United States Patent
Morriss et al.

(10) Patent No.: US 9,655,722 B2
(45) Date of Patent: May 23, 2017

(54) PROSTHETIC HEART VALVE DEVICES, PROSTHETIC MITRAL VALVES AND ASSOCIATED SYSTEMS AND METHODS

(71) Applicant: Twelve, Inc., Redwood City, CA (US)

(72) Inventors: John Morriss, San Francisco, CA (US); Matt McLean, San Francisco, CA (US); Maureen Bensing, Sunnyvale, CA (US); Jean-Pierre Dueri, Los Gatos, CA (US); Hanson Gifford, III, Woodside, CA (US); Katie Miyashiro, San Francisco, CA (US); David Jerry Scott, Redwood City, CA (US); David Trask, Redwood City, CA (US); Kirsten Valley, Los Altos, CA (US)

(73) Assignee: Twelve, Inc., Redwood City, CA (US)

( * ) Notice: Subject to any disclaimer, the term of this patent is extended or adjusted under 35 U.S.C. 154(b) by 0 days.

(21) Appl. No.: 14/776,575

(22) PCT Filed: Mar. 14, 2014

(86) PCT No.: PCT/US2014/029549
§ 371 (c)(1),
(2) Date: Sep. 14, 2015

(87) PCT Pub. No.: WO2014/144937
PCT Pub. Date: Sep. 18, 2014

(65) Prior Publication Data
US 2016/0038280 A1    Feb. 11, 2016

Related U.S. Application Data

(63) Continuation-in-part of application No. 13/946,552, filed on Jul. 19, 2013, now Pat. No. 9,034,032, which
(Continued)

(51) Int. Cl.
*A61F 2/82* (2013.01)
*A61F 2/24* (2006.01)

(52) U.S. Cl.
CPC .......... *A61F 2/2418* (2013.01); *A61F 2/2409* (2013.01); *A61F 2/2436* (2013.01);
(Continued)

(58) Field of Classification Search
CPC ........................................ A61F 2/82
See application file for complete search history.

(56) References Cited

U.S. PATENT DOCUMENTS

| 3,526,219 A | 9/1970 | Balamuth |
| 3,565,062 A | 2/1971 | Kuris |

(Continued)

FOREIGN PATENT DOCUMENTS

| CN | 1440261 | 9/2003 |
| CN | 101076290 | 11/2007 |

(Continued)

OTHER PUBLICATIONS

US 9,265,606, 02/2016, Buchbinder et al. (withdrawn)
(Continued)

*Primary Examiner* — Matthew Schall

(57) ABSTRACT

Prosthetic heart valve devices for percutaneous replacement of native heart valves and associated systems and method are disclosed herein. A prosthetic heart valve device configured in accordance with a particular embodiment of the present technology can include an anchoring member having an upstream portion configured to engage with tissue on or near the annulus of the native heart valve and to deform in a non-circular shape to conform to the tissue. The device can also include a mechanically isolated valve support coupled to the anchoring member and configured to support a prosthetic valve. The device can further include an atrial
(Continued)

extension member extending radially outward from the upstream portion of the anchoring member and which is deformable without substantially deforming the anchoring member. In some embodiments, the upstream portion of the anchoring member and the extension member may be deformed while the valve support remains sufficiently stable.

18 Claims, 124 Drawing Sheets

Related U.S. Application Data is a continuation-in-part of application No. 13/842,785, filed on Mar. 15, 2013, now Pat. No. 9,039,757, which is a continuation-in-part of application No. PCT/US2012/061219, filed on Oct. 19, 2012.

(60) Provisional application No. 61/898,345, filed on Oct. 31, 2013.

(52) U.S. Cl.
CPC ...... *A61F 2/2445* (2013.01); *A61F 2220/005* (2013.01); *A61F 2220/0008* (2013.01); *A61F 2220/0016* (2013.01); *A61F 2220/0025* (2013.01); *A61F 2220/0041* (2013.01); *A61F 2220/0066* (2013.01); *A61F 2220/0075* (2013.01); *A61F 2230/0054* (2013.01); *A61F 2230/0065* (2013.01); *A61F 2230/0067* (2013.01); *A61F 2230/0069* (2013.01); *A61F 2230/0071* (2013.01); *A61F 2230/0078* (2013.01); *A61F 2250/0003* (2013.01); *A61F 2250/006* (2013.01); *A61F 2250/0069* (2013.01)

(56) References Cited

U.S. PATENT DOCUMENTS

| | | | |
|---|---|---|---|
| 3,589,363 A | 6/1971 | Banko et al. |
| 3,667,474 A | 6/1972 | Lapkin et al. |
| 3,823,717 A | 7/1974 | Pohlman et al. |
| 3,861,391 A | 1/1975 | Antonevich et al. |
| 3,896,811 A | 7/1975 | Storz |
| 4,042,979 A | 8/1977 | Angell |
| 4,188,952 A | 2/1980 | Loschilov et al. |
| 4,431,006 A | 2/1984 | Trimmer et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Laughlin et al. |
| 4,602,911 A | 7/1986 | Ahmadi et al. |
| 4,646,736 A | 3/1987 | Auth |
| 4,692,139 A | 9/1987 | Stiles |
| 4,747,821 A | 5/1988 | Kensey et al. |
| 4,750,902 A | 6/1988 | Wuchinich et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,986,830 A | 1/1991 | Owens et al. |
| 4,990,134 A | 2/1991 | Auth |
| 5,058,570 A | 10/1991 | Idemoto et al. |
| 5,069,664 A | 12/1991 | Guess et al. |
| 5,076,276 A | 12/1991 | Sakurai et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,352,199 A | 10/1994 | Tower |
| 5,356,418 A | 10/1994 | Shturman |
| 5,397,293 A | 3/1995 | Alliger et al. |
| 5,411,552 A | 5/1995 | Andersen et al. |
| 5,443,446 A | 8/1995 | Shturman |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,662,671 A | 9/1997 | Barbut et al. |
| 5,681,336 A | 10/1997 | Clement et al. |
| 5,695,507 A | 12/1997 | Auth et al. |
| 5,725,494 A | 3/1998 | Brisken |
| 5,782,931 A | 7/1998 | Yang et al. |
| 5,817,101 A | 10/1998 | Fiedler |
| 5,827,229 A | 10/1998 | Auth et al. |
| 5,840,081 A | 11/1998 | Andersen et al. |
| 5,853,422 A | 12/1998 | Huebsch et al. |
| 5,873,811 A | 2/1999 | Wang et al. |
| 5,904,679 A | 5/1999 | Clayman |
| 5,957,882 A | 9/1999 | Nita et al. |
| 5,972,004 A | 10/1999 | Williamson, IV et al. |
| 5,989,208 A | 11/1999 | Nita |
| 5,989,280 A | 11/1999 | Euteneuer et al. |
| 6,047,700 A | 4/2000 | Eggers et al. |
| 6,056,759 A | 5/2000 | Fiedler |
| 6,085,754 A | 7/2000 | Alferness et al. |
| 6,113,608 A | 9/2000 | Monroe et al. |
| 6,129,734 A | 10/2000 | Shturman et al. |
| 6,132,444 A | 10/2000 | Shturman et al. |
| 6,168,579 B1 | 1/2001 | Tsugita |
| 6,217,595 B1 | 4/2001 | Shturman et al. |
| 6,254,635 B1 | 7/2001 | Schroeder et al. |
| 6,295,712 B1 | 10/2001 | Shturman et al. |
| 6,306,414 B1 | 10/2001 | Koike |
| 6,321,109 B2 | 11/2001 | Ben-Haim et al. |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |
| 6,494,891 B1 | 12/2002 | Cornish et al. |
| 6,505,080 B1 | 1/2003 | Sutton |
| 6,540,782 B1 | 4/2003 | Snyders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,462 B1 | 6/2003 | Andersen et al. |
| 6,595,912 B2 | 7/2003 | Lau et al. |
| 6,605,109 B2 | 8/2003 | Fiedler |
| 6,623,452 B2 | 9/2003 | Chien et al. |
| 6,638,288 B1 | 10/2003 | Shturman et al. |
| 6,648,854 B1 | 11/2003 | Patterson et al. |
| 6,689,086 B1 | 2/2004 | Nita et al. |
| 6,702,748 B1 | 3/2004 | Nita et al. |
| 6,730,121 B2 | 5/2004 | Ortiz et al. |
| 6,746,463 B1 | 6/2004 | Schwartz |
| 6,811,801 B2 | 11/2004 | Nguyen et al. |
| 6,818,001 B2 | 11/2004 | Wulfman et al. |

(56) References Cited

U.S. PATENT DOCUMENTS

| | | |
|---|---|---|
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |
| 6,986,775 B2 | 1/2006 | Morales et al. |
| 7,018,404 B2 | 3/2006 | Holmberg et al. |
| 7,052,487 B2 | 5/2006 | Cohn et al. |
| 7,077,861 B2 | 7/2006 | Spence |
| 7,125,420 B2 | 10/2006 | Rourke et al. |
| 7,186,264 B2 | 3/2007 | Liddicoat et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |
| 7,442,204 B2 | 10/2008 | Schwammenthal et al. |
| 7,473,275 B2 | 1/2009 | Marquez |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |
| 7,942,928 B2 | 5/2011 | Webler et al. |
| 8,002,826 B2 | 8/2011 | Seguin |
| 8,052,750 B2 | 11/2011 | Tuval et al. |
| 8,062,355 B2 | 11/2011 | Figulla et al. |
| 8,109,996 B2 | 2/2012 | Stacchino et al. |
| 8,114,154 B2 | 2/2012 | Righini et al. |
| 8,252,051 B2 | 8/2012 | Chau et al. |
| 8,398,704 B2 | 3/2013 | Straubinger et al. |
| 8,403,981 B2 | 3/2013 | Forster et al. |
| 8,414,643 B2 | 4/2013 | Tuval et al. |
| 8,449,599 B2 | 5/2013 | Chau et al. |
| 8,496,671 B1 | 7/2013 | Hausen |
| 8,512,252 B2 | 8/2013 | Ludomirsky et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,540,767 B2 | 9/2013 | Zhang |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,652,203 B2 | 2/2014 | Quadri et al. |
| 8,685,086 B2 | 4/2014 | Navia et al. |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Rahdert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,812,431 B2 | 8/2014 | Voigt et al. |
| 8,828,043 B2 | 9/2014 | Chambers |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,894,702 B2 | 11/2014 | Quadri et al. |
| 8,900,295 B2 | 12/2014 | Migliazza et al. |
| 8,926,694 B2 | 1/2015 | Costello |
| 8,932,348 B2 | 1/2015 | Solem et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,050,188 B2 | 6/2015 | Schweich, Jr. et al. |
| 9,066,800 B2 | 6/2015 | Clague et al. |
| 9,084,676 B2 | 7/2015 | Chau et al. |
| 9,095,433 B2 | 8/2015 | Lutter et al. |
| 9,119,713 B2 | 9/2015 | Board et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,180,005 B1 | 11/2015 | Lashinski et al. |
| 9,192,466 B2 | 11/2015 | Kovalsky et al. |
| 9,192,471 B2 | 11/2015 | Bolling |
| 9,232,942 B2 | 1/2016 | Seguin et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,254,192 B2 | 2/2016 | Lutter et al. |
| 9,271,833 B2 | 3/2016 | Kim et al. |
| 9,289,291 B2 | 3/2016 | Gorman, III et al. |
| 9,289,297 B2 | 3/2016 | Wilson et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,108 B2 | 6/2016 | Bortlein et al. |
| 9,387,075 B2 | 7/2016 | Bortlein et al. |
| 9,387,078 B2 | 7/2016 | Gross et al. |
| 9,393,111 B2 | 7/2016 | Ma et al. |
| 2001/0021872 A1 | 9/2001 | Bailey et al. |
| 2001/0049492 A1 | 12/2001 | Frazier et al. |
| 2002/0007219 A1 | 1/2002 | Merrill et al. |
| 2002/0013571 A1 | 1/2002 | Goldfarb et al. |
| 2002/0082637 A1 | 6/2002 | Lumauig |
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |

(56) References Cited

U.S. PATENT DOCUMENTS

| | | |
|---|---|---|
| 2004/0092989 A1 | 5/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |
| 2005/0075720 A1 | 4/2005 | Nguyen et al. |
| 2005/0137682 A1 | 6/2005 | Justino |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Salahieh et al. |
| 2005/0267523 A1 | 12/2005 | Devellian et al. |
| 2006/0058872 A1 | 3/2006 | Salahieh et al. |
| 2006/0106456 A9 | 5/2006 | Machold et al. |
| 2006/0149360 A1 | 7/2006 | Schwammenthal et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0061010 A1 | 3/2007 | Hauser et al. |
| 2007/0088431 A1 | 4/2007 | Bourang et al. |
| 2007/0173932 A1 | 7/2007 | Cali et al. |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023117 A1 | 1/2010 | Yoganathan et al. |
| 2010/0030330 A1 | 2/2010 | Bobo et al. |
| 2010/0049313 A1 | 2/2010 | Alon et al. |
| 2010/0076548 A1 | 3/2010 | Konno |
| 2010/0082094 A1* | 4/2010 | Quadri ............... A61F 2/2412 623/1.26 |
| 2010/0094411 A1 | 4/2010 | Tuval et al. |
| 2010/0121436 A1 | 5/2010 | Tuval et al. |
| 2010/0185275 A1 | 7/2010 | Richter et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137409 A1 | 6/2011 | Yang et al. |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0208293 A1 | 8/2011 | Tabor |
| 2011/0224785 A1 | 9/2011 | Hacohen |
| 2011/0319988 A1 | 12/2011 | Schankereli et al. |
| 2012/0022639 A1 | 1/2012 | Hacohen et al. |
| 2012/0035703 A1 | 2/2012 | Lutter et al. |
| 2012/0035713 A1 | 2/2012 | Lutter et al. |
| 2012/0053682 A1 | 3/2012 | Kovalsky et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2013/0172978 A1 | 7/2013 | Vidlund et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guhring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304197 A1 | 11/2013 | Buchbinder et al. |
| 2013/0304198 A1 | 11/2013 | Solem |
| 2013/0304200 A1 | 11/2013 | McLean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | McLean et al. |
| 2013/0325110 A1 | 12/2013 | Khalil et al. |
| 2013/0325114 A1 | 12/2013 | McLean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |

(56) References Cited

U.S. PATENT DOCUMENTS

| | | |
|---|---|---|
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Jonsson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |
| 2014/0194976 A1 | 7/2014 | Starksen et al. |
| 2014/0200397 A1 | 7/2014 | Raman et al. |
| 2014/0200649 A1 | 7/2014 | Essinger et al. |
| 2014/0200657 A1 | 7/2014 | Maurer et al. |
| 2014/0200662 A1 | 7/2014 | Eftel et al. |
| 2014/0214159 A1 | 7/2014 | Vidlund et al. |
| 2014/0219524 A1 | 8/2014 | Takeguchi et al. |
| 2014/0222040 A1 | 8/2014 | Park et al. |
| 2014/0222138 A1 | 8/2014 | Machold et al. |
| 2014/0228942 A1 | 8/2014 | Krahbichler |
| 2014/0228946 A1 | 8/2014 | Chau et al. |
| 2014/0242086 A1 | 8/2014 | Lal et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1 | 9/2014 | Bortlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lamelas et al. |
| 2014/0309730 A1 | 10/2014 | Alon et al. |
| 2014/0309731 A1 | 10/2014 | Quadri et al. |
| 2014/0309732 A1 | 10/2014 | Solem |
| 2014/0316516 A1 | 10/2014 | Vidlund et al. |
| 2014/0324164 A1 | 10/2014 | Gross et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371843 A1 | 12/2014 | Wilson et al. |
| 2014/0371844 A1 | 12/2014 | Dale et al. |
| 2014/0371846 A1 | 12/2014 | Wilson et al. |
| 2014/0379074 A1 | 12/2014 | Spence et al. |
| 2014/0379076 A1 | 12/2014 | Vidlund et al. |
| 2015/0005874 A1 | 1/2015 | Vidlund et al. |
| 2015/0005875 A1 | 1/2015 | Tuval et al. |
| 2015/0025623 A1 | 1/2015 | Granada et al. |
| 2015/0032127 A1 | 1/2015 | Gammie et al. |
| 2015/0045878 A1 | 2/2015 | Rowe |
| 2015/0066140 A1 | 3/2015 | Quadri et al. |
| 2015/0094802 A1 | 4/2015 | Buchbinder et al. |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | Macoviak et al. |
| 2015/0164637 A1 | 6/2015 | Khairkhahan et al. |
| 2015/0164641 A1 | 6/2015 | Annest |
| 2015/0173897 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257881 A1 | 9/2015 | Bortlein et al. |
| 2015/0257882 A1 | 9/2015 | Bortlein et al. |
| 2015/0272737 A1 | 10/2015 | Dale et al. |
| 2015/0305861 A1 | 10/2015 | Annest |
| 2015/0305864 A1 | 10/2015 | Quadri et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0342733 A1 | 12/2015 | Alkhatib et al. |
| 2015/0342737 A1 | 12/2015 | Biancucci et al. |
| 2015/0351908 A1 | 12/2015 | Keranen et al. |
| 2015/0359628 A1 | 12/2015 | Keranen |
| 2015/0359629 A1 | 12/2015 | Ganesan et al. |
| 2015/0359631 A1 | 12/2015 | Sheahan et al. |
| 2015/0366666 A1 | 12/2015 | Khairkhahan et al. |
| 2015/0374495 A1 | 12/2015 | Ruyra Baliarda et al. |
| 2016/0000983 A1 | 1/2016 | Mohl et al. |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0030171 A1 | 2/2016 | Quijano et al. |

(56) References Cited

U.S. PATENT DOCUMENTS

| | | |
|---|---|---|
| 2016/0038246 A1 | 2/2016 | Wang et al. |
| 2016/0038280 A1 | 2/2016 | Morriss et al. |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158001 A1 | 6/2016 | Wallace et al. |
| 2016/0158002 A1 | 6/2016 | Wallace et al. |
| 2016/0158003 A1 | 6/2016 | Wallace et al. |
| 2016/0184095 A1 | 6/2016 | Spence et al. |
| 2016/0206424 A1 | 7/2016 | Al-jilaihawi et al. |

FOREIGN PATENT DOCUMENTS

| | | |
|---|---|---|
| CN | 101291637 | 10/2008 |
| CN | 103491900 | 1/2014 |
| DE | 19605042 | 1/1998 |
| DE | 102006052564 B3 | 12/2007 |
| EP | 186104 | 7/1986 |
| EP | 1512383 | 3/2005 |
| EP | 1545371 | 6/2005 |
| EP | 1551274 | 7/2005 |
| EP | 1629794 | 3/2006 |
| EP | 1646332 | 4/2006 |
| EP | 1702247 | 9/2006 |
| EP | 1734903 | 12/2006 |
| EP | 2026280 | 2/2009 |
| EP | 2037829 | 3/2009 |
| EP | 2081519 | 7/2009 |
| EP | 2111190 | 10/2009 |
| EP | 2142143 | 1/2010 |
| EP | 2167742 | 3/2010 |
| EP | 2278944 | 2/2011 |
| EP | 2306821 | 4/2011 |
| EP | 2327429 | 6/2011 |
| EP | 2400926 | 1/2012 |
| EP | 2410947 | 2/2012 |
| EP | 2416739 | 2/2012 |
| EP | 2444031 | 4/2012 |
| EP | 2488126 | 8/2012 |
| EP | 2509538 | 10/2012 |
| EP | 2549955 | 1/2013 |
| EP | 2549956 | 1/2013 |
| EP | 2566416 | 3/2013 |
| EP | 2586492 | 5/2013 |
| EP | 2618784 | 7/2013 |
| EP | 2623068 | 8/2013 |
| EP | 2626013 | 8/2013 |
| EP | 2629699 | 8/2013 |
| EP | 2633457 | 9/2013 |
| EP | 2637659 | 9/2013 |
| EP | 2641569 | 9/2013 |
| EP | 2654624 | 10/2013 |
| EP | 2656794 | 10/2013 |
| EP | 2656795 | 10/2013 |
| EP | 2656796 | 10/2013 |
| EP | 2667823 | 12/2013 |
| EP | 2670358 | 12/2013 |
| EP | 2676640 | 12/2013 |
| EP | 2688041 | 1/2014 |
| EP | 2697721 | 2/2014 |
| EP | 2713953 | 4/2014 |
| EP | 2714068 | 4/2014 |
| EP | 2723272 | 4/2014 |
| EP | 2723273 | 4/2014 |
| EP | 2723277 | 4/2014 |
| EP | 2739214 | 6/2014 |
| EP | 2741711 | 6/2014 |
| EP | 2750630 | 7/2014 |
| EP | 2750631 | 7/2014 |
| EP | 2755562 | 7/2014 |
| EP | 2755602 | 7/2014 |
| EP | 2757962 | 7/2014 |
| EP | 2777616 | 9/2014 |
| EP | 2777617 | 9/2014 |
| EP | 2782523 | 10/2014 |
| EP | 2785282 | 10/2014 |
| EP | 2790609 | 10/2014 |
| EP | 2793751 | 10/2014 |
| EP | 2809263 | 12/2014 |
| EP | 2810620 | 12/2014 |
| EP | 2814428 | 12/2014 |
| EP | 2814429 | 12/2014 |
| EP | 2819617 | 1/2015 |
| EP | 2819618 | 1/2015 |
| EP | 2819619 | 1/2015 |
| EP | 2833836 | 2/2015 |
| EP | 2838475 | 2/2015 |
| EP | 2849680 | 3/2015 |
| EP | 2849681 | 3/2015 |
| EP | 2852354 | 4/2015 |
| EP | 2873011 | 5/2015 |
| EP | 2875797 | 5/2015 |
| EP | 2882374 | 6/2015 |
| EP | 2886083 | 6/2015 |
| EP | 2886084 | 6/2015 |
| EP | 2895111 | 7/2015 |
| EP | 2901966 | 8/2015 |
| EP | 2907479 | 8/2015 |
| EP | 2945572 | 11/2015 |
| EP | 2948094 | 12/2015 |
| EP | 2948102 | 12/2015 |
| EP | 2964152 | 1/2016 |
| EP | 2967859 | 1/2016 |
| EP | 2967860 | 1/2016 |
| EP | 2967866 | 1/2016 |
| EP | 2968847 | 1/2016 |
| EP | 2981208 | 2/2016 |
| EP | 2982336 | 2/2016 |
| EP | 2999433 | 3/2016 |
| EP | 3003187 | 4/2016 |
| EP | 3003219 | 4/2016 |
| EP | 3003220 | 4/2016 |
| EP | 3010447 | 4/2016 |
| EP | 3013281 | 5/2016 |
| EP | 3017792 | 5/2016 |
| EP | 3021792 | 5/2016 |
| EP | 3023117 | 5/2016 |
| EP | 3027143 | 6/2016 |
| EP | 3033048 | 6/2016 |
| EP | 3037064 | 6/2016 |
| JP | 6504516 | 5/1994 |
| JP | 2002509756 | 4/2002 |
| JP | 2005280917 | 10/2005 |
| JP | 5219518 B2 | 6/2013 |
| WO | WO-9217118 | 10/1992 |
| WO | WO-9516407 | 6/1995 |
| WO | WO-9904730 | 2/1999 |
| WO | WO-9939648 | 8/1999 |
| WO | WO-9949799 | 10/1999 |
| WO | WO-0110343 | 2/2001 |
| WO | WO-0203892 | 1/2002 |
| WO | WO-0228421 | 4/2002 |
| WO | WO-0239908 | 5/2002 |
| WO | WO-03043685 | 5/2003 |
| WO | WO-2004084746 | 10/2004 |
| WO | WO-2004093728 | 11/2004 |
| WO | WO-2004096097 | 11/2004 |
| WO | WO-2004112657 | 12/2004 |
| WO | WO-2005002466 | 1/2005 |
| WO | WO-2005007219 | 1/2005 |
| WO | WO-2005009285 | 2/2005 |
| WO | WO-2005009506 | 2/2005 |
| WO | WO-2005087140 | 9/2005 |

(56) References Cited

FOREIGN PATENT DOCUMENTS

| | | |
|---|---|---|
| WO | WO-2006041877 | 4/2006 |
| WO | WO-2006063199 | 6/2006 |
| WO | WO-2007008371 | 1/2007 |
| WO | WO-2007067820 | 6/2007 |
| WO | WO-2008022077 | 2/2008 |
| WO | WO-2008028569 | 3/2008 |
| WO | WO-2008035337 | 3/2008 |
| WO | WO-2008103497 | 8/2008 |
| WO | WO-2008129405 | 10/2008 |
| WO | WO-2010006627 | 1/2010 |
| WO | WO-2010008549 | 1/2010 |
| WO | WO-2010057262 | 5/2010 |
| WO | WO-2010080594 | 7/2010 |
| WO | WO-2010098857 | 9/2010 |
| WO | WO-2010099032 | 9/2010 |
| WO | WO-2011047168 | 4/2011 |
| WO | WO-2011051043 | 5/2011 |
| WO | WO-2011057087 | 5/2011 |
| WO | WO-2011072084 | 6/2011 |
| WO | WO-2011106137 | 9/2011 |
| WO | WO-2011106544 | 9/2011 |
| WO | WO-2011111047 | 9/2011 |
| WO | WO-2011137531 | 11/2011 |
| WO | WO-2012011018 | 1/2012 |
| WO | WO-2012011108 | 1/2012 |
| WO | WO-2012027487 | 3/2012 |
| WO | WO-2012035279 | 3/2012 |
| WO | WO-2012040655 | 3/2012 |
| WO | WO-2012047644 | 4/2012 |
| WO | WO-2012055498 | 5/2012 |
| WO | WO-2012087842 | 6/2012 |
| WO | WO-2012095455 | 7/2012 |
| WO | WO-2012102928 | 8/2012 |
| WO | WO-2012106602 | 8/2012 |
| WO | WO-2012118508 | 9/2012 |
| WO | WO-2012118816 | 9/2012 |
| WO | WO-2012118894 | 9/2012 |
| WO | WO-2012177942 | 12/2012 |
| WO | WO-2013021374 | 2/2013 |
| WO | WO-2013021375 | 2/2013 |
| WO | WO-2013028387 | 2/2013 |
| WO | WO-2013059743 | 4/2013 |
| WO | WO-2013059747 | 4/2013 |
| WO | WO-2013114214 | 8/2013 |
| WO | WO-2013120181 | 8/2013 |
| WO | WO-2013123059 | 8/2013 |
| WO | WO-2013128432 | 9/2013 |
| WO | WO-2013130641 | 9/2013 |
| WO | WO-2013131925 | 9/2013 |
| WO | WO-2013140318 | 9/2013 |
| WO | WO-2013148017 | 10/2013 |
| WO | WO-2013148018 | 10/2013 |
| WO | WO-2013148019 | 10/2013 |
| WO | WO-2013150512 | 10/2013 |
| WO | WO-2013152161 | 10/2013 |
| WO | WO-2013158613 | 10/2013 |
| WO | WO-2013169448 | 11/2013 |
| WO | WO-2013175468 | 11/2013 |
| WO | WO-2013176583 | 11/2013 |
| WO | WO-2013188077 | 12/2013 |
| WO | WO-2013192107 | 12/2013 |
| WO | WO-2014036113 | 3/2014 |
| WO | WO-2014043527 | 3/2014 |
| WO | WO-2014047111 | 3/2014 |
| WO | WO-2014047325 | 3/2014 |
| WO | WO-2014055981 | 4/2014 |
| WO | WO-2014059432 | 4/2014 |
| WO | WO-2014064694 | 5/2014 |
| WO | WO-2014066365 | 5/2014 |
| WO | WO-2014089424 | 6/2014 |
| WO | WO-2014093861 | 6/2014 |
| WO | WO-2014111918 | 7/2014 |
| WO | WO-2014114794 | 7/2014 |
| WO | WO-2014114795 | 7/2014 |
| WO | WO-2014114796 | 7/2014 |
| WO | WO-2014114798 | 7/2014 |
| WO | WO-2014116502 | 7/2014 |
| WO | WO-2014121280 | 8/2014 |
| WO | WO-2014128705 | 8/2014 |
| WO | WO-2014134277 | 9/2014 |
| WO | WO-2014138194 | 9/2014 |
| WO | WO-2014138284 | 9/2014 |
| WO | WO-2014138482 | 9/2014 |
| WO | WO-2014138868 | 9/2014 |
| WO | WO-2014144100 | 9/2014 |
| WO | WO-2014144937 | 9/2014 |
| WO | WO-2014145338 | 9/2014 |
| WO | WO-2014147336 | 9/2014 |
| WO | WO-2014152306 | 9/2014 |
| WO | WO-2014152375 | 9/2014 |
| WO | WO-2014152503 | 9/2014 |
| WO | WO-2014153544 | 9/2014 |
| WO | WO-2014158617 | 10/2014 |
| WO | WO-2014162181 | 10/2014 |
| WO | WO-2014162306 | 10/2014 |
| WO | WO-2014163705 | 10/2014 |
| WO | WO-2014168655 | 10/2014 |
| WO | WO-2014179391 | 11/2014 |
| WO | WO-2014181336 | 11/2014 |
| WO | WO-2014191994 | 12/2014 |
| WO | WO-2014194178 | 12/2014 |
| WO | WO-2014201384 | 12/2014 |
| WO | WO-2014201452 | 12/2014 |
| WO | WO-2014205064 | 12/2014 |
| WO | WO-2014207699 | 12/2014 |
| WO | WO-2014210124 | 12/2014 |
| WO | WO-2014210299 | 12/2014 |
| WO | WO-2015009503 | 1/2015 |
| WO | WO-2015020971 | 2/2015 |
| WO | WO-2015028986 | 3/2015 |
| WO | WO-2015051430 | 4/2015 |
| WO | WO-2015052663 | 4/2015 |
| WO | WO-2015057407 | 4/2015 |
| WO | WO-2015057735 | 4/2015 |
| WO | WO-2015057995 | 4/2015 |
| WO | WO-2015061378 | 4/2015 |
| WO | WO-2015061431 | 4/2015 |
| WO | WO-2015061463 | 4/2015 |
| WO | WO-2015061533 | 4/2015 |
| WO | WO-2015075128 | 5/2015 |
| WO | WO-2015081775 | 6/2015 |
| WO | WO-2015089334 | 6/2015 |
| WO | WO-2015092554 | 6/2015 |
| WO | WO-2015120122 | 8/2015 |
| WO | WO-2015125024 | 8/2015 |
| WO | WO-2015127264 | 8/2015 |
| WO | WO-2015127283 | 8/2015 |
| WO | WO-2015128739 | 9/2015 |
| WO | WO-2015128741 | 9/2015 |
| WO | WO-2015128747 | 9/2015 |
| WO | WO-2015132667 | 9/2015 |
| WO | WO-2015132668 | 9/2015 |
| WO | WO-2015135050 | 9/2015 |
| WO | WO-2015142648 | 9/2015 |
| WO | WO-2015142834 | 9/2015 |
| WO | WO-2015145241 | 10/2015 |
| WO | WO-2015171190 | 11/2015 |
| WO | WO-2015171743 | 11/2015 |
| WO | WO-2015191604 | 12/2015 |
| WO | WO-2015191839 | 12/2015 |
| WO | WO-2015195823 | 12/2015 |
| WO | WO-2016011185 | 1/2016 |
| WO | WO-2016020918 | 2/2016 |
| WO | WO-2016027272 | 2/2016 |
| WO | WO-2016059533 | 4/2016 |
| WO | WO-2016065158 | 4/2016 |
| WO | WO-2016073741 | 5/2016 |
| WO | WO-2016083551 | 6/2016 |
| WO | WO-2016093877 | 6/2016 |

(56) References Cited

FOREIGN PATENT DOCUMENTS

| WO | WO-2016097337 | 6/2016 |
|---|---|---|
| WO | WO-2016108181 | 7/2016 |

OTHER PUBLICATIONS

"Optison (Perflutren Protein— Type a Microspheres for Injection, USP)." GE Healthcare. General Electric Company. 1997-2005. Web. May 26, 2005. <http://www.amershamhealth-us.com/optison/.
Bernard et al., "Aortic Valve Area Evolution After Percutaneous Aortic Valvuloplasty," European Heart Journal vol. 11, No. 2, Jul. 1990, pp. 98-107.
BlueCross BlueShield of Northern Carolina Corporate Medical Policy "Balloon valvuloplasty, Percutaneous", (Jun. 1994).
Cimino et al., "Physics of Ultrasonic Surgery using Tissue Fragmentation: Part I and Part II", Ultrasound in Medicine and Biologyl, vol. 22, No. 1, pp. 89-100, and pp. 101-117, Jun. 1996.
Cimino, Ultrasonic surgery: power quantification and efficiency optimization. Aesthetic surgery journal, Feb. 2001, 233-241.
Office Action dated Feb. 23, 2011 from Japanese Patent Application No. 2007-545650 together with an English language translation, 10 pages.
Cowell et al., "A randomized Trial of Intensive Lipid-Lowering Therapy in Calcific Aortic Stenosis," NEJM vol. 352 No. 23, pp. 2389-2397 (Jun. 9, 2005).
De Korte et al., "Characterization of plaque components and vulnerability with intravascular ultrasound elastography" Phys. Med. Biol. vol. 45, Feb. 2000, pp. 1465-1475.
Feldman, "Restenosis Following Successful Balloon Valvuloplasty: Bone Formation in Aortic Valve Leaflets," Cathet Cardiovasc Diagn, vol. 29 No. 1, pp. 1-7 (May 1993).
Final Office Action for U.S. Appl. No. 12/870,270, Mailed Jul. 3, 2012, Examiner S. Ganesan, 7 pages.
Final Office Action for U.S. Appl. No. 11/299,246, Mailed Feb. 17, 2010, Examiner S. Ganesan, 6 pages.
Final Office Action for U.S. Appl. No. 11/299,246, Mailed Jun. 6, 2008, Examiner S. Ganesan, 5 pages.
Final Office Action for U.S. Appl. No. 13/329,083, Mailed Jan. 6, 2014, Examiner Prebilic, 9 pages.
Final Office Action for U.S. Appl. No. 13/842,785, mailed Aug. 29, 2014, Examiner Schall, 5 pages.
Final Office Action for U.S. Appl. No. 13/946,552, Examiner Schall, Mailed Aug. 29, 2014, 5 pages.
Final Office Action for U.S. Appl. No. 13/946,628, Mailed Sep. 2, 2014, Examiner Schall, 6 pages.
Final Office Action for U.S. Appl. No. 13/842,785, mailed Jan. 5, 2015, Examiner Schall, 6 pages.
Final Office Action for U.S. Appl. No. 13/946,552, Examiner Schall, Mailed Jan. 8, 2015, 6 pages.
Final Office Action for U.S. Appl. No. 13/946,628, Mailed Jan. 5, 2015, Examiner Schall, 5 pages.
Fitzgerald et al., "Intravascular Sonotherapy Decreased Neointimal Hyperplasia After Stent Implantation in Swine," Circulation, vol. 103, Feb. 2001, pp. 1828-1831.
Freeman et al., "Ultrasonic Aortic Valve Decalcification: Serial Doppler Echocardiographic Follow Up," J Am Coll Cardiol., vol. 16, No. 3, pp. 623-630 (Sep. 1990).
Greenleaf et al., "Selected Methods for Imaging Elastic Properties of Biological Tissues" Annu. Rev. Biomed. Eng., vol. 5, Apr. 2003, pp. 57-78.
Gunn et al., "New Developments in Therapeutic Ultrasoundssisted Coronary Angioplasty," Curr Intery Cardiol Rep., vol. 1 No. 4, pp. 281-290, (Dec. 1990).
Guzman et al., "Bioeffects Caused by Changes in Acoustic Cavitation Bubble Density and Cell Concentration: A Unified Explanation Based on Cell-to-Bubble Ratio and Blast Radius," Ultrasound in Med. & Biol., vol. 29, No. 8, Mar. 2003, pp. 1211-1222.

Hallgrimsson et al., "Chronic Non-Rheumatic Aortic Valvular Disease: a Population Study Based on Autopsies," J Chronic Dis. vol. 32 No. 5, Jun. 1979, pp. 355-363.
International Search Report and Written Opinion dated May 1, 2012; International Application No. PCT/US2011/065627; Applicant: Foundry Newco XII, Inc.; 10 pages.
International Search Report and Written Opinion dated Dec. 10, 2012; International Application No. PCT/US2012/043636; Applicant: Foundry Newco XII, Inc.; 21 pages.
International Search Report and Written Opinion dated Jan. 30, 2013; International Application No. PCT/US2012/061215; Applicant: Foundry Newco XII, Inc.; 11 pages.
International Search Report and Written Opinion dated Jan. 30, 2013; International Application No. PCT/US2012/061219; Applicant: Foundry Newco XII, Inc.; 9 pages.
International Search report and Written Opinion for International App. No. PCT/US2005/044543, dated May 22, 2007, 8 pages.
International Search Report and Written Opinion for International App. No. PCT/US2014/014704, mailed Sep. 4, 2014, 18 pages.
International Search Report and Written Opinion for International Application No. PCT/US2014/038849, mailed Oct. 20, 2014, 14 pages.
International Search Report and Written Opinion for International Application No. PCT/US2014/029549, mailed Mar. 2, 2015, 20 pages.
Isner et al., "Contrasting Histoarchitecture of calcified leaflets from stenotic bicuspid versus stenotic tricuspid aortic valves," J Am Coll Cardiol., vol. 15, No. 5, p. 1104, (Apr. 1990).
Lung et al., "A Prospective Survey of Patients with Valvular Heart Disease in Europe: The Euro Heart Survey on Valvular Heart Disease," Euro Heart Journal, vol. 24, Mar. 2003, pp. 1231-1243.
McBride et al "Aortic Valve Decalcification," J Thorac Cardiovas-Surg, vol. 100, Jul. 1990, pp. 36-42.
Miller et al., "Lysis and Sonoporation of Epidermoid and Phagocytic Monolayer Cells by Diagnostic Ultrasound Activation of Contrast Agent Gas Bodies," Ultrasound in Med. & Biol., vol. 27, No. 8, May 2001, pp. 1107-1113.
Mohler, "Mechanisms of Aortic Valve Calcificaion," Am J Cardiol, vol. 94 No. 11, pp. 1396- 1402, A6 (Dec. 1, 2004).
Non Final Office Action for U.S. Appl. No. 11/299,246, Mailed Apr. 7, 2009, Examiner S. Ganesan, 6 pages.
Non Final Office Action for U.S. Appl. No. 11/299,246, Mailed Oct. 16, 2008, Examiner S. Ganesan, 7 pages.
Non Final Office Action for U.S. Appl. No. 11/299,246, Mailed Aug. 22, 2007, Examiner S. Ganesan, 4 pages.
Non Final Office Action for U.S. Appl. No. 12/870,270, Mailed Nov. 18, 2011, Examiner S. Ganesan, 9 pages.
Non Final Office Action for U.S. Appl. No. 13/329,083, Mailed Jul. 25, 2013, Examiner Paul Prebilic, 16 pages.
Non Final Office Action for U.S. Appl. No. 13/842,785, Mailed Feb. 3, 2014, Examiner Schall, 24 pages.
Non Final Office Action for U.S. Appl. No. 13/946,552, Mailed Feb. 3, 2014, Examiner Schall, 23 pages.
Non Final Office Action for U.S. Appl. No. 13/946,628, Mailed Feb. 4, 2014, Examiner Schall, 24 pages.
Non Final Office Action for U.S. Appl. No. 13/949,098, Mailed Feb. 24, 2014, Examiner Dukert, 28 pages.
Non Final Office Action for U.S. Appl. No. 13/949,098, Mailed Dec. 18, 2014, Examiner Dukert, 11 pages.
Notice of Allowance for U.S. Appl. No. 11/299,246, Mailed May 27, 2010, Examiner S. Ganesan, 6 pages.
Otto et al., "Three-Year Outcome After Balloon Aortic Valvuloplasty. Insights into Prognosis of Valvular Aortic Stenosis," Circulation, vol. 89, Feb. 1994, pp. 642-650.
Passik et al., "Temporal Changes in the Causes of Aortic Stenosis: A Surgical Pathologic Study of 646 Cases," Mayo Clin Proc, vol. 62, Feb. 1987, pp. 19-123.
Quaden et al., "Percutaneous Aortic Valve Replacement: Resection Before Implantation," Eur J Cardiothorac Surg, vol. 27, Jan. 2005, pp. 836-840.
Riebman et al., "New Concepts in the Management of Patients With Aortic Valve Disease." Abstract, Valvular Heart Disease, JACC, Mar. 2004, p. 34A.

(56) References Cited

OTHER PUBLICATIONS

Rosenschein et al., "Percutaneous Transluminal Therapy of Occluded Saphenous Vein Grafts," Circulation, vol. 99, Jan. 1999, pp. 26-29.
Sakata et al., "Percutaneous Balloon Aortic Valvuloplasty: *Antegrade Transseptal* vs. *Conventional Retrograde Transarterial Approach*," Catheter Cardiovasc Interv., vol. 64, No. 3, p. 314, (Mar. 2005).
Sasaki et al., "Scanning electron microscopy and Fourier transformed infrared spectroscopy analysis of bone removal using Er:YAG and CO2 lasers" J Periodontol.; vol. 73, No. 6, pp. 643-652. (Jun. 2002).
The CoreValve System; Medtronic; Dated 2012; 4 pages.
Van Den Brand et al., "Histological Changes in the Aortic Valve after Balloon Dilation: Evidence for a Delayed Healing Process," Br Heart J, Jun. 1992; vol. 67, pp. 445-459.
Verdaadadonk et al., "The Mechanism of Action of the Ultrasonic Tissue Resectors Disclosed Using High-Speed and Thermal Imaging Techniques," SPIE, vol. 3594, pp. 221-231 (Jan. 1999).
Voelker et al., "Inoperative Valvuloplasty in Calcific Aortic Stenosis: a Study Comparing the Mechanism of a Novel Expandable Device with conventional Balloon Dilation," Am Heart J. vol. 122 No. 5, pp. 1327-1333 (Nov. 1991).
Waller et al., "Catheter Balloon Valvuloplasty of Stenotic Aortic Valves. Part II: Balloon Valvuloplasty During Life Subsequent Tissue Examination," Clin Cardiol., vol. 14 No. 11, pp. 924-930, (Nov. 1991).
Wang, "Balloon Aortic Valvuloplasty," Prog Cardiovasc Dis., vol. 40, No. 1, pp. 27-36. (Jul. 1997).
Wilson et al., "Elastography—The movement Begins" Phys. Med. Biol., vol. 45, Jun. 2000, pp. 1409-1421.
Yock et al, "Catheter-Based Ultrasound Thrombolysis," Circulation, vol. 95 No. 6, pp. 1411-1416 (Mar. 18, 1997).
European Search Report for European App. No. 05853460.3, completed Mar. 13, 2015, 3 pages.
Notice of Allowance for U.S. Appl. No. 13/842,785, Examiner Schall, mailed Apr. 7, 2015, 8 pages.
Notice of Allowance for U.S. Appl. No. 13/946,552, Examiner Schall, mailed Mar. 25, 2015, 8 pages.
Notice of Allowance for U.S. Appl. No. 13/946,628, Examiner Schall, mailed Mar. 25, 2015, 8 pages.
Notice of Allowance for U.S. Appl. No. 13/949,098, Examiner B. Dukert, mailed May 8, 2015, 7 pages.
Notice of Allowance for U.S. Appl. No. 14/627,566, Examiner M. W. Schall, mailed Nov. 12, 2015, 7 pages.
Non-Final Office Action for U.S. Appl. No. 13/329,083, mailed Dec. 10, 2015, 9 pages.

* cited by examiner

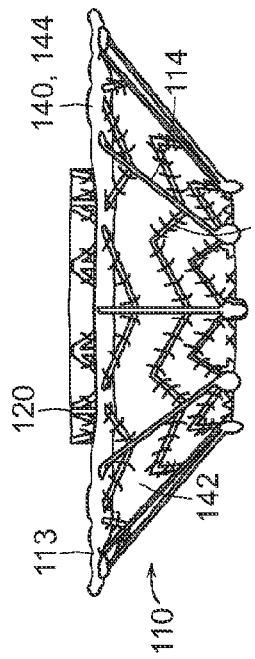
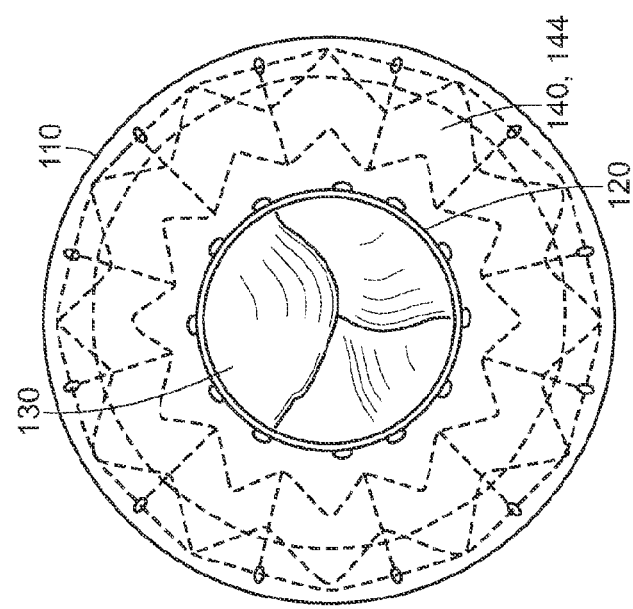
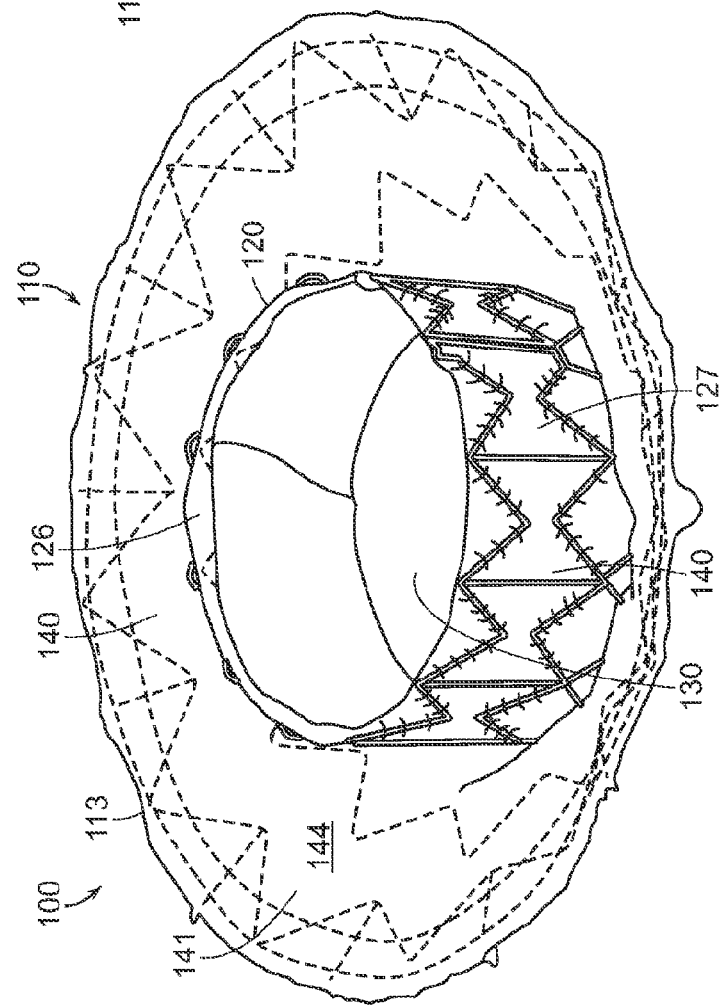
FIG. 19B
FIG. 19C
FIG. 19A

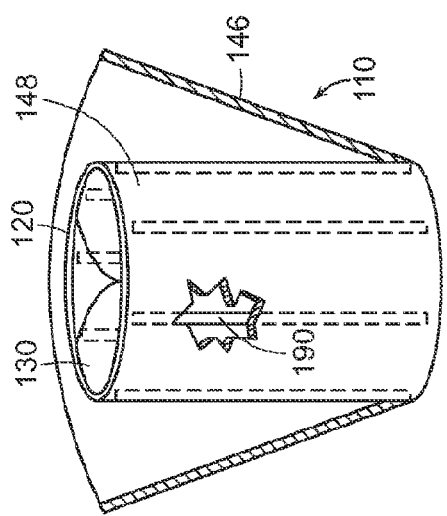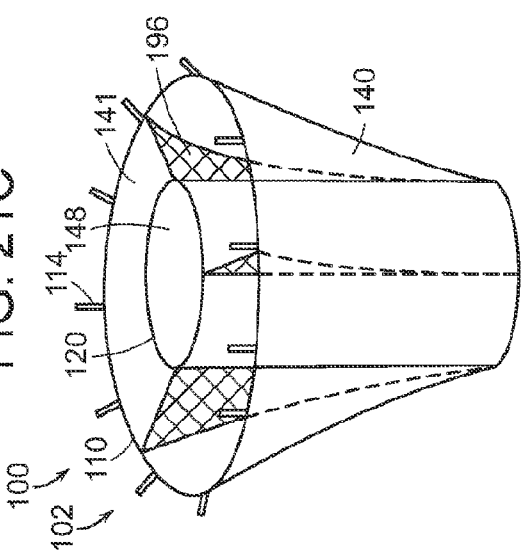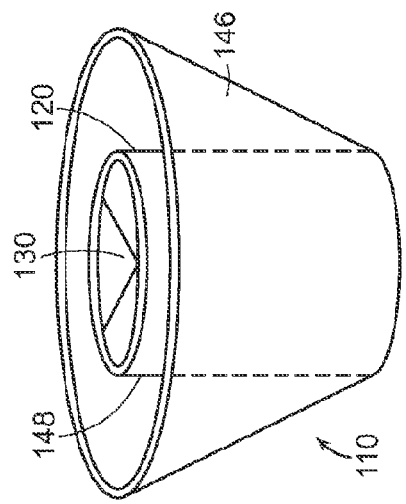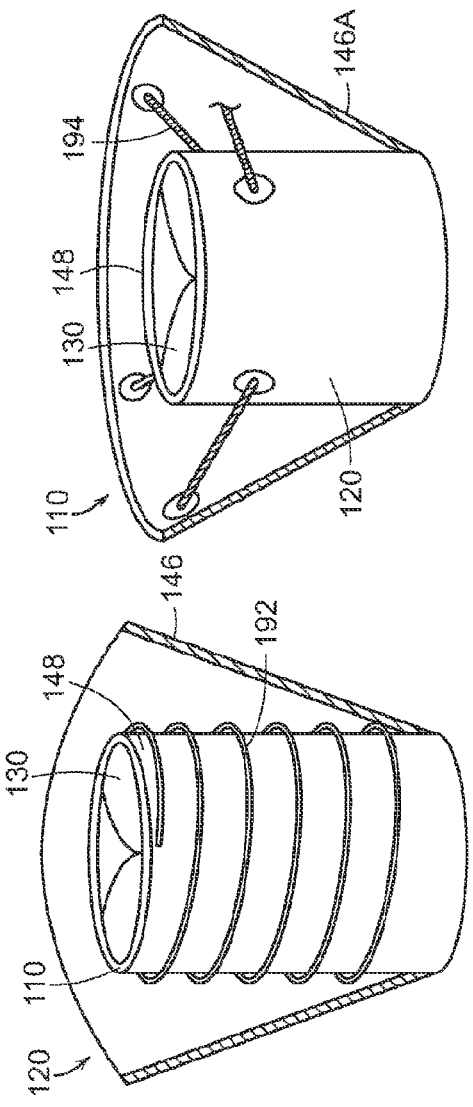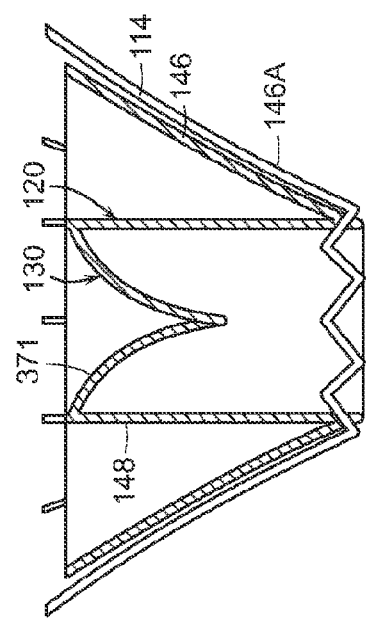

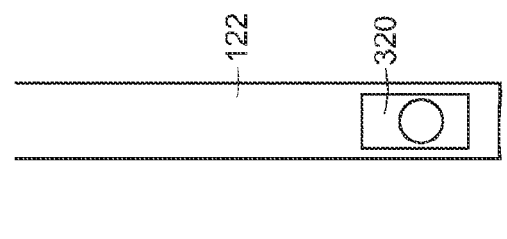
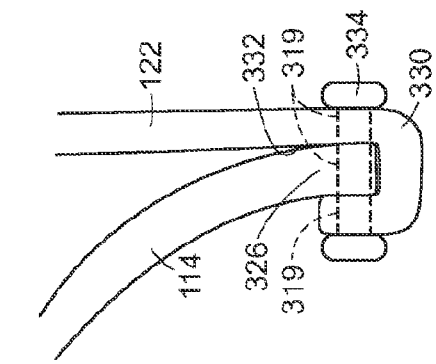
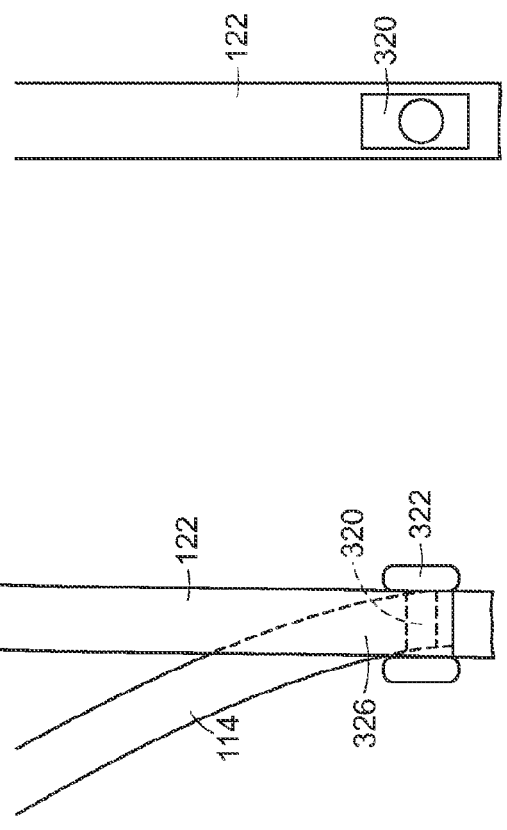
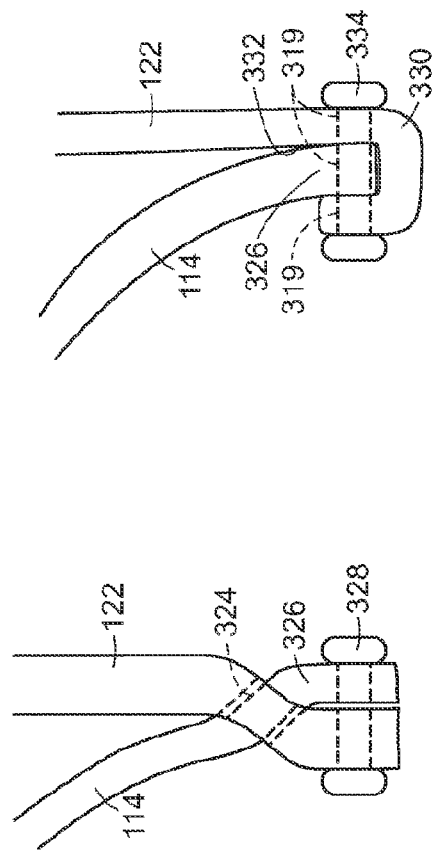
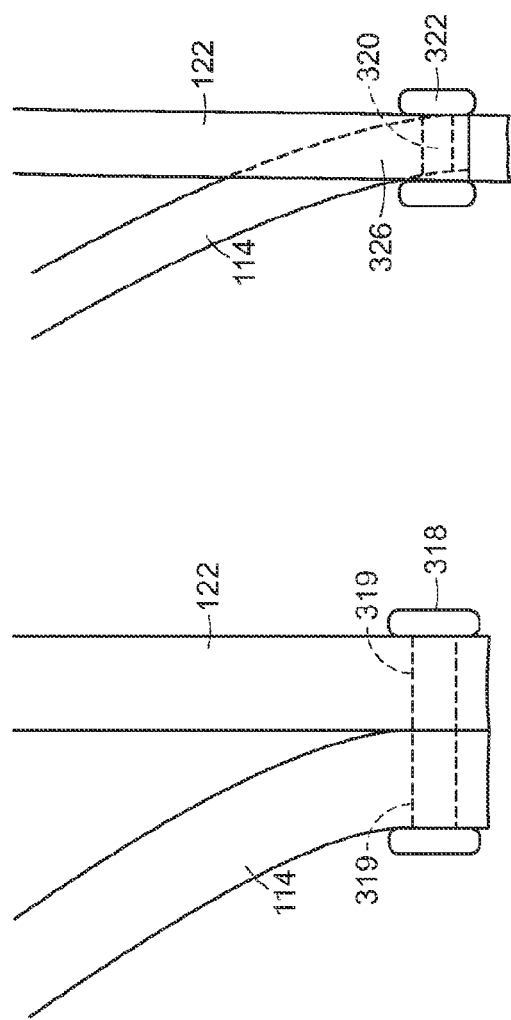
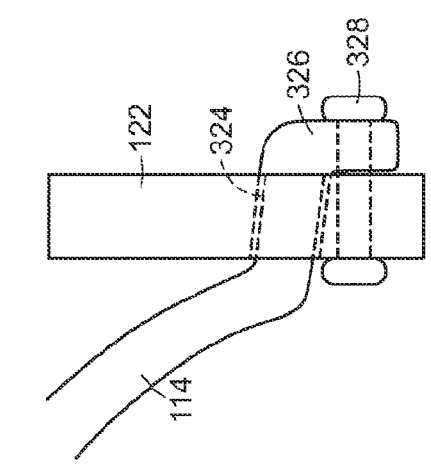

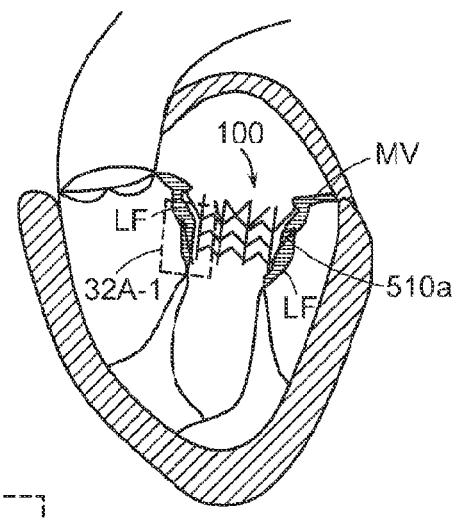
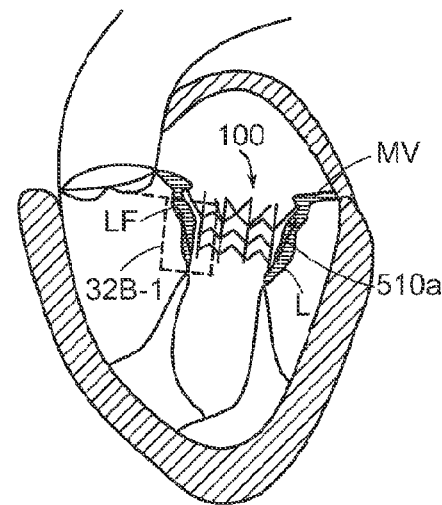
FIG. 32A
FIG. 32B
FIG. 32A-1
FIG. 32B-1
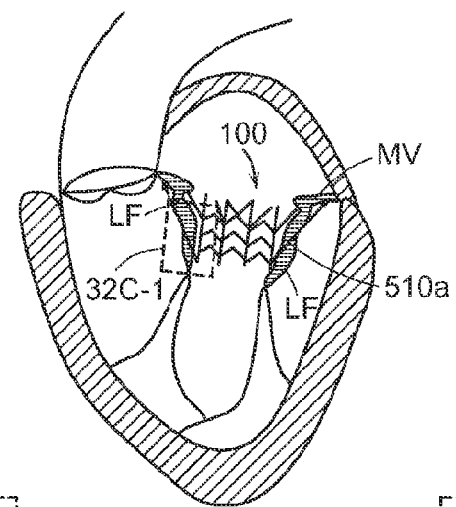
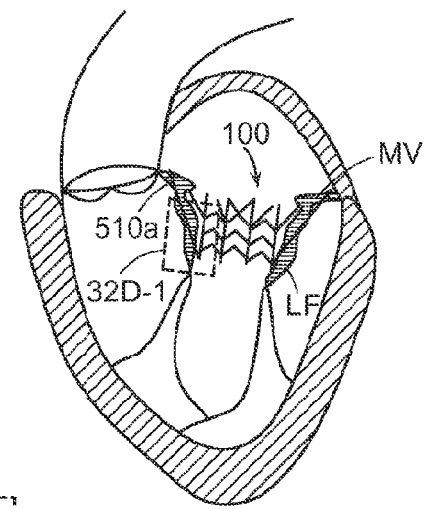
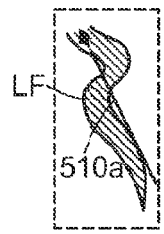
FIG. 32C
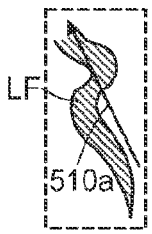
FIG. 32D
FIG. 32C-1
FIG. 32D-1

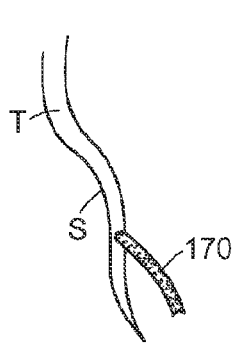
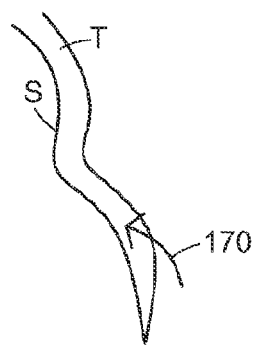
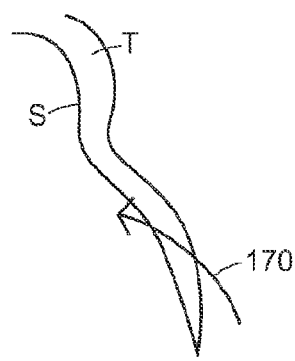
FIG. 33A  FIG. 33B  FIG. 33C
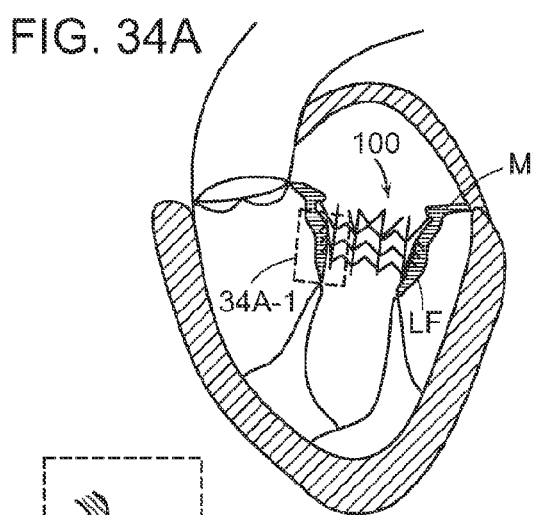
FIG. 34A
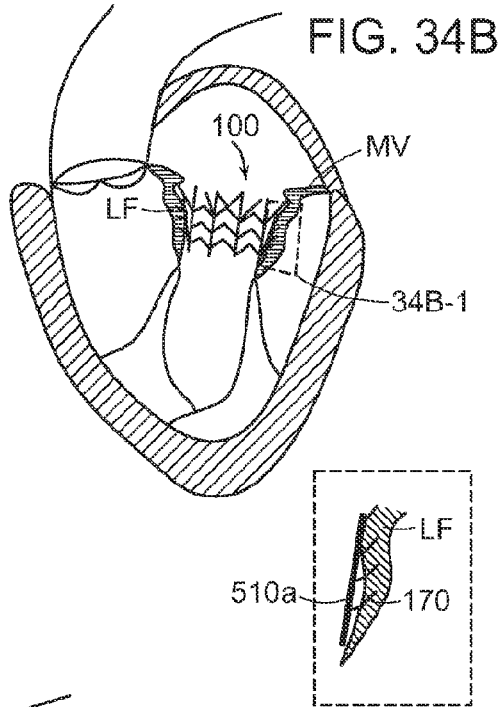
FIG. 34B
FIG. 34A-1
FIG. 34B-1
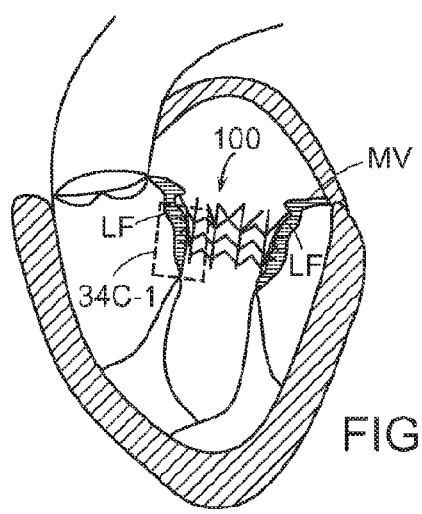
FIG. 34C-1
FIG. 34C

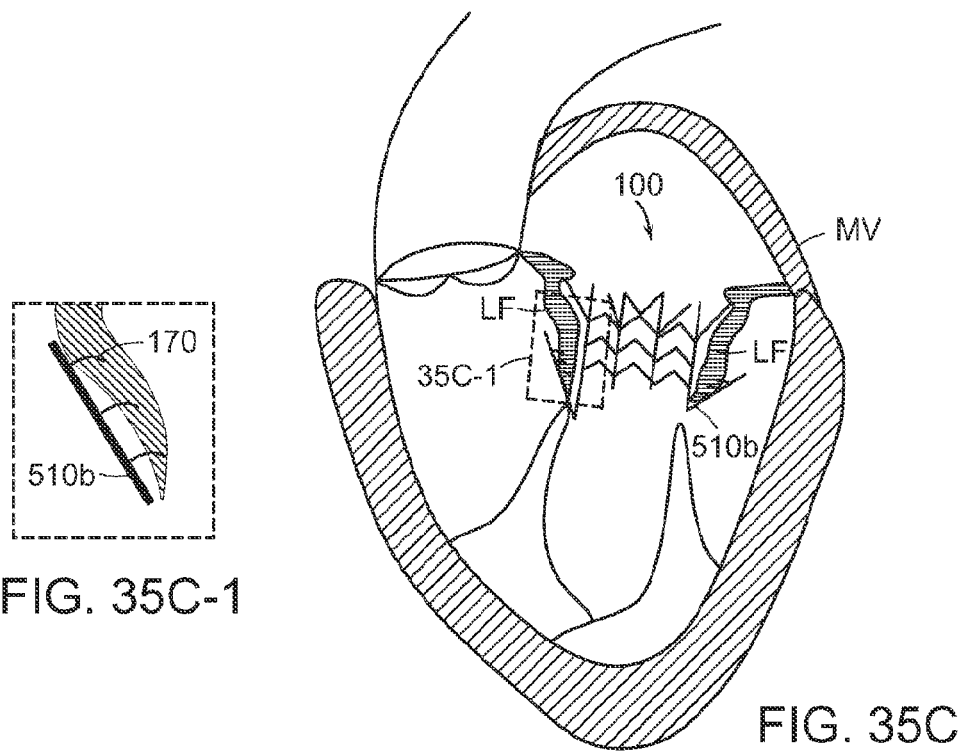
FIG. 35C-1
FIG. 35C
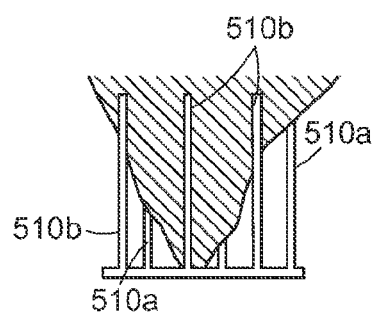
FIG. 36B
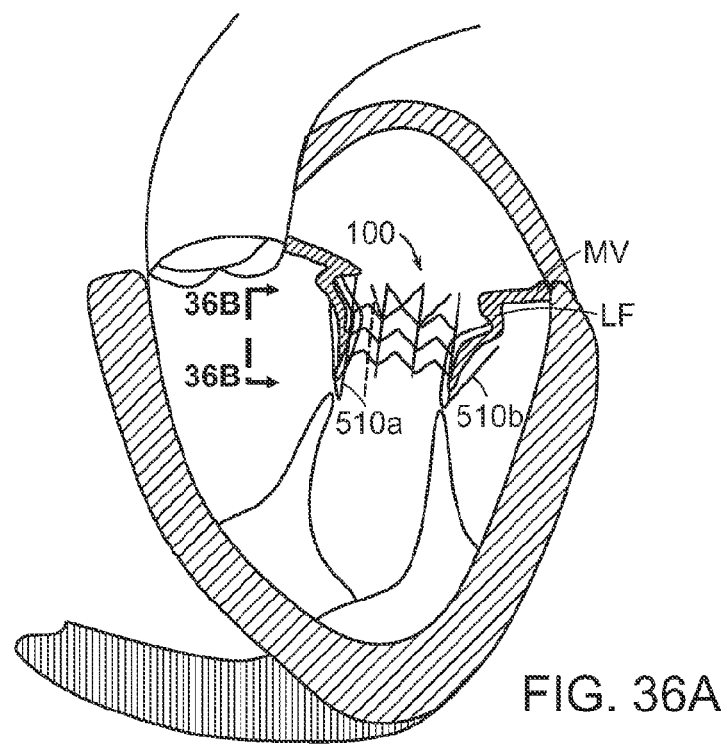
FIG. 36A

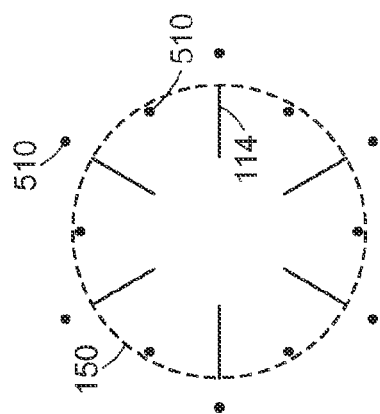
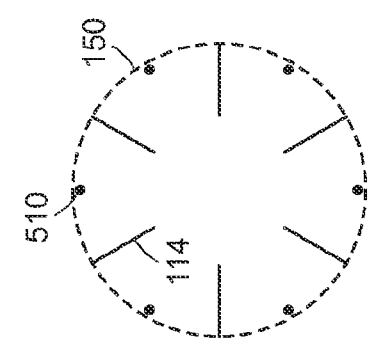
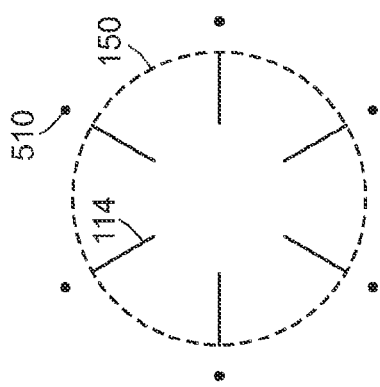
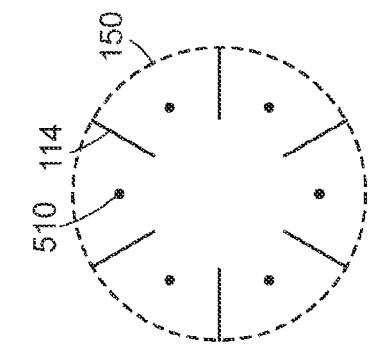

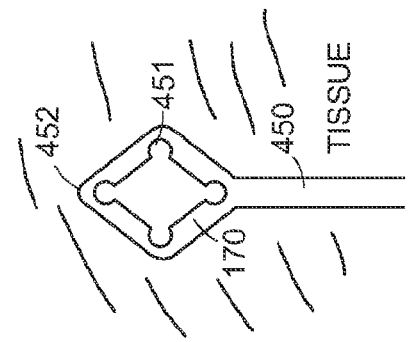
FIG. 40I
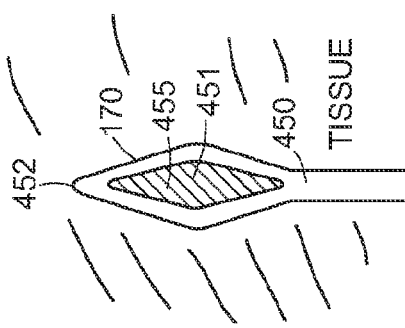
FIG. 40J    FIG. 40K    FIG. 40L
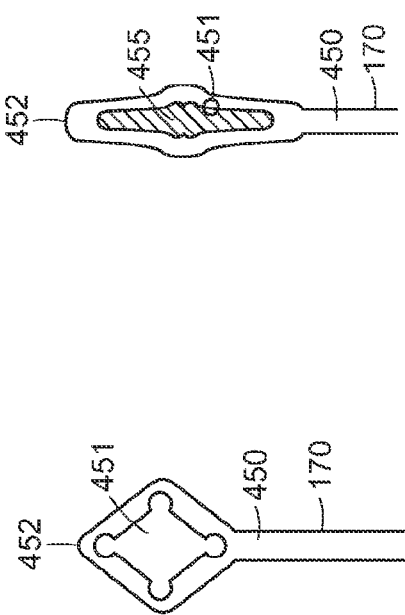
FIG. 40M
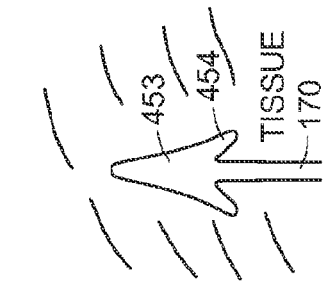
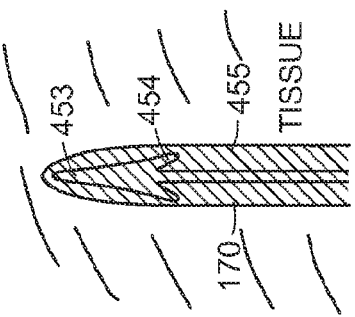
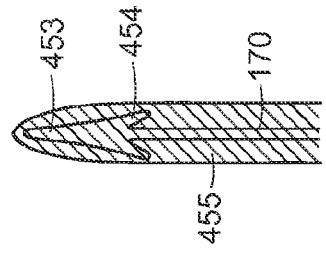
FIG. 40N    FIG. 40O    FIG. 40P

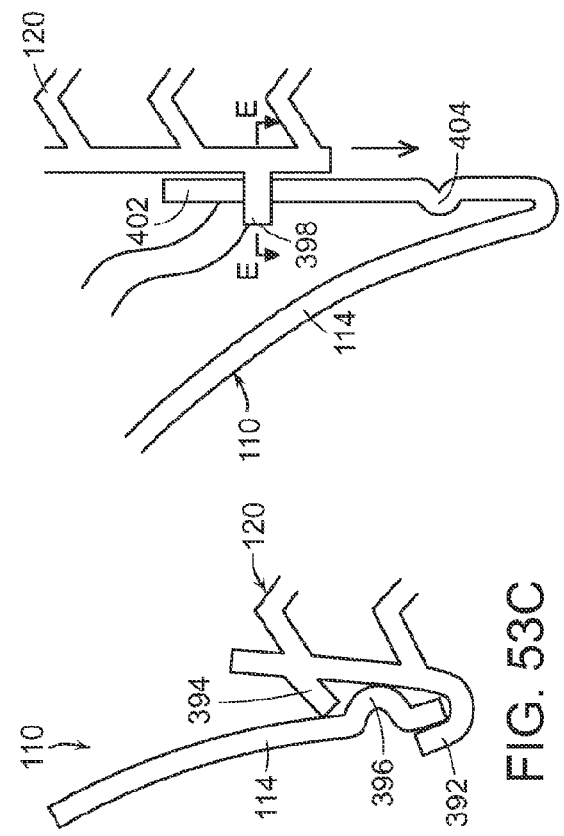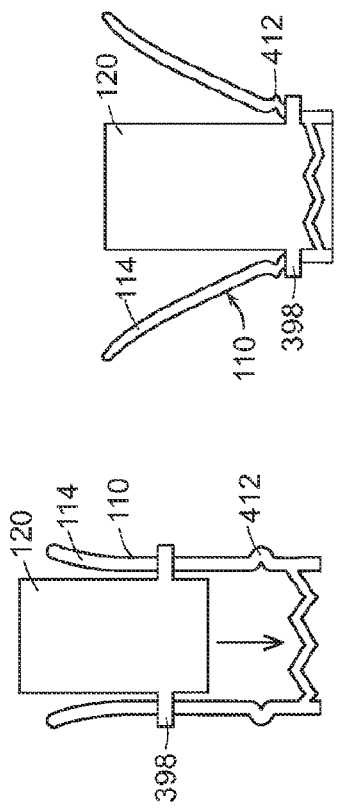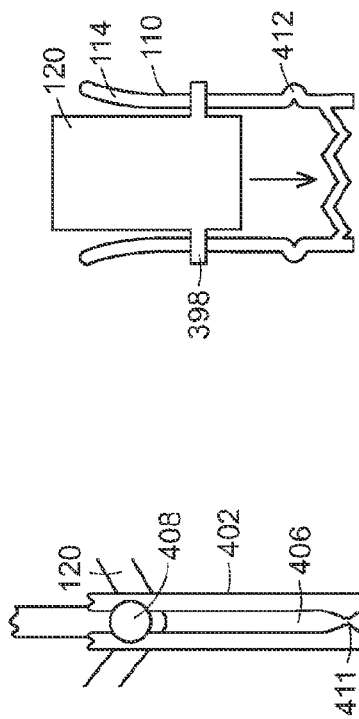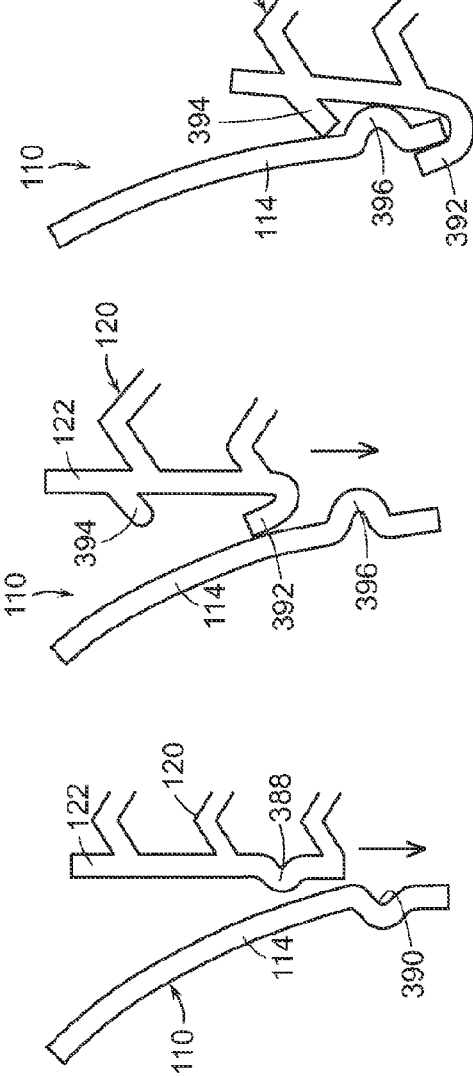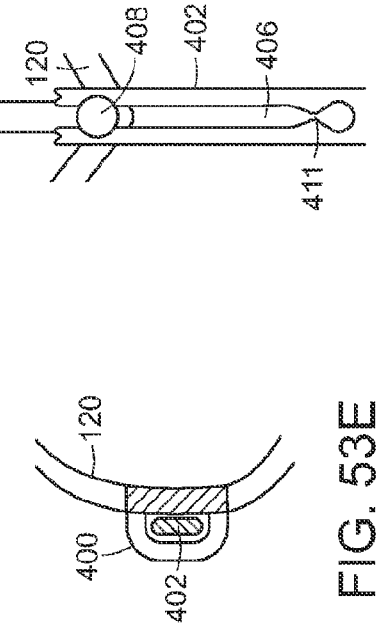

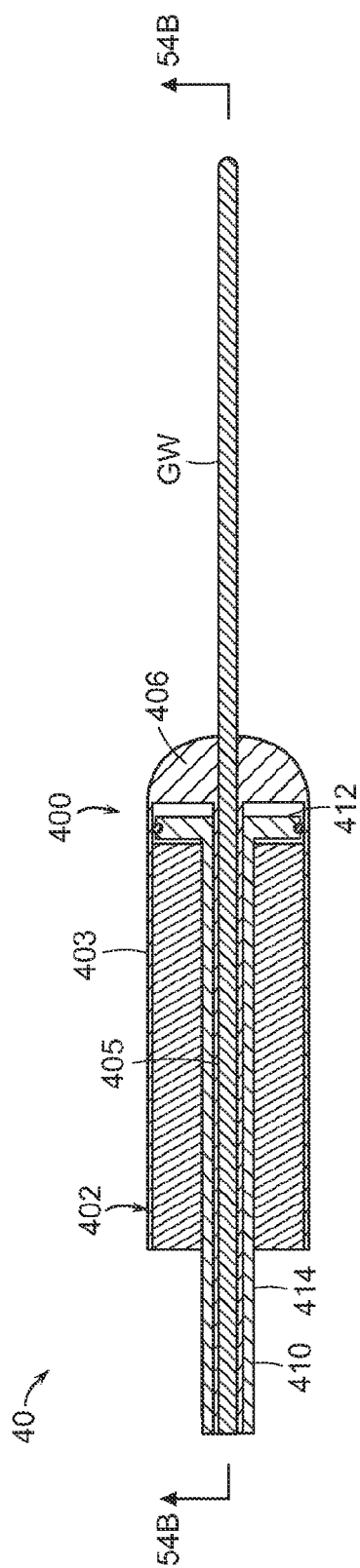
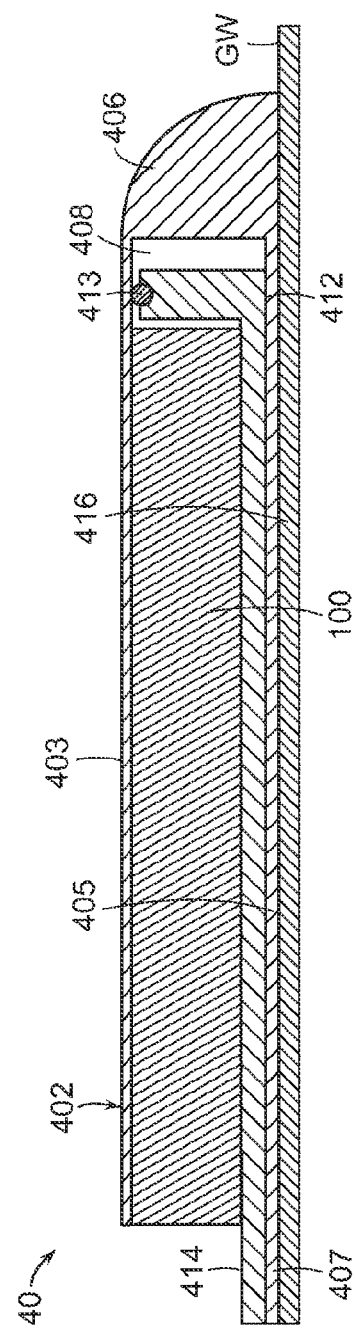
FIG. 54A
FIG. 54B

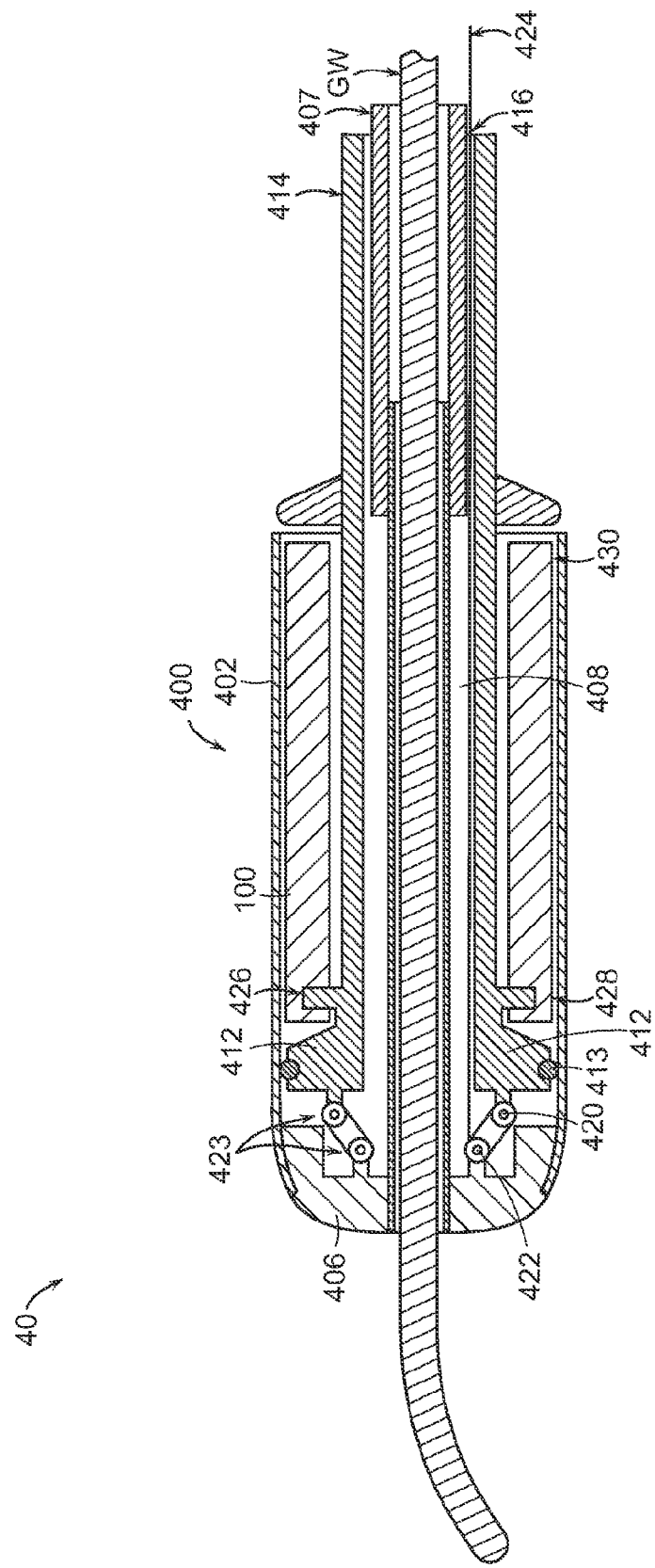

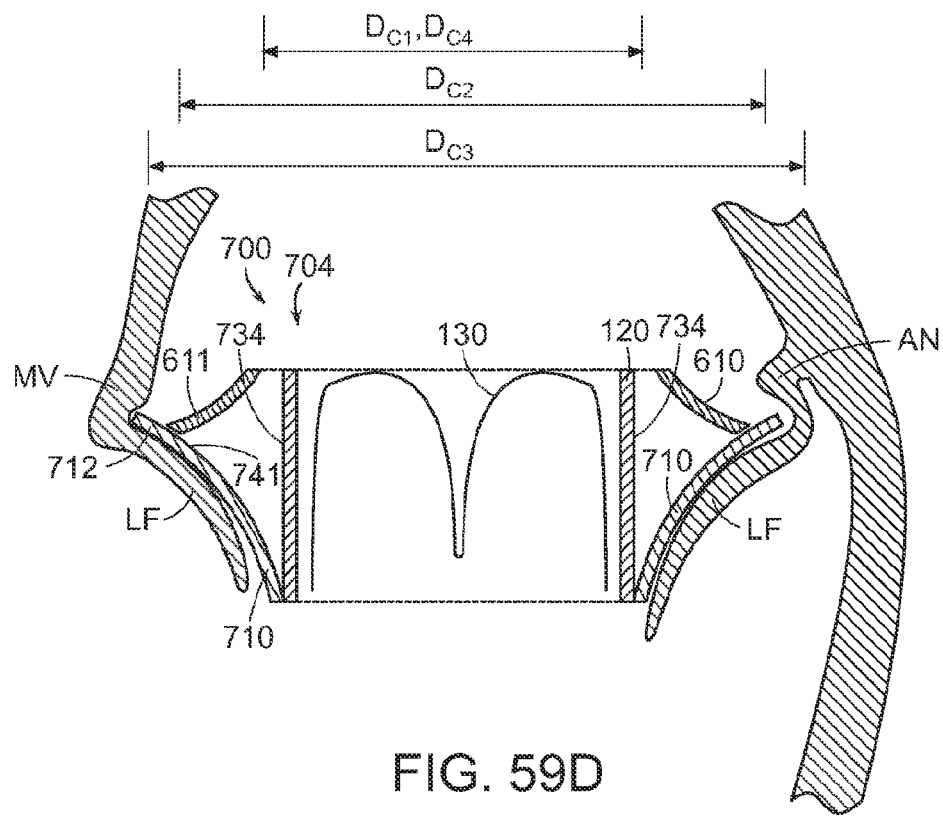
FIG. 59D
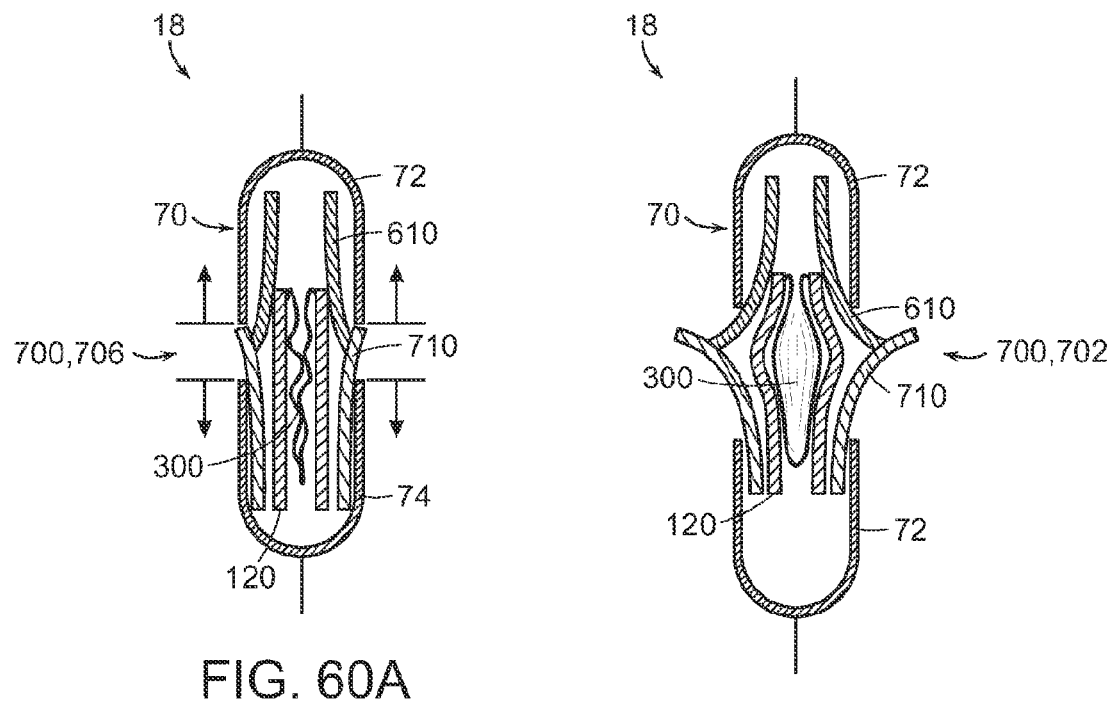
FIG. 60A
FIG. 60B

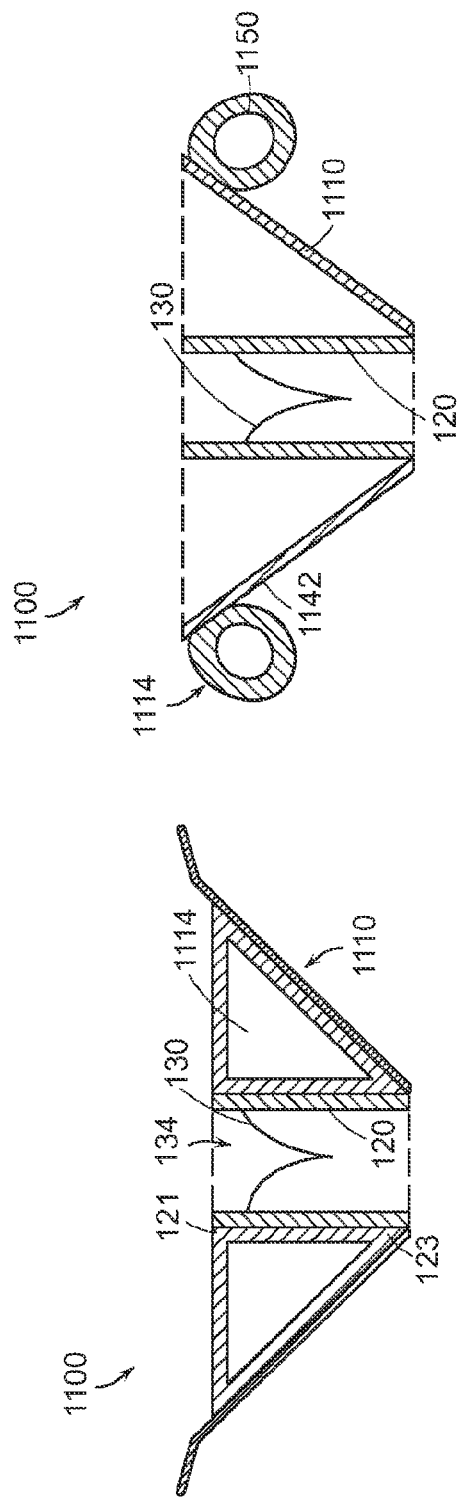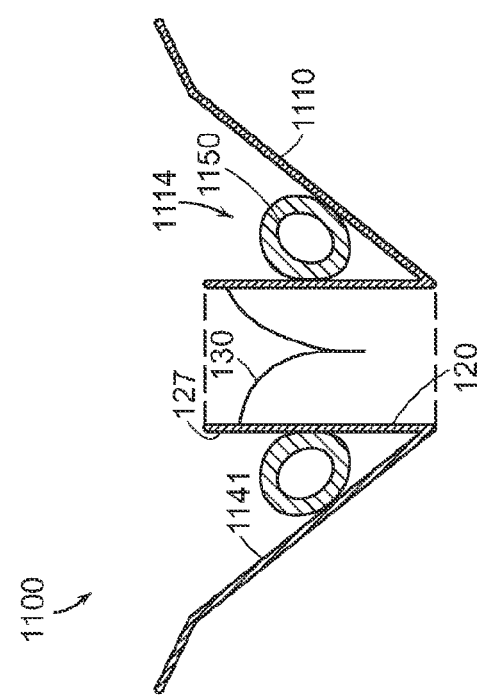

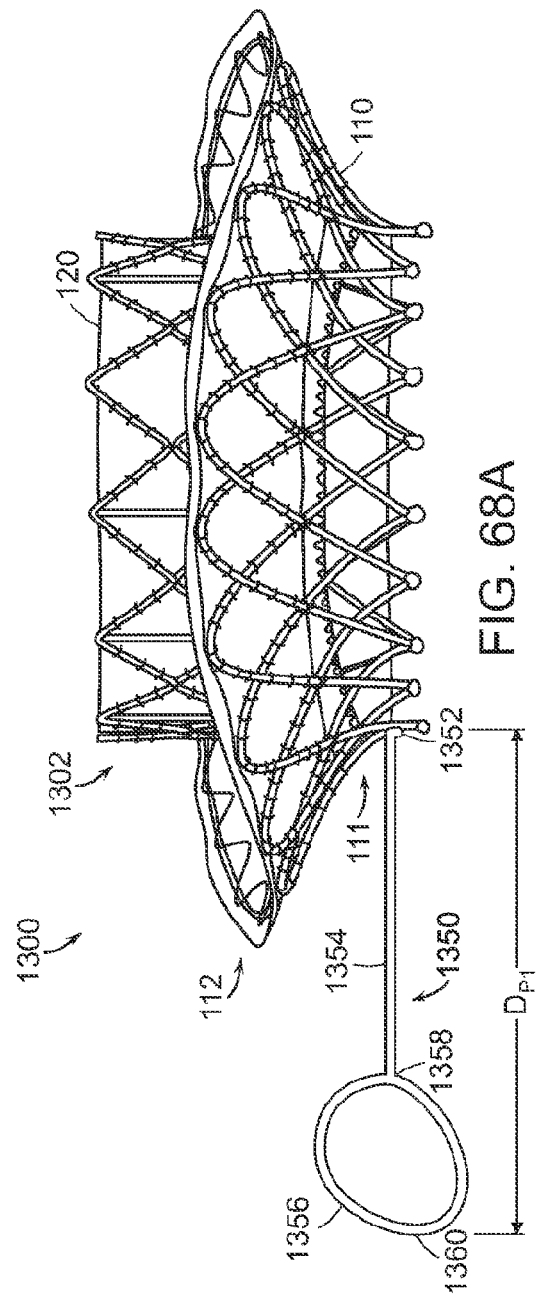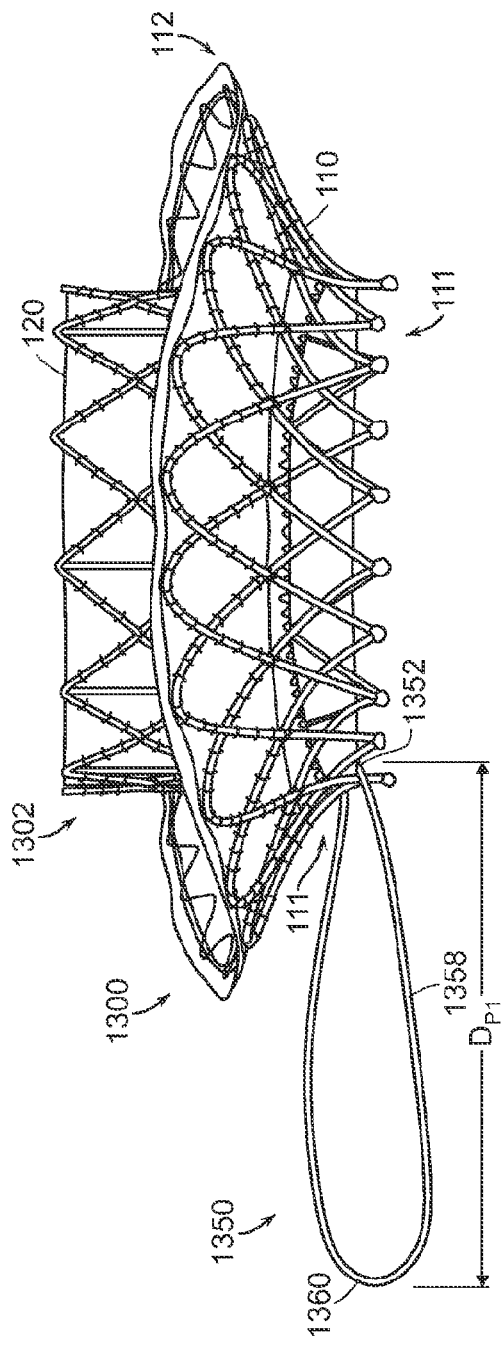
FIG. 68A
FIG. 68B

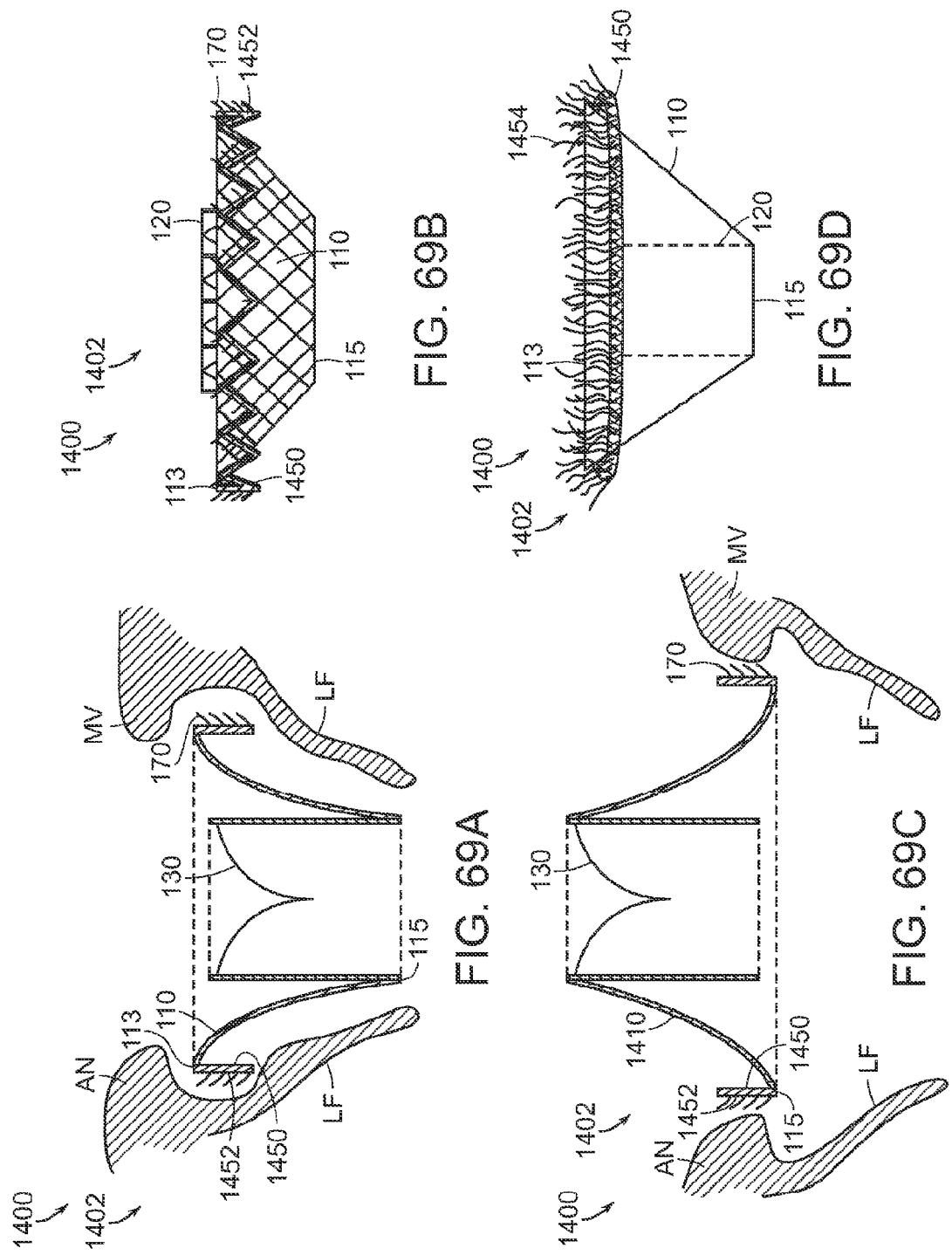

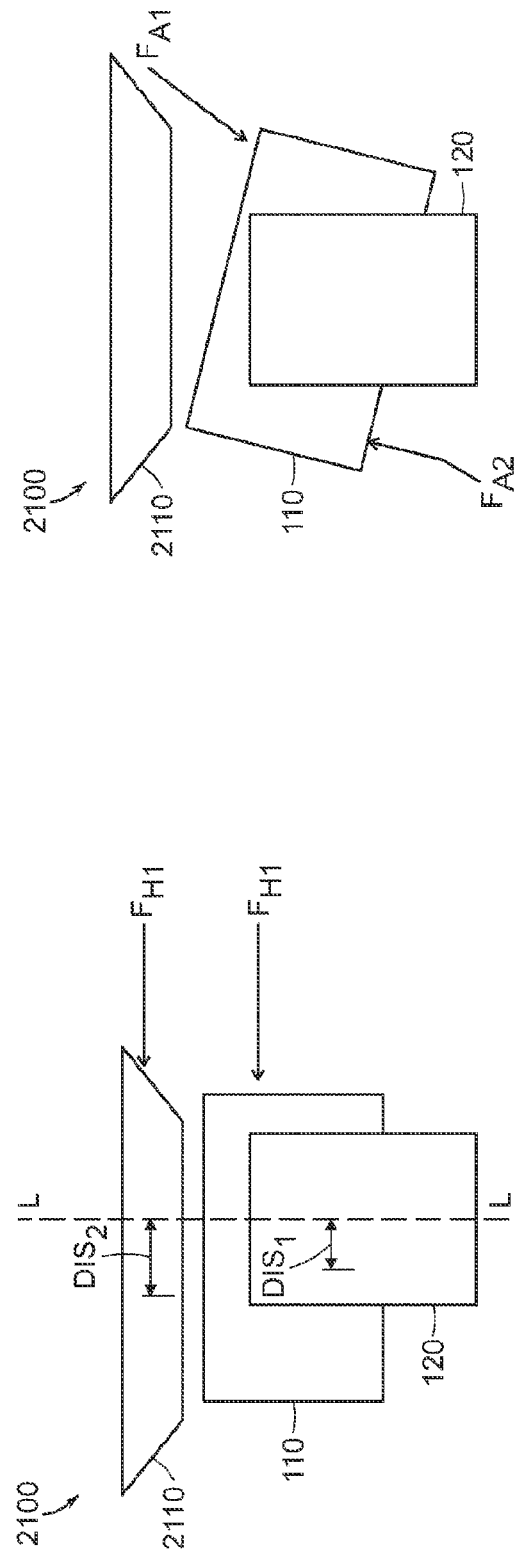
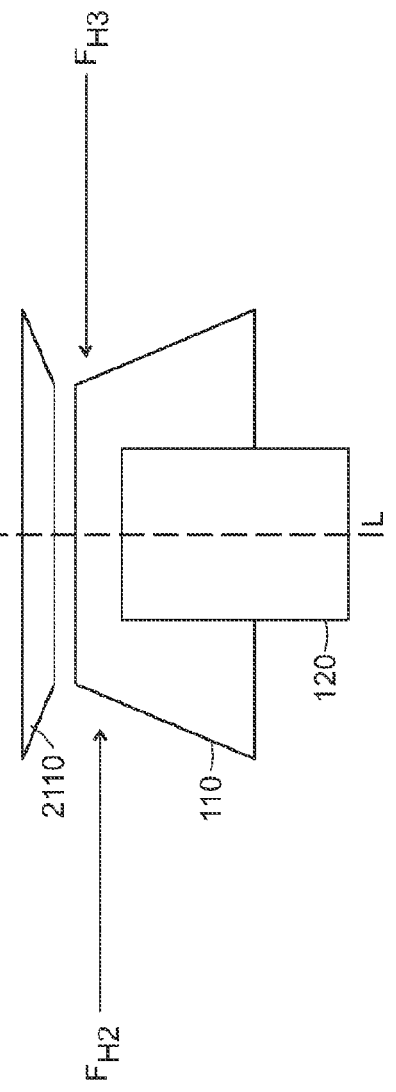

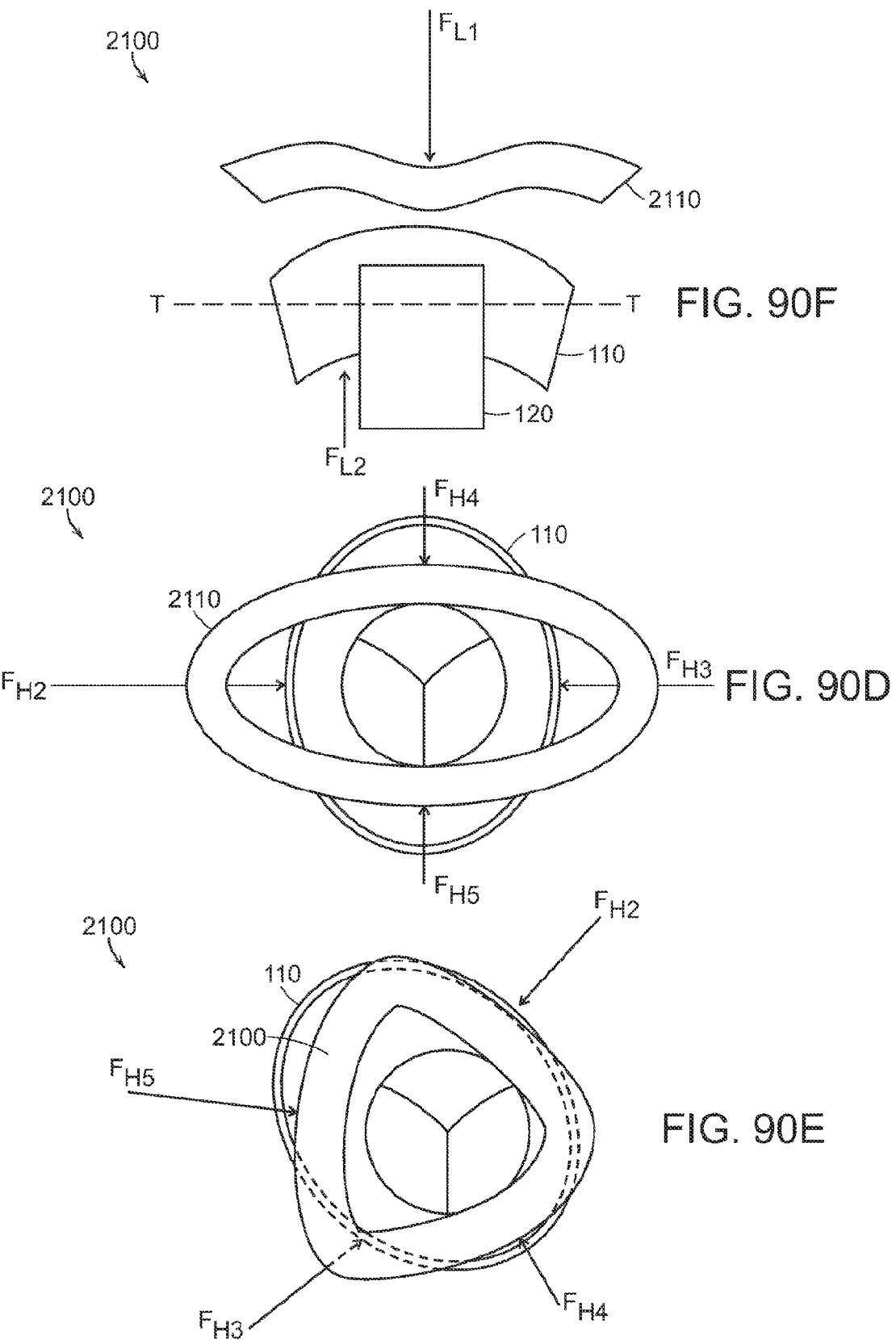

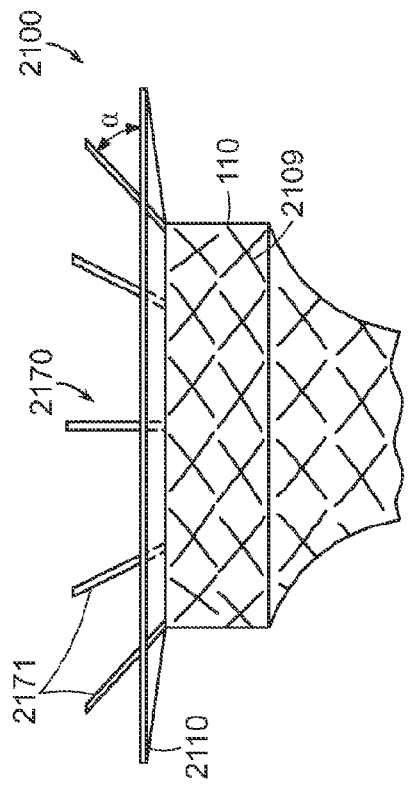
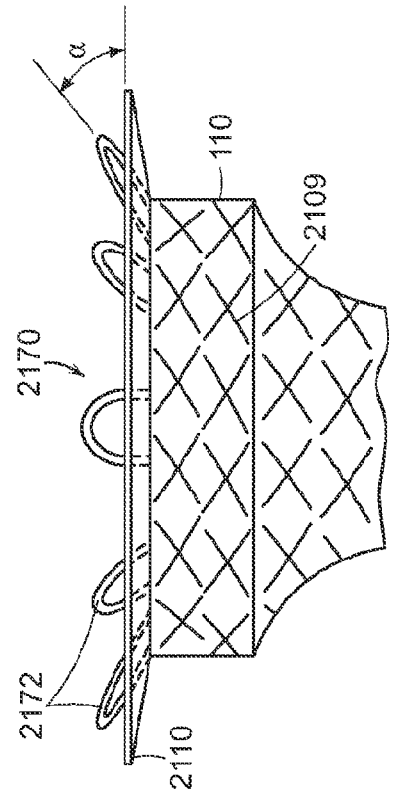
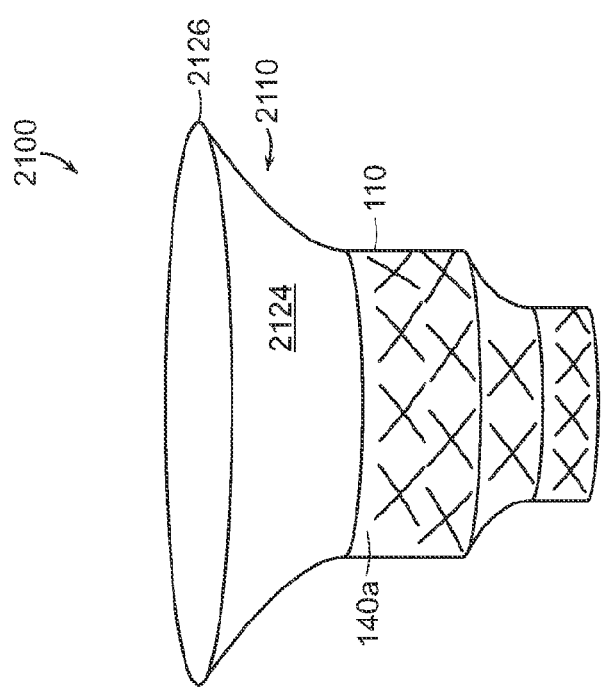

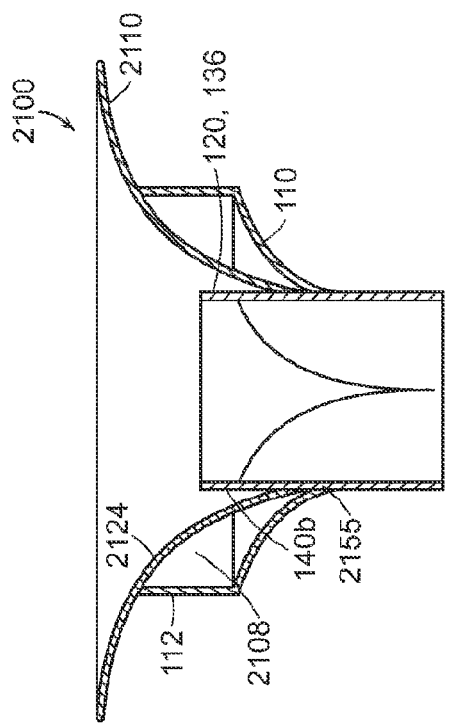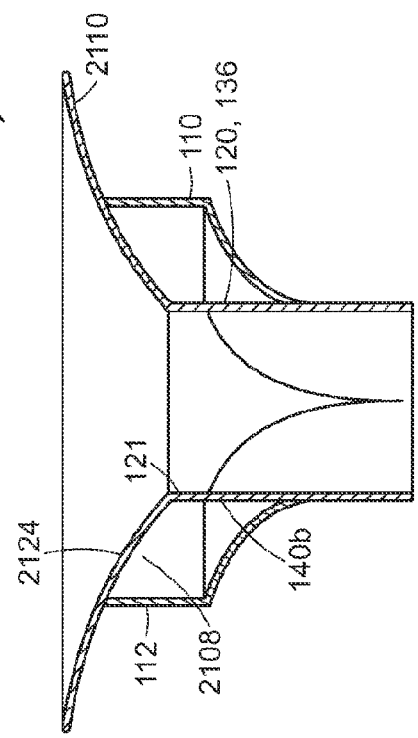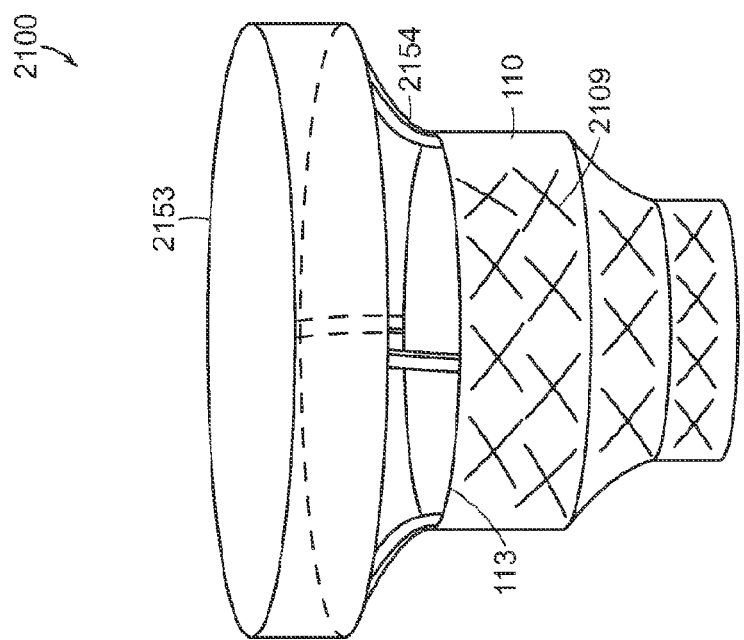

PROSTHETIC HEART VALVE DEVICES, PROSTHETIC MITRAL VALVES AND ASSOCIATED SYSTEMS AND METHODS

CROSS-REFERENCES TO RELATED APPLICATIONS

The present application is a 35 U.S.C. 371 of International Application No. PCT/US2014/129549, filed Mar. 14, 2014, entitled "PROSTHETIC HEART VALVE DEVICES, PROSTHETIC MITRAL VALVES AND ASSOCIATED SYSTEMS AND METHODS," which is a continuation-in-part of U.S. patent application Ser. No. 13/946,552, filed Jul. 19, 2013, now U.S. Pat. No. 9,034,032, entitled "PROSTHETIC HEART VALVE DEVICES, PROSTHETIC MITRAL VALVES AND ASSOCIATED SYSTEMS AND METHODS," which is a continuation-in part of U.S. patent application Ser. No. 13/842,785, filed Mar. 15, 2013, now U.S. Pat. No. 9,039,757, entitled "PROSTHETIC HEART VALVE DEVICES, PROSTHETIC MITRAL VALVES AND ASSOCIATED SYSTEMS AND METHODS," which is a continuation-in-part of International Application No. PCT/US2012/61219, filed on Oct. 19, 2012, entitled "PROSTHETIC HEART VALVE DEVICES, PROSTHETIC MITRAL VALVES AND ASSOCIATED SYSTEMS AND METHODS," which claims priority to U.S. Provisional Patent Application No. 61/605,699, filed Mar. 1, 2012, entitled "SYSTEM FOR MITRAL VALVE REPLACEMENT," and to U.S. Provisional Patent Application No. 61/549,044, filed Oct. 19, 2011, entitled "CONFORMABLE SYSTEM FOR MITRAL VALVE REPLACEMENT," the disclosures of which are incorporated herein in their entireties by reference. International Patent Application No. PCT/US2014/029549 also claims priority to U.S. Provisional Patent Application No. 61/898,345, filed Oct. 31, 2013, entitled "PROSTHETIC HEART VALVE DEVICE," the disclosure of which is incorporated in its entirety by reference. The present application incorporates the subject matter of (1) International Patent Application No. PCT/US2012/043636, entitled "PROSTHETIC HEART VALVE DEVICES AND ASSOCIATED SYSTEMS AND METHODS," filed Jun. 21, 2012; (2) U.S. Provisional Patent Application No. 61/549,037, entitled "SYSTEM FOR MITRAL VALVE REPLACEMENT," filed Oct. 19, 2011; and (3) International Patent Application No. PCT/US2012/61215, entitled "DEVICES, SYSTEMS AND METHODS FOR HEART VALVE REPLACEMENT," filed Oct. 19, 2012, in their entireties by reference.

TECHNICAL FIELD

The present technology relates generally to prosthetic heart valve devices. In particular, several embodiments are directed to prosthetic mitral valves and devices for percutaneous repair and/or replacement of native mitral valves and associated systems and methods.

BACKGROUND

Conditions affecting the proper functioning of the mitral valve include, for example, mitral valve regurgitation, mitral valve prolapse and mitral valve stenosis. Mitral valve regurgitation is a disorder of the heart in which the leaflets of the mitral valve fail to coapt into apposition at peak contraction pressures, resulting in abnormal leaking of blood from the left ventricle into the left atrium. There are a number of structural factors that may affect the proper closure of the mitral valve leaflets. For example, many patients suffering from heart disease experience dilation of the heart muscle, resulting in an enlarged mitral annulus. Enlargement of the mitral annulus makes it difficult for the leaflets to coapt during systole. A stretch or tear in the chordae tendineae, the tendons connecting the papillary muscles to the inferior side of the mitral valve leaflets, may also affect proper closure of the mitral annulus. A ruptured chordae tendineae, for example, may cause a valve leaflet to prolapse into the left atrium due to inadequate tension on the leaflet. Abnormal backflow can also occur when the functioning of the papillary muscles is compromised, for example, due to ischemia. As the left ventricle contracts during systole, the affected papillary muscles do not contract sufficiently to effect proper closure.

Mitral valve prolapse, or when the mitral leaflets bulge abnormally up in to the left atrium, causes irregular behavior of the mitral valve and may also lead to mitral valve regurgitation. Normal functioning of the mitral valve may also be affected by mitral valve stenosis, or a narrowing of the mitral valve orifice, which causes impedance of filling of the left ventricle in diastole.

Typically, treatment for mitral valve regurgitation has involved the application of diuretics and/or vasodilators to reduce the amount of blood flowing back into the left atrium. Other procedures have involved surgical approaches (open and intravascular) for either the repair or replacement of the valve. For example, typical repair approaches have involved cinching or resecting portions of the dilated annulus.

Cinching of the annulus has been accomplished by the implantation of annular or peri-annular rings which are generally secured to the annulus or surrounding tissue. Other repair procedures have also involved suturing or clipping of the valve leaflets into partial apposition with one another.

Alternatively, more invasive procedures have involved the replacement of the entire valve itself where mechanical valves or biological tissue are implanted into the heart in place of the mitral valve. These invasive procedures are conventionally done through large open thoracotomies and are thus very painful, have significant morbidity, and require long recovery periods.

However, with many repair and replacement procedures, the durability of the devices or improper sizing of annuloplasty rings or replacement valves may result in additional problems for the patient. Moreover, many of the repair procedures are highly dependent upon the skill of the cardiac surgeon where poorly or inaccurately placed sutures may affect the success of procedures.

Less invasive approaches to aortic valve replacement have been developed in recent years. Examples of pre-assembled, percutaneous prosthetic valves include, e.g., the CoreValve Revalving® System from Medtronic/Corevalve Inc. (Irvine, Calif., USA) and the Edwards-Sapien® Valve from Edwards Lifesciences (Irvine, Calif., USA). Both valve systems include an expandable frame housing a tri-leaflet bioprosthetic valve. The frame is expanded to fit the substantially symmetric, circular and rigid aortic annulus. This gives the expandable frame in the delivery configuration a symmetric, circular shape at the aortic valve annulus, suitable to supporting a tri-leaflet prosthetic valve (which requires such symmetry for proper coaptation of the prosthetic leaflets). Thus, aortic valve anatomy lends itself to an expandable frame housing a replacement valve since the aortic valve anatomy is substantially uniform, symmetric, and fairly rigid.

Mitral valve replacement, compared with aortic valve replacement, poses unique anatomical obstacles, rendering percutaneous mitral valve replacement significantly more challenging than aortic valve replacement. First, unlike the relatively symmetric and uniform aortic valve, the mitral valve annulus has a non-circular D-shape or kidney-like shape, with a non-planar, saddle-like geometry often lacking symmetry. Such unpredictability makes it difficult to design a mitral valve prosthesis having the ability to conform to the mitral annulus. Lack of a snug fit between the prosthesis and the native leaflets and/or annulus may leave gaps therein, creating backflow of blood through these gaps. Placement of a cylindrical valve prosthesis, for example, may leave gaps in commissural regions of the native valve, potentially resulting in perivalvular leaks in those regions.

Current prosthetic valves developed for percutaneous aortic valve replacement are unsuitable for adaptation to the mitral valve. First, many of these devices require a direct, structural connection between the device structure which contacts the annulus and/or leaflets and the device structure which supports the prosthetic valve. In several devices, the same stent posts which support the prosthetic valve also contact the annulus or other surrounding tissue, directly transferring to the device many of the distorting forces exerted by the tissue and blood as the heart contracts during each cardiac cycle. Most cardiac replacement devices further utilize a tri-leaflet valve, which requires a substantially symmetric, cylindrical support around the prosthetic valve for proper opening and closing of the three leaflets over years of life. If these devices are subject to movement and forces from the annulus and other surrounding tissues, the prostheses may be compressed and/or distorted causing the prosthetic leaflets to malfunction. Moreover, the typical diseased mitral annulus is much larger than any available prosthetic valve. As the size of the valve increases, the forces on the valve leaflets increase dramatically, so simply increasing the size of an aortic prosthesis to the size of a dilated mitral valve annulus would require dramatically thicker, taller leaflets, and might not be feasible.

In addition to its irregular, unpredictable shape, which changes size over the course of each heartbeat, the mitral valve annulus lacks a significant amount of radial support from surrounding tissue. The aortic valve, for example, is completely surrounded by fibro-elastic tissue, helping to anchor a prosthetic valve by providing native structural support. The mitral valve, on the other hand, is bound by muscular tissue on the outer wall only. The inner wall of the mitral valve is bound by a thin vessel wall separating the mitral valve annulus from the inferior portion of the aortic outflow tract. As a result, significant radial forces on the mitral annulus, such as those imparted by an expanding stent prostheses, could lead to collapse of the inferior portion of the aortic tract with potentially fatal consequences.

The chordae tendineae of the left ventricle may also present an obstacle in deploying a mitral valve prosthesis. This is unique to the mitral valve since aortic valve anatomy does not include chordae. The maze of chordae in the left ventricle makes navigating and positioning a deployment catheter that much more difficult in mitral valve replacement and repair. Deployment and positioning of a prosthetic valve or anchoring device on the ventricular side of the native mitral valve is further complicated by the presence of the chordae.

The triscuspid valve on the right side of the heart, although it normally has three leaflets, poses similar challenges to less invasive treatment as the mitral valve. Therefore there is a need for a better prosthesis to treat tricuspid valve disease as well.

Given the difficulties associated with current procedures, there remains the need for simple, effective, and less invasive devices and methods for treating dysfunctional heart valves.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIGS. 19A-19C are isometric, side and top views, respectively, of a prosthetic heart valve device having a sealing member in accordance with a further embodiment of the present technology.

FIGS. 21A-21B are cross-sectional side and isometric views of a prosthetic heart valve device having a tubular valve support member in accordance with a further embodiment of the present technology.

FIGS. 21C-21F are partial cross-sectional side views and an isometric view of prosthetic heart valve devices having a tubular valve support member in accordance with other embodiments of the present technology.

FIGS. 22A-22G and 22I-22K are enlarged side views of various mechanisms of coupling a valve support to an anchoring member in accordance with additional embodiments of the present technology.

FIG. 22H is a side view of a post in the prosthetic heart valve device of FIG. 40G.

FIGS. 32A, 32B, 32C, and 32D are cross-sectional views of a heart with an implanted prosthetic heart valve device having arms disposed on an inward-facing surface of the leaflets in accordance with various embodiments of the present technology.

FIGS. 32A-1, 32B-1, 32C-1 and 32D-1 are enlarged views of the arms engaging the inward-facing surface of the leaflets as shown in FIGS. 32A, 32B, 32C and 32D, respectively in accordance with various embodiments of the present technology.

FIGS. 33A-33C are schematic views illustrating various embodiments of tissue engaging elements for use with prosthetic heart valve devices in accordance with the present technology.

FIGS. 34A, 34B and 34C are cross-sectional views of a heart with an implanted prosthetic heart valve device having arms with tissue engaging elements disposed on an inward-facing surface of the leaflets in accordance with various embodiments of the present technology.

FIGS. 34A-1, 34B-1 and 34C-1 are enlarged views of the arms engaging the inward-facing surface of the leaflets as shown in FIGS. 34A, 34B and 34C, respectively in accordance with various embodiments of the present technology.

FIGS. 35A-35C are side views of prosthetic heart valve devices and shown implanted at a mitral valve (illustrated in cross-section), the devices having arms for engaging an outward-facing surface of the native leaflets in accordance with further embodiments of the present technology.

FIG. 35C-1 is an enlarged view of the arm engaging the inward-facing surface of the leaflets as shown in FIG. 35C in accordance with various embodiments of the present technology.

FIG. 36A is a side view of a prosthetic heart valve device and shown implanted at a mitral valve (illustrated in cross-section), the device having arms for engaging an outward-facing surface of the native leaflets and arms for engaging an inward-facing surface of the native leaflets in accordance with an additional embodiment of the present technology.

FIG. 36B is an enlarged view of the arms engaging the inward-facing and outward-facing surfaces of the leaflets as shown in FIG. 36A.

FIGS. 39A-39D are schematic top views of arm location patterns in accordance with additional embodiments of the present technology.

FIGS. 40I-40T are enlarged side views of embodiments of tissue engaging elements suitable for use with prosthetic heart valve devices in accordance with additional embodiments of the present technology.

FIGS. 53A-53D are partial side views showing various mechanisms for movably coupling the valve support to the anchoring member in accordance with additional embodiments of the present technology.

FIG. 53E is a partial top view of the device of FIG. 53D.

FIG. 53F is a side view of an alternative mechanism for slideably coupling a valve support and anchoring member in accordance with another embodiment of the present technology.

FIGS. 53G-53H are schematic side views of a prosthetic heart valve device showing yet another mechanism for coupling the valve support to the anchoring member in accordance with a further embodiment of the present technology.

FIG. 54A is a cross-sectional side view of another embodiment of a delivery system for the prosthetic heart valve device in accordance with other aspects of the present technology.

FIG. 54B is a partial cross-sectional side view of a distal portion of the delivery system of FIG. 54A.

FIG. 56 is a side cross-sectional view of a further embodiment of a delivery system for the prosthetic treatment device of the invention.

FIG. 59D is a schematic cross-sectional view of a prosthetic heart valve device implanted at a native mitral valve in accordance with another embodiment of the present technology.

FIGS. 60A-60B are cross-sectional side views of a distal end of a delivery catheter for delivering the prosthetic heart valve device of FIG. 59C to a native mitral valve in the heart in accordance with another embodiment of the present technology.

FIGS. 66A-66D are cross-sectional views of prosthetic heart valve devices having fillable chambers in accordance with additional embodiments of the present technology.

FIGS. 68A-68B are side views of prosthetic heart valve devices having a positioning element in accordance with an additional embodiments of the present technology.

FIGS. 69A-69E are cross-sectional and side views of prosthetic heart valve devices shown in an expanded configuration and configured in accordance with an additional embodiment of the present technology.

FIG. 83 is a schematic cross-sectional view of a prosthetic heart valve device in accordance with another embodiment of the present technology.

FIGS. 84A-84C are schematic cross-section views of the operation of prosthetic heart valve devices in accordance with the present technology.

FIGS. 85A-85C are schematic side views of a portion of prosthetic heart valve devices in accordance with the present technology.

FIGS. 86A-86B are side and isometric views of a prosthetic heart valve device in accordance with another embodiment of the technology.

FIGS. 87A-87B are side and top views of another prosthetic heart valve device in accordance with another embodiment of the technology.

FIGS. 88A-88C are cross-sectional views of a heart showing a method of delivering a prosthetic heart valve device to a native mitral valve in the heart using a trans-apical approach in accordance with another embodiment of the present technology.

FIGS. 89A and 89B are schematic top views of a native mitral valve in the heart viewed from the left atrium and showing the prosthetic treatment device of FIGS. 86A and 86B implanted at the native mitral valve in accordance with the present technology.

FIGS. 90A-90F are schematic illustrations showing how the prosthetic heart valve device of FIGS. 86A and 86B mechanically isolates the valve support in accordance with additional embodiments of the present technology.

FIG. 91A is an isometric illustration of a prosthetic heart valve device in accordance with yet another embodiment of the technology.

FIG. 91B is a cross-sectional view of the device shown in FIG. 91A.

FIG. 92 is a top view of a prosthetic heart valve device in accordance with a further embodiment of the technology.

FIG. 93 is a top view of a prosthetic heart valve device in accordance with another embodiment of the technology.

Figure 94:
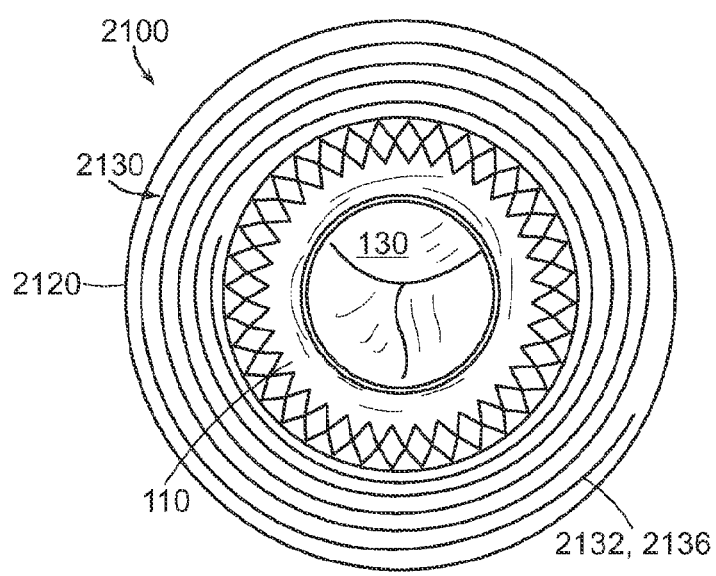

FIG. 94 is a top view of a prosthetic heart valve device in accordance with yet another embodiment of the technology.

Figure 95A:
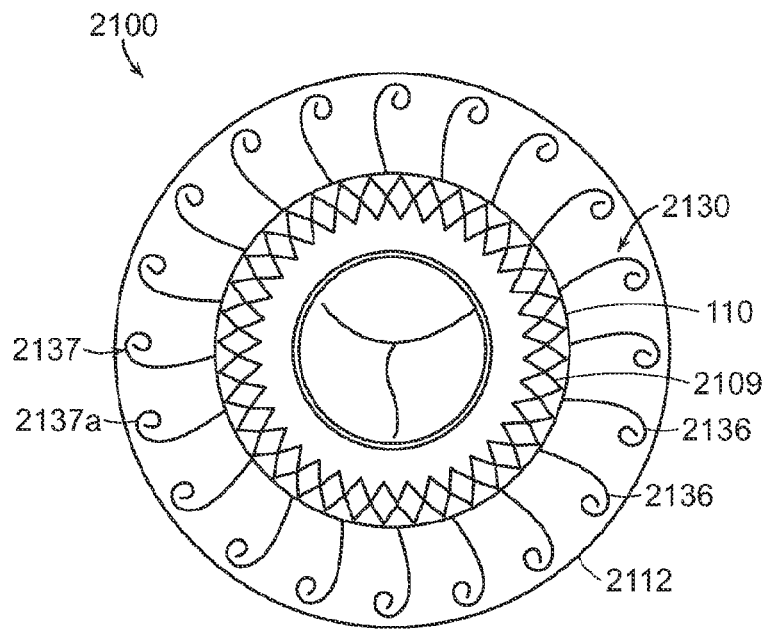
Figure 95B:
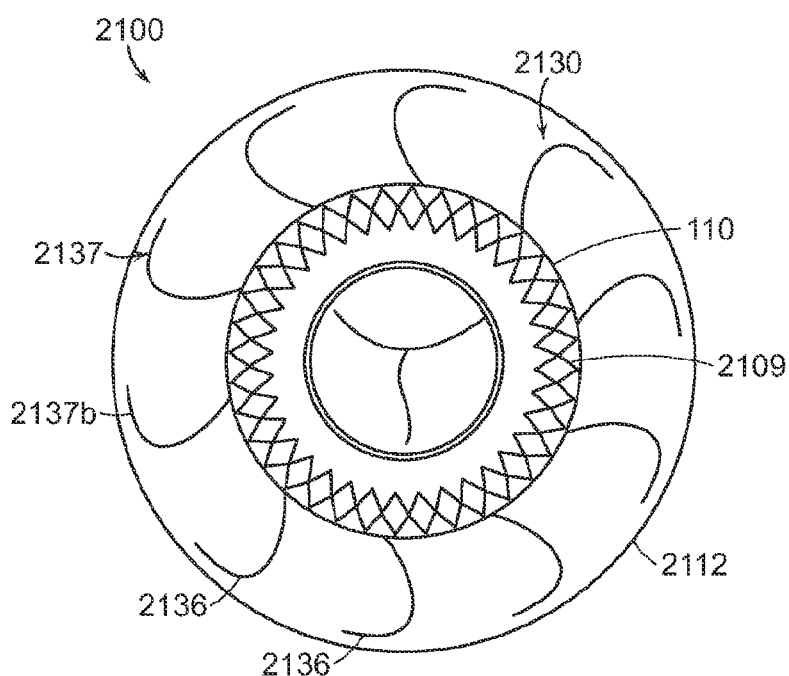

FIGS. 95A and 95B are top views of prosthetic heart valve devices in accordance with further embodiments of the technology.

Figure 96C:
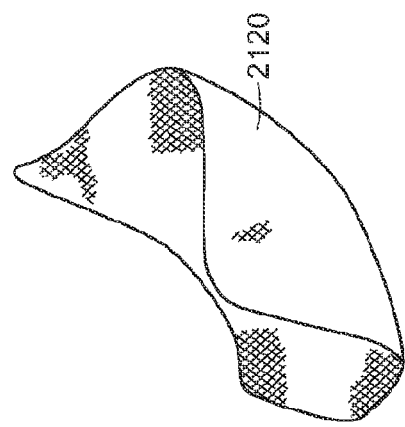
Figure 96A:
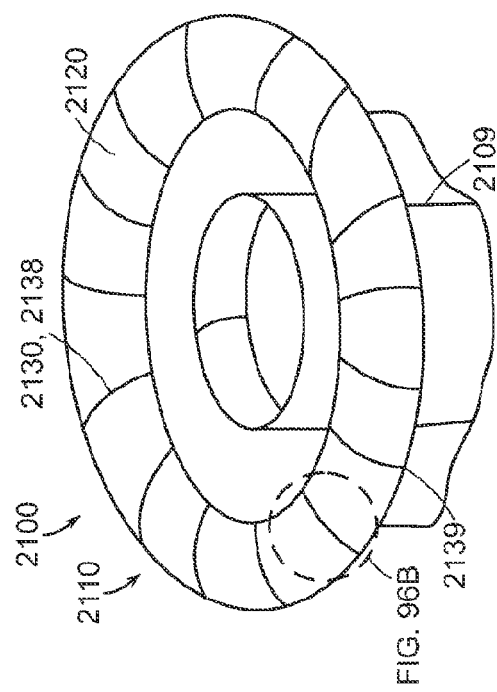

FIG. 96A is an isometric view a prosthetic heart valve device in accordance with yet another embodiment of the technology.

Figure 96B:
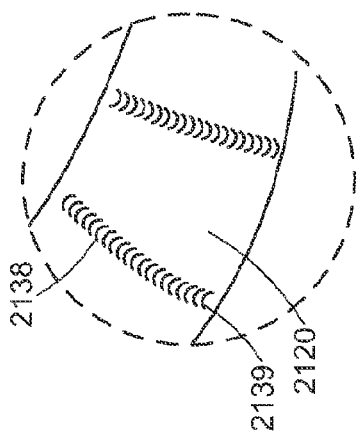

FIGS. 96B and 96C are enlarged schematic views of portions of the prosthetic heart valve device of FIG. 96A.

Figure 97B:
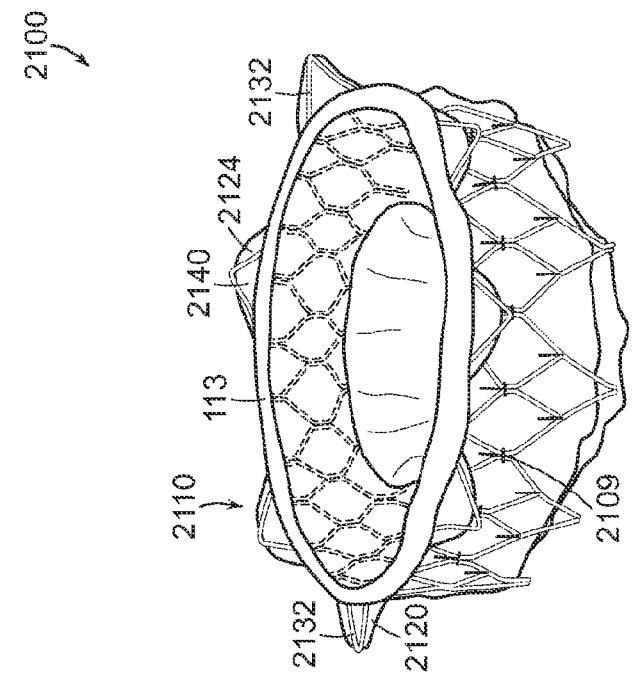
Figure 97A:
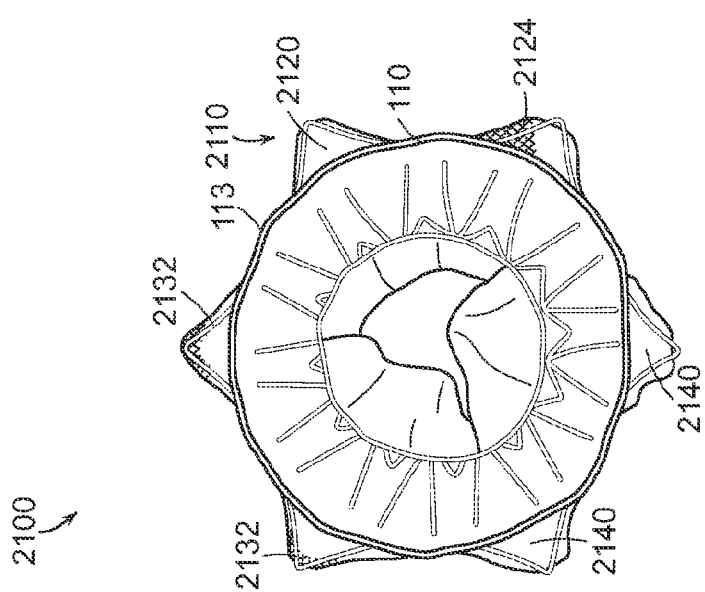

FIGS. 97A and 97B are top and isometric views of a prosthetic heart valve device in accordance with an embodiment of the technology.

Figure 98A:
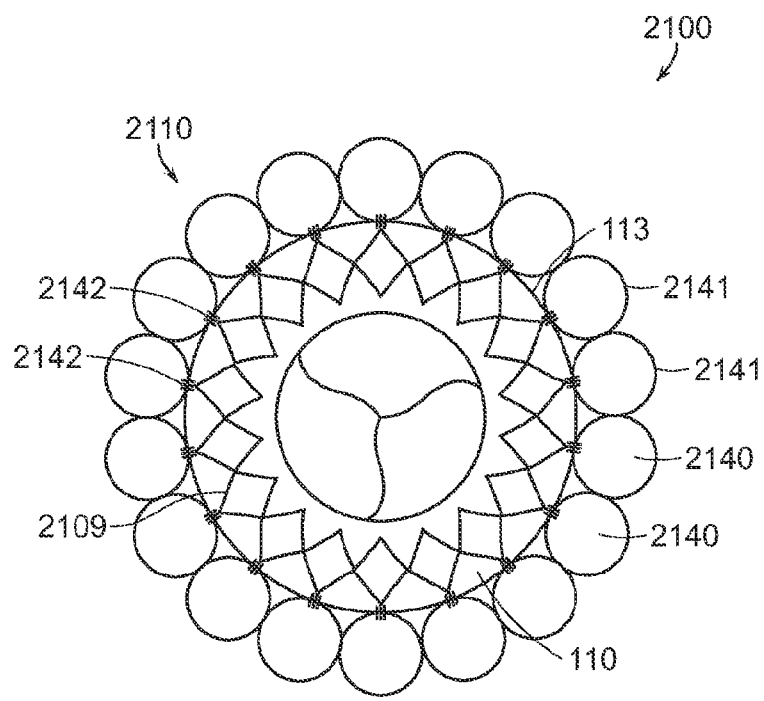
Figure 98B:
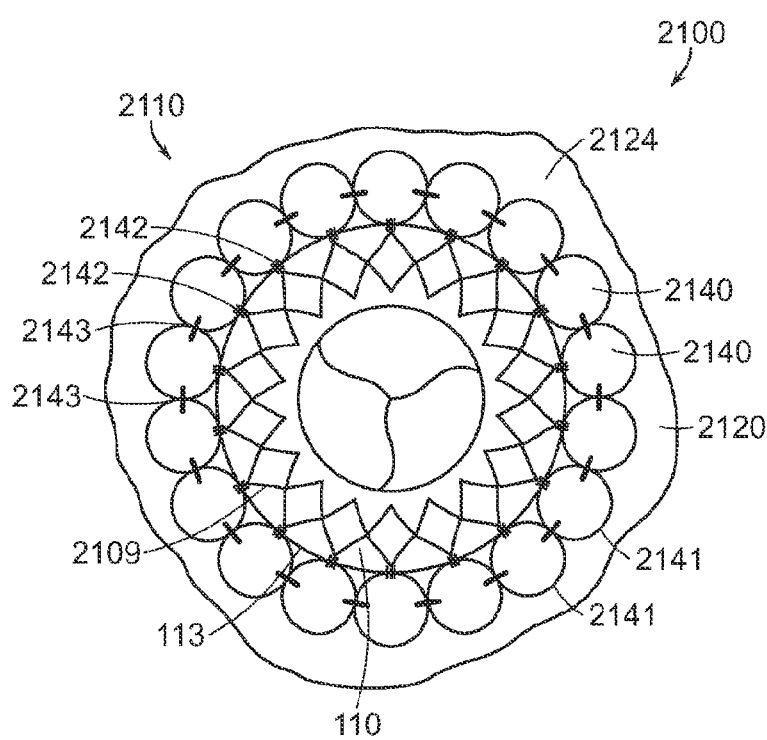
Figure 98C:
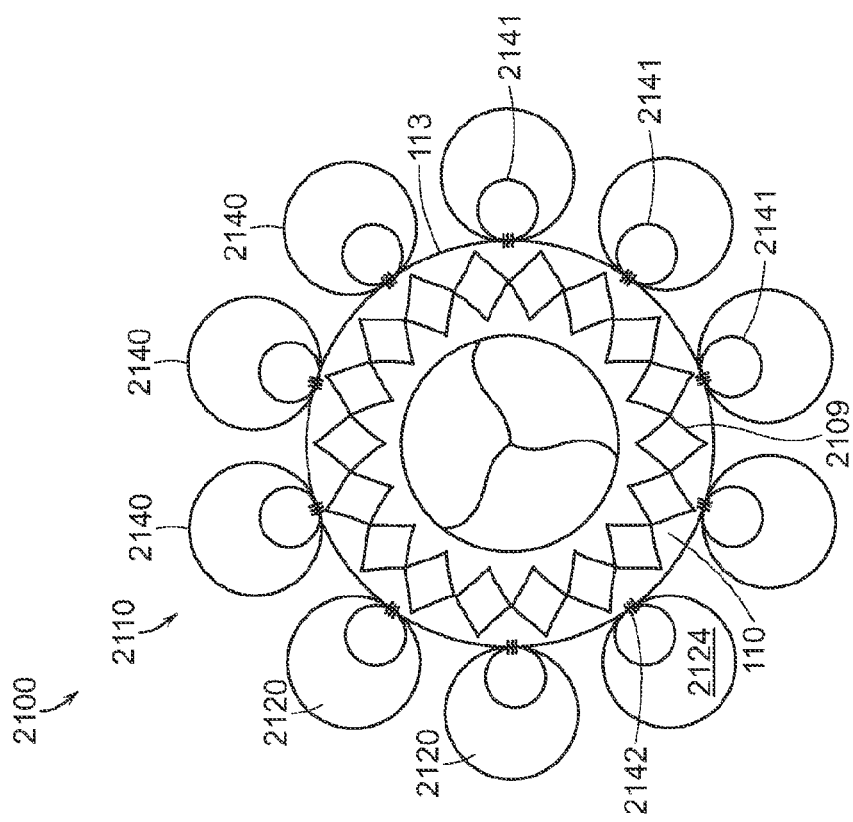

FIGS. 98A-98C are top views of prosthetic heart valve devices in accordance with further embodiments of the technology.

Figure 99:
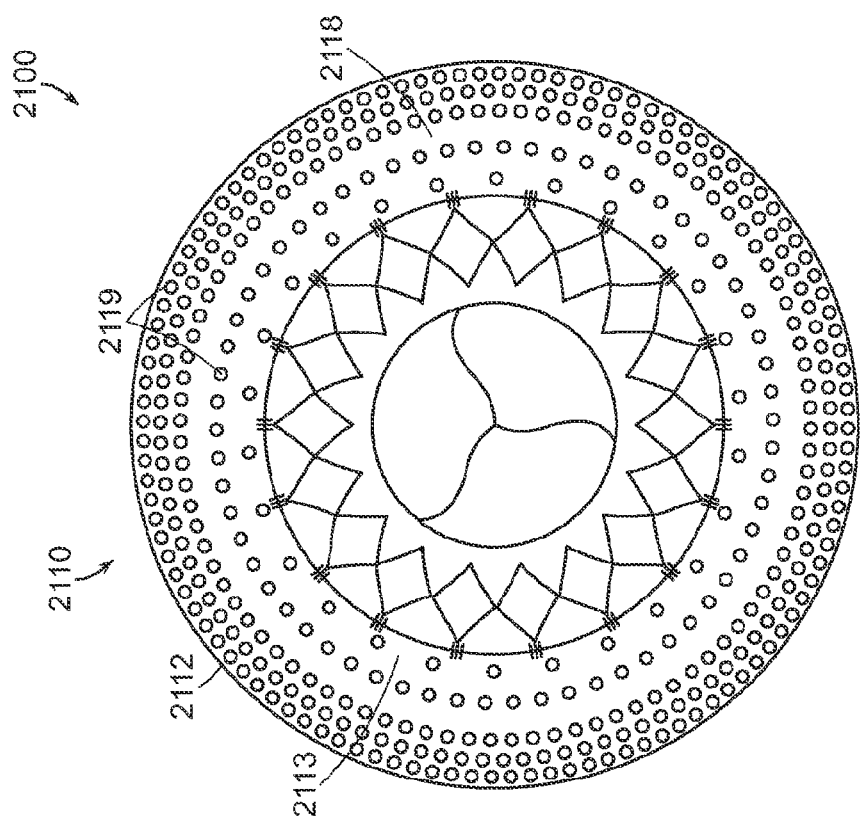

FIG. 99 is a top view of a prosthetic heart valve device in accordance with yet another embodiment of the technology.

Figure 100A:
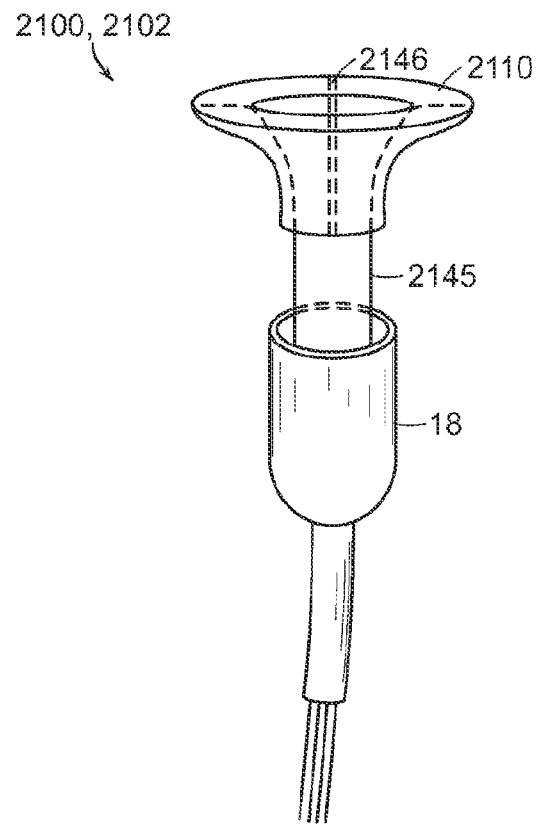

FIG. 100A is a side view showing a method of delivering a prosthetic heart valve device in accordance with a further embodiment of the technology.

Figure 100B:
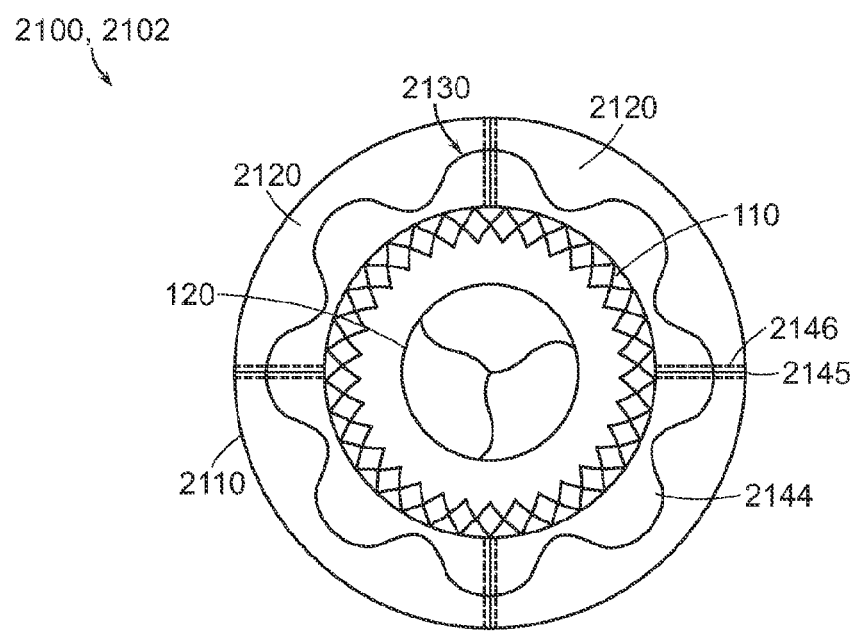

FIG. 100B is a top view of the prosthetic heart valve device of FIG. 100A.

Figure 101:
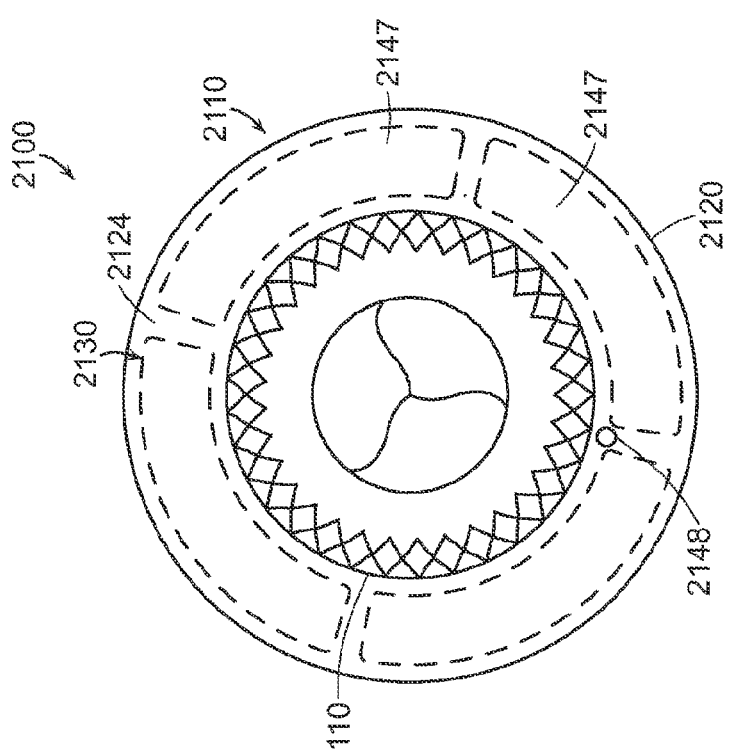

FIG. 101 is a top view of a prosthetic heart valve device in accordance with another embodiment of the technology.

Figure 102:
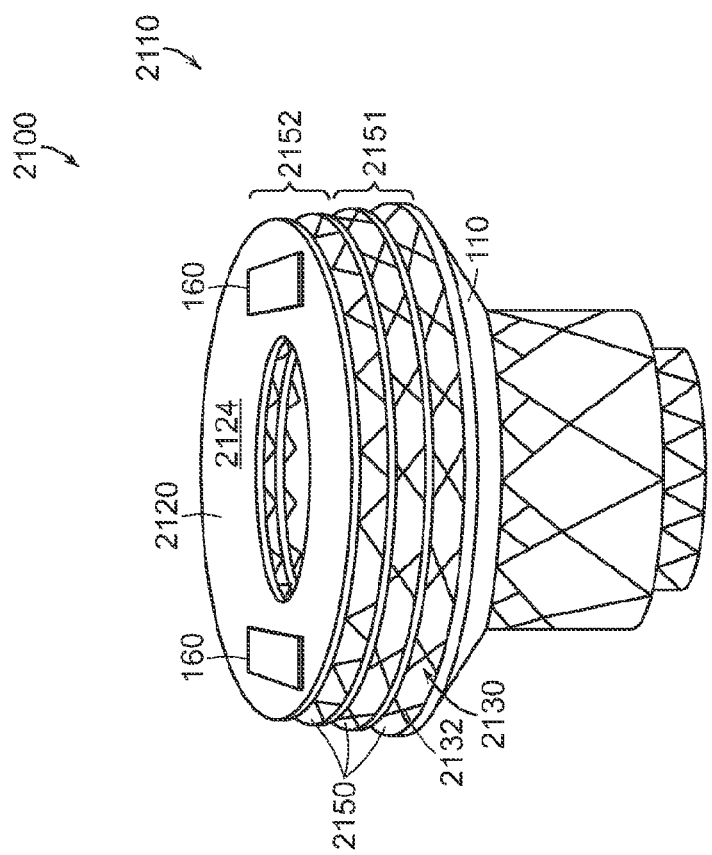

FIG. 102 is an isometric view of a prosthetic heart valve device in accordance with an embodiment of the technology.

FIG. 103 isometric view of a prosthetic heart valve device in accordance with a further embodiment of the technology.

FIGS. 104A and 104B are side views of prosthetic heart valve devices in accordance with further embodiments of the technology.

FIG. 105 is an isometric view of a prosthetic heart valve device in accordance with a yet another embodiment of the technology.

FIGS. 106A and 106B are schematic cross-sectional views of embodiments of prosthetic heart valve devices in accordance with the present technology.

Figure 107A:
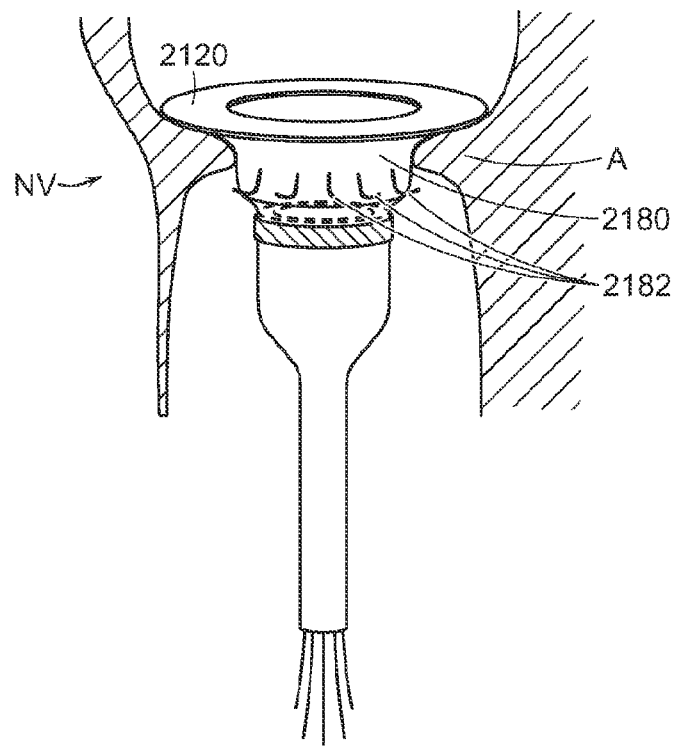
Figure 107B:
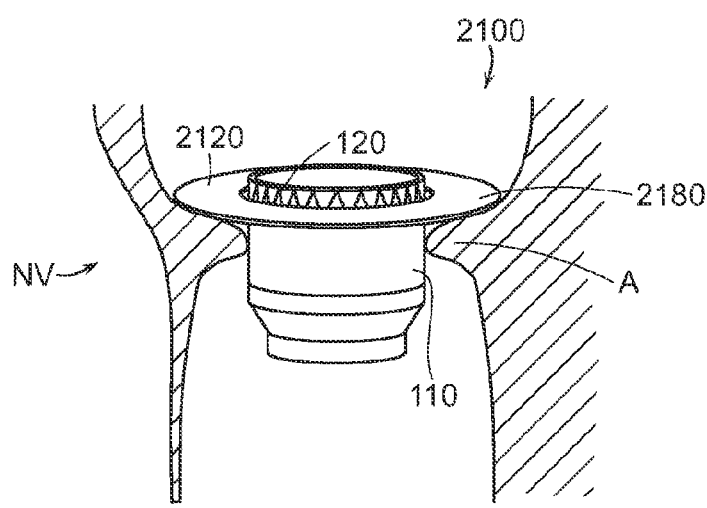

FIGS. 107A and 107B are isometric views showing a method of delivering a prosthetic heart valve device in accordance with a further embodiment of the technology.

DETAILED DESCRIPTION

Specific details of several embodiments of the technology are described below with reference to FIGS. 1-107B. Although many of the embodiments are described below with respect to devices, systems, and methods for percutaneous replacement of a native mitral valve using prosthetic valve devices, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-107B.

With regard to the terms "distal" and "proximal" within this description, unless otherwise specified, the terms can reference a relative position of the portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a position of blood inflow, and distal can refer to a downstream position or a position of blood outflow. For ease of reference, throughout this disclosure identical reference numbers and/or letters are used to identify similar or analogous components or features, but the use of the same reference number does not imply that the parts should be construed to be identical. Indeed, in many examples described herein, the identically numbered parts are distinct in structure and/or function. The headings provided herein are for convenience only.

Overview

Systems, devices and methods are provided herein for percutaneous replacement of native heart valves, such as mitral valves. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the claims but are not described in detail.

Embodiments of the present technology provide systems, methods and apparatus to treat valves of the body, such as heart valves including the mitral valve. The apparatus and methods enable a percutaneous approach using a catheter delivered intravascularly through a vein or artery into the heart. Additionally, the apparatus and methods enable other less-invasive approaches including trans-apical, trans-atrial, and direct aortic delivery of a prosthetic replacement valve to a target location in the heart. The apparatus and methods enable a prosthetic device to be anchored at a native valve location by engagement with a subannular surface of the valve annulus and/or valve leaflets. Additionally, the embodiments of the devices and methods as described herein can be combined with many known surgeries and procedures, such as known methods of accessing the valves of the heart (e.g., the mitral valve or triscuspid valve) with antegrade or retrograde approaches, and combinations thereof.

The devices and methods described herein provide a valve replacement device that has the flexibility to adapt and conform to the variably-shaped native mitral valve anatomy while mechanically isolating the prosthetic valve from the anchoring portion of the device. Several embodiments of the device effectively absorb the distorting forces applied by the native anatomy. The device has the structural strength and integrity necessary to withstand the dynamic conditions of the heart over time, thus permanently anchoring a replacement valve and making it possible for the patient to resume a substantially normal life. The devices and methods further deliver such a device in a less-invasive manner, providing a patient with a new, permanent replacement valve but also with a lower-risk procedure and a faster recovery.

In accordance with various embodiments of the present technology, a device for repair or replacement of a native valve of a heart is disclosed. The native valve has an annulus and leaflets, and the device includes an anchoring member having a first portion configured to engage tissue on or under the annulus and to deform in a non-circular shape to conform to the tissue. The anchoring member also can include a second portion. The device also includes a valve support coupled to the second portion of the anchoring member and configured to support a prosthetic valve and having a cross-sectional shape. In various embodiments, the first portion of the anchoring member is mechanically isolated from the valve support such that the cross-sectional shape of the valve support remains sufficiently stable so that the prosthetic valve remains competent when the anchoring member is deformed in the non-circular shape.

Some embodiments of the disclosure are directed to prosthetic heart valve devices for implantation at a native mitral valve wherein the mitral valve has an annulus and leaflets. In one embodiment, the device can have an anchoring member positionable in a location between the leaflets, wherein a first portion of the anchoring member is expandable to a dimension larger than a corresponding dimension of the annulus. In this embodiment, upstream movement of the anchoring member is blocked by engagement of the upstream portion with tissue on or near the annulus. The anchoring member can also include a second portion. The device can also include a valve support coupled to the second portion of the anchoring member, wherein an upstream region of the valve support is spaced radially inward from at least the first portion of the anchoring member. The valve support can be configured to support a prosthetic valve.

In another arrangement, a device for implantation at a native valve having an annulus and leaflets can include a hyperboloidic anchoring member having an upstream end configured to engage an inward facing surface of the leaflets downstream of the annulus and a downstream end, wherein the upstream end has a larger cross-sectional area than the downstream end. The device can also include a valve support positioned in the anchoring member and configured to support a prosthetic valve. The valve support is coupled to the anchoring member at a location spaced substantially downstream from the upstream end and is uncoupled to the anchoring member at the upstream end.

Other aspects of the disclosure are directed to prosthetic heart valve devices for repair or replacement of a native heart valve of a patient, wherein the heart valve has an annulus and leaflets. In one embodiment, the device includes an anchoring member having a first portion having a first cross-sectional dimension and second portion having a second cross-sectional dimension less than the first cross-sectional dimension. The first portion is configured to engage cardiac tissue to retain the anchoring member in a fixed longitudinal position relative to the annulus. The device can also include a valve support coupled to the second portion of the anchoring member and configured to support a prosthetic valve. The valve support can be radially separated from the first portion of the anchoring member such that the first portion can deform inwardly without substantially deforming the valve support.

In a further arrangement, the present disclosure also is directed to a device for implantation at a native heart valve. The device can include an anchoring member having an upstream end configured to engage tissue on or downstream of a native annulus of the heart valve, and a valve support configured to support a prosthetic valve. The valve support can be coupled to the anchoring member. In some arrangements, the anchoring member can resist upstream migration of the device without an element of the device extending behind native valve leaflets.

In another embodiment, the device can include an anchoring member positionable between the leaflets of the native valve. The anchoring member can have a plurality of tissue engaging elements on an upstream end and/or on an exterior surface which are configured to engage cardiac tissue on or near the annulus so as to prevent migration of the device in the upstream direction. The device can also include a valve support positioned within an interior of the anchoring member and coupled to a downstream portion of the anchoring member, wherein the valve support is radially separated from at least an upstream portion of the anchoring member.

Further embodiments of the disclosure are directed to a device for repair or replacement of a native mitral valve having an annulus and a pair of leaflets that include a support structure having an upper region, a lower region, and an interior to retain a prosthetic valve. The device can also include an anchoring member surrounding at least a portion of the support structure, wherein the anchoring member is positionable between the leaflets and has a plurality of flexible elements (e.g., wires, laser cut metal elements, etc.) arranged in a diamond pattern, an upper portion, and a lower portion. The upper portion of the anchoring member can be flared outwardly in a proximal direction such that proximal ends of the flexible elements point radially outward so as to engage cardiac tissue on or near the annulus and inhibit migration of the device in the upstream direction. The lower region of the support structure can be coupled to the lower portion of the anchoring member, and the lower region of the support structure can be mechanically isolated from at least deformation of the flared upper portion of the anchoring member.

Other embodiments of the disclosure are directed to prosthetic heart valve devices having a cylindrical support and an anchor defined by a structure separate from the cylindrical support. The cylindrical support can have a longitudinal axis and an interior along the longitudinal axis through which blood may flow. The anchor can have a non-circular cross-section with an outwardly flared upstream end configured to engage subannular tissue of a mitral valve. The anchor can also surround the cylindrical support and be coupled to the support at a downstream end opposite the upstream end.

In a further embodiment, the device can include an expandable valve support configured for placement between the two leaflets. The support can have a first region, a second region and an interior in which a valve may be coupled. The device can also include an anchoring member having a first portion and a second portion, the second portion coupled to the second region of the valve support. The first portion of the anchoring member can extend outwardly away from the second portion. The anchoring member can have a first perimeter at the first portion configured to engage tissue on or near the annulus. The anchoring member can be mechanically isolated from the valve support such that a force exerted radially at or near the first perimeter will not substantially alter a shape of the valve support.

Additional embodiments are directed to devices to treat a heart valve of a patient that include an inner frame and an outer frame coupled to the inner frame. The inner frame can have an outer surface and an inner surface that is configured to support a prosthetic valve. The outer frame can have an upper portion with a cross-sectional dimension greater than a corresponding cross-sectional dimension of an annulus of the mitral valve, wherein the upper portion is configured to engage tissue at or below the annulus of the mitral valve. The upper portion can also prevent migration of the device in an upward or upstream direction during ventricular systole. Further, the upper portion of the outer frame can be mechanically isolated from the inner frame.

In a further embodiment, the device can include a cylindrical inner skeleton and an outer skeleton coupled to the inner skeleton and positionable between the leaflets downstream of the annulus. The outer skeleton can be deformable to a non-circular cross-section while the inner skeleton remains substantially circular in cross-section. The inner skeleton can have an interior to which a prosthetic valve may be coupled. The outer skeleton can have a plurality of flexible elements (e.g., wires, laser cut metal elements, etc.), wherein at least a portion of the flexible elements can be configured to engage native subannular tissue so as to prevent migration of the device in an upstream direction. In one embodiment, the plurality of flexible wires are arranged in a diamond configuration.

In yet a further embodiment, a prosthetic mitral valve device can include a valve support having upstream and downstream ends, an interior in which a valve may be coupled, and a perimeter. The device can also include an anchoring member having a flared upstream portion and a downstream portion coupled to the perimeter of the valve support. The upstream portion can be mechanically isolated from the valve support and can be configured to engage subannular tissue of a native mitral valve. Additionally, the device can be moveable into a plurality of configurations including a first configuration in which the valve support and the anchoring member are radially contracted, and wherein the valve support has a first cross-sectional shape. The device can also move into a second configuration in which the valve support and the anchoring member are radially expanded and in which the valve support has a second cross-sectional shape. Additionally, the device can move into a third configuration in which the anchoring member is engaged with and deformed by the subannular tissue while the valve support remains in the second cross-sectional shape.

In some embodiments, the device may comprise an atrial retainer extending from the anchoring member or the valve support to a position at least partially upstream of the native mitral annulus. The atrial extension member may comprise an atrial engagement structure adapted to engage an upstream surface (e.g., supra-annular surface) of the annulus and/or an interior wall of the atrium for further stabilizing or anchoring the device. For example, the atrial retainer can block downstream movement of the device.

Some embodiments of the device may further comprise one or more stabilizing members to inhibit the device from tilting or being displaced laterally. The stabilizing members may comprise a plurality of arms extending radially outwardly from the valve support and/or the anchoring member. The arms may be configured to extend behind the native leaflets and/or into engagement with the ventricular wall or papillary muscles.

A further embodiment, in accordance with another aspect of the present disclosure, is directed to a device for implantation at a native mitral valve, wherein the native mitral valve has an annulus and leaflets. The device can include a valve support having upstream and downstream ends, an interior in which a valve may be coupled, and an outer surface, and include a first anchoring member having a first flared upstream portion and a first downstream portion coupled to the outer surface of the valve support. In other embodiments, the first downstream portion can be coupled to inner surface of the valve support, or in some embodiments, to an end of the valve support. The device can also include a second anchoring member at least partially surrounding the first anchoring member. The first upstream portion of the first anchoring member can be mechanically isolated from the valve support and configured to engage supra-annular tissue of the native mitral valve. The second anchoring member can have a second flared upstream portion and a second downstream portion coupled to the outer surface of the valve support, wherein the second upstream portion can be mechanically isolated from the valve support and is configured to engage subannular tissue of the native mitral valve.

In yet a further embodiment, the device for implantation can include a radially expandable anchoring member configured to engage native tissue on or downstream of the annulus. The anchoring member can have a first longitudinal length on a posterior leaflet-facing side and a second length on an anterior leaflet-facing side. In certain embodiments, the first length can be greater than the second length such that occlusion of a left ventricle outflow tract (LVOT) is limited. The device can also include a valve support, or alternatively a prosthetic valve, coupled to an interior or to an end of the anchoring member.

Other embodiments of the present technology provide a device for implantation at a native mitral valve having an annulus and leaflets, wherein the device includes a valve support having upstream and downstream ends, an interior in which a valve may be coupled, and an outer surface. The device can also include an anchoring member having a flared upstream portion and a downstream portion coupled to the outer surface of the valve support, wherein the upstream portion can have an upper ring and a lower ring coupled to the upper ring. The device can further include a plurality of flexible annulus engaging elements distributed around a circumference of the anchoring member and coupling the upper ring to the lower ring. The lower ring is configured to move in an upstream direction toward the upper ring such that the annulus is received between the upper and lower rings and within the annulus engaging elements.

The disclosure further provides systems for delivery of prosthetic valves and other devices using endovascular or other minimally invasive forms of access. For example, embodiments of the present technology provide a system to treat a mitral valve of a patient, in which the mitral valve has an annulus. The system comprises a device to treat the mitral valve as described herein and a catheter having a lumen configured to retain the device within the catheter.

In other aspects, a system for replacing a native valve in a patient is provided. The system can include an elongated catheter body having a distal end and a proximal end, and a housing coupled to the distal end of the catheter body and having a closed end and an open end. The system can also include a plunger within the housing which is axially movable relative to the housing, and an actuator at the proximal end of the catheter body and coupled to the plunger such that moving the actuator moves the housing axially relative to the plunger. The system can further include a prosthetic valve device having a collapsed configuration and an expanded configuration. The prosthetic valve device can be positionable in the housing in the collapsed configuration and can be releasable proximally from the housing by moving the actuator.

In yet another aspect, embodiments of the present technology provide a method of treating a heart valve of a patient. The mitral valve has an annulus and leaflets coupled to the annulus. The method can include implanting a device as described herein within or adjacent to the annulus. The device, in some embodiments, can include a valve support coupled to and at least partially surrounded by an anchoring member. The anchoring member can be disposed between the leaflets and an upstream portion of the anchoring member can be configured to engage tissue on or downstream of the annulus to prevent migration of the device in an upstream direction. Further, the valve support can be mechanically isolated from the anchoring member at least at the upstream portion.

In yet a further aspect, embodiments of the present technology provide a method for replacement of a native mitral valve having an annulus and leaflets. The method can include positioning a device as described herein between the leaflets, while the device is in a collapsed configuration. The method can also include allowing the prosthetic device to expand such that an anchoring member of the prosthetic device is in a subannular position in which it engages tissue on or downstream of the annulus. The anchoring member can have a diameter larger than a corresponding diameter of the annulus in the subannular position. The method can further include allowing a valve support to expand within the anchoring member, wherein the valve support is coupled to the anchoring member. In various embodiments, the valve support can be mechanically isolated from the anchoring member such that deformation of the anchoring member when the anchoring member engages the tissue does not substantially deform the valve support. In some arrangements, certain regions of the valve support may deform, but a support region suitable for retaining a prosthetic valve does not substantially deform such that leaflet coaptation of the prosthetic valve would not be compromised.

The disclosure further provides prosthetic heart valve devices that can include an anchoring member having a tubular fixation frame with an inlet end and an outlet end. The device can also include a tubular valve support that has a first portion coupled to the anchoring member and a second portion mechanically isolated from the anchoring member such that the inlet end of the anchoring member is radially deformable without substantially deforming the second portion. The device can further include a valve coupled to the valve support. The valve can have at least one leaflet movable from a closed position in which blood flow is blocked through the valve support and an open position in which blood flow is allowed through the valve support in a downstream direction. The device can also include an extension member coupled to the fixation frame and extending radially outward therefrom. A deformable portion of the extension member can be mechanically isolated from the anchoring member such that the deformable portion of the extension member is radially deformable without substantially deforming the anchoring member.

Additional aspects of the disclosure are directed to prosthetic heart valve devices that can include an anchoring member that has a connection structure and a radially expandable fixation frame. The connection structure can have a first end coupled to the fixation frame, a second end coupled to a valve support and a lateral portion that spaces the fixation frame apart from the valve support. The device can also include a valve coupled to the valve support and which has at least one leaflet movable from a closed position in which blood flow is blocked through an interior and an open position in which blood flow is allowed through the interior in a flow direction from an inlet end toward an outlet end. The Device can further include an extension member having a brim and a support structure coupled to the brim. The brim can include a sheet of flexible material coupled to the fixation frame and extending radially outward therefrom. In various embodiments, the support structure can be more rigid than the brim. In one embodiment, the brim can be deflectable relative to the fixation frame about an axis transverse to the flow direction and the fixation frame is configured to deform at least partially independently of the valve support.

Additional prosthetic heart valve devices can include an anchoring member having a tubular fixation frame with an interior and having an upstream end and a downstream end, and a valve coupled to the anchoring member. The valve can have at least one leaflet movable from a closed position in which blood flow is blocked through the interior and an open position in which blood flow is allowed through the interior in a flow direction from the upstream end toward the downstream end. The device can also include an extension member having a brim and a resilient support structure coupled to the brim. The brim can include a sheet of flexible material coupled to the anchoring member near the upstream end thereof and extending radially outward therefrom. The support structure can be structurally independent from the fixation frame. Further, the extension member can be radially deformable without substantially deforming the anchoring member.

In yet a further aspect, a prosthetic heart valve device can include an anchoring member having a radially expandable frame with an interior and having an upstream end and a downstream end. In some embodiments, the upstream end includes a tissue fixation portion configured to engage tissue located at and/or downstream of a native annulus of a heart valve in a subject and configured to be at least partially deformable to conform to a shape of the tissue. The device can also include a valve positioned relative to the anchoring member and having at least one leaflet movable from a closed position in which blood flow is blocked through the interior and an open position in which blood flow is allowed through the interior in a flow direction from the upstream end toward the downstream end. The valve can be spaced inwardly apart from the tissue fixation portion of the anchoring member such that the valve remains competent when the tissue fixation portion is deformed to conform to the shape of the tissue. The device can further include an extension member flexibly coupled to the anchoring member proximate the upstream end of the expandable frame, wherein the extension member extends longitudinally along the flow direction in a low-profile configuration and is biased to project laterally relative to the flow direction in a deployed configuration. The extension member can be configured to deform relative to the expandable frame in the deployed configuration.

Additional aspects of the technology are directed to methods of replacing a native heart valve. In one embodiment, a method can include positioning a prosthesis in a first heart chamber upstream of a native annulus with a delivery device when the prosthesis being is a collapsed configuration, and deploying an extension member of the prosthesis in the first heart chamber so that the extension member at least partially expands into an expanded shape while an anchoring member of the prosthesis remains at least partially collapsed. The method can also include moving the prosthesis to cause an indicator portion of the extension member to deflect by engagement with a wall of the first heart chamber surrounding the native heart valve, and visualizing the indicator portion of the extension member to determine a position of the prosthesis relative to a native annulus based on the deflection of the indicator portion. The method can further include deploying the anchoring member of the prosthesis such that it expands into engagement with heart tissue downstream of the native annulus so as to anchor the prosthesis in place.

Another method of replacing a native heart valve can include positioning a prosthesis in a first heart chamber upstream of a native annulus with a delivery device when the prosthesis is in a collapsed configuration, and deploying an extension member of the prosthesis in the first heart chamber so that the extension member at least partially expands into an expanded shape while an anchoring member of the prosthesis remains at least partially collapsed. The method can also include deploying the anchoring member of the prosthesis such that it expands into engagement with heart tissue downstream of the native annulus so as to anchor the prosthesis in place. The method can further include allowing the extension member to radially deform to a greater extent than any deformation of the anchoring member.

An additional method of replacing a native heart valve can include positioning a collapsed prosthesis in a first heart chamber upstream of a native annulus with a delivery device, and deploying an extension member of the prosthesis in the first heart chamber so that the extension member at least partially expands into an expanded shape while a fixation member of the prosthesis remains at least partially collapsed. The method can also include moving the prosthesis in a downstream direction such that the expanded extension member folds at least partially inwardly and positions the fixation member at a desired location relative to the native valve annulus. The method can further include deploying the fixation member of the prosthesis such that it expands into engagement with heart tissue downstream of the native annulus so as to anchor the prosthesis in place.

The devices and methods disclosed herein can be configured for treating non-circular, asymmetrically shaped valves and bileaflet or bicuspid valves, such as the mitral valve. It can also be configured for treating other valves of the heart such as the tricuspid valve. Many of the devices and methods disclosed herein can further provide for long-term (e.g., permanent) and reliable anchoring of the prosthetic device even in conditions where the heart or native valve may experience gradual enlargement or distortion.

Cardiac and Mitral Valve Physiology

Figure 1:
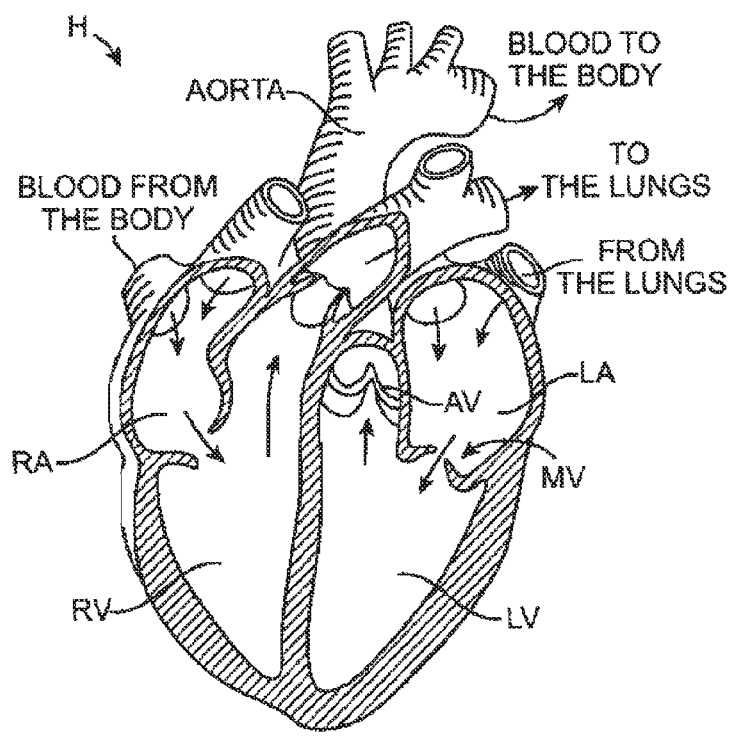
FIGS. 1 and 2 are schematic illustrations of a mammalian heart having native valve structures suitable for replacement with various prosthetic heart valve devices in accordance with embodiments of the present technology.
Figure 2:
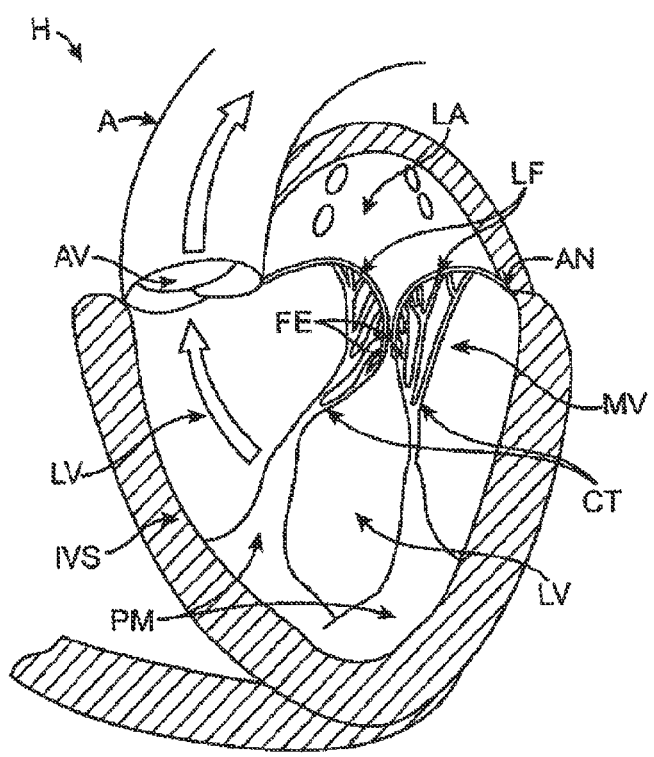

FIGS. 1 and 2 show a normal heart H. The heart comprises a left atrium that receives oxygenated blood from the lungs via the pulmonary veins PV and pumps this oxygenated blood through the mitral valve MV into the left ventricle LV. The left ventricle LV of a normal heart H in systole is illustrated in FIG. 2. The left ventricle LV is contracting and blood flows outwardly through the aortic valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA.

Figure 3:
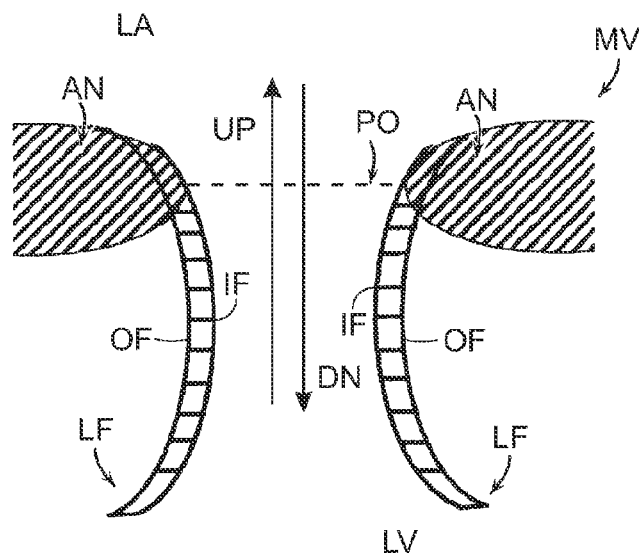
FIG. 3 is a schematic cross-sectional side view of a native mitral valve showing the annulus and leaflets.

The mitral valve MV comprises a pair of leaflets having free edges FE which meet evenly, or "coapt" to close, as illustrated in FIG. 2. The opposite ends of the leaflets LF are attached to the surrounding heart structure via an annular region of tissue referred to as the annulus AN. FIG. 3 is a schematic cross-sectional side view of an annulus and leaflets of a mitral valve. As illustrated, the opposite ends of the leaflets LF are attached to the surrounding heart structure via a fibrous ring of dense connective tissue referred to as the annulus AN, which is distinct from both the leaflet tissue LF as well as the adjoining muscular tissue of the heart wall. The leaflets LF and annulus AN are comprised of different types of cardiac tissue having varying strength, toughness, fibrosity, and flexibility. Furthermore, the mitral valve MV may also comprise a unique region of tissue interconnecting each leaflet LF to the annulus AN, referred to herein as leaflet/annulus connecting tissue LAC (indicated by overlapping cross-hatching). In general, annular tissue AN is tougher, more fibrous, and stronger than leaflet tissue LF.

Referring to FIG. 2, the free edges FE of the mitral leaflets LF are secured to the lower portions of the left ventricle LV through chordae tendineae CT (referred to hereinafter "chordae") which include a plurality of branching tendons secured over the lower surfaces of each of the valve leaflets LF. The chordae CT in turn, are attached to the papillary muscles PM, which extend upwardly from the lower wall of the left ventricle LV and interventricular septum IVS.

Figure 4A:
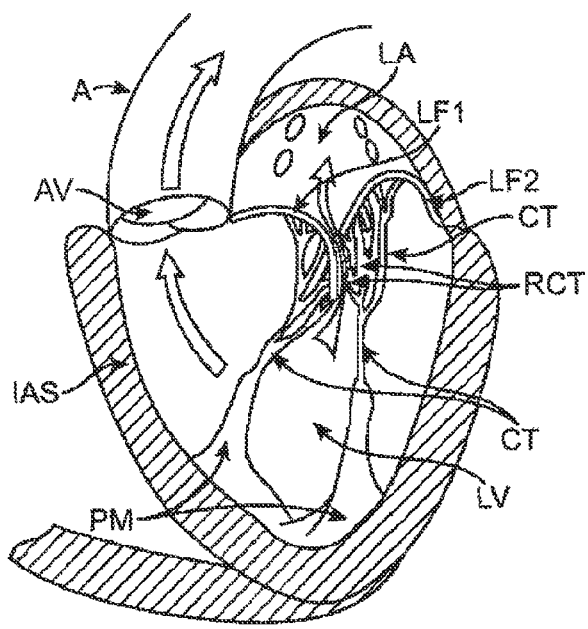
FIG. 4A is a schematic illustration of the left ventricle of a heart having either i) prolapsed leaflets in the mitral valve, or ii) mitral valve regurgitation in the left ventricle of a heart having impaired papillary muscles, and which are suitable for combination with various prosthetic heart valve devices in accordance with embodiments of the present technology.
Figure 4B:
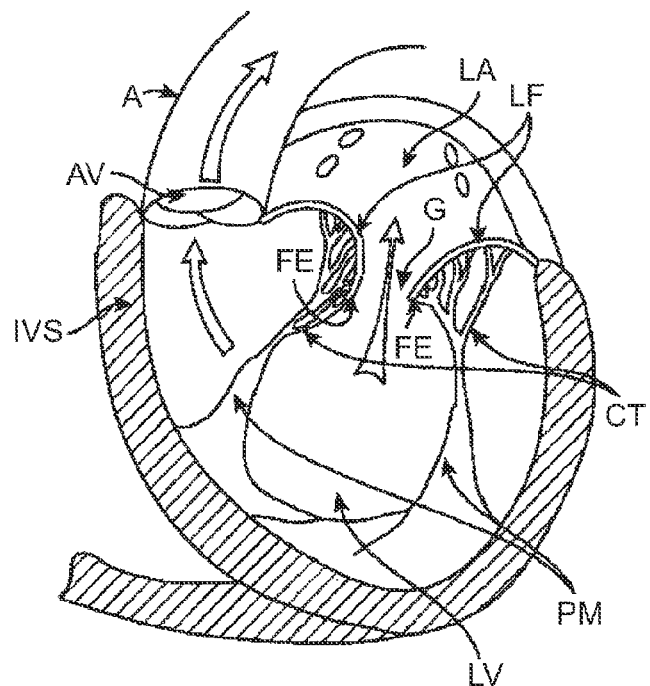
FIG. 4B is a schematic illustration of a heart in a patient suffering from cardiomyopathy, and which is suitable for combination with various prosthetic heart valve devices in accordance with embodiments of the present technology.

Referring now to FIGS. 4A to 4B, a number of structural defects in the heart can cause mitral valve regurgitation. Ruptured chordae RCT, as shown in FIG. 4A, can cause a valve leaflet LF2 to prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Regurgitation also occurs in the patients suffering from cardiomyopathy where the heart is dilated and the increased size prevents the valve leaflets LF from meeting properly, as shown in FIG. 4B. The enlargement of the heart causes the mitral annulus to become enlarged, making it impossible for the free edges FE to meet during systole. The free edges of the anterior and posterior leaflets normally meet along a line of coaptation C as shown in FIG. 5A, but a significant gap G can be left in patients suffering from cardiomyopathy, as shown in FIG. 5B.

Mitral valve regurgitation can also occur in patients who have suffered ischemic heart disease where the functioning of the papillary muscles PM is impaired, as illustrated in FIG. 4A. As the left ventricle LV contracts during systole, the papillary muscles PM do not contract sufficiently to effect proper closure. One or both of the leaflets LF1 and LF2 then prolapse. Leakage again occurs from the left ventricle LV to the left atrium LA.

Figure 5A:
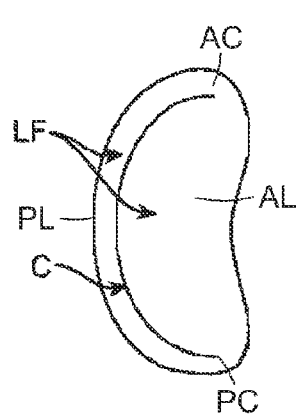
FIG. 5A is a schematic illustration of a native mitral valve of a heart showing normal closure of native mitral valve leaflets.
Figure 5B:
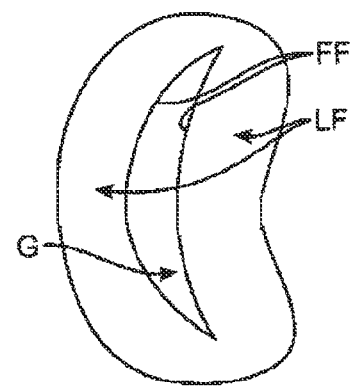
FIG. 5B is a schematic illustration of a native mitral valve of a heart showing abnormal closure of native mitral valve leaflets in a dilated heart, and which is suitable for combination with various prosthetic heart valve devices in accordance with embodiments of the present technology.
Figure 5C:
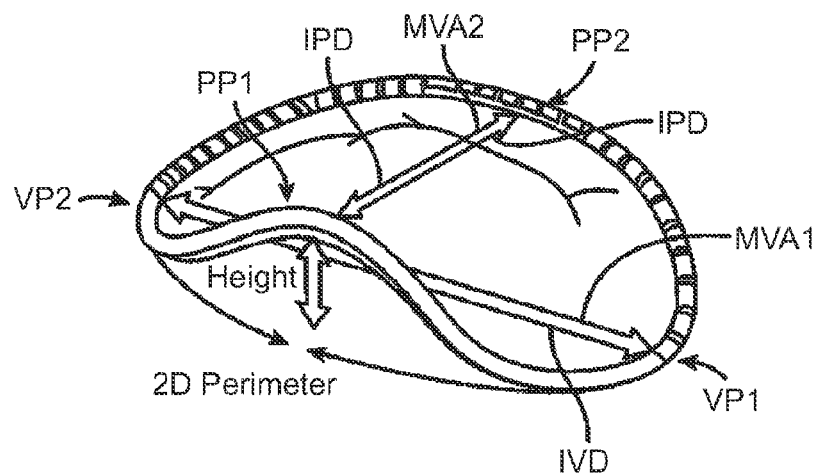
FIG. 5C is a schematic illustration of a mitral valve of a heart showing dimensions of the annulus, and which is suitable for combination with various prosthetic heart valve devices in accordance with embodiments of the present technology.

FIGS. 5A-5C further illustrate the shape and relative sizes of the leaflets L of the mitral valve. Referring to FIG. 5C, it may be seen that the overall valve has a generally "D"-shape or kidney-like shape, with a long axis MVA1 and a short axis MVA2. In healthy humans the long axis MVA1 is typically within a range from about 33.3 mm to about 42.5 mm in length (37.9+/−4.6 mm), and the short axis MVA2 is within a range from about 26.9 to about 38.1 mm in length (32.5+/−5.6 mm) However, with patients having decreased cardiac function these values can be larger, for example MVA1 can be within a range from about 45 mm to 55 mm and MVA2 can be within a range from about 35 mm to about 40 mm. The line of coaptation C is curved or C-shaped, thereby defining a relatively large anterior leaflet AL and substantially smaller posterior leaflet PL (FIG. 5A). Both leaflets appear generally crescent-shaped from the superior or atrial side, with the anterior leaflet AL being substantially wider in the middle of the valve than the posterior leaflet. As illustrated in FIG. 5A, at the opposing ends of the line of coaptation C the leaflets join together at corners called the anterolateral commissure AC and posteromedial commissure PC, respectively.

FIG. 5C shows the shape and dimensions of the annulus of the mitral valve. The annulus is an annular area around the circumference of the valve comprised of fibrous tissue which is thicker and tougher than that of the leaflets LF and distinct from the muscular tissue of the ventricular and atrial walls. The annulus may comprise a saddle-like shape with a first peak portion PP1 and a second peak portion PP2 located along an interpeak axis IPD, and a first valley portion VP1 and a second valley portion VP2 located along an intervalley axis IVD. The first and second peak portion PP1 and PP2 are higher in elevation relative to a plane containing the nadirs of the two valley portions VP1, VP2, typically being about 8-19 mm higher in humans, thus giving the valve an overall saddle-like shape. The distance between the first and second peak portions PP1, PP2, referred to as interpeak span IPD, is substantially shorter than the intervalley span IVD, the distance between first and second valley portions VP1, VP2.

A person of ordinary skill in the art will recognize that the dimensions and physiology of the patient may vary among patients, and although some patients may comprise differing physiology, the teachings as described herein can be adapted for use by many patients having various conditions, dimensions and shapes of the mitral valve. For example, work in relation to embodiments suggests that some patients may have a long dimension across the annulus and a short dimension across the annulus without well-defined peak and valley portions, and the methods and device as described herein can be configured accordingly.

Access to the Mitral Valve

Access to the mitral valve or other atrioventricular valve can be accomplished through the patient's vasculature in a percutaneous manner. By percutaneous it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well-known and described in the patent and medical literature. Depending on the point of vascular access, the approach to the mitral valve may be antegrade and may rely on entry into the left atrium by crossing the inter-atrial septum. Alternatively, approach to the mitral valve can be retrograde where the left ventricle is entered through the aortic valve. Once percutaneous access is achieved, the interventional tools and supporting catheter(s) may be advanced to the heart intravascularly and positioned adjacent the target cardiac valve in a variety of manners, as described herein.

Using a trans-septal approach, access is obtained via the inferior vena cava IVC or superior vena cava SVC, through the right atrium RA, across the inter-atrial septum IAS and into the left atrium LA above the mitral valve MV.

Figure 6A:
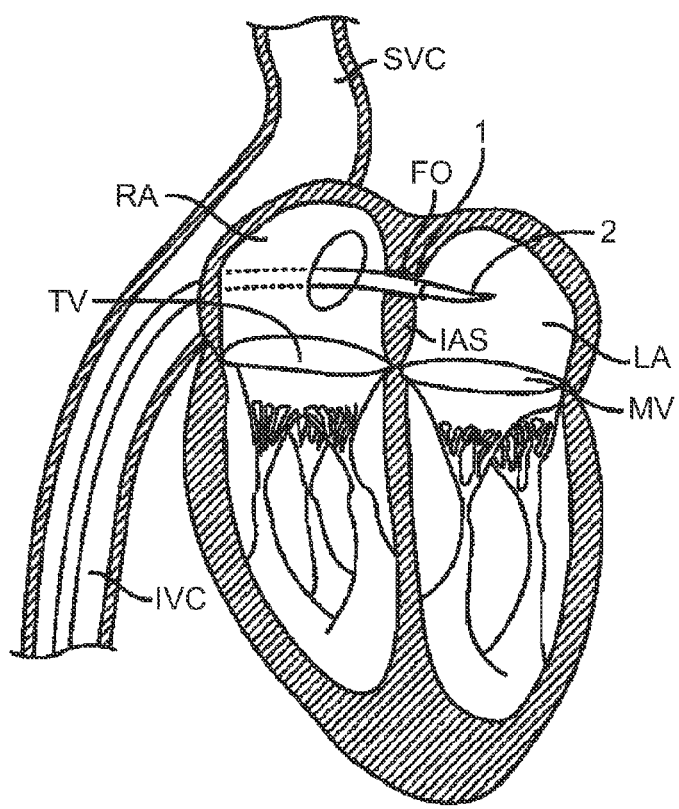
FIG. 6A is a schematic, cross-sectional illustration of the heart showing an antegrade approach to the native mitral valve from the venous vasculature, in accordance with various embodiments of the present technology.

As shown in FIG. 6A, a catheter 1 having a needle 2 may be advanced from the inferior vena cava IVC into the right atrium RA. Once the catheter 1 reaches the anterior side of the inter-atrial septum IAS, the needle 2 may be advanced so that it penetrates through the septum, for example at the fossa ovalis FO or the foramen ovale into the left atrium LA. At this point, a guidewire may be exchanged for the needle 2 and the catheter 1 withdrawn.

Figure 6B:
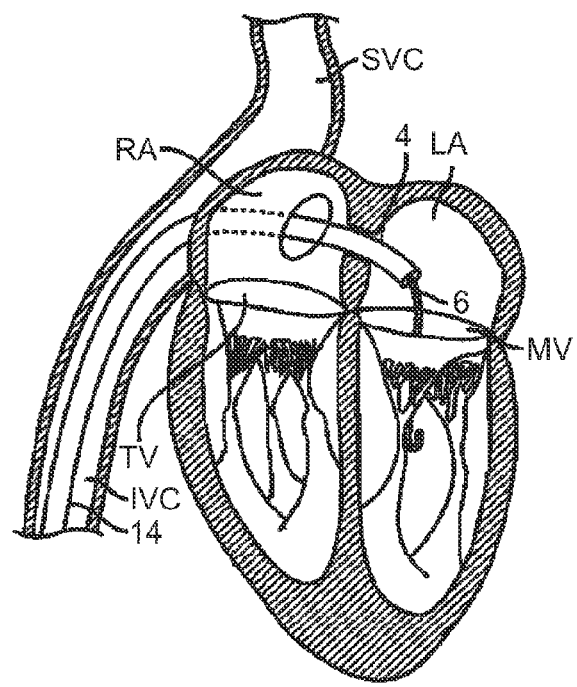
FIG. 6B is a schematic, cross-sectional illustration of the heart showing access through the inter-atrial septum (IAS) maintained by the placement of a guide catheter over a guidewire, in accordance with various embodiments of the present technology.

As shown in FIG. 6B, access through the inter-atrial septum IAS may usually be maintained by the placement of a guide catheter 4, typically over a guidewire 6 which has been placed as described above. The guide catheter 4 affords subsequent access to permit introduction of the device to replace the mitral valve, as described in more detail herein.

In an alternative antegrade approach (not shown), surgical access may be obtained through an intercostal incision, preferably without removing ribs, and a small puncture or incision may be made in the left atrial wall. A guide catheter may then be placed through this puncture or incision directly into the left atrium, sealed by a purse string-suture.

The antegrade or trans-septal approach to the mitral valve, as described above, can be advantageous in many respects. For example, the use of the antegrade approach will usually allow for more precise and effective centering and stabilization of the guide catheter and/or prosthetic valve device. Precise positioning facilitates accuracy in the placement of the prosthetic valve device. The antegrade approach may also reduce the risk of damaging the chordae tendinae or other subvalvular structures during catheter and interventional tool introduction and manipulation. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 7:
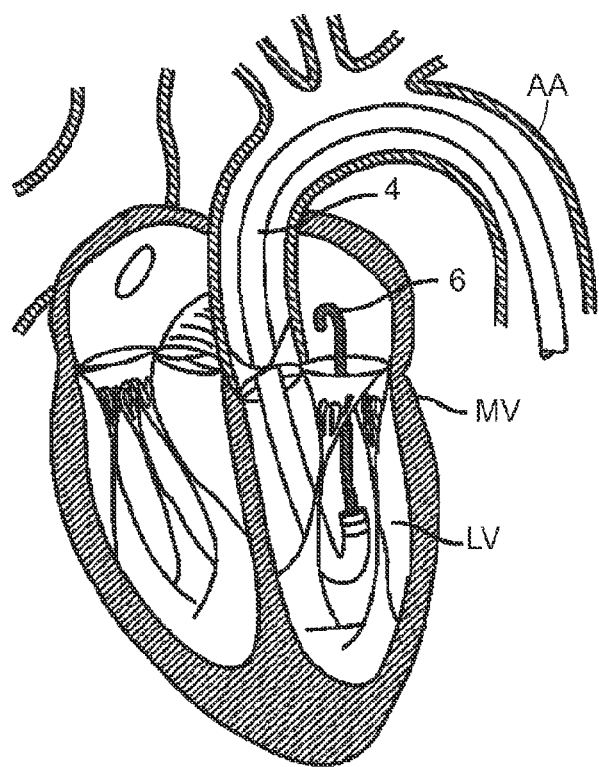
FIGS. 7 and 8 are schematic, cross-sectional illustrations of the heart showing retrograde approaches to the native mitral valve through the aortic valve and arterial vasculature, in accordance with various embodiments of the present technology.
Figure 8:
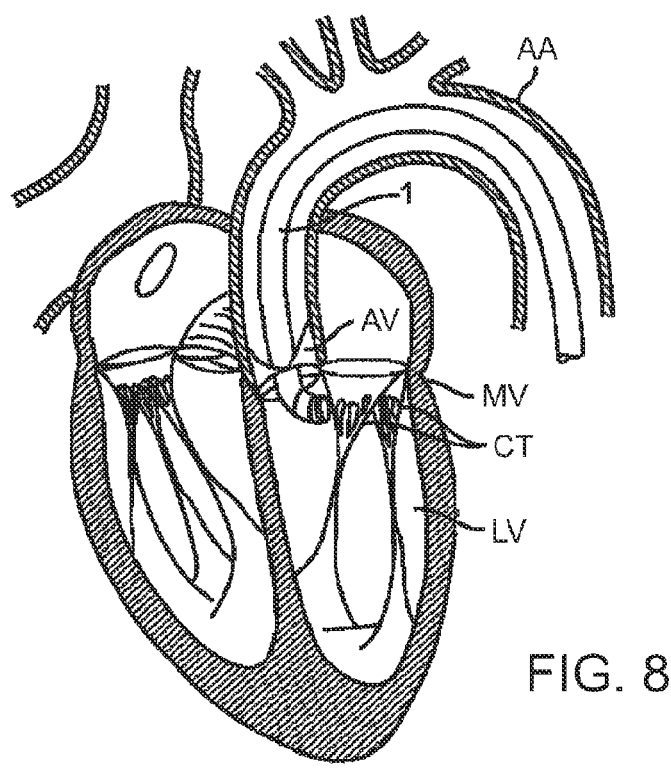

An example of a retrograde approach to the mitral valve is illustrated in FIGS. 7 and 8. The mitral valve MV may be accessed by an approach from the aortic arch AA, across the aortic valve AV, and into the left ventricle LV below the mitral valve MV. The aortic arch AA may be accessed through a conventional femoral artery access route, as well as through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein.

In some specific instances, a retrograde arterial approach to the mitral valve may be selected due to certain advantages. For example, use of the retrograde approach can eliminate the need for a trans-septal puncture. The retrograde approach is also more commonly used by cardiologists and thus has the advantage of familiarity.

Figure 9:
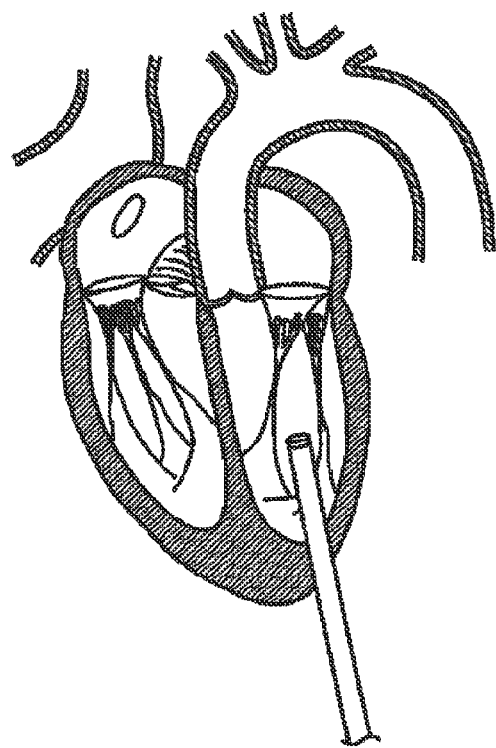
FIG. 9 is a schematic, cross-sectional illustration of the heart showing an approach to the native mitral valve using a trans-apical puncture in accordance with various embodiments of the present technology.

An additional approach to the mitral valve is via trans-apical puncture, as shown in FIG. 9. In this approach, access to the heart is gained via thoracic incision, which can be a conventional open thoracotomy or sternotomy, or a smaller intercostal or sub-xyphoid incision or puncture. An access cannula is then placed through a puncture, sealed by a purse-string suture, in the wall of the left ventricle at or near the apex of the heart. The catheters and prosthetic devices of the invention may then be introduced into the left ventricle through this access cannula.

The trans-apical approach has the feature of providing a shorter, straighter, and more direct path to the mitral or aortic valve. Further, because it does not involve intravascular access, the trans-apical procedure can be performed by surgeons who may not have the necessary training in interventional cardiology to perform the catheterizations required in other percutaneous approaches.

The prosthetic treatment device may be specifically designed for the approach or interchangeable among approaches. A person of ordinary skill in the art can identify an appropriate approach for an individual patient and design the treatment apparatus for the identified approach in accordance with embodiments described herein.

Orientation and steering of the prosthetic valve device can be combined with many known catheters, tools and devices. Such orientation may be accomplished by gross steering of the device to the desired location and then refined steering of the device components to achieve a desired result.

Gross steering may be accomplished by a number of methods. A steerable guidewire may be used to introduce a guide catheter and the prosthetic treatment device into the proper position. The guide catheter may be introduced, for example, using a surgical cut down or Seldinger access to the femoral artery in the patient's groin. After placing a guidewire, the guide catheter may be introduced over the guidewire to the desired position. Alternatively, a shorter and differently shaped guide catheter could be introduced through the other routes described above.

A guide catheter may be pre-shaped to provide a desired orientation relative to the mitral valve. For access via the trans-septal approach, the guide catheter may have a curved, angled or other suitable shape at its tip to orient the distal end toward the mitral valve from the location of the septal puncture through which the guide catheter extends. For the retrograde approach, as shown in FIGS. 7 and 8, guide catheter 4 may have a pre-shaped J-tip which is configured so that it turns toward the mitral valve MV after it is placed over the aortic arch AA and through the aortic valve AV. As shown in FIG. 7, the guide catheter 4 may be configured to extend down into the left ventricle LV and to assume a J-shaped configuration so that the orientation of an interventional tool or catheter is more closely aligned with the axis of the mitral valve MV. In either case, a pre-shaped guide catheter may be configured to be straightened for endovascular delivery by means of a stylet or stiff guidewire which is passed through a lumen of the guide catheter. The guide catheter might also have pull-wires or other means to adjust its shape for more fine steering adjustment.

Selected Embodiments of Prosthetic Heart Valve Devices and Methods

Embodiments of the present technology as described herein can be used to treat one or more of the valves of the heart as described herein, and in particular embodiments, can be used for treatment of the mitral valve. Introductory examples of prosthetic heart valve devices, system components and associated methods in accordance with embodiments of the present technology are described in this section with reference to FIGS. 10A-56. It will be appreciated that specific elements, substructures, advantages, uses, and/or other features of the embodiments described with reference to FIGS. 10A-56 can be suitably interchanged, substituted or otherwise configured with one another and/or with the embodiments described with reference to FIGS. 57A-71 in accordance with additional embodiments of the present technology. Furthermore, suitable elements of the embodiments described with reference to FIGS. 10A-71 can be used as stand-alone and/or self-contained devices.

Figure 10A:
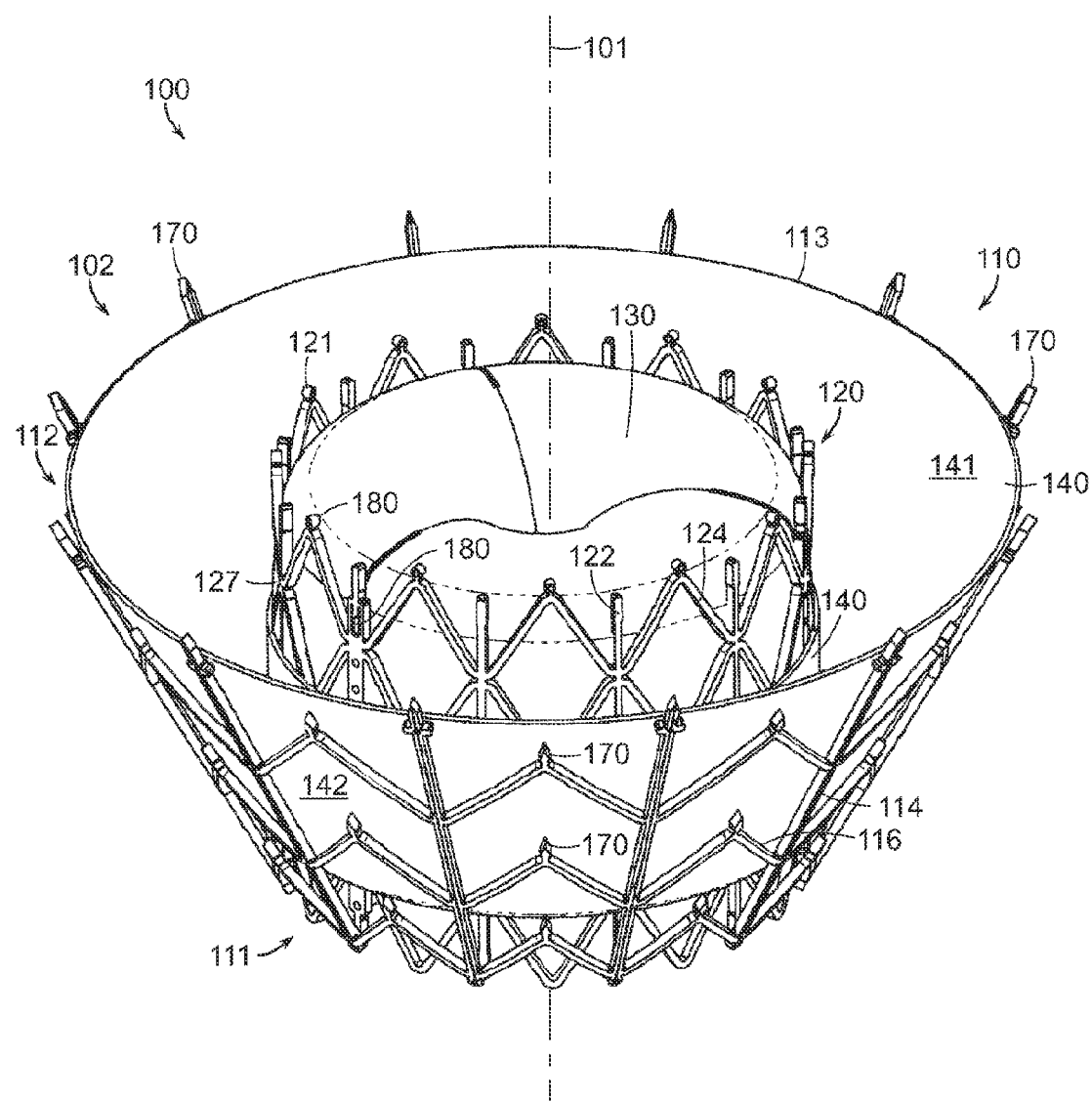
FIG. 10A shows an isometric view of a prosthetic heart valve device in accordance with an embodiment of the present technology.
Figure 10B:
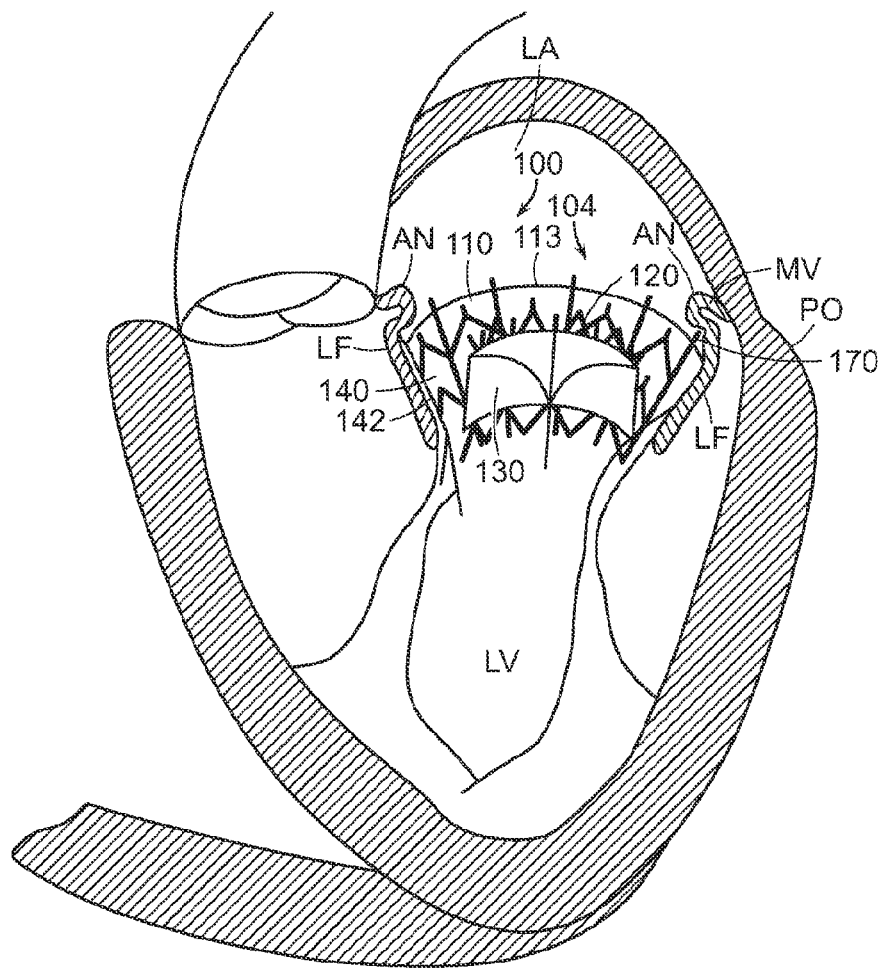
FIG. 10B illustrates a cut-away view of a heart showing the prosthetic treatment device of FIG. 10A implanted at a native mitral valve in accordance with an embodiment of the present technology.
Figure 10C:
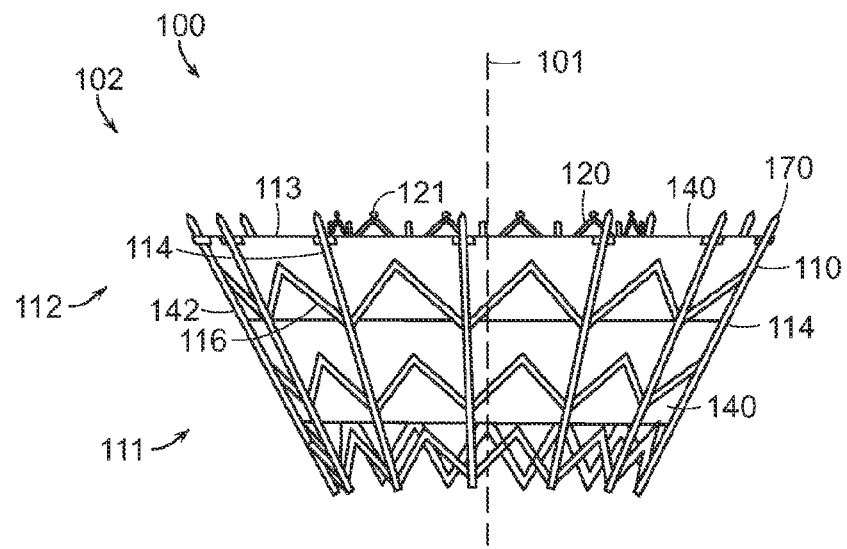
FIGS. 10C-10F are side, perspective cut-away, top, and bottom views, respectively, of a prosthetic heart valve device in accordance with an embodiment of the present technology.

Systems, devices and methods are provided herein for percutaneous implantation of prosthetic heart valves in a heart of a patient. In some embodiments, methods and devices are presented for the treatment of valve disease by minimally invasive implantation of artificial replacement heart valves. In one embodiment, the artificial replacement valve can be a prosthetic valve device suitable for implantation and replacement of a mitral valve between the left atrium and left ventricle in the heart of a patient. In another embodiment, the prosthetic valve device can be suitable for implantation and replacement of another valve (e.g., a bicuspid or tricuspid valve) in the heart of the patient. FIG. 10A shows an isometric view of a prosthetic heart valve device 100 in an expanded configuration 102 in accordance with an embodiment of the present technology, and FIG. 10B is a schematic illustration of a cross-sectional view of a heart depicting the left atrium, left ventricle, and native mitral valve of the heart. FIG. 10B also shows an embodiment of the expandable prosthetic valve device 100 implanted in the native mitral valve region of the heart.

As shown in FIG. 10A, the device 100 can include a flexible anchoring member 110 at least partially surrounding and coupled to an inner valve support 120. The device 100 can further include a prosthetic valve 130 coupled to, mounted within, or otherwise carried by the valve support 120. FIGS. 10C-10F are side, perspective cut-away, top, and bottom views, respectively, of the prosthetic heart valve device 100 in accordance with the present technology. The device 100 can also include one or more sealing members 140 and tissue engaging elements 170. For example, the sealing member 140 can, in one embodiment, extend around an inner wall 141 of the anchoring member 110 and/or around an exterior surface 127 of the valve support 120 to prevent paravalvular (e.g., paraprosthetic) leaks between the device 100 and the native tissue and/or between the anchoring member 110 and the valve support 120. In another specific embodiment, and as shown in FIG. 10A, the tissue engaging elements 170 can be spikes disposed on an upstream perimeter 113 of the anchoring member 110 and extend in an upward and/or radially outward direction to engage, and in some embodiments, penetrate the native tissue to facilitate retention or maintain position of the device in a desired implanted location. The tissue engaging elements 170 may also be included around an outer wall 142 of the anchoring member 110 and can extend outwardly to engage and, in some embodiments, penetrate the native valve leaflets or other adjacent tissue. Additionally, the valve support 120 can have a plurality of coupling features 180, such as eyelets, around an upstream end 121 to facilitate loading, retention and deployment of the device 100 within and from a delivery catheter (not shown), as further described herein.

The prosthetic heart valve device 100 can be movable between a delivery configuration (not shown), an expanded configuration 102 (FIG. 10A), and a deployed configuration 104 (FIG. 10B). In the delivery configuration, the prosthetic heart valve device 100 has a low profile suitable for delivery through small-diameter guide catheters positioned in the heart via the trans-septal, retrograde, or trans-apical approaches described herein. In some embodiments, the delivery configuration of the prosthetic heart valve device 100 will preferably have an outer diameter no larger than about 8-10 mm for trans-septal approaches, about 8-10 mm for retrograde approaches, or about 8-12 mm for trans-apical approaches to the mitral valve MV. As used herein, "expanded configuration" refers to the configuration of the device when allowed to freely expand to an unrestrained size without the presence of constraining or distorting forces. "Deployed configuration," as used herein, refers to the device once expanded at the native valve site and subject to the constraining and distorting forces exerted by the native anatomy.

Referring back to FIG. 3, "subannular," as used herein, refers to a portion of the mitral valve MV that lies on or downstream DN of the plane PO of the native orifice. As used herein, the plane PO of the native valve orifice is a plane generally perpendicular to the direction of blood flow through the valve and which contains either or both the major axis MVA1 or the minor axis MVA2 (FIG. 5C). Thus, a subannular surface of the mitral valve MV is a tissue surface lying on the ventricular side of the plane PO, and preferably one that faces generally downstream, toward the left ventricle LV. The subannular surface may be disposed on the annulus AN itself or the ventricular wall behind the native leaflets LF, or it may comprise a surface of the native leaflets LF, either inward-facing IF or outward-facing OF, which lies below the plane PO. The subannular surface or subannular tissue may thus comprise the annulus AN itself, the native leaflets LF, leaflet/annulus connective tissue, the ventricular wall or combinations thereof.

In operation, the prosthetic heart valve device 100 can be intravascularly delivered to a desired location in the heart, such as an intracardiac location near the mitral valve MV, while in the delivery (e.g., collapsed) configuration within a delivery catheter (not shown). Referring to FIG. 10B, the device 100 can be advanced to a position within or downstream of the native annulus AN where the device 100 can be released from the delivery catheter to enlarge toward the expanded configuration 102 (FIG. 10A). The device 100 will engage the native tissue at the desired location, which will deform or otherwise alter the shape of the device 100 into the deployed configuration 104 (FIG. 10B). Once released from the catheter, the device 100 can be positioned such that at least a portion of the flexible anchoring member 110 engages a subannular surface of the native valve so as to resist systolic forces and prevent upstream migration of the device 100 (FIG. 10B). In the embodiment illustrated in FIG. 10B, the upstream perimeter 113 of the anchoring member 110 engages the inward-facing surfaces IF (FIG. 3) of the native leaflets LF, which are pushed outwardly and folded under the native annulus AN. The leaflets LF engage a ventricular side of the annulus AN and are prevented from being pushed further in the upstream direction, thus maintaining the anchoring member 110 below the plane of the native valve annulus. The tissue engaging elements 170 can penetrate the tissue of the leaflets LF and/or the annulus AN to stabilize and firmly anchor the device 100. In some embodiments, however, some portions of the anchoring member 110 may extend above the annulus AN, with at least some portions of the anchoring member 110 engaging tissue in a subannular location to prevent migration of the device 100 toward the left atrium LA. As shown in FIG. 10B, the leaflets LF can lie in apposition against the outer wall 142 of the anchoring member 110 forming a blood-tight seal with the sealing member 140. The tissue engaging elements 170 can apply pressure against or, in another embodiment, penetrate the annulus AN or leaflets LF along the outer wall 142 of the anchoring member 110 to further stabilize the device 100 and prevent migration.

In accordance with aspects of the present technology, the proximal or upper end of the anchoring member 110, while in a deployed configuration 104, conforms to the irregularly-shaped mitral annulus AN, effectively sealing the device 100 against the native annulus AN to anchor the device and to prevent paravalvular leaks. As described further herein, the anchoring member 110 mechanically isolates the valve support 120 from distorting forces present in the heart such that the anchoring member 110 may adapt and/or conform to native forces while the valve support 120 maintains its structural integrity. Accordingly, the anchoring member 110 can be sufficiently flexible and resilient and/or coupled to the valve support 120 in such a manner as to mechanically isolate the valve support 120 from the forces exerted upon the anchoring member 110 by the native anatomy. Alternatively, or in addition to the above features, the valve support 120 may be more rigid and/or have greater radial strength than the radial strength of the anchoring member 110 so as to maintain its cylindrical or other desired shape and to ensure proper opening and closing of the prosthetic valve 130 housed within the valve support structure 120. In some embodiments, the valve support 120 has a radial strength of at least 100%, or in other embodiments at least 200%, and in further embodiments at least 300%, greater than a radial strength of the anchoring member 110. In one embodiment, the valve support 120 can have a radial strength of approximately 10 N to about 12 N. Thus, if deformed from its unbiased shape by exerting a radially compressive force against its circumference, the valve support 120 can exhibit a hoop force which is about 2 to about 20 times greater for a given degree of deformation than will be exhibited by the anchoring member 110.

Figure 10D:
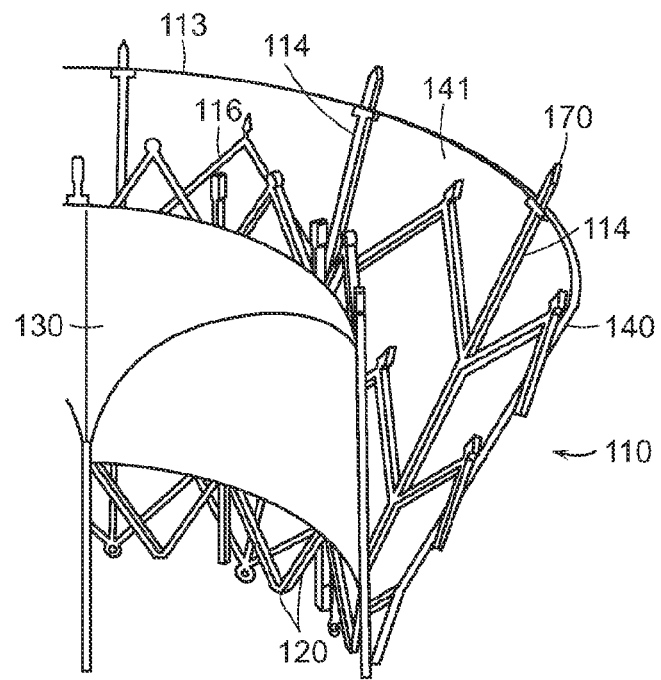
Figure 10E:
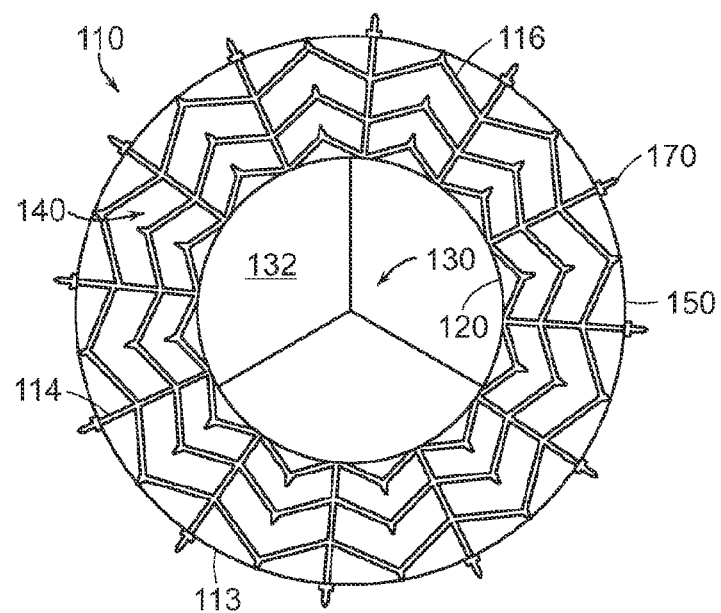
Figure 10F:
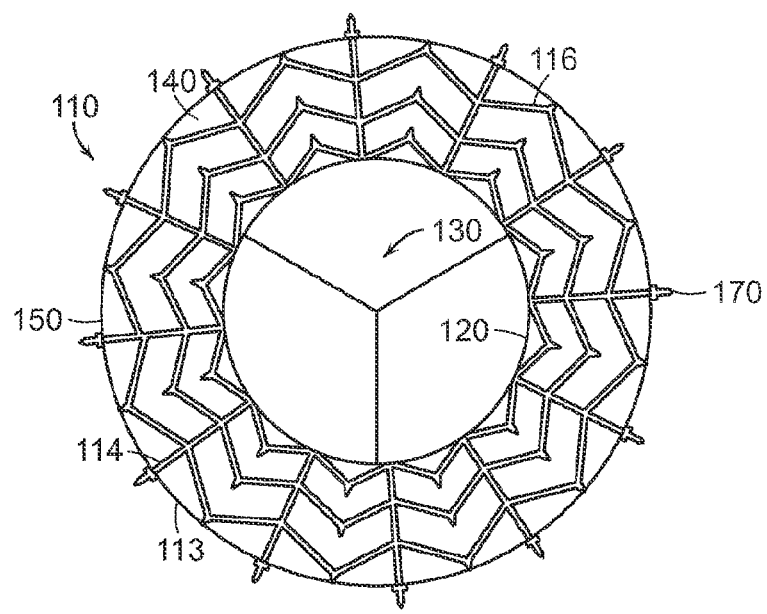

As illustrated in FIGS. 10A-10F, the anchoring member 110 has a downstream portion 111 and an upstream portion 112 opposite the downstream portion 111 relative to a longitudinal axis 101 of the device 100. The upstream portion 112 of the anchoring member 110 can be a generally outward oriented portion of the device 100, as shown in FIG. 10D. In one embodiment the anchoring member 110 has a generally hyperboloidic shape, such as the shape of a two-sheet hyperboloid. In another example, the downstream portion 111 can be substantially circular in cross-section while the upstream portion 112 can be generally non-circular. In some embodiments, the anchoring member 110 can include a series of circumferentially positioned, resiliently deformable and flexible longitudinal ribs 114 which, in some embodiments, are connected circumferentially by deformable and/or flexible connectors 116. Once deployed, at least a portion of the upstream ends of the longitudinal ribs 114 engage a subannular surface of the native valve (e.g., mitral valve). As described in more detail below, certain embodiments of longitudinal ribs 114 are configured to penetrate subannular tissue to anchor and further stabilize the device 100.

Additionally, FIGS. 10A-10F also illustrate that the longitudinal ribs 114 and/or circumferential connectors 116 may be arranged in a variety of geometrical patterns. In the examples shown in FIGS. 10A-10F, the connectors 116 are formed in a chevron configuration. One of ordinary skill will recognize that diamond-shaped patterns, sinusoidal configurations, closed cells, open cells, or other circumferentially expandable configurations are also possible. In some embodiments, the longitudinal ribs 114 may be divided along their length into multiple, separated segments (not shown), e.g. where the connectors 116 interconnect with the longitudinal ribs 114. The plurality of connectors 116 and ribs 114 can be formed from a deformable material or from a resilient or shape memory material (e.g., Nitinol). In other embodiments, the anchoring member 110 can comprise a mesh or woven construction in addition to or in place of the longitudinal ribs 114 and/or circumferential connectors 116. For example, the anchoring member 110 could include a tube or braided mesh formed from a plurality of flexible wires or filaments arranged in a diamond pattern or other configuration. In another example, a metal tube can be laser cut to provide a desired rib or strut geometry. The diamond configuration can, in some embodiments, provide column strength sufficient to inhibit movement of the device 100 relative the annulus under the force of systolic blood pressure against the valve 130 mounted in the valve support 120. In a particular example, the anchoring member 120 can be formed of a preshaped Nitinol tube having, for example, a wall thickness of approximately 0.010 inches to about 0.030 inches.

Figure 11A:
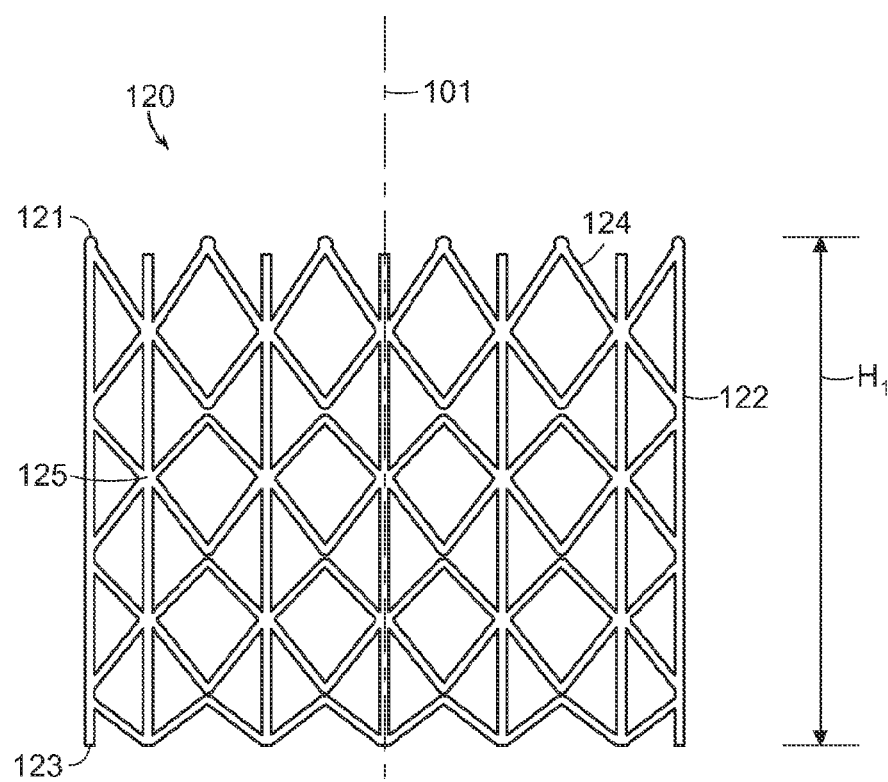
FIG. 11A is a side view of a valve support in an expanded configuration in accordance with an embodiment of the present technology.
Figure 11B:
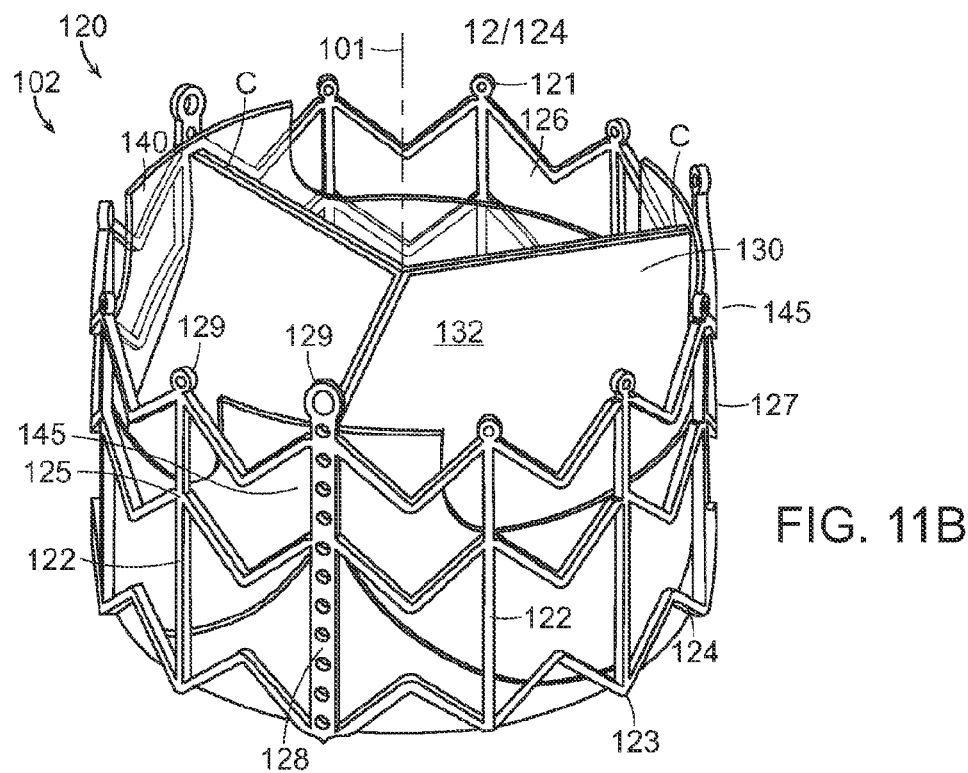
FIGS. 11B-11D are isometric views of additional embodiments of valve supports with prosthetic valves mounted therein in accordance with the present technology.
Figure 11C:
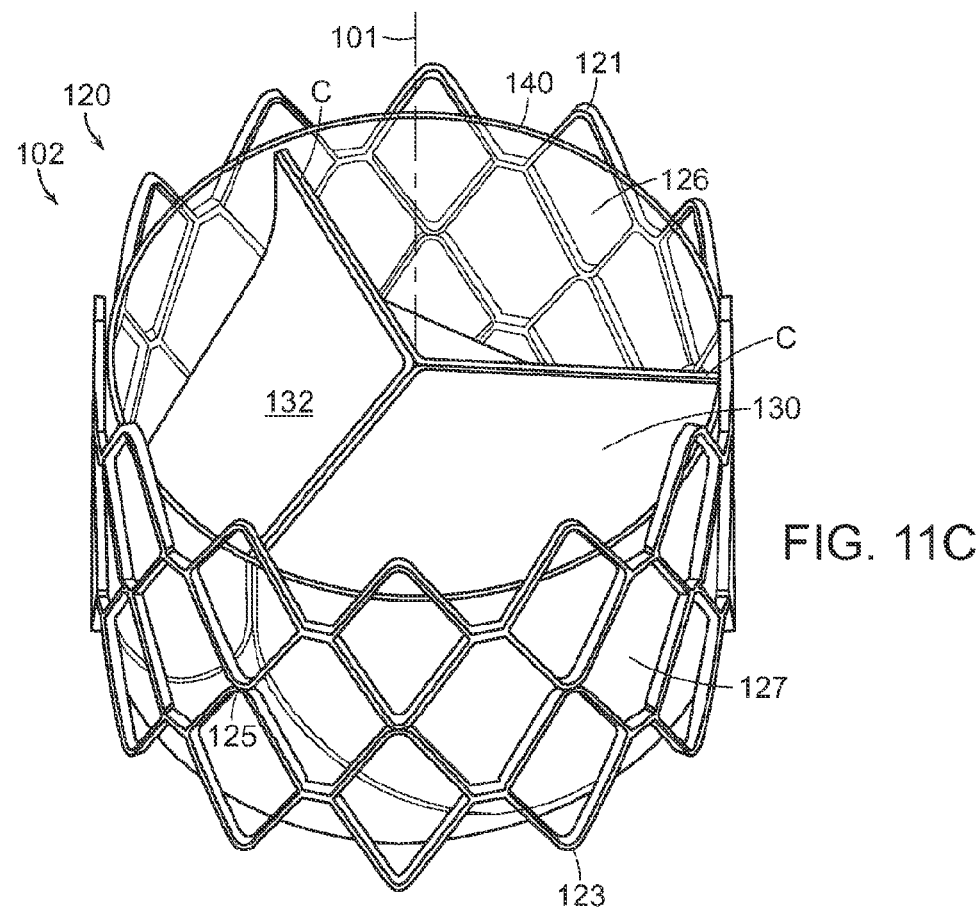
Figure 11D:
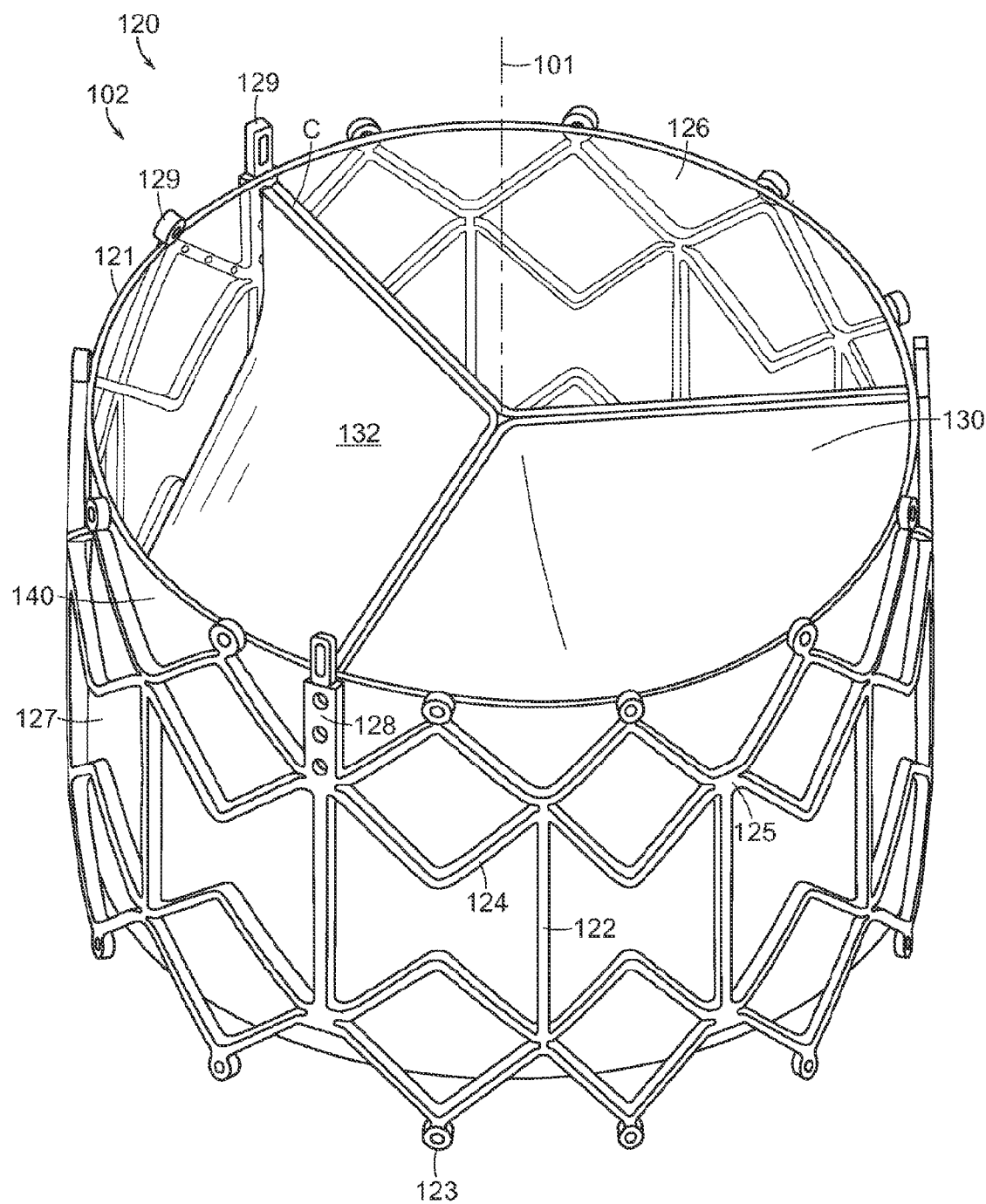
Figure 11E:
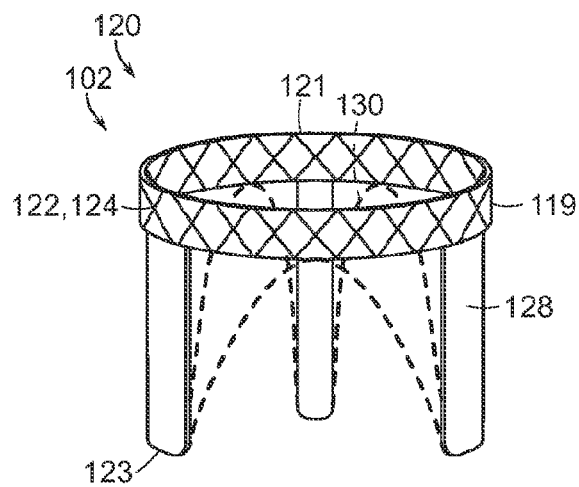
FIGS. 11E-11G are side views of a valve support having support bands and prosthetic valves mounted therein in accordance with the present technology.
Figure 11F:
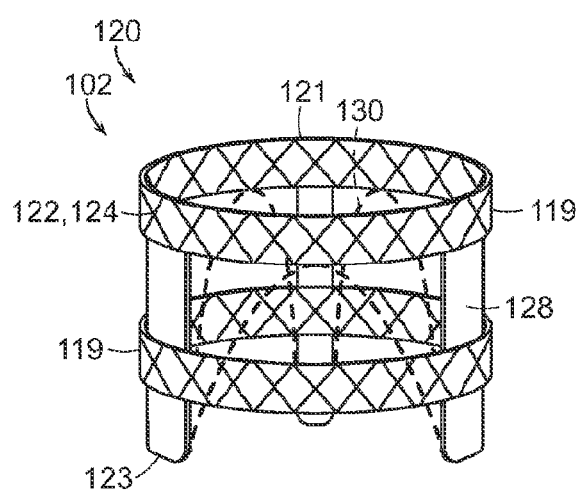
Figure 11G:
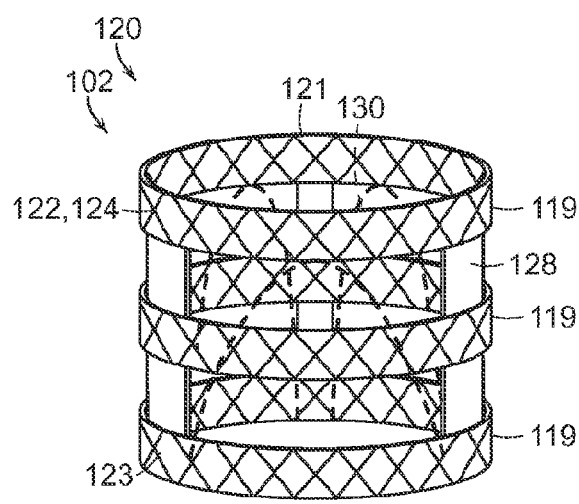
Figure 11H:
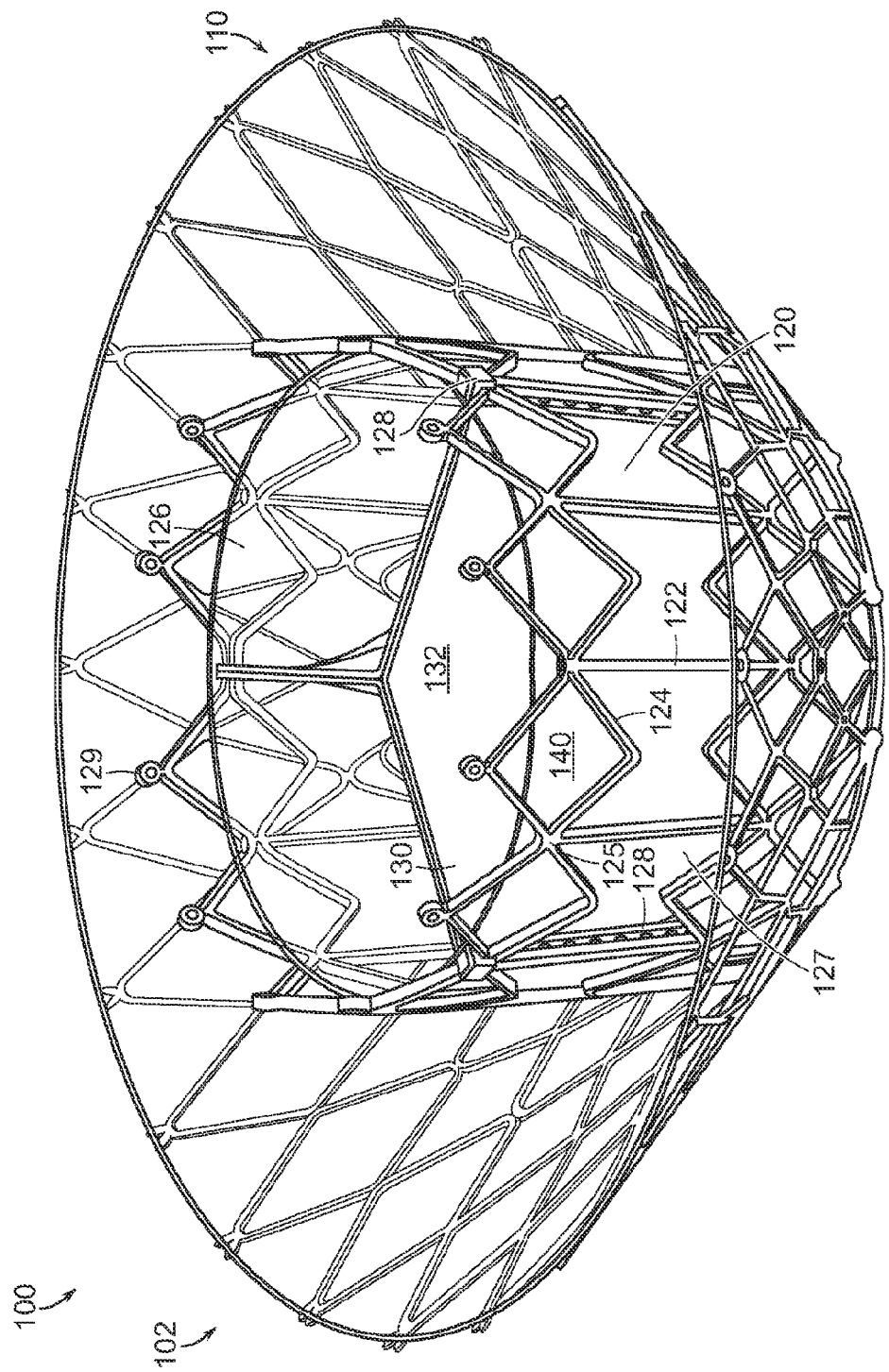
FIG. 11H shows an isometric view of a prosthetic heart valve device in accordance with another embodiment of the present technology.

FIGS. 11A-11H show several embodiments of valve supports 120 that can be used in embodiments of the prosthetic heart valve device 100 shown in FIGS. 10A-10F. FIGS. 11A-11G are side and isometric views of the valve support 120 shown in an expanded configuration 102, and FIG. 11H is an isometric view of another embodiment of a prosthetic heart valve device 100 disposed in an expanded configuration 102 in accordance with the present technology. Referring to FIGS. 10A-10F and 11A-11H together, several embodiments of the valve support 120 can be generally cylindrical having an upstream end 121 and a downstream end 123 formed around a longitudinal axis 101 with a circular, oval, elliptical, kidney-shaped, D-shaped, or other suitable cross-sectional shape configured to support a tricuspid or other prosthetic valve 130. In some embodiments, the valve support 120 includes a plurality of posts 122 connected circumferentially by a plurality of struts 124. The posts 122 and struts 124 can be arranged in a variety of geometrical patterns that can expand and provide sufficient resilience and column strength for maintaining the integrity of the prosthetic valve 130. For example, the plurality of posts 122 can extend longitudinally across multiple rows of struts 124 to provide column strength to the valve support 120. However, in other embodiments, the valve support 120 can include a metallic, polymeric, or fabric mesh or a woven construction.

Generally, the plurality of posts 122 can extend along an axial direction generally parallel to the longitudinal axis 101 and the struts 124 can extend circumferentially around and transverse to the longitudinal axis 101. The posts 122 can extend an entire longitudinal height $H_1$ of the valve support 120 (FIG. 11A), or in another embodiment, the posts 122 can include a plurality of independent and separate post segments (not shown) along the valve support height $H_1$. In one embodiment the height $H_1$ can be approximately 14 mm to about 17 mm. The struts 124 can form a series of rings around the longitudinal axis 101, wherein each ring has a circumferentially expandable geometry. In the example shown in FIGS. 11A, 11D and 11H, the struts 124 are formed in a series of zig-zags and arranged in pairs 180 degrees out of phase with each other so as to form a series of diamonds. Alternative expandable geometries can include sinusoidal patterns, chevron configurations (FIG. 11B), closed cells (FIG. 11C), open cells, or other expandable configurations. The plurality of struts 124 can attach to the plurality of posts 122 so as to define a plurality of nodes 125 where the struts and posts intersect. The plurality of struts 124 and the plurality of posts 122 can be formed from a deformable material or a resilient or shape memory material (e.g., Nitinol).

The anchoring member 110 and the valve support 120 may be made of the same or, in some embodiments, different materials. In some embodiments, both the anchoring member 110 and the valve support 120 include a resilient biocompatible metal, such as stainless steel, nickel cobalt or cobalt chromium alloys such as MP35N, or nickel titanium alloys such as Nitinol. Superelastic shape memory materials such as Nitinol can allow the device to be collapsed into a very low profile delivery configuration suitable for delivery through the vasculature via catheter, and allow self-expansion to a deployed configuration suitably sized to replace the target valve. In some embodiments, the anchoring member 110 and/or the valve support 120 can be laser cut from a single metal tube into the desired geometry, creating a tubular scaffold of interconnected struts. Anchoring member 110 may then be shaped into a desired configuration, e.g. a flared, funnel-like or hyperboloid shape, using known shape-setting techniques for such materials.

As shown in FIGS. 11B-11E, the valve support 120 has an interior surface 126 and an exterior surface 127, and the valve support 120 is configured to receive or support the prosthetic valve 130 within an interior lumen of the valve support 120 to inhibit retrograde blood flow (e.g., blood flow from the left ventricle into the left atrium). Accordingly, the valve support 120 can provide a scaffold to which prosthetic valve tissue can be secured and provide a scaffold that has sufficient axial rigidity to maintain a longitudinal position of the prosthetic valve 130 relative to the anchoring member 110. The valve support 120 can further provide such a scaffold having radial rigidity to maintain circularity (or other desired cross-sectional shape) to ensure that leaflets 132 of the prosthetic valve 130 coapt or otherwise seal when the device 100 is subject to external radial pressure. In one embodiment, the valve support 120 can have a support region 145 along the longitudinal axis 101 that is configured to attach to the prosthetic valve, or in other embodiments, be aligned with the coaptation portion of the leaflets 132 (shown in FIG. 11B).

The valve 130 may comprise a temporary or permanent valve adapted to block blood flow in the upstream direction and allow blood flow in the downstream direction through the valve support 120. The valve 130 may also be a replacement valve configured to be disposed in the valve support 120 after the device 100 is implanted at the native mitral valve. The valve 130 can have a plurality of leaflets 132, and may be formed of various flexible and impermeable materials including PTFE, Dacron®, pyrolytic carbon, or other biocompatible materials or biologic tissue such as pericardial tissue or xenograft valve tissue such as porcine heart tissue or bovine pericardium. Other aspects of valve 130 are described further below. The interior surface 126 within the lumen of the valve support 120 can be covered at least partially by an impermeable sealing member 140 to prevent blood flow from inside the valve support 120 to the outside of the valve support 120, where it could leak around the exterior of the valve support 120. In another embodiment, the sealing member 140 may be affixed to the exterior surface 127 of the valve support 120 and, in either embodiment, may be integrally formed with or attached directly to valve 130. In an additional embodiment, the sealing member 140 can be applied on at least portions of both the interior surface 126 and the exterior surface 127 of the valve support 120.

As shown in FIGS. 11B-11H, the prosthetic valve 130 can be sutured, riveted, glued, bonded, mechanically interlocked, or otherwise fastened to posts 122 or commissural attachment structures 128, which are configured to align with valve commissures C. The posts 122 or commissural attachment structures 128 can include eyelets 129, loops, or other features formed thereon to facilitate attachment of sutures or other fastening means to facilitate attachment of the prosthetic valve 130. In one embodiment, shown in FIG. 11B, the attachment structures 128 can be integrated into the structural frame of the valve support 120 such that the attachment structures 128 are distributed around the circumference of the valve support 120 and function as posts 122. In another embodiment, shown in FIG. 11D, the attachment structures 128 can be attachment pads formed on parts of the posts 122 (e.g., along an upper end of the posts 122). In the embodiments illustrated in FIGS. 11E-11G, the valve support 120 includes support bands 119 to which the attachment structures 128 are incorporated. In one embodiment, the attachment structures 128 can be integral with the support bands 119 (e.g., laser cut from a single metal tube into the desired geometry, creating one or more tubular support bands having interconnected struts with longitudinal attachment structures). In other embodiments, the support bands 119 can be separate component that are fastened to the attachment structures 128. In a further embodiment, shown in FIG. 11H, the attachment structures 128 can be separate structures that can be coupled to posts 122, struts 124 or other components along the interior surface 126 of the valve support 120.

As illustrated in FIG. 11C, the prosthetic valve 130 may also be attached to the sealing member 140 or sleeve which is attached to the interior surface 126 of the valve support 120, as described above. Once attached, the prosthetic valve 130 can be suitable to collapse or compress with the device 100 for loading into a delivery catheter (not shown). In one embodiment, the prosthetic valve 130 has a tri-leaflet configuration, although various alternative valve configurations may be used, such as a bi-leaflet configuration. The design of the prosthetic valve 130, such as the selection of tri-leaflet vs. bi-leaflet configurations, can be used to determine the suitable shape of the valve support 120. For example, for a tri-leaflet valve, the valve support 120 can have a circular cross-section, while for a bi-leaflet valve, alternative cross-sectional shapes are possible such as oval or D-shaped cross-sections. In particular examples, the valve support can have a circular cross-sectional diameter of approximately 25 mm to about 32 mm, such as 27 mm.

In some arrangements, the valve support 120 can have a permanent prosthetic valve pre-mounted therein, or the valve support 120 may be configured to receive a separate catheter-delivered valve following implantation of the device 100 at the native mitral valve. In arrangements where a permanent or replacement valve is desirable, the valve support 120 can further include a temporary valve pre-mounted within the interior lumen. If a period of time between placement of the device 100 and further implantation of the permanent prosthetic valve is desirable, a temporary valve sewn into or otherwise secured within the valve support 120 can assure regulation of blood flow in the interim. For example, temporary valves may be used for a period of about 15 minutes to several hours or up to a several days. Permanent or replacement prosthetic valves may be implanted within a temporary valve or may be implanted after the temporary valve has been removed. Examples of pre-assembled, percutaneous prosthetic valves include, e.g., the CoreValve ReValving® System from Medtronic/CorevalveInc. (Irvine, Calif., USA), or the Edwards-Sapien® valve from Edwards Lifesciences (Irvine, Calif., USA). If adapted to receive a separate catheter-delivered valve, the valve support 120 may have features within its interior lumen or on its upper or lower ends to engage and retain the catheter-delivered valve therein, such as inwardly extending ridges, bumps, prongs, or flaps. Additional details and embodiments regarding the structure, delivery and attachment of prosthetic valves, temporary valves and replacement valves suitable for use with the prosthetic heart valve devices disclosed herein can be found in International PCT Patent Application No. PCT/US2012/043636, entitled "PROSTHETIC HEART VALVE DEVICES AND ASSOCIATED SYSTEMS AND METHODS," filed Jun. 21, 2012, the entire contents of which are incorporated herein by reference.

In some arrangements, the anchoring member 110 is defined by a structure separate from the valve support 120. For example, the anchoring member 110 can be a first or outer frame or skeleton and the valve support 120 can be a second or inner frame or skeleton. As such, the anchoring member 110 can at least partially surround the valve support 120. In some embodiments, the downstream portion 111 of the anchoring member 110 can be coupled to the valve support 120 while the upstream portion 112 is not connected or coupled to the valve support 120 in a manner that unduly influences the shape of the valve support 120. For example, in some embodiments, the upstream portion 112 of the anchoring member 110 can be configured to engage and deform to the shape of the native tissue on or under the annulus while the cross-sectional shape of the valve support 120 remains sufficiently stable. For example, the valve support 120 (e.g., at least at the upstream end 121) can be spaced radially inward from the upstream portion 112 of the anchoring member 110 such that if the anchoring member 110 is deformed inwardly, at least the upstream end 121 of the valve support 120 remains substantially undeformed. As used herein, "substantially undeformed" can refer to situations in which the valve support 120 is not engaged or deformed, or can refer to scenarios in which the valve support 120 can deform slightly but the prosthetic valve 130 remains intact and competent (e.g., the leaflets 132 coapt sufficiently to prevent retrograde blood flow). In such arrangements, leaflets 132 of the prosthetic valve 130 can close sufficiently even when the device 100 is under systolic pressures or forces from the pumping action of the heart.

The longitudinal ribs 114 and/or circumferential connectors 116 can be less rigid than the posts 122 and/or struts 124 of the valve support 120, allowing greater flexibility in the anchoring member 110 and/or more stability to the shape and position of the valve support 120. In some embodiments, the flexibility of the anchoring member 110 can allow the anchoring member 110 to absorb distorting forces as well as allow the device 100 to conform to the irregular, non-circular shape of the native annulus (while leaving the valve support 120 substantially unaffected), encouraging tissue ingrowth and creating a seal to prevent leaks between the device 100 and the native tissue. In addition, the longitudinal ribs 114 and/or connectors 116 can be configured to press radially outward against the native valve, ventricular and/or aortic structures so as to anchor the device 100 in a desired position, as well as maintain an upstream deployed circumference 150' larger than that of the native annulus such that subannular positioning effectively prevents upstream migration of the device 100 (described further below in FIG. 14C). Furthermore, the longitudinal ribs 114 can have sufficient resilience and column strength (e.g., axial stiffness) to prevent longitudinal collapse or eversion of the anchoring member 110 and/or the device 100 and to resist movement of the device in an upstream direction.

By structurally separating the anchoring member 110 from the valve support 120, the valve 130 and valve support 120 are effectively mechanically isolated from the distorting forces exerted on the anchoring member 110 by the native tissue, e.g., radially compressive forces exerted by the native annulus and/or leaflets, longitudinal diastolic and systolic forces, hoop stress, etc. For example, deformation of the anchoring member 110 by the native tissue can change a cross-section of the anchoring member 110 (e.g., to a non-circular or non-symmetrical cross-section), while the valve support 120 may be substantially undeformed. In one embodiment, at least a portion of the valve support 120 can be deformed by the radially compressive forces, for example, where the anchoring member 110 is coupled to the valve support 120 (e.g., the downstream end 123). However, the upstream end 121 of the valve support 120 and/or the valve support region 145 (FIG. 11B) is mechanically isolated from the anchoring member 110 and the compressive forces such that at least the valve support region 145 can be substantially undeformed. Thus the valve support 120, and at least the valve support region 145, can maintain a circular or other desirable cross-section so that the valve remains stable and/or competent. The flexibility of the longitudinal ribs 114 can contribute to the absorption of the distorting forces, and also aid in mechanically isolating the valve support 120 and valve 130 from the anchoring member 110.

At an upstream end of the device 100 oriented toward the left atrium, the valve support 120 can be configured to sit below, even with, or above the uppermost terminal of the upstream portion 112 of the anchoring member 110. At a downstream end of the device 100 oriented toward and residing within the left ventricle, the anchoring member 110 can be coupled to the valve support 120. Alternatively, the anchoring member 110 can be coupled to the valve support 120 anywhere along a length of the valve support 120. The valve support 120 and anchoring member 110 may be coupled by a variety of methods known in the art, e.g., suturing, soldering, welding, staples, rivets or other fasteners, mechanical interlocking, friction, interference fit, or any combination thereof. In other embodiments, the valve support 120 and the anchoring member 110 can be integrally formed with one another. In yet another embodiment, a sleeve or other overlaying structure (not shown) may be attached to both the anchoring member 110 and the valve support 120 to interconnect the two structures.

Figure 12C:
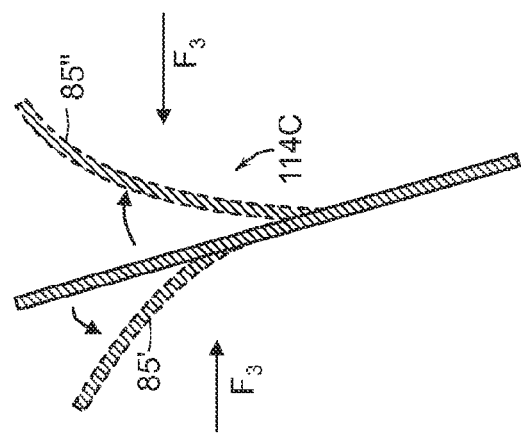
FIGS. 12A-12C are side views of various longitudinal ribs flexing in response to a distorting force in accordance with further embodiments of the present technology.
Figure 12B:
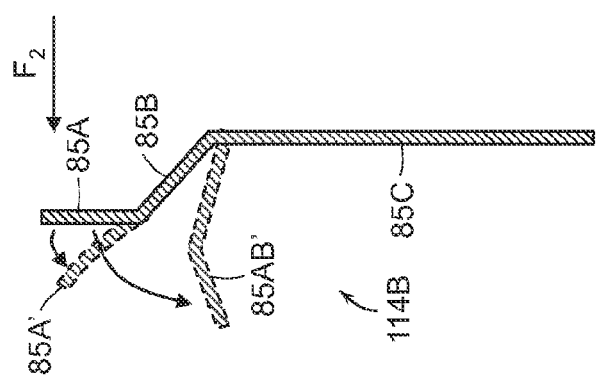
Figure 12A:
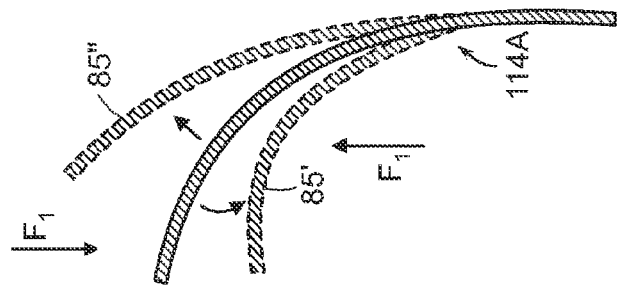

FIGS. 12A-12C are side views of various longitudinal ribs 114 flexing in response to a distorting force F in accordance with further embodiments of the present technology. The degree of flexibility of individual longitudinal ribs 114 (and thus the anchoring member 110) may be consistent among all ribs of an anchoring member 110, or, alternatively, some ribs 114 may be more flexible than other ribs 114 within the same anchoring member 110. Likewise, a degree of flexibility of individual ribs 114 may be consistent throughout an entire length of the rib 114 or the degree of flexibility can vary along the length of each rib 114.

As shown FIGS. 12A-12C, the longitudinal ribs 114 (shown individually as 114A-114C) may flex along their respective lengths in response to distorting forces F that can be applied by the surrounding tissue during or after implantation of the device 100. In FIG. 12A, the rib 114A may flex downward to a position 75' or upward to a position 75" in response to an upward or downward force $F_1$, respectively. Similarly, in FIG. 12B, a rib 114B with multiple distinct segments 85A, 85B, 85C may flex and/or rotate inwardly/outwardly or side-to-side in response to a laterally-directed force $F_2$. The distinct segment 85A at the end of the rib 114B may flex and/or rotate inwardly/outwardly or side-to-side (e.g., to position 85A') in response to the laterally directed force $F_2$ separate from lower distinct segments 85B and 85C. In other arrangements, the segment 85A may flex and/or rotate (e.g., to position 85AB') with the distinct segment 85B or with both segments 85B and 85C together (not shown). As shown in FIG. 12C, the rib 114C having a generally linear shape when in a relaxed state, may also flex and/or rotate inwardly/outwardly or side-to-side (e.g., to positions 95' or 95") in response to a laterally-directed force $F_3$, by bending to create a curved shape, or in another embodiment not shown, by bending so as to create two substantially linear segments.

Figure 13A:
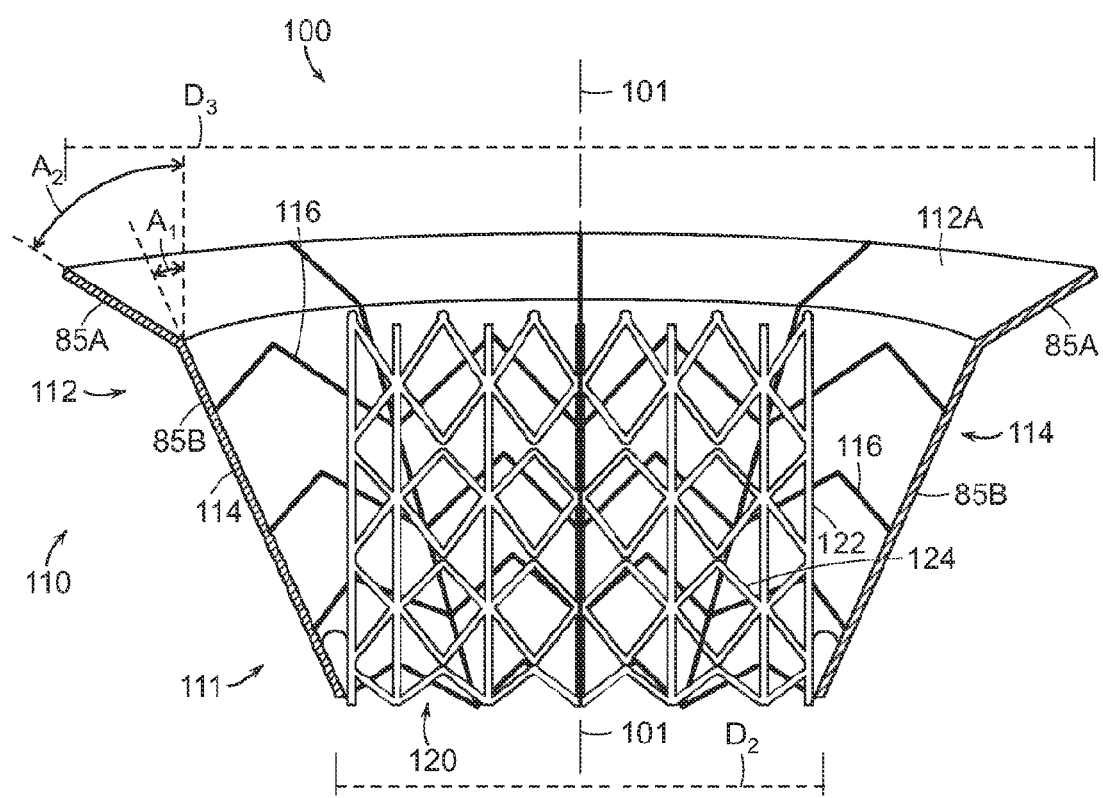
FIG. 13A is a schematic, cross-sectional view of a prosthetic heart valve device in accordance with another embodiment of the present technology.
Figure 13F:
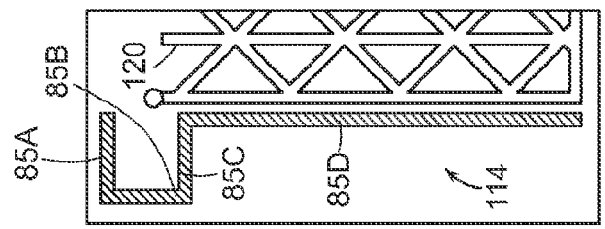
FIGS. 13B-13F are partial side views of prosthetic heart valve devices illustrating a variety of longitudinal rib configurations in accordance with additional embodiments of the present technology.

Individual ribs 114 can also have a variety of shapes and be placed in a variety of positions around a circumference of the anchoring member 110. In some embodiments, the device 100 can include a first and second plurality of ribs wherein the first plurality of ribs have a characteristic different than the second plurality of ribs. Various characteristics could include size of the rib, rib shape, rib stiffness, extension angle and the number of ribs within a given area of the anchoring member. In other embodiments, the longitudinal ribs can be unevenly or evenly spaced around an outer perimeter of the anchoring member, The ribs 114 can be positioned around a circumference oriented along the longitudinal axis 101 of the anchoring member 110 to create any number of overall cross-sectional geometries for the anchoring member 110, e.g., circular, D-shaped, oval, kidney, irregular, etc. FIG. 13A is a schematic, cross-sectional view of a prosthetic heart valve device in accordance with another embodiment of the present technology, and FIGS. 13B-13F are partial side views of prosthetic heart valve devices illustrating a variety of longitudinal rib configurations in accordance with additional embodiments of the present technology. Referring to FIG. 13A, an individual rib 114 can comprise a plurality of linear segments, such as segments 85A and 85B. In the illustrated example, the rib segment 85B is angled radially outwardly (e.g., angled away from the longitudinal axis 101) by a first angle $A_1$. The rib segment 85B extends in an upstream direction from its point of attachment to the valve support 120 at the downstream end of the segment 85B, thereby giving the anchoring member 110 a conical or flared shape, with a larger diameter $D_2$ at the upstream portion 112 and a smaller diameter $D_3$ at the downstream portion 111 of the anchoring member 110. In one embodiment, the upper rib segment 85A can be angled at a steeper second angle $A_2$ relative to the longitudinal axis 101 than lower rib segment 85B, resulting in a wider flared upstream portion 112A at the upstream portion 112 of the anchoring member 110. In some arrangements, the wider flared upstream portion 112A may enhance sealing between the anchoring member 110 and the native tissue, while the downstream portion 111 can provide a more rigid geometry for resisting upstream movement of the device 100 when systolic forces are exerted on the device 100. Alternatively, the rib 114 can be arcuate over all or a portion of its length, as shown in the partial side view of FIG. 13B.

Figure 13E:
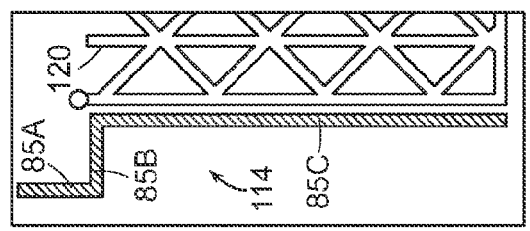
Figure 13D:
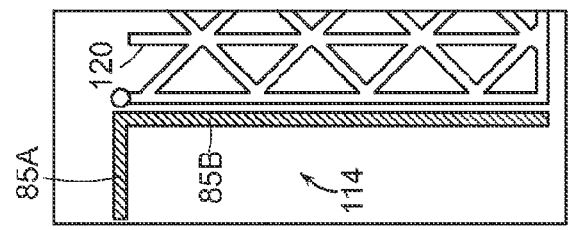
Figure 13C:
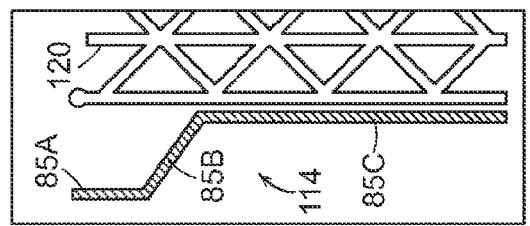
Figure 13B:
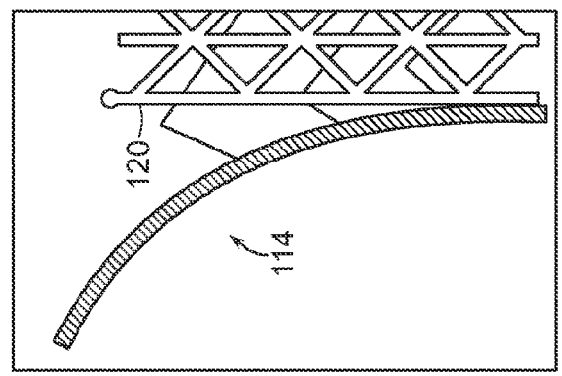

In yet other embodiments, as illustrated by FIGS. 13C-13F, the rib 114 can have a more complex shape defined by multiple distinct segments 85A, 85B, 85C, etc. For example, as shown in FIG. 13C, the rib 114 includes a linear rib segment 85C generally parallel to the longitudinal axis 101 connected at its upstream end to a linear and radially outwardly extending rib segment 85B, where rib segment 85B is connected at its upstream end to a more vertical rib segment 85A which is about parallel with the longitudinal axis 101. Referring to FIG. 13D, the rib 114 can include a linear rib segment 85B generally parallel to longitudinal axis 101 and connected at its upstream end to a linear and radially outwardly extending rib segment 85A, which is generally perpendicular to longitudinal axis 101. Referring to FIG. 13E, the rib 114 can include a linear rib segment 85C generally parallel to the longitudinal axis 101 and connected at its upstream end to a linear and radially outwardly extending rib segment 85B which is generally perpendicular to the longitudinal axis 101. The rib segment 85B can further be connected at its most radially outward end to a vertical rib segment 85C generally parallel with the longitudinal axis 101. In reference to FIG. 13F, the rib 114 includes a linear segment 85D generally parallel with the longitudinal axis 101 and connected at its upstream end to a radially outwardly extending segment 85C which is generally perpendicular to the longitudinal axis 101. The rib segment 85C can further be connected at its most radially outward end to a linear, vertical segment 85B generally parallel with the longitudinal axis 101, and where 85B is connected at its most radially outward end to a linear and radially inward extending segment 85A.

In the embodiments illustrated in FIGS. 13C-13F, the ribs 114 can be coupled to the valve support 120 (e.g., coupled to posts 122) in a manner to enhance mechanical isolation of the valve support 120. For example, the ribs 114 may be attached to the valve support 120 near the downstream end of the ribs 114 such that a substantial portion of each rib 114 upstream of the attachment point is movable and deformable relative to the valve support 120, thereby allowing the rib 120 to flex radially outward or circumferentially back and forth relative to the valve support 120. Additionally, one of ordinary skill in the art will recognize that in any of the embodiments illustrated in FIGS. 13A-13F, any or all of the rib segments may have a curvature, and any interconnections of segments shown as angled may instead be curved. Accordingly, any of these various geometries may be configured to allow the anchoring member 110 to conform to the native anatomy, resist migration of the device 100, and mechanically isolate the valve support 120 and/or the prosthetic valve 130 contained therein from forces exerted on the anchoring member 110 by the native tissue.

Figure 14A:
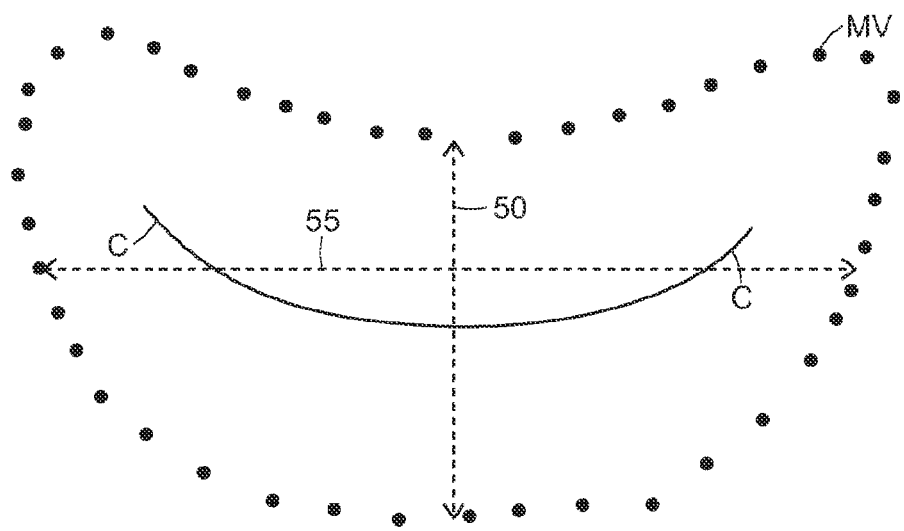
FIG. 14A is a schematic top view of a native mitral valve illustrating the major and minor axes.

The flexible characteristics of the individual ribs 114 can allow for the flexibility and conformability of the anchoring member 110 to engage and seal the device 100 against uneven and uniquely-shaped native tissue. Additionally, the flexibility can assist in creating a seal between the device 100 and the surrounding anatomy. FIG. 14A is a schematic top view of a native mitral valve MV illustrating the minor axis 50 and major axis 55, and FIGS. 14B-14C are schematic top views of an anchoring member 110 in an expanded configuration 102 and in a deployed configuration 104, respectively, overlaying the schematic of the native mitral valve MV in accordance with an embodiment of the present technology.

Figure 14B:
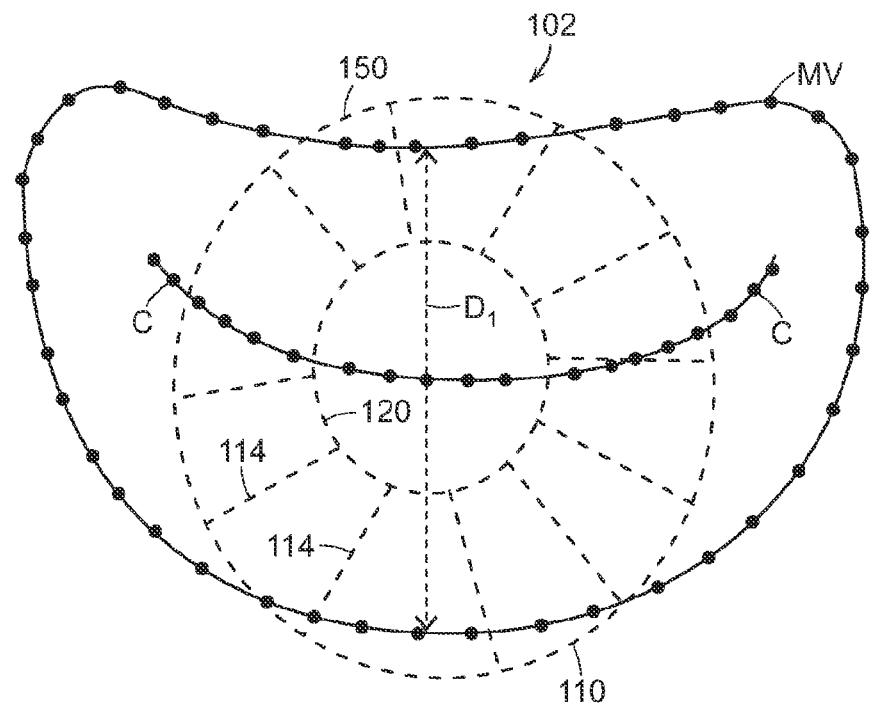
FIGS. 14B-14C are schematic top views of an anchoring member in an expanded configuration and in a deployed configuration, respectively, in accordance with an embodiment of the present technology.

Referring to FIG. 14B, the upstream portion 112 (FIG. 10A) of the anchoring member 110 can have an outer circumference 150 with a diameter $D_1$ that is greater than the minor axis 50 (FIG. 14A) of the native annulus, and usually less than the major axis 55 of the annulus, when the anchoring member 110 is in an expanded configuration 102 (shown as dashed lines). In other embodiments, the anchoring member 110 may have a diameter $D_1$ at least as large as the distance between the native commissures C, and may be as large as or even larger than the major axis 55 of the native annulus. In some embodiments, the outer circumference 150 of the anchoring member 110 has the diameter $D_1$ which is approximately 1.2 to 1.5 times the diameter (not shown) of the valve support 120 (or the prosthetic valve 130), and can be as large as 2.5 times the diameter of the valve support 120 (or the prosthetic valve 130). While conventional valves must be manufactured in multiple sizes to treat diseased valves of various sizes, the valve support 120 and the prosthetic valve 130, in accordance with aspects of the present technology, may be manufactured in just a single diameter to fit a multitude of native valve sizes. For example, the valve support 120 and the prosthetic valve 130 do not need to engage and fit the native anatomy precisely. In a specific example, the valve support 120 may have a diameter (not shown) in the range of about 25 mm to about 32 mm for adult human patients. Also in accordance with aspects of the present technology, the anchoring member 110 may be provided in multiple diameters to fit various native valve sizes, and may range in diameter at an upstream end from about 28 mm to about 80 mm, or in other embodiments, greater than 80 mm.

Figure 14C:
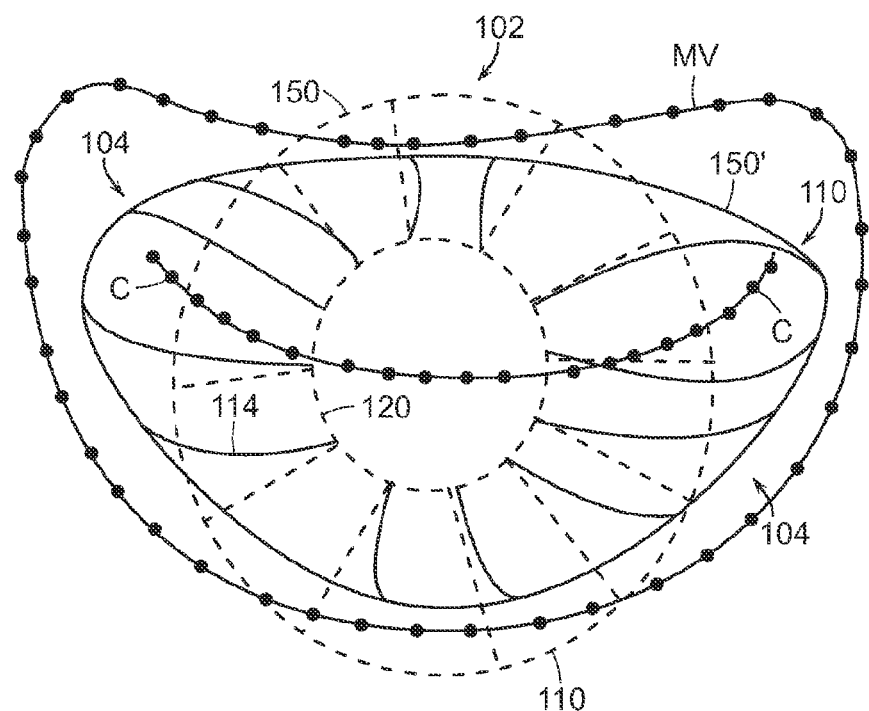

The top view of the anchoring member 110 shown in FIG. 14C illustrates how flexibility and/or deformation of one or more longitudinal ribs 114 and/or rib segments allows the anchoring member 110 to distort relative to the expanded configuration 102, as shown by the dashed lines, into a deployed configuration 104, as shown by the bolded lines. As shown in FIG. 14C, the anchoring member 110, when deployed or implanted at or under the mitral valve annulus, can conform to the highly variable native mitral valve tissue shape MV, as shown in the dotted lines, while the ribs 114 bend, twist, and stretch such that the overall shape of the anchoring member 110 has a deployed (e.g., a generally more oval or D-shaped, or other irregular shape) configuration 104 instead of a fully expanded configuration 102. Referring to FIGS. 14B-14C together, the anchoring member 110 covers the mitral valve commissures C in the deployed configuration 104, whereas the commissures C would be left unsealed or exposed in the more circular expanded configuration 102, potentially allowing paravalvular leaks. The anchoring member 110 could also be pre-shaped to be in a generally oval or D-shape, or other shape, when in an unbiased condition.

Figure 15:
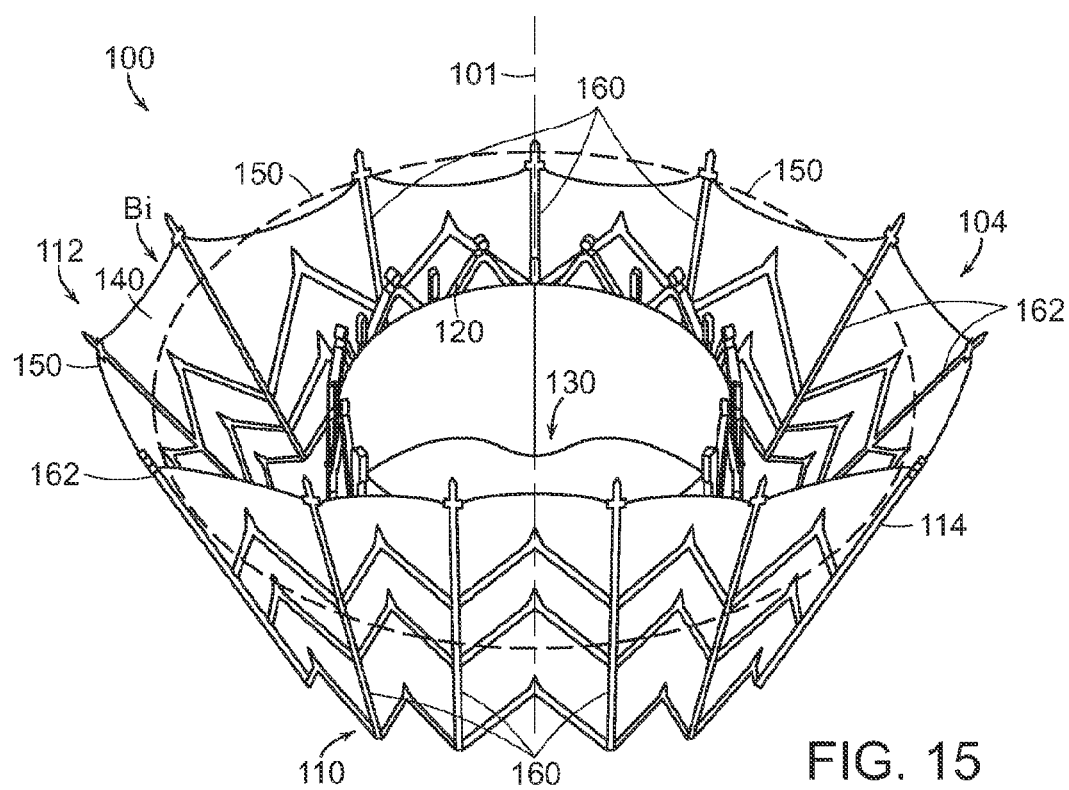
FIG. 15 is an isometric view of a prosthetic heart valve device illustrated in a deployed configuration in accordance with an additional embodiment of the present technology.

FIG. 15 is an isometric view of an embodiment of the prosthetic heart valve device 100 illustrated in a deployed configuration 104 in accordance with an embodiment of the present technology. FIG. 15 illustrates the device 100 having a plurality of ribs 114, wherein a first set of ribs 160 can be configured to bend inwards or compress toward the center longitudinal axis 101 of the device 100 and a second set of ribs 162 can be configured to bend outwards or flex in response to an distorting forces present in a subannular space of the native valve. As a result, the outer circumference 150 of the anchoring member 110 may distort from a more circular shape in the expanded configuration 102, as shown by the dashed line, to a generally more oval or D-shape in the expanded configuration 104, as shown by the solid line, thus conforming to the shape of the native anatomy. In a further arrangement, the upstream portion 112 of the anchoring member 110 may be sized slightly larger than the subannular space into which it is deployed, such that the anchoring member 110 is compressed to a slightly smaller diameter in its deployed configuration 104. This may cause a slight relaxation of the sealing member 142, such that sealing member sections between adjacent ribs 114 are sufficiently slack to billow or curve inwards or outwards to form a slack section Bi, as shown in FIG. 15. Such billowing can be desirable in some arrangements because the curvature of the relaxed sleeve segment Bi can engage and conform to the mitral leaflet tissue, thereby enhancing a seal formed between the device 100 and the native tissue.

As shown in FIG. 15, the unbiased, expanded configuration of the valve support 120, which in the illustrated embodiment is circular in cross-section, remains substantially unaffected while the anchoring member 110 conforms to the non-circular shape of the native mitral valve annulus MV. Accordingly, the valve support 120 is mechanically isolated from these forces and maintains its structural shape and integrity. The mechanical isolation of the valve support 120 from the anchoring member 110 may be attributed to several aspects of the prosthetic heart valve device 100. For example, the relative high flexibility of the anchoring member 110 compared with the lower flexibility of the valve support 120 allows the anchoring member 110 to deform significantly when deployed and when in operation (e.g., conform to the shape and motion of the anatomy under ventricular systole forces) while the valve support 120 remains substantially undeformed (e.g., generally circular) in these same conditions. Additionally, radial spacing between the anchoring member 110 and the valve support 120, particularly at the upstream portion/upstream end where the anchoring member 110 engages the native annulus and/or subannular tissue, allows the anchoring member 110 to be deformed inwardly a substantial amount without engaging the valve support 110. Further, the anchoring member 110 can be coupled to the valve support 120 at a location (e.g. the downstream portion 111 of the anchoring member 110) which is spaced apart longitudinally a substantial distance from the location (e.g., the upstream portion 112 of the anchoring member 110) at which the anchoring member 110 engages the native annulus, allowing the ribs 114 of the anchoring member 110 to absorb much of the distorting forces exerted upon it rather than transmitting those forces directly to the valve support 120. Moreover, the coupling mechanisms employed to attach the anchoring member 110 to the valve support 120 can be configured (e.g., to be flexible or moveable) so as to reduce the transmission of forces from the anchoring member 110 to the valve support 120 (discussed in more detail herein).

In many embodiments, the anchoring member 110 can have sufficient flexibility such that the anchoring member 110 conforms to the native mitral annulus when in the deployed configuration 104 (FIGS. 14C and 15); however, the anchoring member 110 can be configured to remain biased towards its expanded configuration 102 (e.g., FIGS. 10A and 14B) such that, when in the deployed configuration 104, the anchoring member 110 pushes radially outwards against the native annulus, leaflets, and/or ventricular walls just below the annulus. In some arrangements, the radial force generated by the biased anchoring member shape may be sufficient to deform the native anatomy such that the minor axis 50 (FIG. 14A) of the native valve is increased slightly, and/or the shape of the annulus is otherwise altered. Such radial force can enhance anchoring of the device 100 to resist movement toward the atrium when the valve 130 is closed during ventricular systole as well as movement toward the ventricle when the valve 130 is open. Furthermore, the resulting compression fit between the anchoring member 110 and leaflets and/or ventricular walls or other structures helps create a long-term bond between the tissue and the device 100 by encouraging tissue ingrowth and encapsulation.

Figure 16A:
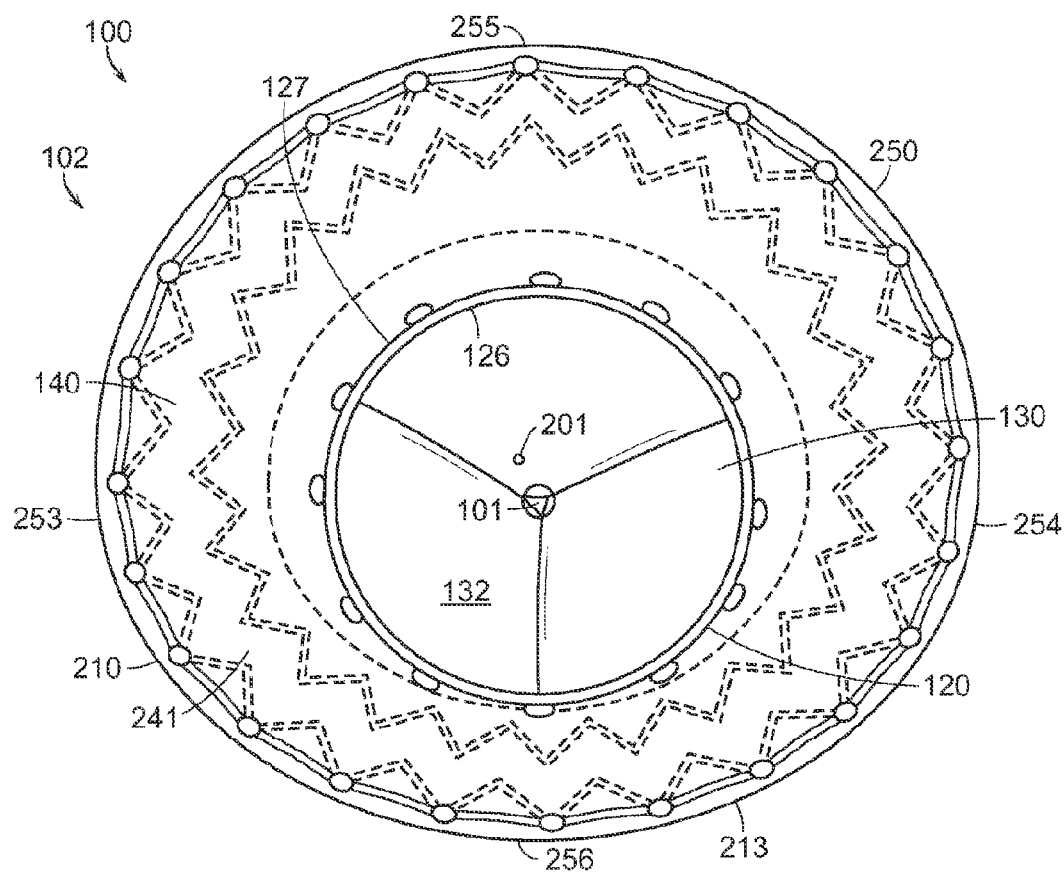
FIG. 16A is a top view of a prosthetic heart valve device illustrated in an expanded configuration in accordance with a further embodiment of the present technology.

FIGS. 16A-17C illustrate a prosthetic heart valve device 100 configured in accordance with additional embodiments of the present disclosure. FIGS. 16A-16C include a top view and first and second side views of a prosthetic heart valve device 100 illustrated in an expanded configuration 102 that includes features generally similar to the features of the prosthetic heart valve device 100 described above with reference FIGS. 10A-15. For example, the device 100 includes the valve support 120 and the prosthetic valve 130 housed within an interior lumen of the valve support 120. However, in the embodiment shown in FIGS. 16A-16C, the device 100 includes an anchoring member 210 having an oval or D-shaped upstream perimeter 213 and a plurality of elevations around a circumference 250 of the anchoring member 210 such that the anchoring member 210 is suitable for engaging and conforming with tissue in the subannular region of the mitral valve.

Figure 16B:
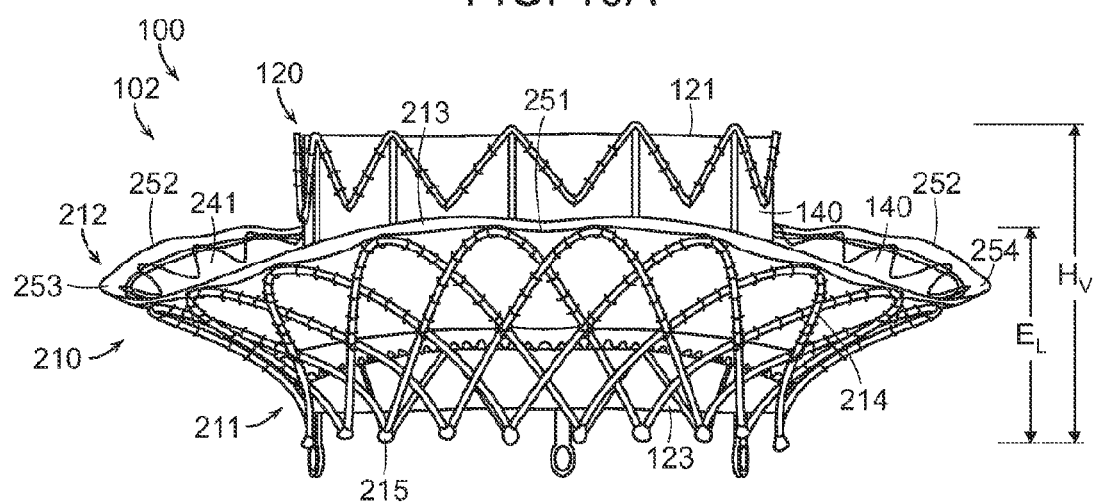
FIGS. 16B-16C are a first side view and a second side view, respectively, of the prosthetic heart valve device of FIG. 16A.
Figure 16C:
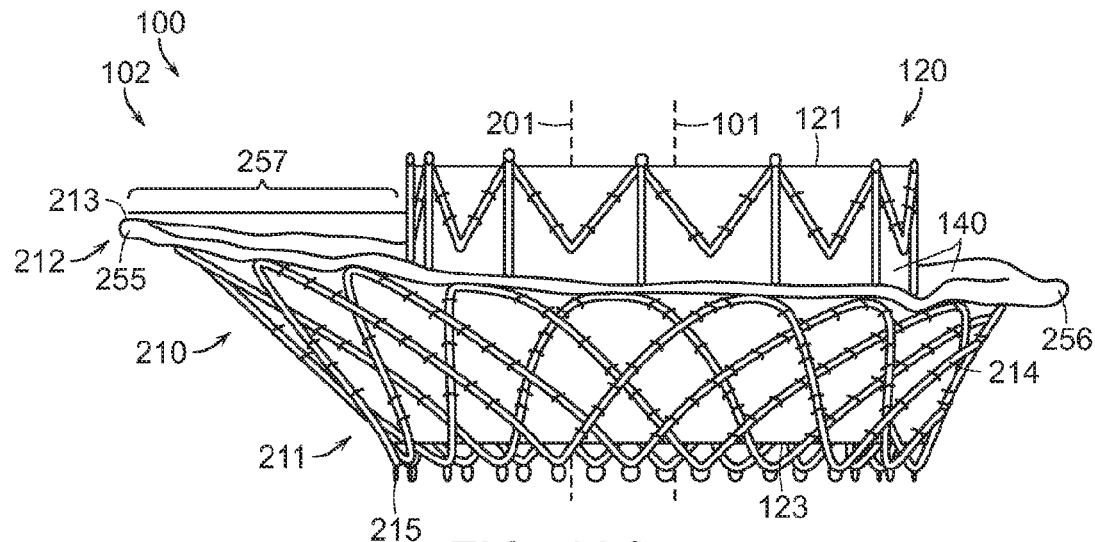

Referring to FIGS. 16A-16C together, the device 100 can include the flexible anchoring member 210 at least partially surrounding and coupled to the valve support 120 at a downstream portion 211 of the anchoring member 210. The device 100 can also include one or more sealing members 140 extending around an inner wall 241 of the anchoring member 210 and/or around the exterior surface 127 or the interior surface 126 of the valve support 120 to prevent paravalvular leaks between the device 100 and the native tissue and/or between the anchoring member 210 and the valve support 120. In one embodiment, the sealing member 140 can wrap around and/or cover the upstream perimeter 213 of the anchoring member 210. For example, the sealing member 140 can be sewn, sutured, or adhered to a wall 241, 242 and have an extended portion (not shown) that folds over the upstream perimeter 213. In one embodiment, the sealing member 140 can be adhered to an opposite wall (e.g., extend from the inner wall 241 to cover the upstream perimeter 213 and attached to an upper portion of the outer wall 242). However, in other embodiments, the sealing member 140 can have a longer free edge (not shown) left unattached. The free edge of the sealing member 140 can be suitable in some arrangements to inhibit blood flow between the upper perimeter 213 and the native tissue.

As illustrated in FIGS. 16B-16C, the anchoring member 210 has the downstream portion 211 and an upstream portion 212 opposite the downstream portion 111 along a longitudinal axis 201 of the device 100. Similar to the anchoring member 110 of device 100 (FIG. 10A), the upstream portion 212 of the anchoring member 210 can be a generally outward oriented portion of the device 100. In some embodiments, the anchoring member 110 can include of a series of circumferentially positioned, resiliently deformable and flexible ribs 214 which can be in a crisscross pattern around the circumference 250 of the anchoring member 210 to form a diamond pattern. In one embodiment, the ribs 214 can be flexible wires or filaments arranged in a diamond pattern or configuration. The diamond configuration, in some embodiments, provides hoop strength sufficient to provide a frictional attachment to the native annulus and leaflet tissue to inhibit movement of the device 100 relative the annulus under the force of systolic blood pressure against the valve 130 mounted in the valve support 120. In a particular example, the anchoring member 120 can be formed of a preshaped Nitinol tube having, for example, a wall thickness of approximately 0.010 inches to about 0.030 inches. The diamond pattern or configuration can, for example, include one or more rows of diamonds, and in some embodiments, between approximately 12 and approximately 36 columns of diamonds around the circumference 250 of the anchoring member 210.

In some embodiments, the upstream perimeter 213 of the anchoring member 210 does not lie in a single plane. For example, the ribs 214 can have variable lengths and/or be off-set from each other at variable angles such that a distance (e.g., elevation) between a downstream perimeter 215 and the upstream perimeter 213 can vary around the circumference 250. For example, the upstream perimeter 213 can form a rim having a plurality of peaks 251 and valleys 252 (FIG. 16B) for adapting to the shape of the native mitral valve (see FIG. 5C). As used herein, "peaks" and "valleys" do not refer to diamond peaks and diamond valleys of a diamond pattern formed by the plurality of ribs 214, but refers to portions of the upstream perimeter 213 having an undulating shape formed by changes in elevation with respect to the downstream perimeter 215. In one embodiment, the distance between the downstream perimeter 215 and the upstream perimeter (e.g., elevation) can vary from about 6 mm to about 20 mm, and in another embodiment, between about 9 mm and about 12 mm.

In one embodiment, the upstream perimeter 213 of the anchoring member 210 can have two peaks 251 that are separated by two valleys 252. In some embodiments, a first peak can have a different shape or elevation than that of a second peak. In other embodiments, the shape of a valley 252 can be different than a shape of an inverted peak 251. Accordingly, the peaks 251 and valleys 252 can be asymmetrically positioned and shaped around the circumference 250 of the anchoring member 210. In various arrangements, the valleys 252 can be configured for positioning along commissural regions of the native annulus, and the peaks 251 can be configured for positioning along leaflet regions of the native annulus. In one embodiment, the peaks 251 can have apices configured to be positioned near midpoint regions of the leaflets. The anchoring member might also be circumferentially symmetric when in the unconstrained position, but form the aforementioned "peaks and valleys" when deployed in a non-circular annulus, so that the more radially expanded portions, typically corresponding to the commissures, are lower than the less expanded areas, near the centers of the leaflets. Such an effect might be facilitated by the specific geometry of the ribs and diamond patterns of the anchoring member.

Figure 17A:
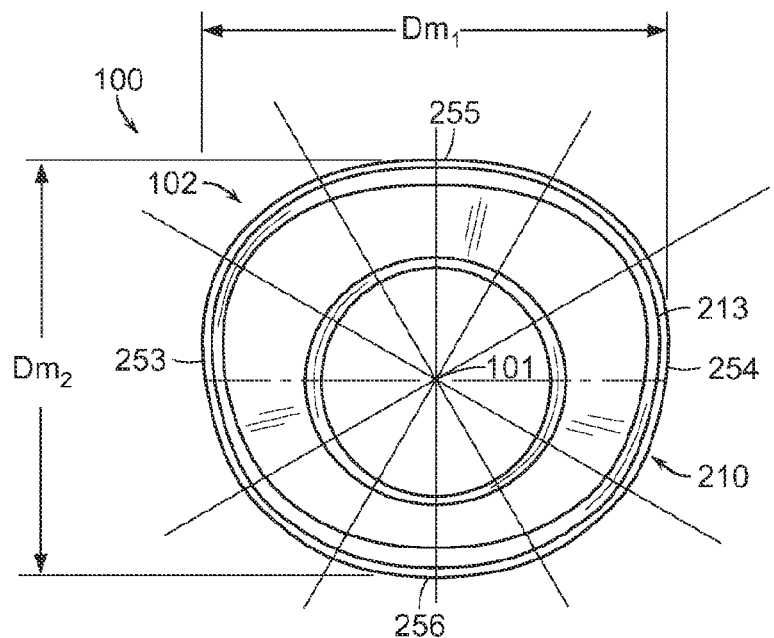
FIGS. 17A-17C are schematic top and first and second side views of the prosthetic heart valve device of FIG. 16A showing dimensions and taper angles of various aspects of the device in accordance with embodiments of the present technology.
Figure 17B:
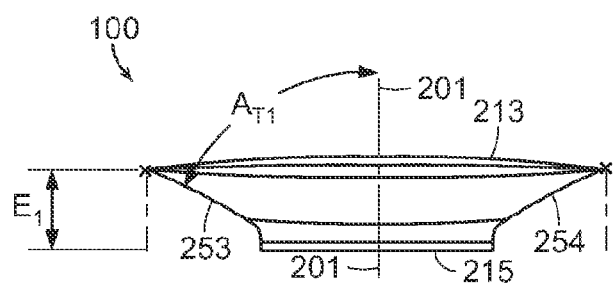
Figure 17C:
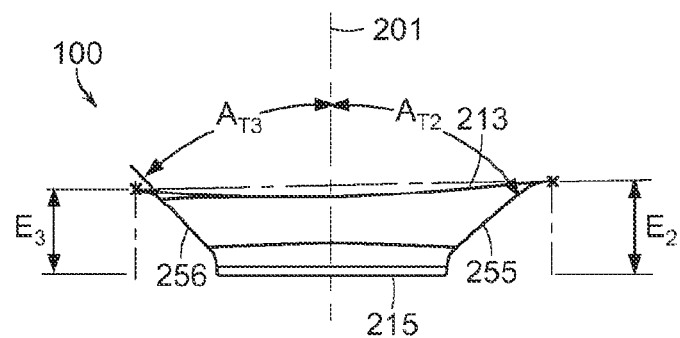

Referring to FIGS. 17A-17C, one specific example of the anchoring member 210 can have a first elevation $E_1$ between the downstream perimeter 215 and the upstream perimeter 213 of approximately 7 mm to about 8 mm at first and second regions 253, 254 of the anchoring member. The first and second regions 253, 254 are configured to align with the first and second commissures (e.g., anterolateral commissure AC and posteromedial commissure PC, FIG. 5A) of the native mitral valve. The anchoring member 210 can also have a second elevation $E_2$ between the downstream perimeter 215 and the upstream perimeter 213 of approximately 9 mm to about 11 mm at a third region 255 of the anchoring member 210, wherein the third region 255 is configured to align with an anterior leaflet AL (FIG. 5A) of the native mitral valve. The anchoring member 210 can further have a third elevation $E_3$ between the downstream perimeter 215 and the upstream perimeter 213 of approximately 12 mm to about 13 mm at a fourth region 256 of the anchoring member 210 opposite the third region 255, wherein the fourth region 256 is configured to align with a posterior leaflet PL (FIG. 5A) of the native mitral valve. One of ordinary skill in the art will recognize that the elevations $E_1$, $E_2$ and $E_3$ can have other measurements, and in some embodiments, the elevations $E_1$, $E_2$ and $E_3$ can be different from one another or the same.

Figure 16D:
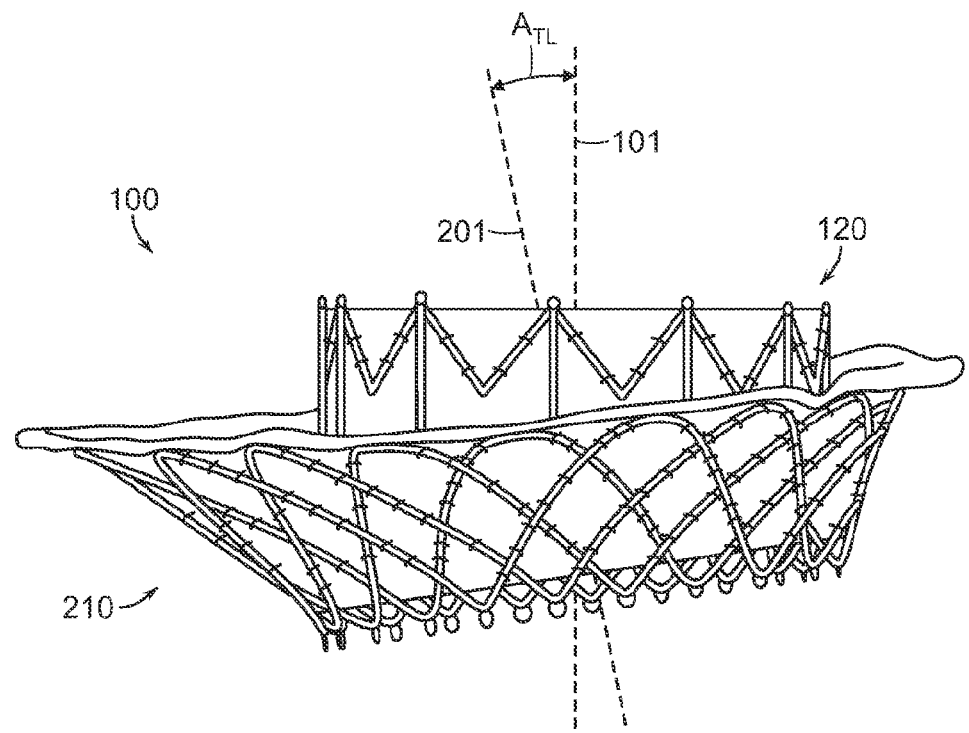
FIG. 16D is a side view of a prosthetic heart valve device showing the longitudinal axis of the anchoring member off-set from the longitudinal axis of the valve support by a tilt angle in accordance with another embodiment of the present technology.
Figure 16E:
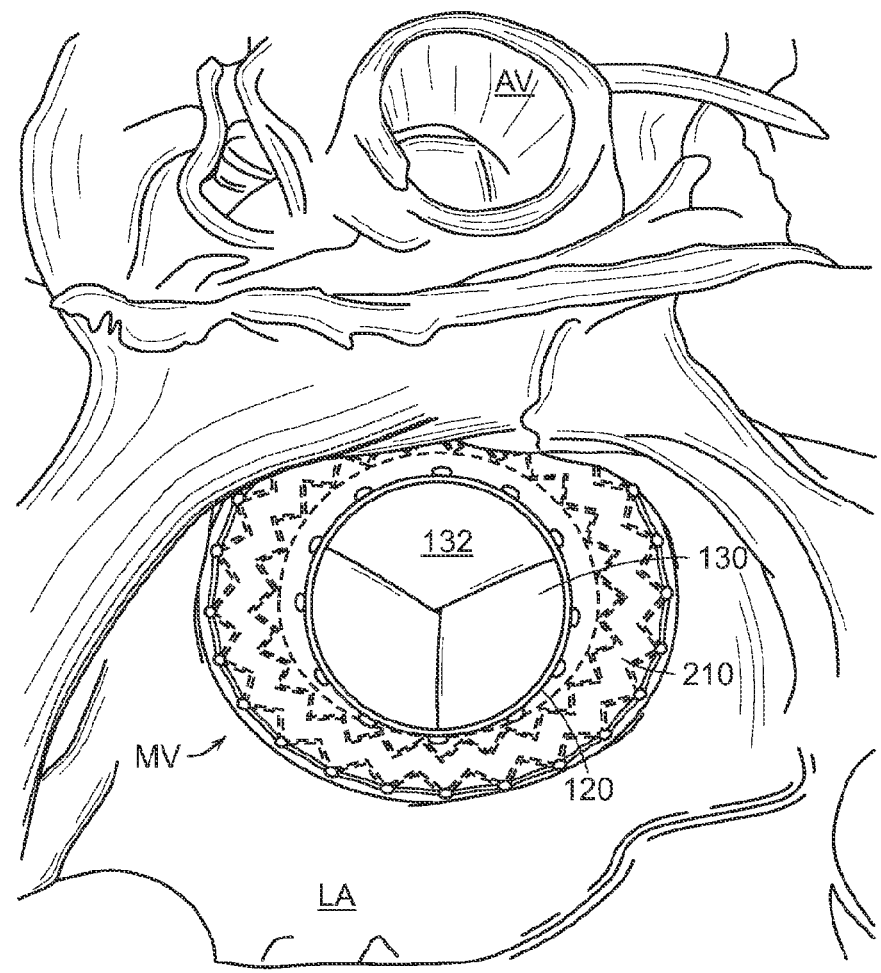
FIG. 16E is a schematic top view of a native mitral valve in the heart viewed from the left atrium and showing the prosthetic treatment device of FIG. 16A-16C implanted at the native mitral valve in accordance with an embodiment of the present technology.

Additionally, the upstream perimeter 213 can form a rim having a generally oval or D-shape, or other irregular shape for adapting to the shape of the native mitral valve. For example, and referring to FIG. 17A, the upstream perimeter 213 of the anchoring member 210 can have a major perimeter diameter $D_{m1}$ and a minor perimeter diameter $D_{m2}$ perpendicular to the major perimeter diameter $D_{m1}$. In one embodiment, the major perimeter diameter $D_{m1}$ is greater than the long axis MVA1 of the native mitral valve (shown in FIG. 5C) when the device 100 is in the expanded configuration 102 (FIG. 17A). In another embodiment, the major perimeter diameter $D_{m1}$ is less than the long axis MVA1 when the device 100 is in the expanded configuration 102. In such embodiments, the device 100 can be configured to have a major perimeter diameter $D_{m1}$ that is greater than the long axis MVA1 when the device is in the deployed configuration (e.g., when engaging the tissue on or under the native annulus, see FIG. 16E). Further, the minor perimeter diameter $D_{m2}$ can be greater than the short axis MVA2 of the native mitral valve (shown in FIG. 5C) when the device 100 is in the expanded configuration 102 (FIG. 17A), or alternatively in the deployed configuration (FIG. 16E). In one embodiment, the major perimeter diameter $D_{m1}$ and/or minor perimeter diameter $D_{m2}$ can be approximately 2 mm to approximately 22 mm, or in another embodiment, approximately 8 mm to approximately 15 mm greater than the long axis MVA1 and/or the short axis MVA2, respectively, of the native mitral valve. In some embodiments, the major perimeter diameter can be approximately 45 mm to about 60 mm and the minor perimeter diameter can be approximately 40 mm to about 55 mm.

Again referring to FIG. 16C, the upstream portion 212 of the anchoring member 210 can be radially separated from the valve support 120 by a gap 257. In one embodiment, the gap 257 is greater on an anterior leaflet facing side of the device 100 (e.g., along the third region 255) than on a posterior leaflet-facing side of the device 100 (e.g., along the fourth region 256).

Referring back to FIGS. 16A and 16C, the valve support 120 can be oriented along the first longitudinal axis 101 and the anchoring member 210 can be oriented along the second longitudinal axis 201. The second longitudinal axis 201 can be off-set from the first longitudinal axis 101. "Off-set" can refer to an arrangement where the axes 101, 201 are parallel but separated such that the gap 257 can vary around the circumference 250 (FIG. 16C). FIG. 16D shows another embodiment in which "off-set" can refer to an arrangement wherein the second axis 201 can be angled from the first axis 101 (e.g., the first and second 101, 201 axes are non-collinear or non-parallel) such that the anchoring member 210 is generally tilted with respect to the valve support 120. In one embodiment, the second longitudinal axis 201 is disposed at a tilt angle $A_{TL}$ between 15° and 45° relative to the first longitudinal axis 101.

Figure 18:
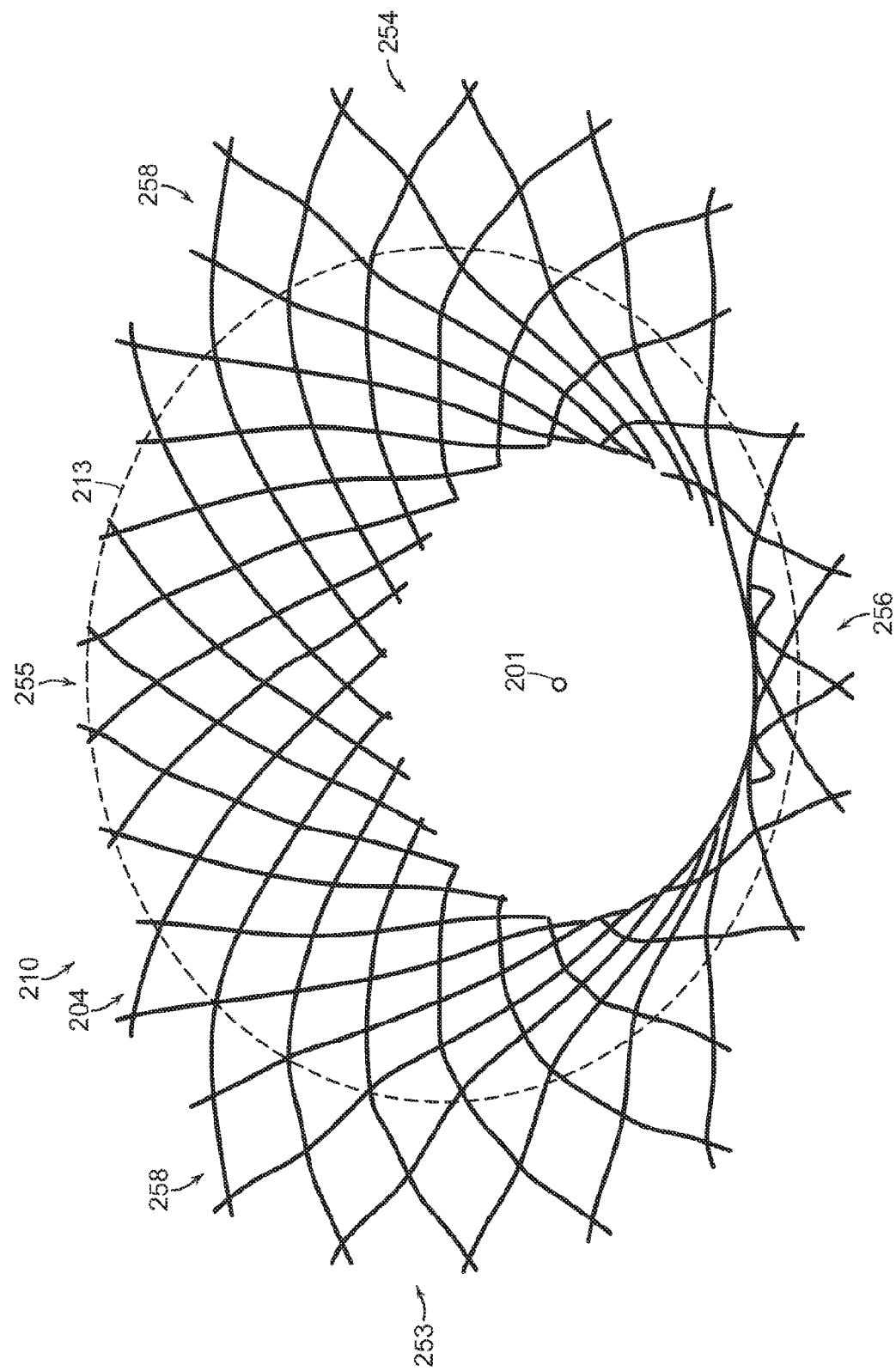
FIG. 18 is an isometric view of an anchoring member illustrated in an expanded configuration in accordance with yet another embodiment of the present technology.

In additional embodiments, and as shown in more detail in FIG. 18, the first and second regions 253 and 254 of the upstream perimeter 213 can extend further from the longitudinal axis 201 than the third 255 and fourth regions 256. For example, the anchoring member 210 can have a generally conical body (shown in dotted lines) and have upstream rim extensions 258 in the first and second regions 253 and 254. In some embodiments, the third region 255 of the upstream perimeter 213 can extend further from the longitudinal axis 201 than the fourth region 256. In some arrangements, the third region 255 can have a size and shape that allows the anchoring member 210 to engage the inward facing surface of the anterior leaflet without substantially obstructing the left ventricular outflow tract (LVOT).

Referring to FIGS. 17A-17C together, the valve support 120 can be oriented along the longitudinal axis 101, and the upstream portion 212 of the anchoring member 210 can flare outward from the longitudinal axis 101 by a taper angle $A_T$. In embodiments where the ribs 214 are generally curved outward from the downstream portion 211 to the upstream portion 212 (rather than linear), the taper angle $A_T$ can continuously change between the downstream portion and the upstream portion. In some embodiments, the taper angle $A_T$ can be the same around the circumference 250 of the upstream portion 212 of the anchoring member 210; however, in other embodiments, the taper angle $A_T$ can vary around the circumference 250. For example, the anchoring member 210 can have a first taper angle $A_{T1}$ at the first and second regions 253 and 254 (FIG. 17B) which can be configured to align with the anterolateral commissure AC and posteromedial commissure PC (see FIG. 5C), respectively. The anchoring member 210 can further have a second taper angle $A_{T2}$ at the third region 255 which can be configured to align with the anterior leaflet, and a third taper angle $A_{T3}$ at the fourth region 256 which can be configured to align with the posterior leaflet (FIG. 17C). In one embodiment, the taper angle can be approximately 30° to about 75°, and in another embodiment, between approximately 40° and about 60°.

One important aspect of having asymmetric rib lengths for the anchoring members is that different lengths might mean that one side or segment of the anchoring member is exposed from the delivery system before the others, allowing the physician deploying the device to optimize the orientation of the device prior to full deployment.

These variations in shaping of the anchoring member can serve several functions. One is to ensure a better fit with the native valve annulus. Another is to optimize the bending load on each rib and section of the anchoring member in the deployed position, in part to minimize long-term fatigue stresses on the ribs. A third reason is to ensure that the anchoring member, when deployed in the mitral annulus, does not impart asymmetric forces on the valve support member. A fifth is to reduce the force of the deployed device against the anterior leaflet, so the leaflet isn't excessively displaced towards the aortic valve. By making sure that the middle of the anterior leaflet is less radially expanded, the radius of curvature of the circumference of the anchoring member will be higher in that area, and per Laplace's law, the radial force of that area will be lower.

FIG. 16E is a schematic top view of a native mitral valve in the heart viewed from the left atrium and showing the prosthetic treatment device 100 of FIG. 16A-16C implanted at the native mitral valve MV in accordance with an embodiment of the present technology. Once deployed, and as illustrated in FIG. 16E, at least a portion of the upstream ends of the ribs 214 (shown in FIGS. 16B-16C) engage a subannular surface of the native valve (e.g., mitral valve). As described in more detail below, certain embodiments of ribs 114 or 214 are configured to penetrate subannular tissue to anchor and further stabilize the devices 100.

Although the anchoring member 210 is deformable in response to distorting forces exerted by the native anatomy, the valve support 120 can have sufficient rigidity to maintain a circular or other original cross-sectional shape, thus ensuring proper functioning of the prosthetic valve leaflets 132 when opening and closing. Such mechanical isolation from the anchoring member 210 may be achieved by the valve support 120 having sufficient rigidity to resist deformation while anchoring member 210 is deformed, and by selecting a location and means for coupling the valve support 120 to the anchoring member 210 so as to mitigate the transmission of forces through the anchoring member 210 to the valve support 120 or the prosthetic valve 130 contained therein. For example, the valve support 120 may be coupled to the anchoring member 210 only at the downstream end 123 of the valve support 120, which is separated from the upstream end 121 where the anchoring member 210 engages the annulus. On the upstream end 121, the valve support 120 may be completely unconnected to and spaced radially apart from the anchoring member 210 by the gap 257 to allow deformation of the anchoring member 210 without impacting the shape of valve support 120 (see FIGS. 16A-16C where the prosthetic valve 130 is located). Thus, forces exerted on the anchoring member 210 by the annulus can be absorbed by the flexible ribs 214 of the anchoring member 210 to mitigate transmission of such forces to the downstream end 123 of valve support 120.

In some embodiments, it may be desirable to limit a distance the device 100 extends downstream of the annulus into the left ventricle (e.g., to limit obstruction of the left ventricle outflow tract (LVOT)). Accordingly, some embodiments of the device 100 can include anchoring members 210 having a relatively low overall elevation (e.g., elevations $E_1$, $E_2$ and $E_3$, FIGS. 17B-17C), such that the anchoring member 210 does not extend into or obstruct the LVOT. As shown in the side view of FIG. 16B, for example, the anchoring member 110 can have a low overall elevation $E_L$ (e.g., the distance between the upstream perimeter 213 and the downstream perimeter 215 of the anchoring member 210) with respect to a height $H_V$ of the valve support 120. In such embodiments, the upstream perimeter 213 of the anchoring member 110 may be just below, adjacent to, or positioned within the annulus of the native mitral valve while the downstream perimeter 215 of the anchoring member 210 is configured to extend minimally into the left ventricle below the native mitral valve annulus when the device 100 is implanted. In some arrangements, the valve support 120 can be coupled to anchoring member 210 so as to also minimize protrusion into the left ventricle, and in some embodiments, may extend upwardly through the plane of the native annulus into the left atrium.

Additional Components and Features Suitable for Use with the Prosthetic Heart Valve Devices Additional components and features that are suitable for use with the prosthetic heart valve devices (e.g., devices 100 described above) are described herein. It will be recognized by one of ordinary skill in the art that while certain components and features are described with respect to a particular device (e.g., device 100), the components and features can also be suitable for use with or incorporated with other devices as described further herein.

As discussed above with respect to FIG. 10A, some embodiments of the prosthetic heart valve device 100 can include a sealing member 140 that extends around portions of the anchoring member 110 and/or the valve support 120. For example, the embodiment illustrated in FIG. 10A has a sealing member 140 around the inner wall 141 of the anchoring member 110 and around an exterior surface 127 of the valve support 120 to prevent paravalvular leaks both between the device 100 and the anatomy but also through components of the device 100.

FIGS. 19A-19C are isometric, side and top views, respectively, of a prosthetic heart valve device 100 having a sealing member 140 in accordance with a further embodiment of the present technology. Referring to FIGS. 19A-19C together, the device 100 includes a sealing member 140, such as a skirt 144. The skirt 144 can be disposed on the outer wall 142 or disposed on the inner wall 141 and at least partially over the upstream perimeter 113 of the anchoring member 110. Accordingly, the skirt 144 can be fixed and/or coupled to any surface of the anchoring member 110. The skirt 144 can also overlay an interior surface 126 (shown in FIG. 19A) and/or exterior surface 127 of the valve support 120. Variations of the skirt 144 and/or other sealing members 140 can be configured to (1) create a blood flow-inhibiting seal between the anchoring member 110 and the native tissue, (2) block blood flow through the walls 141, 142 of the anchoring member 110 and/or through the surfaces 126, 127 of the valve support 120, and (3) block blood flow through the space between the valve support 120 and the anchoring member 110. In some embodiments, the sealing member 140 can be configured to promote in-growth of adjacent tissue. The sealing member 140 can help to seal between the anchoring member 110 and the valve support 120, as well as between the device 100 and the surrounding anatomy such that blood flow is restricted to flowing through the prosthetic valve 130 from the left atrium to the left ventricle. Additionally, the sealing member 140 can provide circumferential support for the anchoring member 110 when in the expanded configuration 102 (FIGS. 10A, 16A and 19A) or deployed configuration 104 (FIGS. 10B and 16B). In some embodiments, the sealing member 140 may further serve to attach the anchoring member 110 to the valve support 120. For example, the skirt 144 can be coupled to the inner wall 141 of the anchoring member 110 and integrally formed with or otherwise attached to the sealing member 140 that is coupled to the valve support 120. In other embodiments, the sealing member 140 can be used to couple the valve support 120 to the prosthetic valve 130 housed in the interior of the valve support 120. Sealing members 140, such as skirts 144, can be coupled to the anchoring member 110 and/or valve support 120 with sutures, rivets or other known mechanical fasteners. In other embodiments, adhesives, glues and other bonding materials can be used to couple the sealing members to components of the device 100.

Figure 20A:
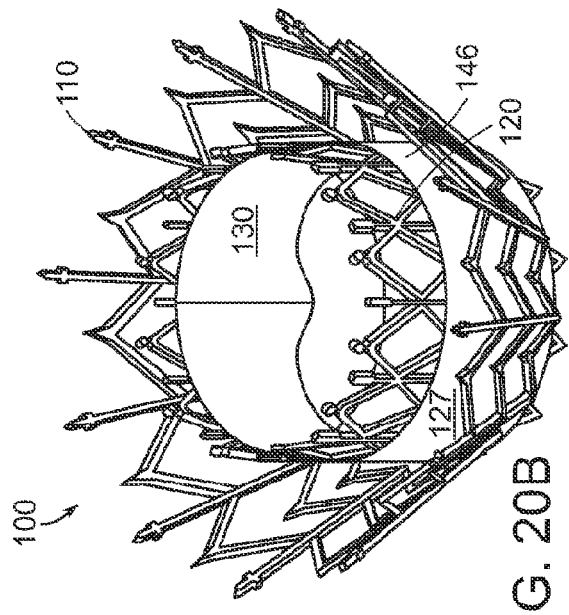
FIG. 20A is an isometric view of a prosthetic heart valve device without a sealing member in accordance with an embodiment of the present technology.
Figure 20B:
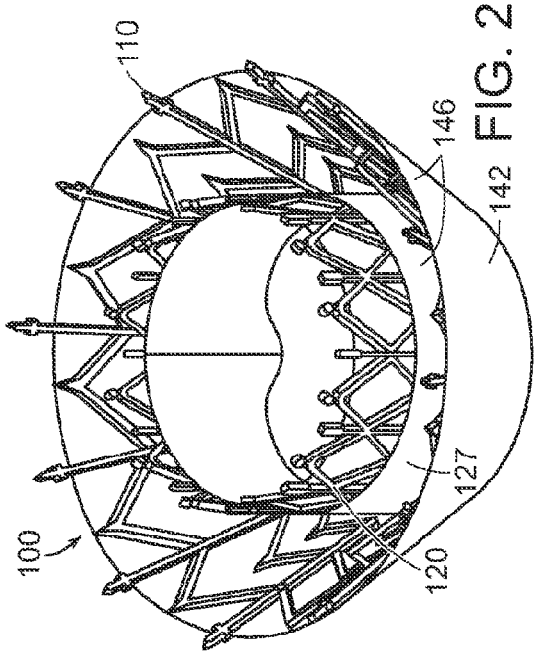
FIGS. 20B-20E are isometric views of prosthetic heart valve devices having sealing members in accordance with additional embodiments of the present technology.
Figure 20C:
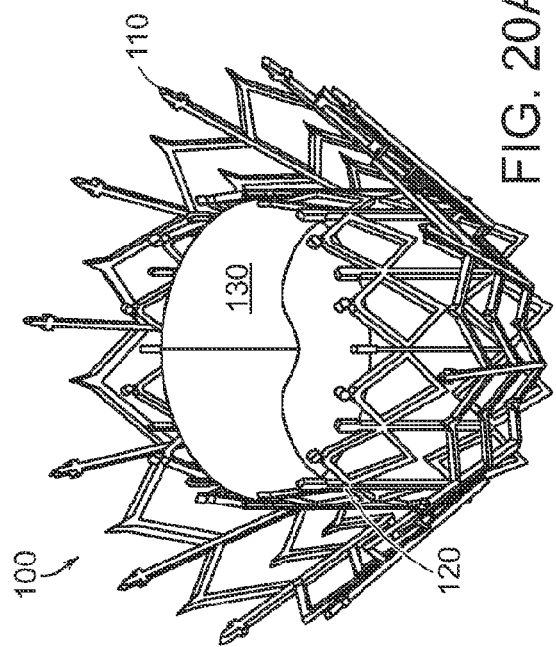
Figure 20D:
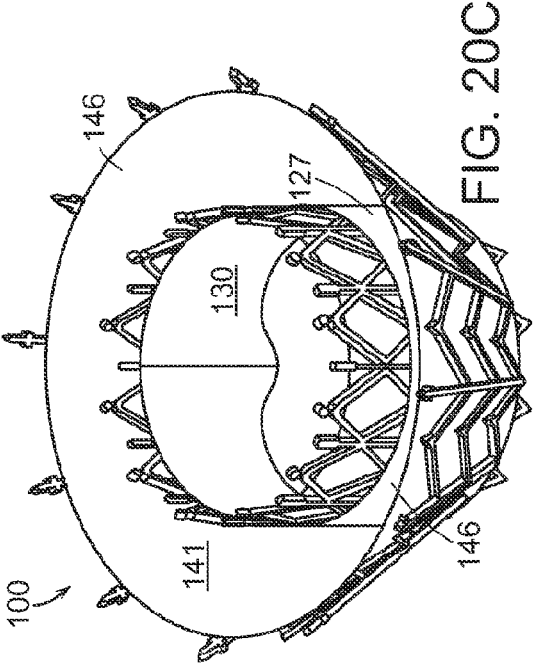
Figure 20E:
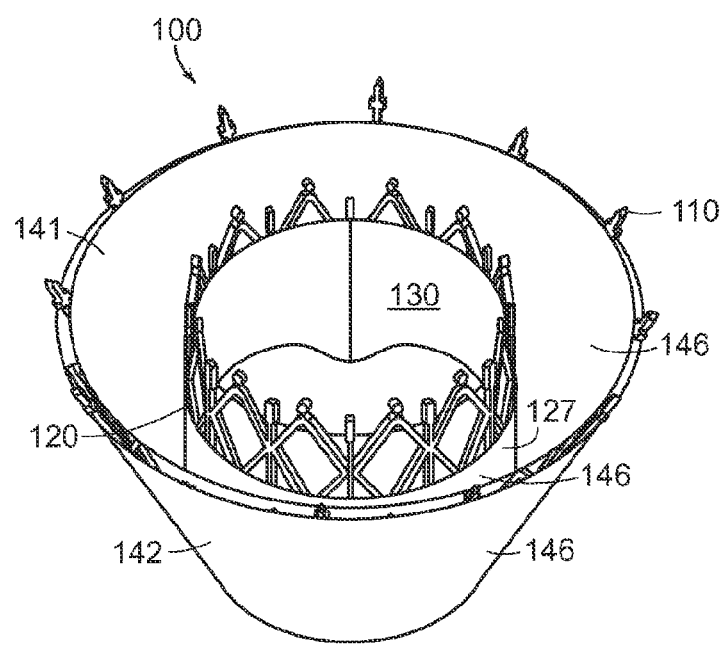

FIG. 20A is an isometric view of a prosthetic heart valve device 100 without a sealing member 140, and FIGS. 20B-20E are isometric views of prosthetic heart valve devices 100 having sealing members 140 in accordance with additional embodiments of the present technology. For example, FIGS. 20B-20C show embodiments of the device 100 in which the sealing member 140 is a sleeve 146. The sleeve 146 can include an impermeable sealing material that is cylindrical and configured to fit within or over various frame or skeleton structures of the device 100 as further described below. In FIG. 20B the sleeve 146 is on the exterior surface 127 of the valve support 120, whereas in FIG. 20C, the sleeve 146 is also disposed on the inner wall 141 of the anchoring member 110 and on the exterior surface 127 of the valve support 120. FIG. 20D illustrates an embodiment of the device 100 in which the sleeve 146 is disposed on the outer wall 142 of the anchoring member 110 and on the exterior surface 127 of the valve support 120. Referring to FIG. 20E, the device 100 can also incorporate the sleeve 146 on both the outer wall 142 and inner wall 141 of the anchoring member 110 as well as on the exterior surface 127 of the valve support 120.

One of ordinary skill in the art will recognize that the sealing members 140, such as the skirts 144 and sleeves 146 shown in FIGS. 19A-20E, can fully cover the walls 141, 142 or surfaces 126,127, or in other embodiments, at least partially cover the walls 141, 142, and/or the surfaces 126, 127 of the anchoring member 110 and the valve support 120, respectively. Any combination of sealing members 140 is contemplated. Additionally, the sealing member 140 can comprise a single continuous sheet of fluid impervious material (e.g., for covering the inner surface 141 of the anchoring member 110 and the exterior surface 127 of the valve support 120), which could create a seal between the anchoring member 110 and the valve support 120. In various embodiments, the sealing member 140, such as the skirt 144 or sleeve 146, can comprise a fabric or other flexible and biocompatible material such as Dacron®, ePTFE, bovine pericardium, or other suitable flexible material to integrate with tissue and minimize paravalvular leaks. In other embodiments, the sealing member 140 can include a polymer, thermoplastic polymer, polyester, Gore-Tex®, a synthetic fiber, a natural fiber or polyethylene terephthalate (PET). The valve 130 may also be attached to the sealing member 140 or integrally formed with the sealing member 140.

In a further embodiment, shown in FIGS. 21A-21F, the valve support 120 may comprise a tubular member 148 of fabric, polymer, or pericardium with little or no metallic or other structural support. Referring to FIGS. 21A-21B, the tubular member 148 may be a thicker and more rigid portion of a sleeve 146 which is capable of retaining its shape and has sufficient strength to resist radial and axially tensile forces during systole, and axial compressive forces during diastole. The leaflets 132 of the prosthetic valve 130 may be integrally formed with, sewn or otherwise attached to the tubular member 148. In one embodiment, the tubular member 148 can be integrally formed with an outer portion 146A of the sleeve 146 that extends around the anchoring member 110 (shown in FIG. 21A), or in another embodiment, the tubular member 148 can be a separate and/or thicker member which is sewn, bonded, or otherwise fastened to the sleeve 146 in a blood-tight manner. The tubular member 148 can optionally include reinforcing members to give it greater strength and to help it retain a desirable shape suitable for operating the valve 130. For example, a series of relatively stiff longitudinal struts 190 of metal or polymer can be coupled to or embedded within the walls of tubular member 148 (FIG. 21C), and/or a wire coil 192 may extend around or be embedded within walls of the tubular member 148 (FIG. 21D). In a further embodiment, a series of tethers 194 can be coupled between the outer portion 146A of the sleeve 146 and tubular member 148 (FIG. 21E). In one arrangement, the tethers 194 can extend at a downstream angle from the upstream portion 112 of the anchoring member 110 so as to inhibit collapse or structural compromise of the tubular member 148 during atrial systole. In yet another embodiment, a plurality of vertical septa 196 may be interconnected between the anchoring member 110 (and/or a sealing member 140 coupled to the inner wall 141 of the anchoring member 110) and the tubular member 148 (FIG. 21F). The plurality of vertical septa 196 coupled between the anchoring member 110 and the valve support 120 can be a flexible fabric or polymer, and in some embodiments, can be the same material used for the sleeve 146. The septa 196, which can be collapsed with the anchoring member 110 to a low profile delivery configuration (not shown) can also constrain the outward deflection of the ribs 114 when the device 100 is in the expanded configuration 102.

As described herein, the anchoring member 110 can be a structure or component separate from the valve support 120. In one embodiment, the anchoring member 110 can be coupled to the valve support 120 at, for example, a downstream end 123 of the valve support 120, while the upstream portion of the anchoring member 110 can remain uncoupled to the valve support 120 and/or other otherwise be mechanically isolated from the valve support 120. The anchoring member 110 can be coupled to the valve support 120 using a variety of mechanisms, including flexible, or non-rigid, coupling mechanisms. FIGS. 22A-22G and 22I-22K are enlarged side views of various mechanisms of coupling the valve support 120 to the anchoring member 110 that allow relative movement between the downstream portions or the anchoring member 110 and the valve support 120 or otherwise provide mechanical isolation of the valve support 120 from the anchoring member 110 in accordance with additional embodiments of the present technology.

Figure 22A:
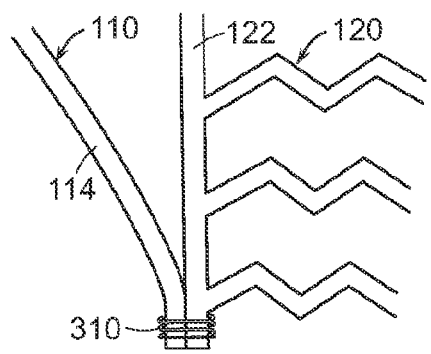
Figure 22B:
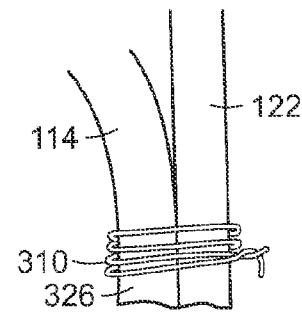
Figure 22C:
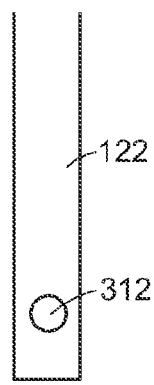
Figure 22D:
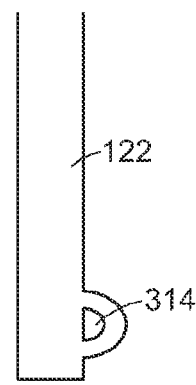
Figure 22E:
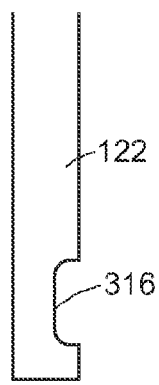

FIGS. 22A-22B illustrate a downstream end 326 of a rib 114 of the anchoring member 110 coupled to a post 122 of the valve support 120. In a first embodiment, the rib 114 can be coupled to the post 122 by a suture, wire or other suitable filament 310 which is wrapped around the adjacent elements and tied (FIG. 22B). In some embodiments, either or both the rib 114 and the post 122 may have a feature to which the filament 310 may be secured, such as a through-hole 312 (FIG. 22C), a loop or eyelet 314 (FIG. 22D), or a groove 316 configured to retain the filament 310 therein and inhibit sliding along the rib 114 or post 122.

In another embodiment shown in FIG. 22F, the rib 114 can be coupled to the post 122 by a rivet, screw, pin, or other fastener 318 which passes through aligned holes 319 in the rib 114 and the post 122. Alternatively, and as shown in FIGS. 22G-22H, the post 122 may have a cavity 320 in its outer wall configured to receive a downstream end 326 of rib 144, and the two elements 114, 122 can be fastened together by a filament or fastener 322. In this arrangement, a substantial portion of the systolic force exerted on the valve support 110 can be translated directly to the rib 114 because the downstream end of the rib 114 engages the floor of the cavity 320, thereby relieving the suture or fastener 322 from having to resist such force.

In further embodiments shown in FIGS. 22I-22J, a downstream end 326 of the rib 114 passes through a passage 324 formed through the post 122. The downstream end 326 is then secured to post 122 by a fastener 328 or a filament like those described above. Additionally, because the rib 114 is held within the passage 324, the systolic loads exerted on the valve support 120 can be translated directly to the ribs 114 rather than to the fastener 328. In yet another embodiment shown in FIG. 22K, a downstream end 330 of the post 122 is formed radially outward in a hook or J-shape, forming a channel 332 in which a downstream end 326 of the rib 114 can be received. The ends 330, 326 of the two elements may be secured by a fastener 334 passing through holes 319 in the rib 114 and the post 122. Systolic loads applied to the post 122 can be translated directly to the rib 114 via channel 332, relieving fastener 334 from bearing a substantial portion of the load.

Figure 23A:
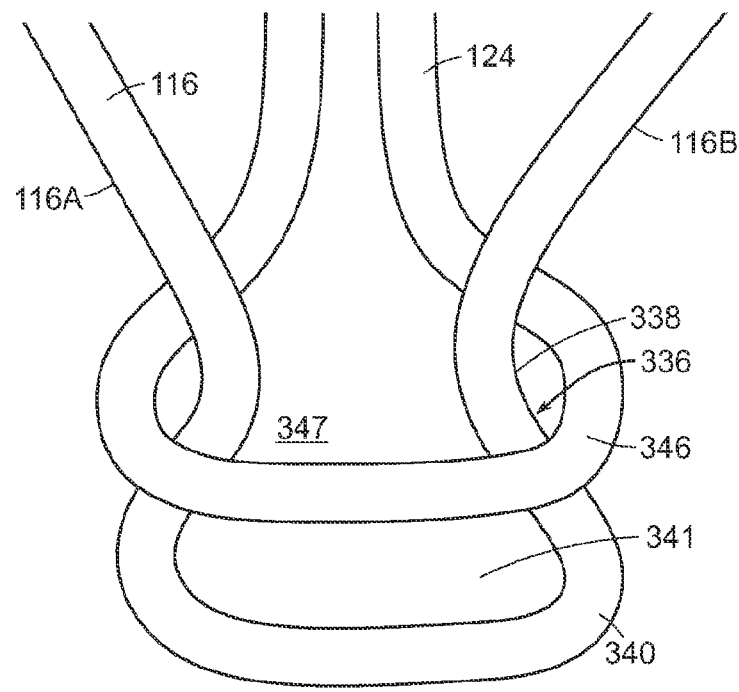
FIGS. 23A-23B are enlarged side views of additional mechanisms for coupling an anchoring member to a valve support member in accordance with further embodiments of the present technology.
Figure 23B:
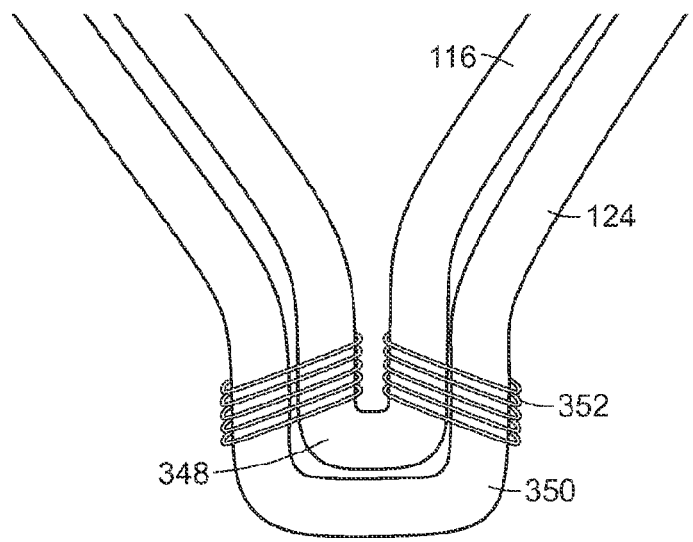

FIGS. 23A-23B illustrate further embodiments of mechanisms suitable for coupling the anchoring member 110 to the valve support 120. In the embodiments shown in FIGS. 23A-23B, circumferential connectors 116 of the anchoring member 110 are coupled to the struts 124 of the valve support 120. For example, in FIG. 23A, the connectors 116 are formed so as to have an hourglass-shaped portion 336 forming a waist 338 and an enlarged connector head 340 forming a connector cell 341. Struts 124 similarly have an enlarged strut head 346 forming a strut cell 347. The hourglass portion 336 of the connector 116 can be configured to pass through the strut cell 347 such that the strut head 346 extends around the waist 338 of the connector 116. The connector head 340 can be sufficiently large that it is prevented from being released from the strut cell 347. Further, due to the diverging angles of connector segments 116A, 116B, the strut head 346 can be prevented from sliding upward relative to the connector head 340. In such arrangements, systolic loads exerted in the upward direction on the valve support 120 can be translated through the struts 124 to the connectors 116, which in turn translate these forces to the ribs 114 which are driven into the native anatomy to anchor the device 100 in place.

In FIG. 23B, the connectors 116 can be formed so as to have a loop portion 348 extending downwardly which is nested in a concave portion 350 formed in the strut 124. The loop portion 348 can be fastened to the concave portion 350 in various ways, e.g. by a suture 352 wrapped around each member 348, 350. In this arrangement, systolic loads applied to valve support 120 in the upstream direction can be transferred through the concave portion 350 to loop portions 348 of the anchoring member 110.

Figure 24A:
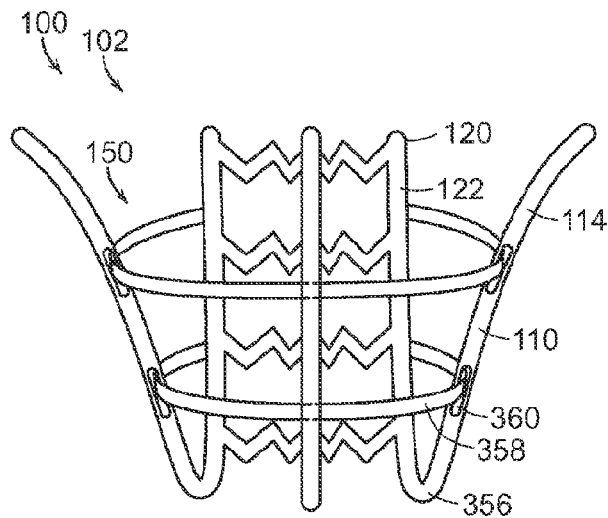
FIG. 24A is a perspective view of an integral connection between a valve support and an anchoring member in accordance with an additional embodiment of the present technology.
Figure 24B:
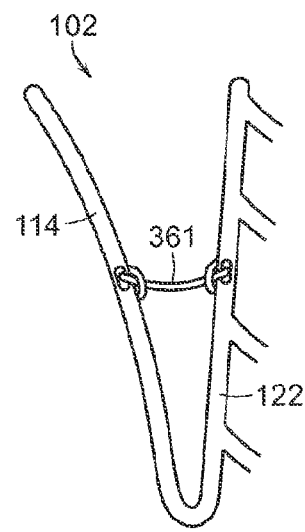
FIGS. 24B-24D are enlarged views of additional embodiments of an integral connection between a valve support and an anchoring member in accordance with the present technology.

In other embodiments, the anchoring member 110, or selected components thereof, can be integrally formed with the valve support 120. As shown in FIG. 24A, the ribs 114 of the anchoring member 110 can be integrally formed with posts 122 of the valve support 120 with a U-shaped bridge member 356 interconnecting each rib 114 to respectively aligned posts 122. The ribs 114 may be circumferentially interconnected by expandable connectors 116 formed integrally therewith. Alternatively, in the embodiment shown in FIG. 24A, a plurality of separate bands or wires 358 extend around the circumference 150 of the anchoring member 110 and are each slideably coupled to the ribs 114, e.g. by extending through a hole 360 formed in each individual rib 114. The flexible bands or wires 358 permit ribs 114 to be collapsed inwardly to a low-profile delivery configuration (not shown), while limiting the outward deflection of the ribs 114 when in the expanded configuration 102. Alternatively, a tether 361 of wire or suture may be coupled between the individual ribs 114 and the posts 122 (shown in FIG. 24B) to limit the outward deflection of the ribs 114 when in the expanded configuration 102.

Figure 24C:
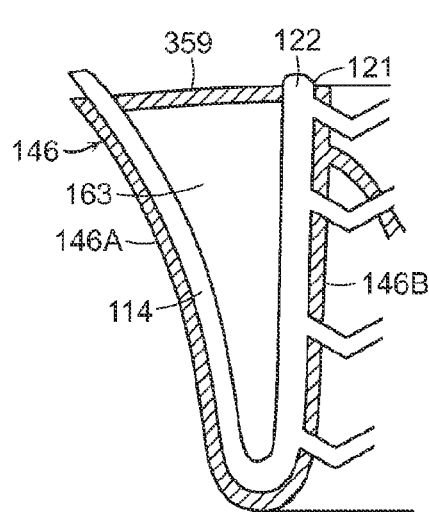
Figure 24D:
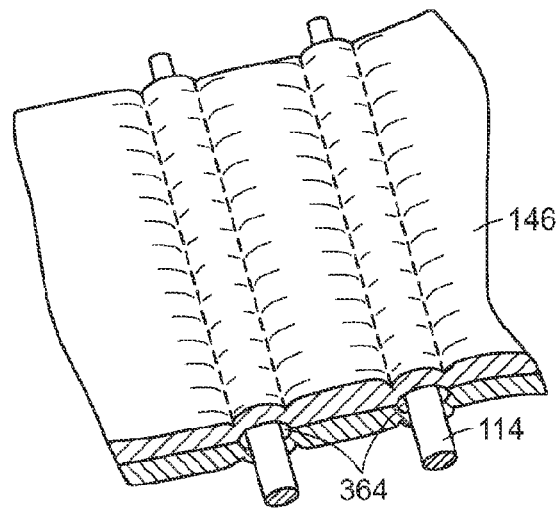

In further embodiments, a sleeve 146 may be secured to the ribs 114 in a manner which limits the outward deflection of the ribs 114 when the device 100 is in the expanded configuration (shown in FIG. 24C). The sleeve 146 may, for example, extend around the outer side of each rib 114 as shown in FIG. 24C to constrain it from expanding outwardly beyond a predetermined limit Optionally, the sleeve 146 may further include a horizontal septum 359 extending between an inner portion 146B of the sleeve 146 that extends around the valve support 120 and an outer portion 146A of the sleeve 146 that extends around the anchoring member 110. The horizontal septum 359 can more rigidly constrain the outward flexion of the ribs 114. In some embodiments, the septum 359 can also seal the annular cavity 163 formed by the septum 359 between the inner portion 146B and the outer portion 146A to limit blood flow into this cavity 163 and minimizing clot formation therein. Alternatively, openings (not shown) may be formed in the sleeve 146 downstream of the septum 359 which can permit blood to flow into the enclosed cavity 163 to form a region of clot, thereby limiting the deflection of the ribs 114 and making the device more rigid and securely anchored. The septum 359, which can be a flexible fabric, polymeric, or pericardial material, can be located at the upstream end of the device 100 as shown, or at a location spaced further downstream from the upstream end 121 of the valve support 120. In a further embodiment shown in FIG. 24D, each individual rib 114 can be constrained within a passage 364 formed in the sleeve 146 by suturing or bonding two layers of sleeve fabric together. In the expanded configuration 102, the movement of the ribs 114 can be limited relative to the sleeve 146.

Figure 25A:
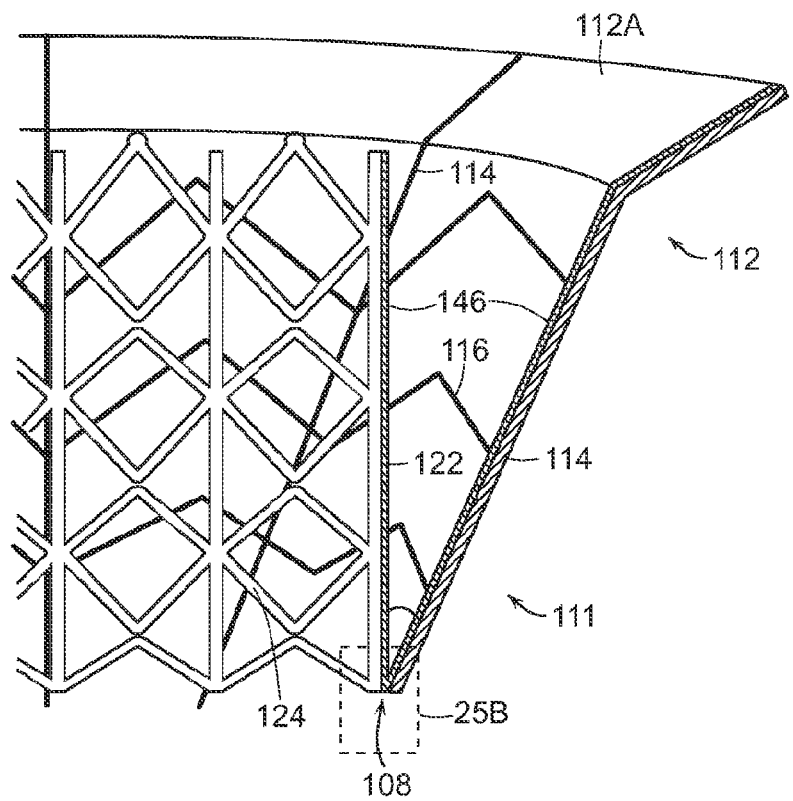
FIG. 25A is a partial cross-sectional view of a prosthetic heart valve device having an anchoring member and a valve support in accordance with an embodiment of the present technology.
Figure 25B:
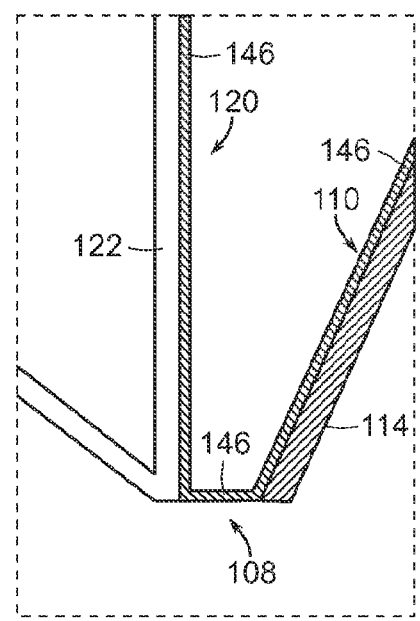
FIG. 25B is an enlarged view of the designated box shown in FIG. 25A

FIG. 25A is a partial cross-sectional view of a prosthetic heart valve device 100 having an anchoring member 110 and a valve support 120, and FIG. 25B is an enlarged view of the designated box shown in FIG. 25A in accordance with an embodiment of the present technology. As shown in FIGS. 25A and 25B, there can be a gap 108 between the valve support 120 and lower portion 111 of the anchoring member 110. If the gap 108 exists, the gap 108 can be protected by a sleeve 146 to prevent blood from leaking between the anchoring member 110 and the valve support 120 in either an upstream or downstream direction.

Figure 26A:
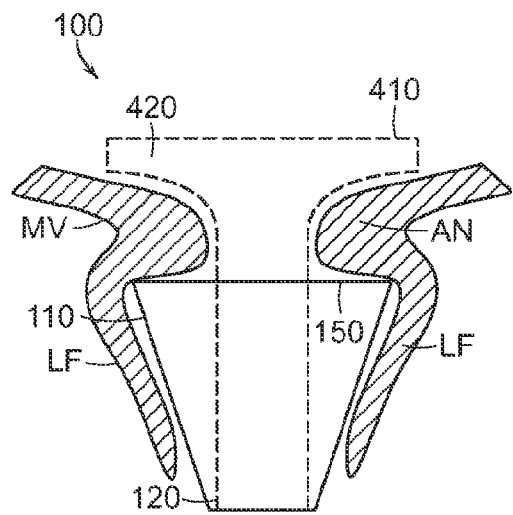
FIGS. 26A-26D are schematic cross-sectional views of prosthetic heart valve devices having atrial retainers and implanted at a native mitral valve in accordance with various embodiments of the present technology.
Figure 26B:
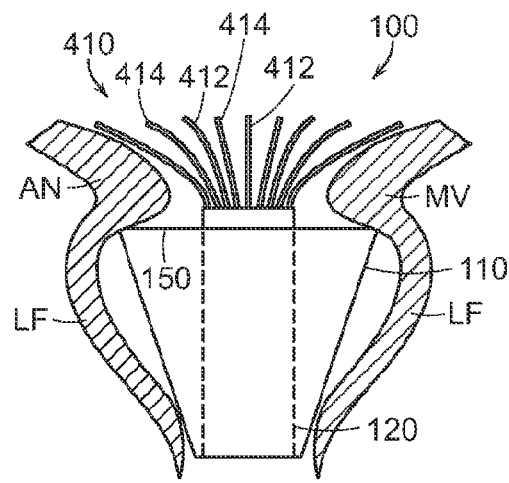
Figure 26C:
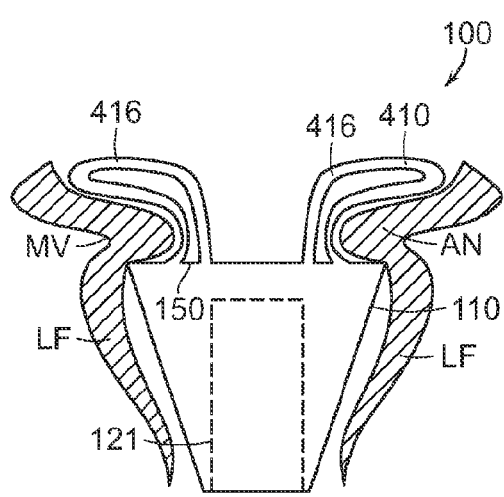

FIGS. 26A-26D are schematic cross-sectional views of prosthetic heart valve devices 100 having atrial retainers 410 and implanted at a native mitral valve MV in accordance with various embodiments of the present technology. FIGS. 26A-26C show several embodiments of the device 100 in which the device 100 includes an atrial retainer 410 configured to engage a supra-annular surface of the annulus AN or other tissue within the left atrium to assist the native leaflets in preventing downstream migration of the device 100 into the left ventricle. In these arrangements, the annulus AN can be sandwiched between a top circumference 150 of the anchoring member 110 and a bottom surface of the atrial retainer 410.

As shown in FIG. 26A, one embodiment of the device 100 can include the atrial retainer 410 coupled to or integrally formed with the inner valve support 120. The atrial retainer 410 can extend upstream through the annulus AN and into a supra-annular space within the atrium and engage the supra-annular surface or other atrial tissue with an outwardly extending flange 420. In another embodiment shown in FIG. 26B, the atrial retainer 410 can comprise a plurality of fingers 412 which may be formed integrally with or otherwise coupled to the valve support 120 (e.g. comprising upward extensions of posts 122 or upward extensions of the anchoring member 110). The fingers 212 can be generally uncovered or exposed within the left atrium as illustrated in FIG. 26B; however, in another embodiment, the fingers 412 can be covered with a sealing member (not shown) or other covering of fabric, polymeric sheet, or pericardial tissue extending around the outside or inside surfaces of the fingers 412 to form a conical shape to help seal the device 100 with the native tissue on the atrial side of the annulus AN and to help funnel blood into the prosthetic valve 130 (FIG. 10A). The fingers 412 may also include circumferential struts (not shown) interconnecting the fingers 412 to limit lateral deflection and enhance the stiffness of the fingers. The fingers 412 can include a resilient shape memory material (e.g., Nitinol) such that the fingers can be straightened and deflected inwardly for delivery and be released to an unbiased, radially projecting outward position in the expanded configuration 102 as shown. For example, the fingers 412 can have finger tips 414 biased outwardly and, in some arrangements, in the downstream direction in the expanded configuration 102. During delivery to a desired position within the native mitral valve MV, the device 100 can be unsheathed in the distal or downstream direction (discussed in more detail below), such that the fingers 412 are first released to engage the atrial side of the valve annulus AN. This indexes the position of the device 100 relative to the native valve to ensure that the anchoring member 110 is positioned on the ventricular side of the native annulus AN but not overextended into the ventricle when it is unsheathed and expanded.

Figure 26D:
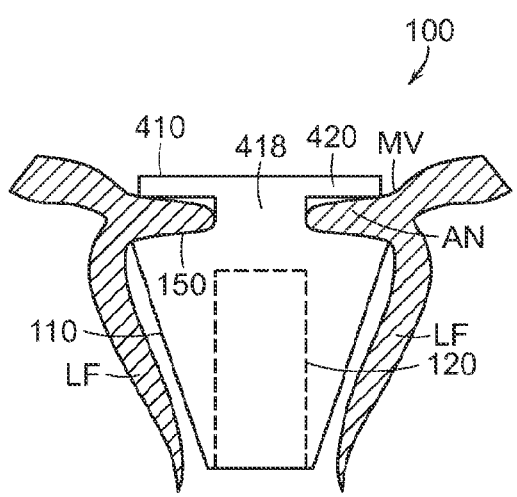

The atrial retainer 410 may alternatively be an extension of the anchoring member 110. In one embodiment shown in FIG. 26C, the atrial retainer 410 can include a plurality of atrial loops 416, which, although depicted in a more vertical plane, may alternatively lie in a plane more parallel to the plane of the native annulus AN, and which extend upstream through the annulus AN, then extend radially outwardly to engage a supra-annular surface. The loops 416, which may comprise extensions of one or more ribs 114 of the anchoring member 110, can include a resilient shape-memory metal (e.g., Nitinol) or other material that may be compressed into a low profile shape for delivery then released to expand to the radially-extended configuration shown in FIG. 26C. Similar to the device 100 of FIG. 26C, FIG. 26D is also a cross-sectional view of a prosthetic heart valve device 100 that includes an atrial retainer 410 formed by an extension of the anchoring member 110. As shown in FIG. 26D, the atrial retainer 410 can include a cylindrical portion 418 which extends upwardly from the anchoring member 110 through the native annulus AN, with a flange 420 at the proximal region which extends over the atrial side of the native annulus AN to engage the supra-annular surface. The flange 420 can include a resilient shape memory material (e.g., Nitinol) that can be collapsed for delivery and expand when deployed at the native mitral valve MV. The cylindrical portion 418 and flange 420 may be integrally formed with the anchoring member 110, e.g. comprised of extensions of the ribs 114, or in another embodiment, can be coupled to one or more portions of the anchoring member 110 and/or the valve support 120.

Figure 27:
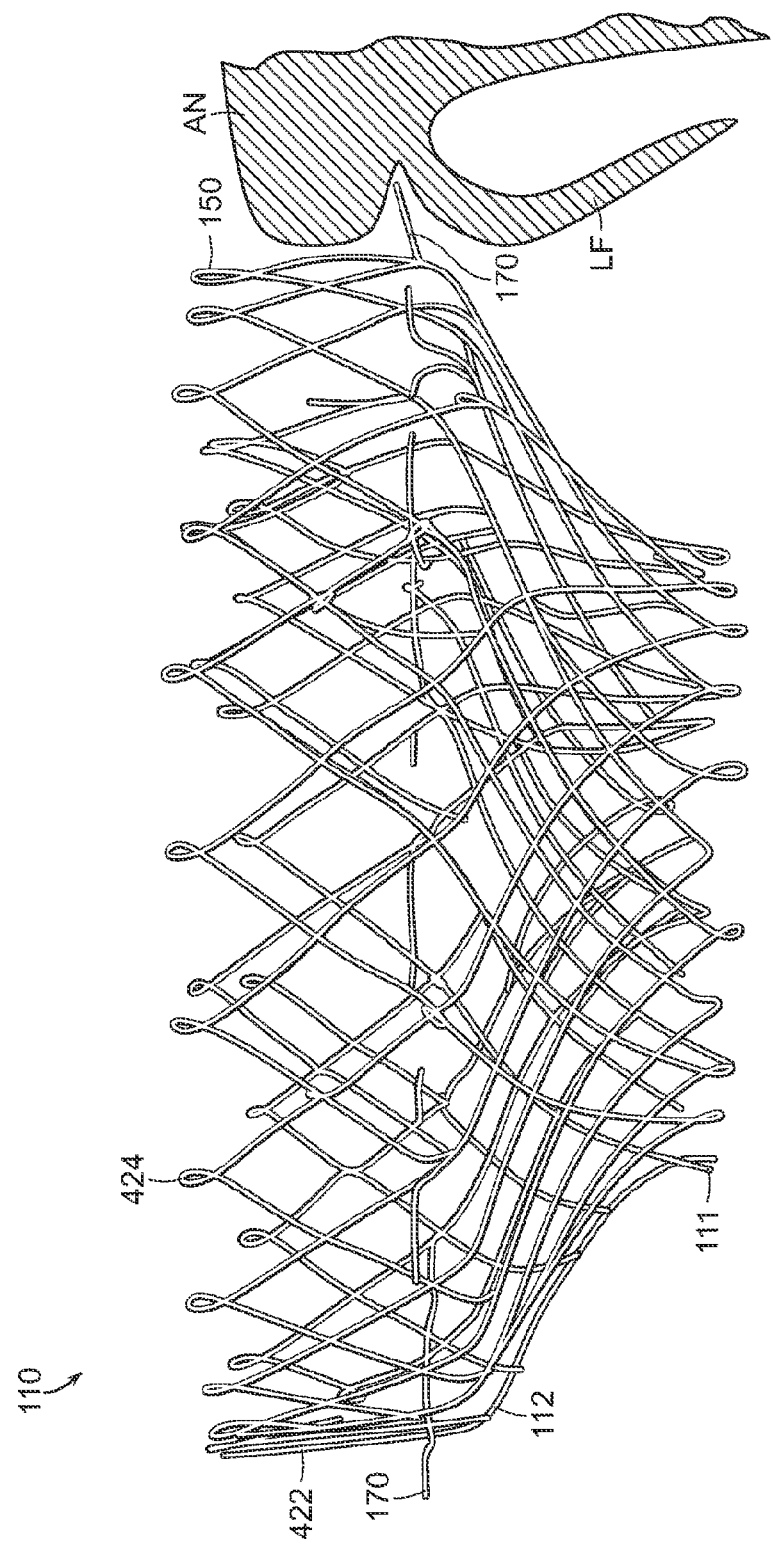
FIG. 27 is a side view of an anchoring member having a vertical portion at the upstream end for engaging the annulus in accordance with another embodiment of the present technology.

In other embodiments, the prosthetic heart valve device 100 can include atrial extending features that assist in retaining the device 100 in a desired location within the native mitral valve, but do not substantially engage atrial or supra-annular tissue. For example, FIG. 27 is a side view of an anchoring member 110 having a vertical portion 422 at the upstream end 424 for engaging the annulus AN in accordance with another embodiment of the present technology. The anchoring member 110 can include the lower portion 111 and the upper flared portion 112 which is positionable in a subannular location between the leaflets LF and downstream of the annulus AN. The upstream portion 112 can be expandable to a dimension that is larger than a corresponding dimension of the subannular tissue and/or inward facing leaflets LF. The vertical portion 422 can be fitted within the annulus orifice so as to engage the annulus AN around an entire upstream circumference 150 of the anchoring member 110. The vertical portion 422 can be expandable to a dimension that is larger than a corresponding dimension of the annulus AN such that radial expansion of the vertical portion 422 presses outwardly against the native tissue to assist retaining the device in the desired location with the native mitral valve. Optionally, the anchoring member 110 can also include a plurality of tissue engaging elements 170, such as spikes. In one embodiment, the spikes (shown here as tissue engaging elements 170) can be distributed around the circumference 150 of the upper portion 112 of the anchoring member 110 and oriented such that the spikes can penetrate tissue in a subannular location and can be configured to help the anchoring member 110 resist movement in either an upstream or downstream direction.

Prosthetic Heart Valve Devices Having Stabilizing Members

Figure 28:
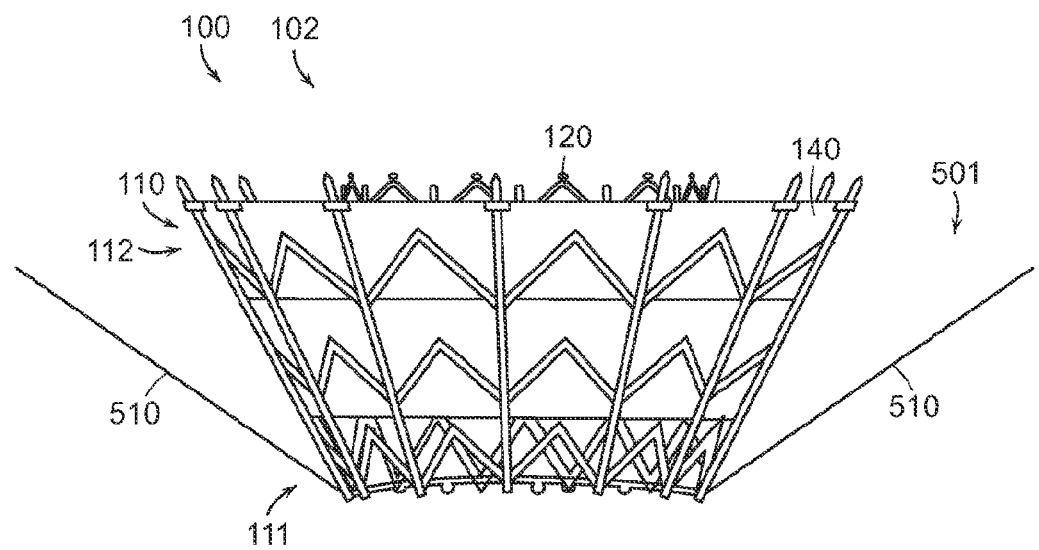
FIG. 28 is a side view of a prosthetic heart valve device in an expanded configuration and having a plurality of stabilizing elements in accordance with an embodiment of the present technology.

FIG. 28 illustrates one embodiment of the prosthetic heart valve device 100 in an expanded configuration 102 that further comprises one or more stabilizing members 501 to help stabilize the device 100 at the native valve site and, in some embodiments, prevent tilting or lateral migration, or to inhibit upstream or downstream migration of the device 100. In some embodiments, the stabilizing members 501 may comprise one or more arms 510 extending from a lower or downstream portion 111 of the anchoring member 110. The arms 510 are configured to engage the native tissue, e.g. the valve leaflets, subannular tissue, or ventricular wall, either inside or outside the native leaflets, depending on the configuration.

Figure 29:
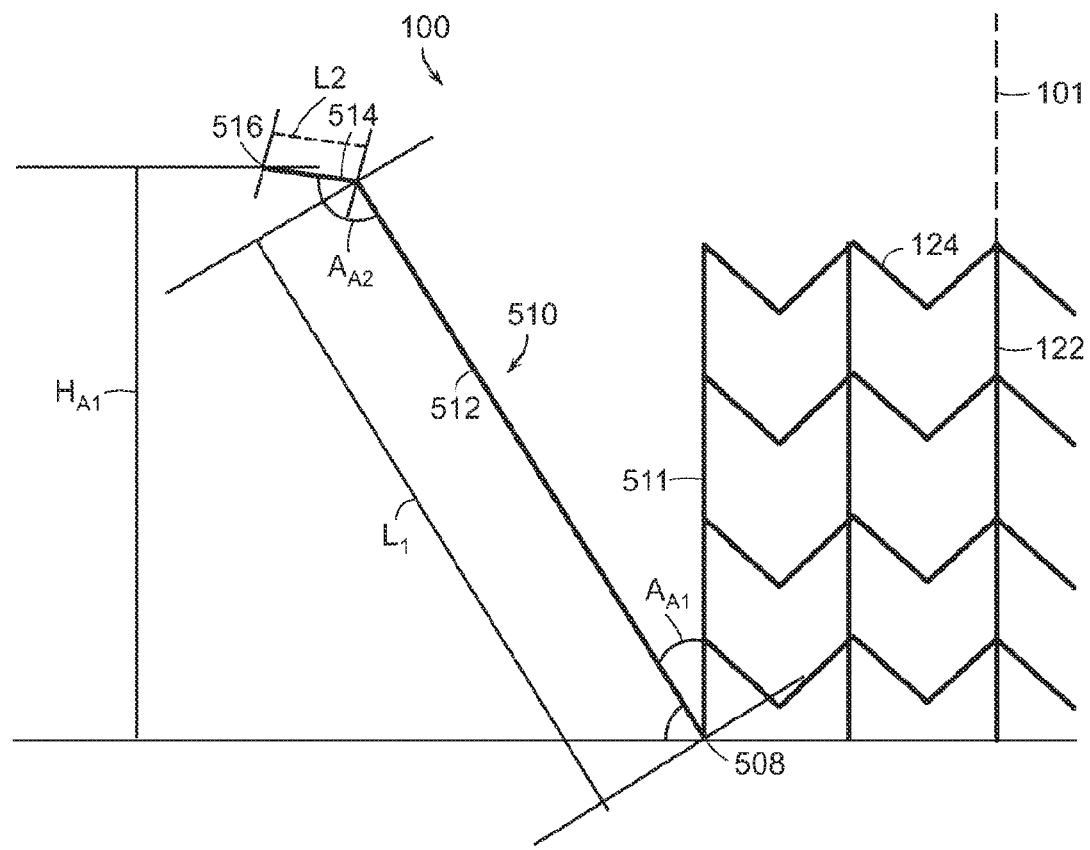
FIG. 29 is an enlarged schematic, side view of a prosthetic heart valve device having an extended arm in accordance with an embodiment of the present technology.
Figure 30A:
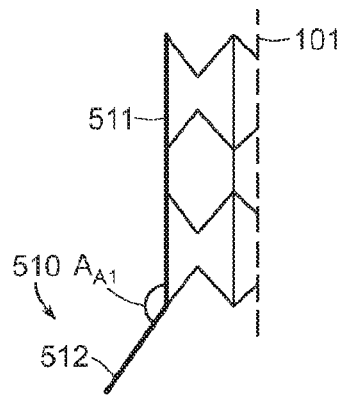
FIGS. 30A-30C are enlarged partial side views of a prosthetic heart valve device having arms coupled to the device at various angles with respect to a longitudinal axis of the device in accordance with further embodiments of the present technology.
Figure 30B:
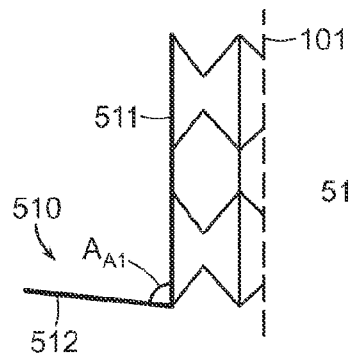
Figure 30C:
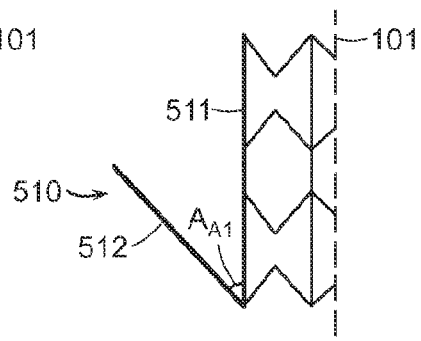

FIG. 29 is an enlarged schematic, side view of a prosthetic heart valve device having an extended arm in accordance with an embodiment of the present technology. As shown in FIG. 29, an individual arm 510 may comprise an arm body 512, an arm extension 514, and an arm tip 516. The arm body 512 has an arm body length $L_1$ and may connect to a valve post 511 at a first joint 508. The post 511 can be a valve support post 122, an anchoring member rib 114, and/or another feature of the device 100 (e.g., strut 124 or connector 116). A first arm angle $A_{A1}$ is formed by the intersection of the axes of post 511 and the arm body 512; the first arm angle $A_{A1}$ selected such that the arm 512 is positionable so that the tip 516 can engage the native tissue at a desired location, e.g. the subannular tissue or ventricular wall behind the native leaflets. FIGS. 30A-30C are enlarged partial side views of a prosthetic heart valve device 100 having arms 510 coupled to the device at various angles with respect to a longitudinal axis 101 of the device in accordance with further embodiments of the present technology. In one embodiment, the first arm angle $A_{A1}$ can be about 10° to about 45°. In other embodiments, the first arm angle $A_{A1}$ can be an obtuse angle (FIG. 30A), generally perpendicular or approximately a 90° angle (FIG. 30B), or an acute angle (FIG. 30C).

Referring back to FIG. 29, the arm body 512 can connect to the arm extension 514 at a distal end of the arm body 512. The arm extension 514 can have an arm extension length $L_2$ which can be selected or optimized for penetrating a desired distance into the native tissue, such as about 0.5-2 mm. The arm extension 514 can extend from the arm body 212 at second arm angle $A_{A2}$. The second arm angle $A_{A2}$ can be formed by the intersection between the arm extension 514 and arm body 512 and be selected to provide the desired angle of engagement with the native tissue, such as about 100° to about 135°. In other embodiments, the arm extension 514 may be parallel or collinear with the arm body 512 (not shown), or may be eliminated entirely. The arm extension 514 terminates at the arm tip 516. In embodiments without an arm extension 514, the arm tip 516 can be the most distal portion of the arm body 512 (not shown).

Figure 31A:
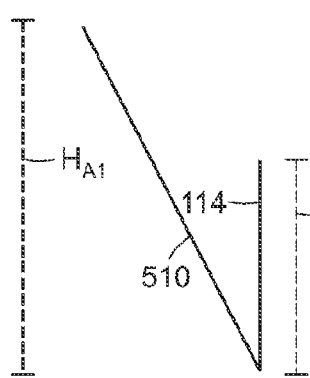
FIGS. 31A-31C are enlarged, partial side views of a prosthetic heart valve device having arms of various lengths coupled to the device in accordance with additional embodiments of the present technology.
Figure 31B:
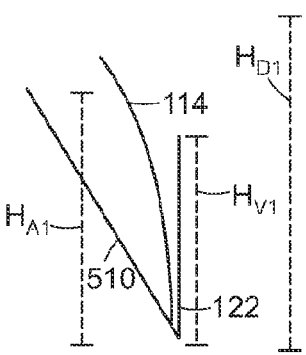
Figure 31C:
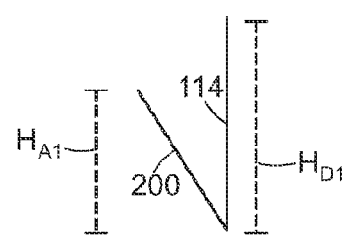

The arm 510 may have an arm height $H_{A1}$ extending from the first joint 508 to the most distal reaching point of the arm, which could be the arm tip 516 (shown in FIG. 29) along an axis parallel to the longitudinal axis 101 of the device 100. The arm height $H_{A1}$ can be selected or optimized such that the arm tip 516 engages a desired location in the subannular anatomy when the device 100 is in a desired longitudinal position relative to the native mitral valve (e.g., when the anchoring member 110 is in engagement with the subannular tissue). The arm height $H_{A1}$ will depend upon of the overall height of the anchoring member 110 and/or valve support 120 as well as the location of the joint 508. FIGS. 31A-31C are enlarged, partial side views of prosthetic heart valve devices having arms 510 of various lengths ($L_1+L_2$), and accordingly having variable heights $H_{A1}$. As shown, the arm height $H_{A1}$ may be greater than the overall height $H_{D1}$ of the anchoring member 110 (represented by rib 114) or valve support (FIG. 31A), be intermediate between the respective heights $H_{D1}$, $H_{V1}$ of the anchoring member 110 (represented by rib 114) and the valve support 120 (represented by post 122) (FIG. 31B), or be less than the overall height $H_{D1}$ of both the anchoring member 110 (represented by rib 114) and the valve support 120 (FIG. 31C).

Additional details and embodiments regarding the structure and attachment of arms or other stabilizing members suitable for use with the device 100 can be found in International PCT Patent Application No. PCT/US2012/043636, entitled "PROSTHETIC HEART VALVE DEVICES AND ASSOCIATED SYSTEMS AND METHODS," filed Jun. 21, 2012, the entire contents of which are incorporated herein by reference.

FIGS. 32A, 32B, 32C, and 32D are cross-sectional views of a heart with an implanted prosthetic heart valve device 100 having arms 510a disposed on an inward-facing surface of the leaflets LF, and FIGS. 32A-1, 32B-1, 32C-1 and 32D-1 are enlarged views of the arms 510a engaging the inward-facing surface of the leaflets as shown in FIGS. 32A, 32B, 32C and 32D, respectively. The embodiments of prosthetic heart valve devices 100 illustrated in FIGS. 32A-32D-1 have arms 510a configured to expand to a position radially inside the leaflets LF, radially outside the leaflets LF, or a combination of inside and outside the leaflets LF. For example, FIGS. 32A and 32A-1, show arms 510a expanding and engaging an inward surface of the leaflets LF and show the arms 510a partially piercing the leaflets LF. In another example illustrated in FIGS. 32B and 32B-1, the arms 510a may fully penetrate the leaflets LF. In a further example, the device 100 can incorporate arms 510a that 1) completely penetrate the leaflets LF and 2) partially pierce subannular tissue (FIGS. 32C and 32C-1). Referring to FIGS. 32D and 32D-1, the device 100 can be configured to incorporate arms 510a that fully penetrate both the leaflets LF and the annular tissue of the mitral valve MV.

FIGS. 33A-33C are schematic views illustrating various embodiments of tissue engaging elements 170 for use with prosthetic heart valve devices 100 in accordance with the present technology. Tissue engaging elements 170 can include any feature that engaged tissue in an atraumatic manner, such as a blunt element, or which partially pierces or fully penetrates cardiac tissue, such as a barb or spike. As used herein, "tissue engaging" refers to an element 170 which exerts a force on the tissue T but does not necessarily pierce the tissue T, such as being atraumatic to the tissue T, as shown in FIG. 33A. As used herein, "partially piercing" refers to a tissue engaging feature 170 which at least partially penetrates the tissue T but does not break through an opposite surface S, as shown in FIG. 33B. As used herein, "fully piercing" refers to a tissue engaging feature 170 which can both enter and exit the tissue T, as shown in FIG. 33C. "Piercing" alone may refer to either partial or full piercing. Tissue engaging elements 170 may take the form of spikes, barbs, or any structure known in art capable of piercing cardiac tissue, or alternatively, any blunt or atraumatic feature configured to apply pressure on the cardiac tissue without piercing the tissue. Further details on positioning of such elements is described herein.

FIGS. 34A, 34B and 34C are cross-sectional views of a heart with an implanted prosthetic heart valve device 100 having arms 510a with tissue engaging elements 170 disposed on an inward-facing surface of the leaflets LF, and FIGS. 34A-1, 34B-1 and 34C-1 are enlarged views of the arms 510a engaging the inward-facing surface of the leaflets LF as shown in FIGS. 34A, 34B and 34C, respectively. As illustrated in FIGS. 34A-34C-1, tissue engaging elements 170 can be incorporated on and extend from the arms 510a in either a downstream direction (FIGS. 34A and 34A-1), upstream direction (FIGS. 34B and 34B-1), or in both the downstream and upstream directions (FIGS. 34C and 34C-1). In other embodiments, the tissue engaging elements 170 can be incorporated on and extend from the components of the anchoring member 110 and/or the valve support 120 in either or both the upstream and downstream directions.

Figure 35A:
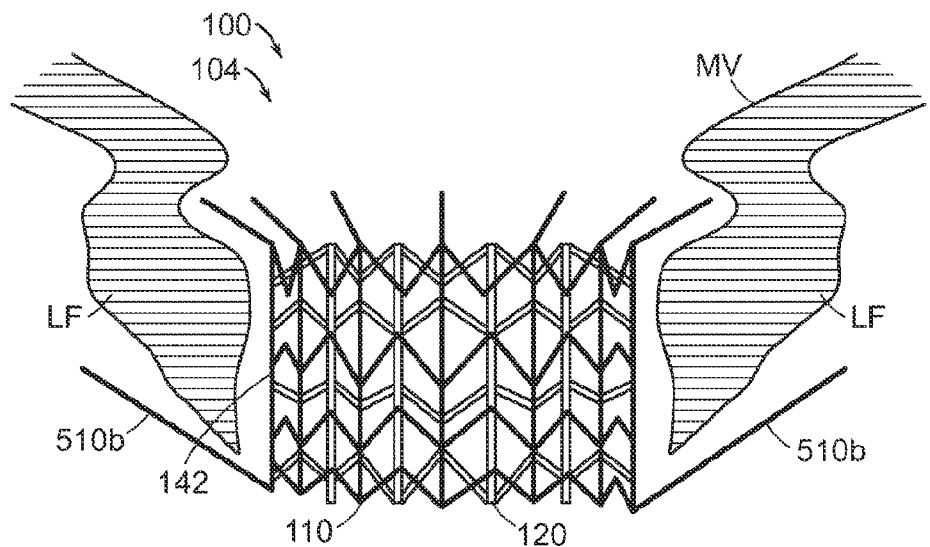
Figure 35B:
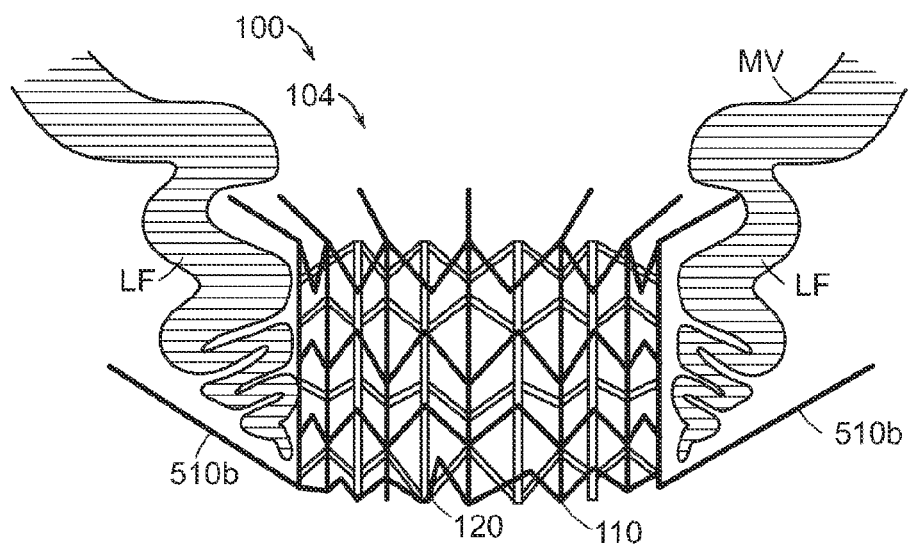

FIGS. 35A-35C are side views showing prosthetic heart valve devices 100 implanted at a mitral valve MV (illustrated in cross-section) in a deployed configuration 104, wherein the devices have arms 510b for engaging an outward-facing surface of the native leaflets LF in accordance with various embodiments of the present technology. FIG. 35A shows an embodiment of the device 100 that includes arms 510b configured to extend from the downstream end of the device 100 (e.g., the ventricular end of a device implanted at a native mitral valve downstream of the leaflets) to reach behind the leaflets LF such that the leaflets LF are effectively sandwiched between the arms 510b and the outer wall 142 of the anchoring member 110. In another embodiment, and as shown in FIG. 35B, the arms 510b may cause leaflets LF to fold upon themselves in the space between the arms 510b and the outer wall 142 of the anchoring member 110. In a further embodiment illustrated in FIG. 35C, the arms 510b can also include the tissue engaging elements 170. FIG. 35C-1 is an enlarged view of the arm 510b having tissue engaging elements 170 for engaging the outward-facing surface of the leaflets LF as shown in FIG. 35C. As shown in FIG. 35C-1, the arms 510b configured to engage an outside-facing surface of the native leaflets LF may include tissue engaging elements 170 on an inside surface of the arms 510b such that they are oriented toward the leaflet tissue.

In accordance with another embodiment of the present technology, FIG. 36A is a side view showing a prosthetic heart valve device 100 implanted at a mitral valve MV (illustrated in cross-section). The device shown in FIG. 36A has arms 510b for engaging an outward-facing surface of the native leaflets LF and arms 510a for engaging an inward-facing surface of the native leaflets LF. Inside/outside arms 510a, 510b may further comprise tissue engaging elements 170 on a radially inside surface or radially outside surface of the arms 510a, 510b, respectively, for engaging or piercing the leaflet tissue. The arrangement of inside/outside arms 510a, 510b around a circumference of the device 100 can alternate in a pre-designed pattern. For example, inside arms 510a can alternate with outside arms 510b as shown in FIG. 36B, or alternatively, arms 510a, 510b may extend radially outward and/or radially inward randomly or at irregular intervals, depending on placement of the device 100 and with respect to alignment with the native posterior and anterior leaflets.

Figure 37A:
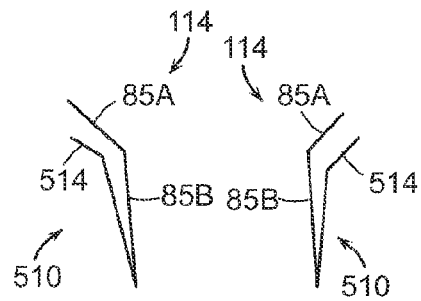
FIGS. 37A-37D are enlarged side views of additional embodiments of arms suitable for use with a prosthetic heart valve device in accordance with the present technology.
Figure 37B:
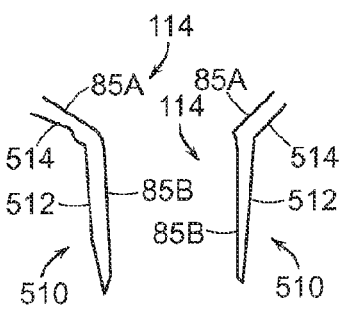
Figure 37C:
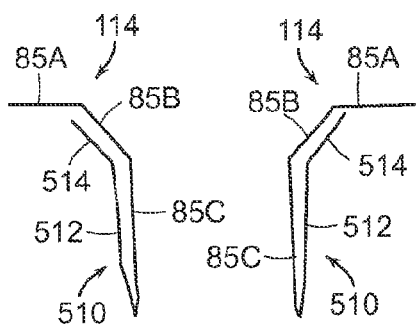
Figure 37D:
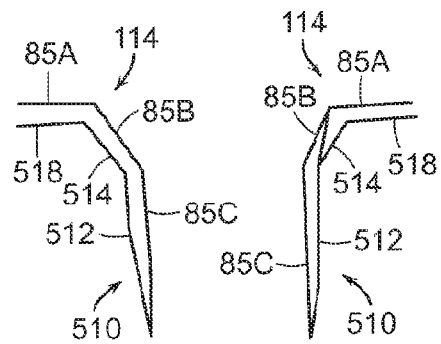

FIGS. 37A-37D are enlarged side views of additional embodiments of arms 510 suitable for use with a prosthetic heart valve device 100 in accordance with the present technology. For example, in FIGS. 37A-37D, the arms 510 can have a similar overall profile as a profile of the anchoring member 110. The anchoring member 110 can include ribs having varying shapes, sizes and/or outwardly or inwardly oriented rib segments 85 for forming the overall anchoring member profile. Accordingly, the arms 510 can also have varying shapes, sizes and/or outwardly or inwardly oriented arm segments that mimic the anchoring member 110 profile. In some arrangements, the embodiments shown in FIGS. 37A-37D are configured to clamp leaflets LF and/or the annulus AN tissue between the arms 510 and the ribs 114 so as to conform the leaflet tissue to the shape of the anchoring device 110 for enhanced sealing and anchoring of the device. For example, FIG. 37A illustrates one embodiment in which arm extensions 514 and/or arm bodies 512 may partially mimic the shape of the ribs 114 and/or rib segments 85, and FIG. 37B illustrates another embodiment in which arm extensions 514 and/or arm bodies 512 more closely follow the shape of the ribs 114. Embodiments encompassed by FIGS. 37A-37B can apply to outward surface engaging arms 510b and/or inward surface engaging arms 510a. Additionally, as shown in FIGS. 37A-37B, the arm extensions 514 can extend radially outwardly so as to be generally parallel with an upstream segment 85A of the rib 114. The arm extension 514 can be configured to extend partially along the length of the rib 114 and/or rib segments 85 (FIGS. 37A and 37C) or fully along the length of the rib 114 and/or rib segments 85. In FIG. 37D, the arms 510 have second arm extensions 518 connected to an upstream portion of the first arm extension 514 and extending outwardly so as to be generally parallel to a second rib segment 85B and third rib segment 85A.

Figure 38A:
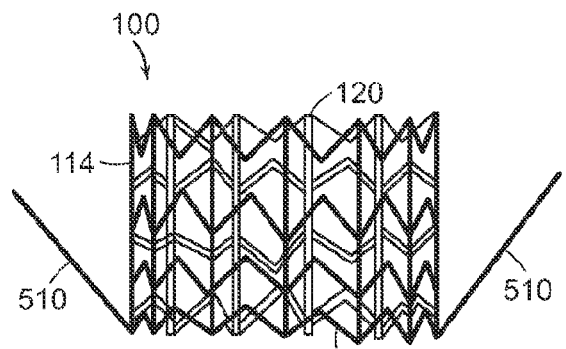
FIG. 38A is a side view of a prosthetic heart valve device having a plurality of non-interconnected arms in accordance with a further embodiment of the present technology.
Figure 38B:
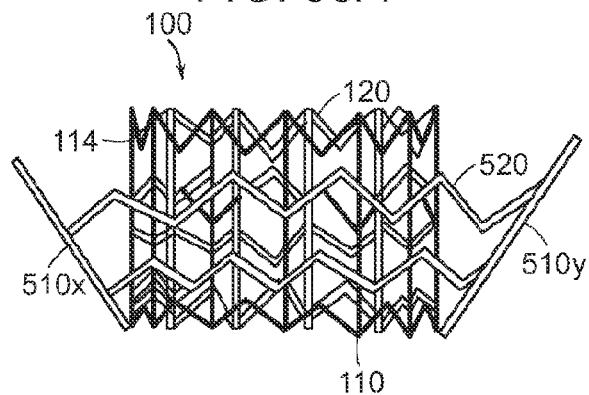
FIG. 38B is a side view of a prosthetic heart valve device having a plurality of circumferentially connected arms in accordance with a further embodiment of the present technology.

In some embodiments, the prosthetic heart valve device 100 may incorporate a plurality of arms 510 around a circumference of the device 100; however, in other embodiments, the device may include the plurality of arms in groupings (e.g., first and second groupings so as to engage the posterior and anterior leaflets, respectively). Additionally, the arms 510 may extend from the anchoring member 110 and/or valve support 120 independently of other components including other arms 510, such as shown in FIG. 38A. In other embodiments and as shown in FIG. 38B, the device 100 may further include at least one first arm 510x interconnected with at least one second arm 510y by interconnecting arm struts 520. The arm struts 520 can be configured to be circumferentially expandable and may connect all arms 510 (e.g., arm 510x and 510y) or one or more groups of arms 510. In some embodiments, the arm struts 520 can limit the outward extension of the arms 510x, 510y away from the device 100.

In accordance with aspects of the present technology, the arms 510 can be coupled to and/or extend from components of the device 100 symmetrically and/or asymmetrically around the circumference 150 of the device 100. FIGS. 39A-39D are schematic top views of arm location patterns with respect to the ribs 114 of the anchoring member 110 (e.g., as shown in FIG. 38A). The arms 510 can be interspersed with ribs 114 (FIGS. 39A and 39C), in the same radial plane as the ribs 114 of the anchoring member 110 (FIG. 39B), or both interspersed and in plane with the ribs 114 (FIG. 39D). Further, the arms 510 may be configured to extend outside the expanded outer circumference 150 of the anchoring member 110 (FIG. 39B), inside the expanded outer circumference 150 of the anchoring member 110 (FIG. 39A), extend to the same outer circumference 150 of the anchoring member 110 (FIG. 39C), or a combination of these configurations (FIG. 39D).

In the above-described embodiments, the arms 510 may be configured to engage tissue independently of the deployment of anchoring member 110. For example, delivery catheters suitable for the delivery of the prosthetic heart valve devices 100 may be equipped with separate mechanisms operable to deploy the arms 510 and the anchoring members 110 individually or otherwise independently of each other. In this way, the anchoring member 110 may be first released into engagement with the native tissue so that the position of device 100 may be assessed and adjusted by the operator until the desired final position has been attained. Following deployment and positioning of the anchoring member 110, the arms 510 can be released to engage the tissue. Such deployment systems and methods are useful when the arms 510 are equipped with tissue engaging elements 170 which, once deployed, may prohibit any repositioning of the device 100. In some embodiments, the anchoring member 110 will be equipped with atraumatic tissue engagement elements 170 which do not penetrate tissue or inhibit device relocation once the anchoring member 110 has been deployed. Accordingly, some embodiments of the device 100 may be repositionable even with the anchoring member 110 expanded so long as the arms 510 are constrained in an undeployed configuration, with the device 100 becoming permanently anchored only when the arms 510 are released.

Figure 40A:
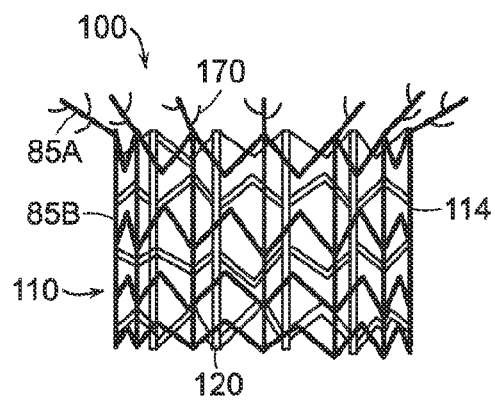
FIGS. 40A-40D are side views of prosthetic heart valve devices having tissue engaging elements on varying structures of the device in accordance with additional embodiments of the present technology.
Figure 40B:
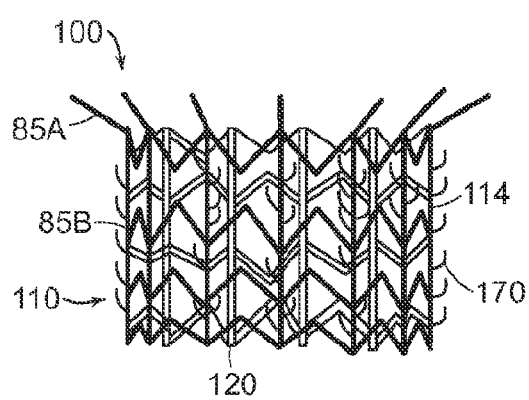
Figure 40C:
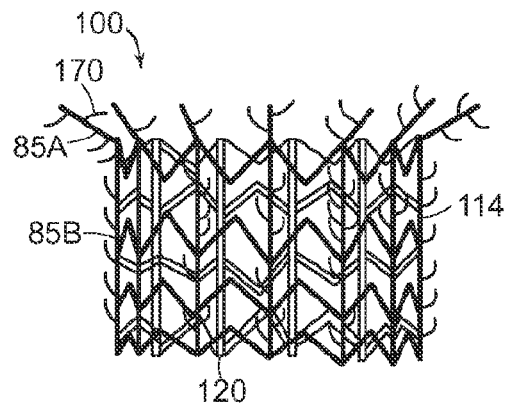

Alternatively or in addition to tissue engaging elements 170 present on the arms 510 as described above, tissue engaging elements 170 may be present on other components of the device 100. FIGS. 40A-40E are side views of prosthetic heart valve devices 100 having tissue engaging elements 170 on varying structures of the device 100 in accordance with additional embodiments of the present technology. For example, tissue engaging elements 170 can be incorporated on the ribs 114 of the anchoring member 110. FIG. 40A shows tissue engaging elements 170 incorporated on the upper rib segment 85A, and FIG. 40B shows the tissue engaging elements 170 incorporated on lower rib segment 85B. FIG. 40C illustrates an embodiment of the device having the tissue engaging elements 170 along the entire rib 114. The tissue engaging elements 170 are shown in FIGS. 40A-40C schematically, but one of ordinary skill in the art will recognize that the elements can be any of a variety of tissue engaging elements 170 described herein (e.g., atraumatic, partially piercing, fully penetrating, etc.), or in other embodiments, a combination of different types of tissue engaging elements 170. Additionally, the tissue engaging elements 170 are shown oriented in an upstream direction (e.g., to inhibit upstream migration of the device 100); however, in other embodiments, the tissue engaging elements 170 can be oriented in a downstream direction (e.g., to inhibit downstream migration of the device 100), or in a combination of downstream and upstream oriented directions. The tissue engaging elements 170 can be incorporated symmetrically around a circumference of the device 100, or in other embodiments, the tissue engaging elements 170 can be incorporated asymmetrically. For example, in some embodiments, the tissue engaging elements 170 can be present on a side of the device 100 aligned with the posterior leaflet, but absent or have a different arrangement on a side of the device 100 aligned with the anterior leaflet such that the wall separating the aortic valve from the left ventricle will not be affected by the tissue engaging elements 170.

Figure 40D:
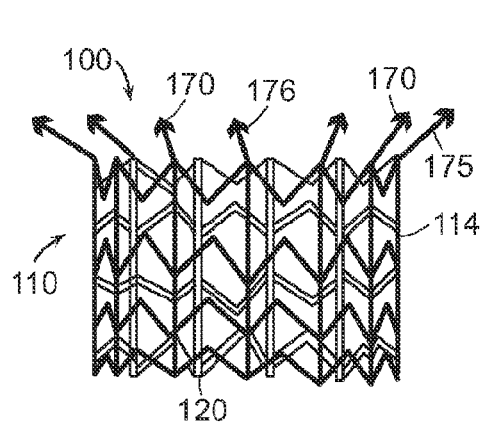
Figure 40E:
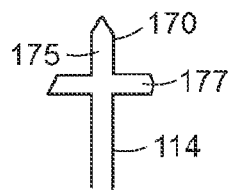
FIGS. 40E-40G are enlarged side views of tissue engaging elements suitable for use with prosthetic heart valve devices in accordance with other embodiments of the present technology.
Figure 40F:
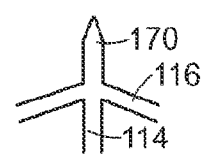
Figure 40G:
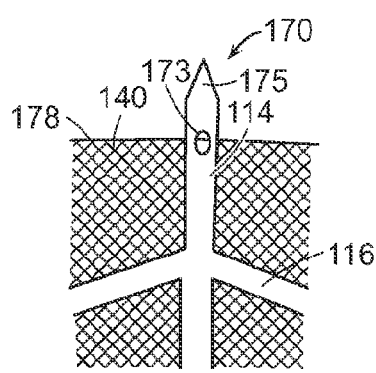
Figure 40T:
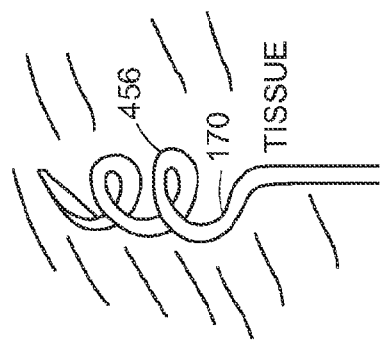
Figure 40S:
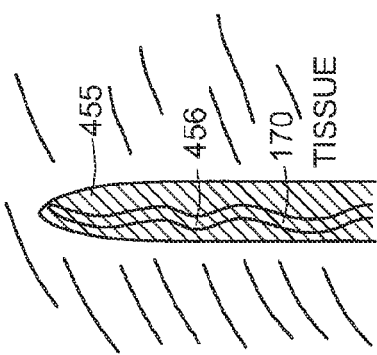

FIG. 40D illustrates an embodiment of the device 100 having tissue engaging elements 170, such as spikes on an upstream tip 175 of the rib 114, wherein the spikes can be configured to fully or partially penetrate subannular tissue when the device 100 is deployed on or under the annulus of the mitral valve. In some embodiments, the tissue engaging elements 170 (e.g., spikes) can include barbs 176 or other features for retaining the tissue engaging elements 170 (e.g., spikes) in the tissue. In other embodiments, the tissue engaging elements 170 (e.g., spikes) can be blunt so as to engage but not penetrate the subannular tissue. FIGS. 40E-40G are enlarged side views of tissue engaging elements 170 (e.g., spikes) suitable for use on upstream tips 175 of the ribs 114. Devices 100 having tissue engaging elements 170 on the upstream tips 175 can also incorporate features for limiting the distance of penetration into the tissue. For example, the upstream tip 175 can have a hilt 177 formed a short distance, e.g. 1-5 mm, proximal to the tip of each tissue engaging element 170 to limit the distance to which the tissue engaging element 170 can penetrate the subannular tissue (FIG. 40E). Alternatively, as shown in FIG. 40F, the depth penetration of the tissue engaging element 170 into the tissue can be limited by positioning connectors 116 a desired distance from the tips of the tissue engaging element 170. In a further embodiment shown in FIG. 40G, a sealing member 140 may be attached to the ribs 114 such that the upstream edge 178 of the sealing member 140 can limit the depth of penetration of the tissue engaging element 170. In order to prevent slippage of the sealing member 140 downward, an attachment feature such as a hole 173 configured to receive a suture may be formed in the rib 114 at the desired distance from its upstream tip 175 to which the sealing member 140 can be firmly secured.

Alternatively, tissue engaging elements 170, such as bumps, ridges, or other protrusions configured to exert frictional forces on cardiac tissue, may be also present on one or more valve support struts 124, valve support posts 122, and/or other components (e.g., sealing members 140). These tissue engaging elements 170 can be disposed on an outer portion of these features and can be configured to extend outwardly to engage the native leaflets and to stabilize and firmly anchor the device 100 in the desired location. Alternatively, ridges, scales, bristles, or other features having directionality may be formed on the surface of the ribs 114, connectors 116, or sealing member 140 to allow movement relative to native tissue in one direction, while limiting movement in the opposite direction.

The tissue engaging elements 170 on the anchoring member 110 can be barbs, spikes, or other retention features configured to have a delayed deployment so as to allow the device to be repositioned or removed for a period of time until these elements become fully deployed. For example, the tissue engaging element 170 may be constructed of a shape memory material (e.g., Nitinol) which is preshaped in a deployed configuration and adapted to retain the tissue engaging element 170 in the native tissue. The tissue engaging element 170 may be deformed into a contracted configuration which permits removal from tissue, and retained in this shape by a bioerodible material or adhesive. Once immersed in tissue, this material can erode over a period of time (e.g., 10 minutes-2 hours) allowing the tissue engaging element 170 to return to its unbiased deployed shape which will assist in retaining the tissue engaging element 170 in the tissue.

Several examples of such delayed, deployable tissue engaging elements 170 are shown in FIGS. 40I-40T. In the embodiment of FIG. 40I, the tissue engaging element 170 comprises a shape memory alloy shaft 450 laser cut so as to have a diamond-shaped window 451 near its distal tip 452, which can be sharp enough to penetrate tissue. The shape set so that window 451 is biased toward being open in an expanded configuration as shown in FIG. 40I. Prior to delivery of the device, window 451 may be pinched closed and a bioerodible glue 455 may be injected into window 451 to hold it in a closed configuration as shown in FIG. 40J. Upon deployment of the device, the distal tip 452 can penetrate the native tissue, e.g. valve leaflet or annulus, as shown in FIG. 40K. The glue 455 within window 451 maintains it in a closed configuration for a period of time to allow the operator to reposition or remove the device if necessary. If left in position, the glue 455 erodes, allowing the window 451 to reopen into the expanded configuration which will retain the tissue engaging element 170 in the tissue as shown in FIG. 40L.

In the embodiment shown in FIGS. 40M-40P, the tissue engaging element 170 comprises an arrowhead-shaped tip 453 having two or more wings 454 biased to be angled radially outward and pointing in a proximal direction as shown in FIG. 40M. A bioerodible glue or coating 455 is applied over the arrowhead tip 453 to hold the wings 454 in a radially contracted configuration as shown in FIG. 40N. In the contracted configuration, the device 100 is deployed such that the tissue engaging element 170 pierces the native tissue as shown in FIG. 40O. The bioerodible coating 455 then erodes gradually until it allows the wings 454 to return to the laterally expanded configuration shown in FIG. 40P, thus retaining the tissue engaging element 170 in the tissue.

Figure 40R:
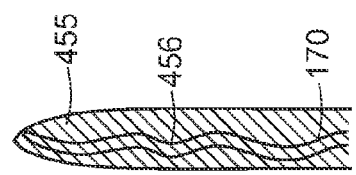
Figure 40Q:
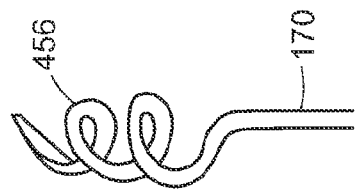

A further embodiment is shown in FIGS. 40Q-40T. In this embodiment, the tissue engaging element 170 comprises a helical tip 456 in an unbiased state. A bioerodible coating 455 may be used to retain the helical tip 456 in a straightened configuration as shown in FIG. 40R. The tissue engaging element 170 can penetrate the tissue in the contracted configuration, and when the bioerodible coating 455 erodes sufficiently to allow the helical tip 456 to return to its deployed configuration, the tissue engaging element 170 can be retained in the tissue.

Figure 41:
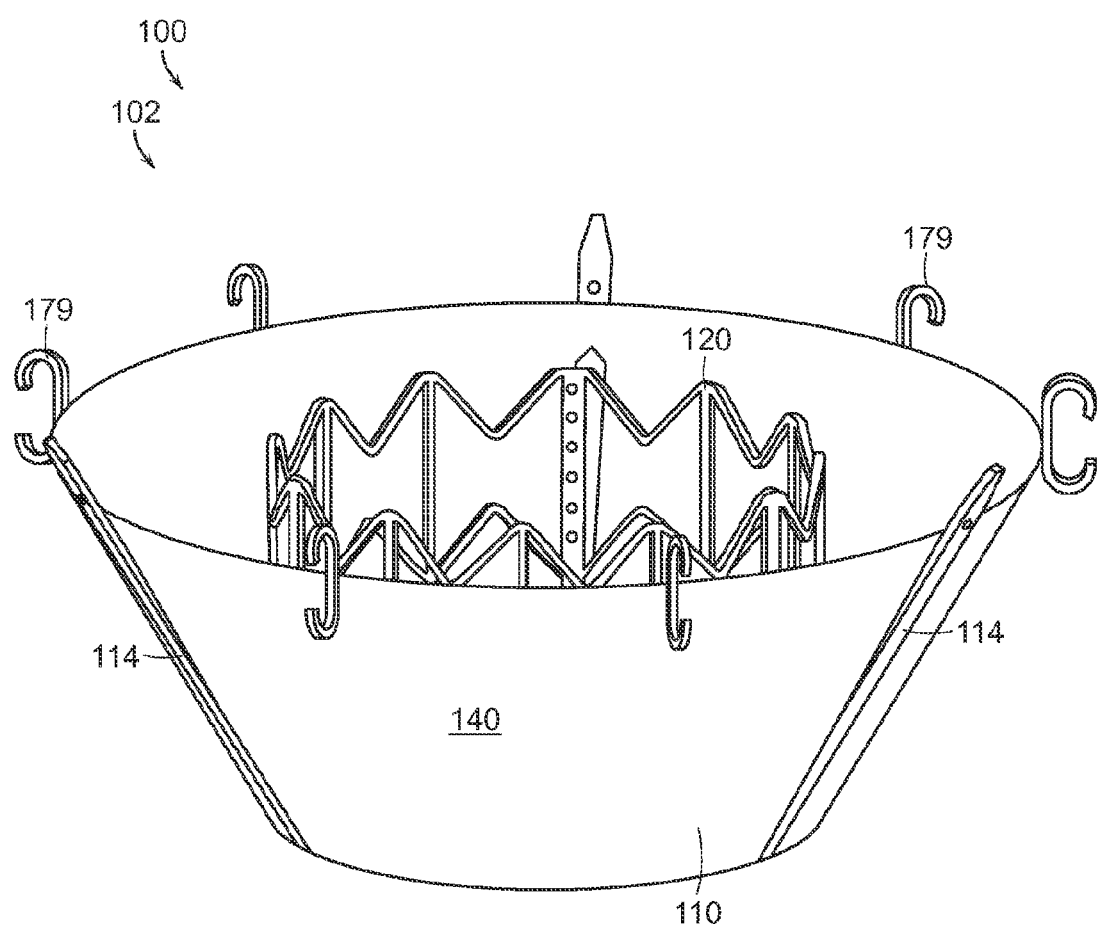
FIG. 41 is an isometric view of a prosthetic heart valve device having a plurality of annulus engaging elements in accordance with a further embodiment of the present technology.

The prosthetic heart valve device 100 can also be configured to have additional tissue engaging elements 170 for engaging the annulus. For example, FIG. 41 is an isometric view of a prosthetic heart valve device 100 having a plurality of annulus engaging elements 179 in accordance with a further embodiment of the present technology. The annulus engaging elements 179 can be a C-shaped hook feature or other shape that allows the element 179 to engage tissue on the annulus, as well as a portion of supra-annular tissue and subannular tissue. As shown, the annulus engaging elements 179 can be symmetrically (shown in FIG. 41) or asymmetrically interspersed around the upstream perimeter of the anchoring member 110 and coupled to ribs 114, connectors 116 (not shown), or to a sealing member 140. The annulus engaging elements 179 may also be coupled to the anchoring member 110 at other locations downstream of the upstream perimeter 113, or in other embodiments to a portion of the valve support 120 that extends through at least the annulus plane PO (FIG. 3). Additionally, the annulus engaging elements 179 may be blunt (e.g., for pressing but not penetrating into the annular tissue), or they may be sharp for penetrating the annulus tissue on either or both of the supra-annular or subannular surfaces. The annulus engaging element 179 can be suitable for both positioning the device 100 in the desired location (e.g., with anchoring member 110 below the annulus), as well as to inhibit movement of the device in either an upstream or downstream direction.

Figure 42A:
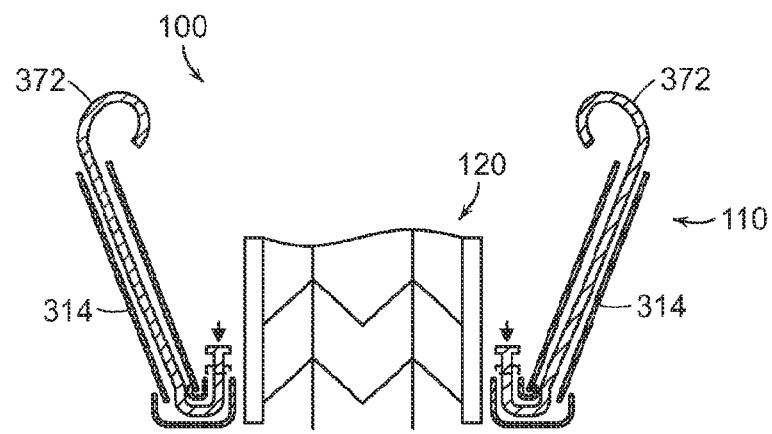
FIGS. 42A-42B are cross-sectional side and enlarged views of a prosthetic heart valve device having tissue engaging elements deployable from a plurality of tubular ribs in accordance with another embodiment of the present technology.
Figure 42B:
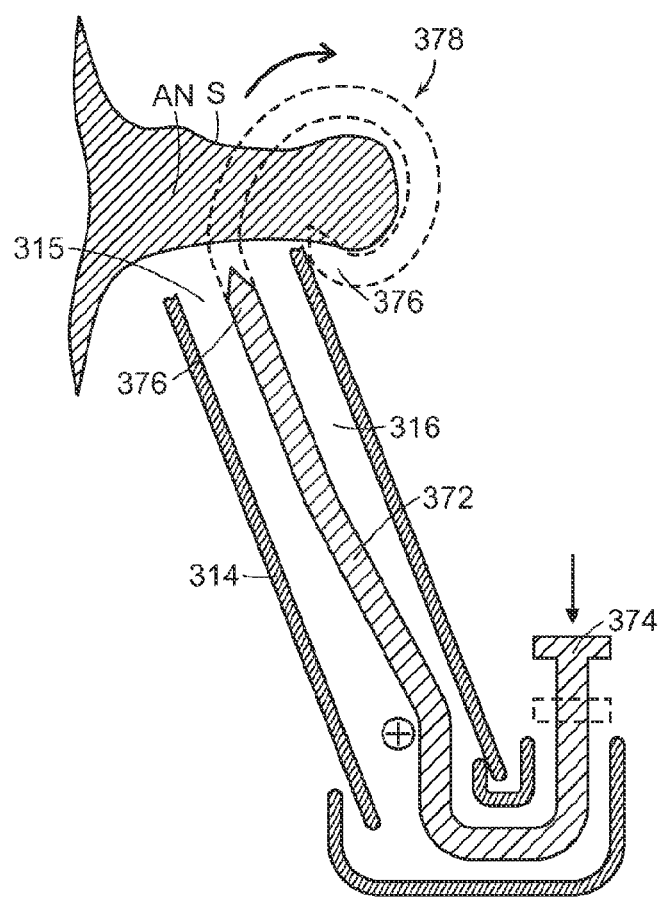

In another embodiment shown in FIGS. 42A-42B, a prosthetic heart valve device 100 can have tissue engaging elements 372 deployable from a plurality of tubular ribs 314. Referring to FIG. 42A, the prosthetic heart valve device 100 can have an anchoring member 110 having a plurality of tubular ribs 314 configured to retain a plurality of deployable tissue engaging elements 372. FIG. 42B is an enlarged view of the tubular rib 314 and a deployable tissue engaging element 372 retained within a lumen 316 of the rib 314 and shown before deployment of the element 372. The tissue engaging element 372 can comprise a shape memory material (e.g., Nitinol) configured to deploy to a preformed shape upon release of the tissue engaging element 372 from the inner lumen 316 of the rib 314. Release of the tissue engaging element 372 can be achieved by engaging a proximal end 374 of the tissue engaging element 372. For example, the proximal end 374 can be engaged during the deployment of the device 100 to release the tissue engaging element 372 after the anchoring member 110 is positioned at the desired location below the annulus AN. The tubular rib 314 can include a U-shaped deflector 318 and a pivot point 320 configured to guide the tissue engaging element 372 distally through a distal opening 315 of the rib 314. As illustrated in dotted lines in FIG. 42B, engagement of the proximal end 374 of element 372 will encourage a distal end 376 of the tissue engaging element 372 from the distal opening 315 of the tubular rib 314 to penetrate adjacent subannular tissue. Once deployed and after exiting an opposing surface S, such as the supra-annular surface, the tissue engaging element 372 can transition into its preformed shape, such as a curled shape 378 that can resist retraction of the distal end 376 from the tissue.

Figure 43A:
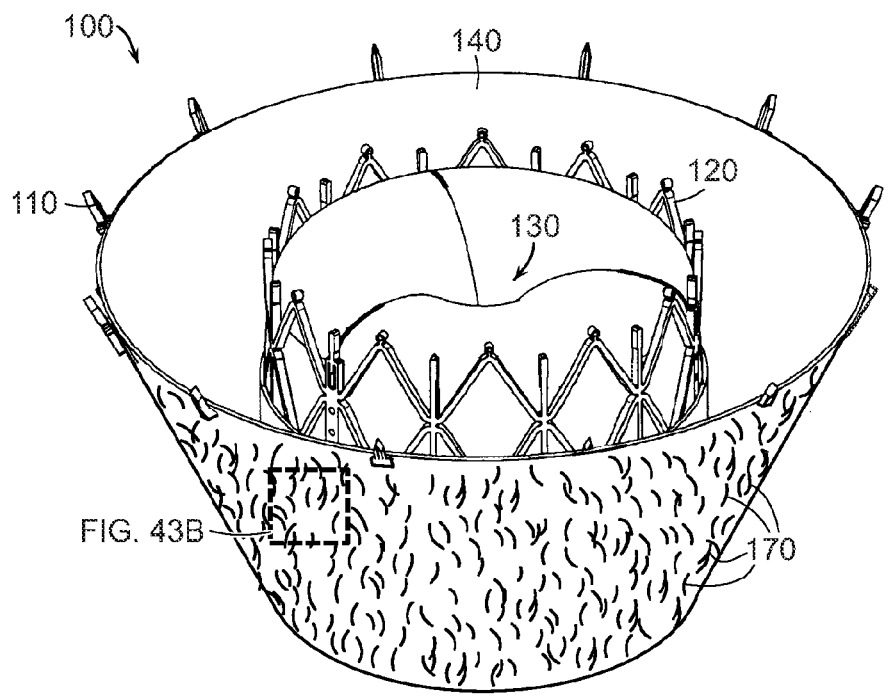
FIGS. 43A-43B are an isometric view and an enlarged detail view of a prosthetic heart valve device having a sealing member configured with tissue engaging elements in accordance with another embodiment of the present technology
Figure 43B:
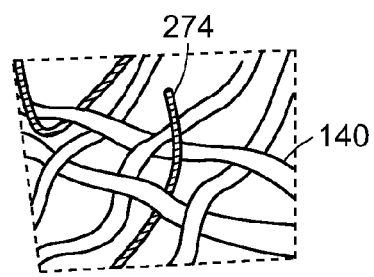

In accordance with another embodiment of the prosthetic treatment device 100, tissue engaging elements 170 can be incorporated into sealing members 140 (e.g., sleeve 146). FIGS. 43A-43B are an isometric view and an enlarged detail view of a prosthetic heart valve device 100 having a sealing member 140 configured with tissue engaging elements 170. Referring to FIGS. 43A-43B together, the tissue engaging elements 170 can comprise metallic or polymeric wires 274 or fibers, rigid and sharp enough to penetrate tissue, which are woven into or otherwise coupled to sealing member 140 materials. The sealing member 140 can then be attached to outer and/or inner walls 141, 142 of the anchoring member 110 and/or interior and/or exterior surfaces 126, 127 of the valve support 120 such that tissue engaging elements 170 extend radially outward from the sealing member 140 to engage the adjacent leaflets or other tissue.

Tissue engaging elements 170 may alternatively comprise an array of relatively short barbs, points, rods, tines, or similar protrusions configured to frictionally engage the tissue, or dent or slightly penetrate the surface of the tissue, to inhibit motion of the anchoring member 110 relative to the native leaflets or annulus. These tissue engaging elements, in exemplary embodiments, may be polymeric or metallic, about 0.2-5 mm in length, about 0.1-0.5 mm in diameter, flexible enough to deflect slightly in engagement with tissue, and distributed over the surface of the sealing member 140 in densities of 4-100 per square centimeter. The tissue engaging elements 170 may be integrally formed with the material of the sealing member 140, woven into such material, or formed in or mounted to a flexible sheet which is bonded, riveted, or otherwise fastened to the sealing member 140. The tissue engaging elements 170 may be angled, curved, or bent so as to point preferentially in a non-perpendicular direction, preferably in an upstream direction, to impart higher retention force against movement in the upstream direction while allowing movement more easily in the downstream direction. In some embodiments, the tissue engaging elements may be composed of a bioerodible material that lasts, following implantation, a sufficient time to allow tissue ingrowth or encapsulation to retain the device 100 in position. The tissue engaging elements 170, and/or the material of sealing member 140, may also be coated with a permanent or temporary friction-enhancing coating or adhesive that enhances retention at least until the device has been encapsulated in tissue sufficiently to prevent movement.

Figure 44A:
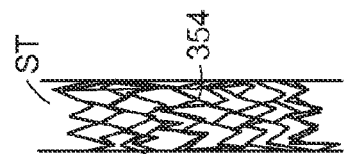
FIGS. 44A-44F are enlarged side views of embodiments of tissue engaging elements suitable for use with prosthetic heart valve devices in accordance with additional embodiments of the present technology.
Figures 44B, 44C:
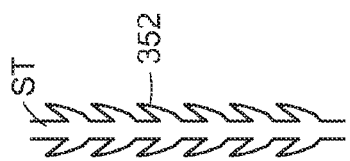
Figure 44D:
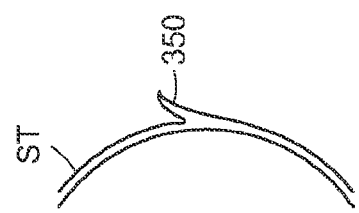
Figure 44E:
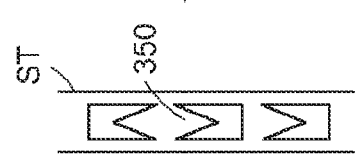
Figure 44F:
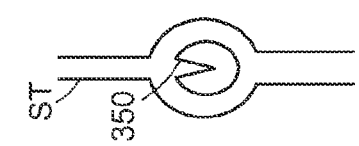

FIGS. 44A-44F are enlarged side views of embodiments of additional tissue engaging elements that can be incorporated on various device structures (referred collectively as "ST"), such struts, connectors, posts, arms, and/or ribs which may be incorporated into device features, such as the anchoring member 110 or valve support 120. For example, the additional tissue engaging elements may comprise one or more cut-out protrusions 350 (FIGS. 44A and 44B) in place of or in addition to tissue engaging elements 170. In a collapsed or straightened configuration, as shown by the side view of FIG. 44C, cut-out protrusion 350 maintains low relief relative to the surface of structure ST to maintain a low profile during delivery. As the device 100 expands and structure ST changes to its deployed configuration (e.g. a curvature as shown in FIG. 44D), the protrusion separates from the ST to a higher relief. The protrusion 350 may also be configured to grab subannular tissue, pulling the cut-out protrusions even farther away from structure ST. The device structures ST may also be shaped to include sharp protrusions 352 along one or more of its edges or faces, as illustrated in FIG. 44E, or may also include pointed scale-like protrusions 354, as shown in FIG. 44F.

Figure 45A:
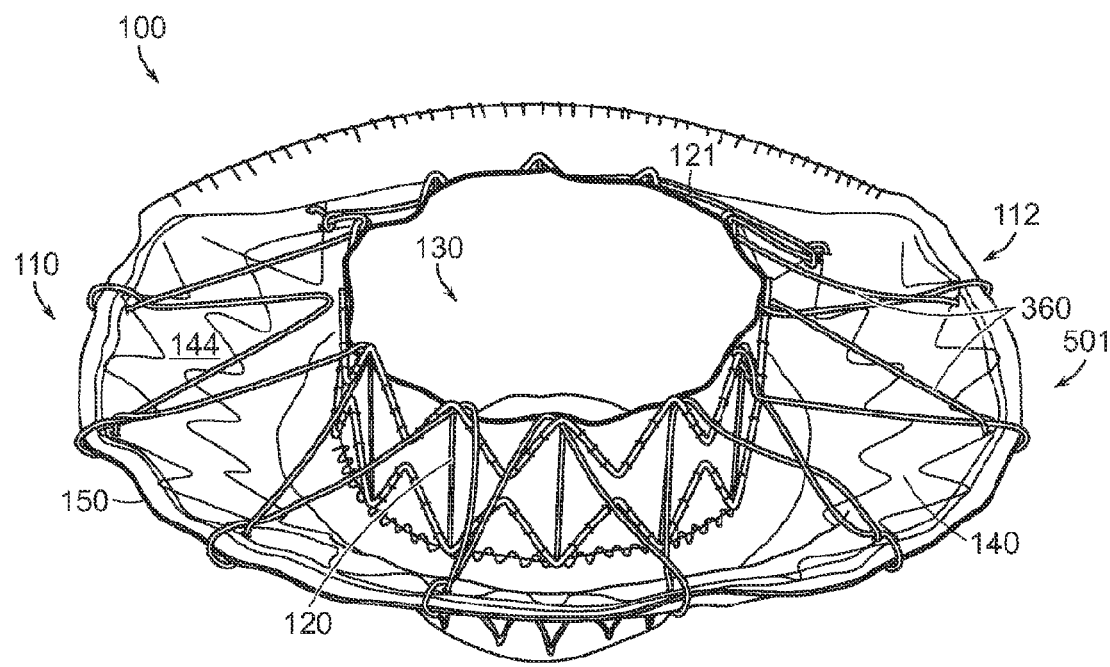
FIG. 45A is an isometric view of a prosthetic heart valve device having a plurality of tethers between the anchoring member 110 and the valve support 120 in accordance with an embodiment of the present technology.

In addition to the stabilizing members 501 described above, the prosthetic heart valve devices described herein (e.g., devices 100) may also include support features such as tethers 360 and sealing member septa 370 for stabilizing the anchoring member 110 and/or the valve support 120, and/or for spreading pressure gradient loads evenly over a greater area of the device 100 (e.g., during ventricular systole). Referring to FIG. 45A, one example of the device 100 can incorporate a plurality of tethers 360 at least loosely coupling the upper portion 112 of the anchoring member 110 to the upstream end 121 of the valve support 120. In one embodiment, the tethers 360 can include a single suture that is run continuously around the circumference 150 of the anchoring member 110. In another embodiment, the device 100 can include several sutures of discreet lengths tied between the anchoring member 110 and the valve support 120. In one embodiment the tethers can be a suture comprising polytetrafluoroethylene (PTFE). Generally, the tethers 360 assist in distributing forces evenly along the anchoring member 110 without deforming the valve support 120 or compromising the closure of the prosthetic valve 130. In some arrangements, the tethers 360 can assist in limiting radial expansion of the upstream portion. Accordingly, even with the incorporation of the tethers 360, the valve support 120 remains mechanically isolated from at least the upstream portion of the anchoring member 110.

Figure 45B:
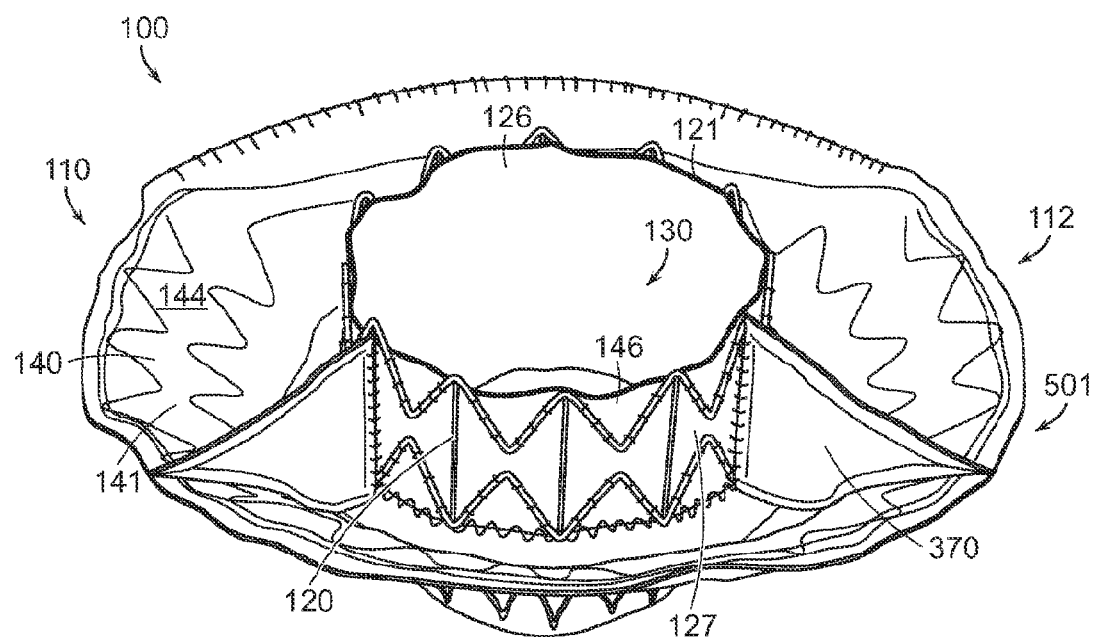
FIG. 45B is an isometric view of a prosthetic heart valve device having a plurality of septa between the anchoring member 110 and the valve support 120 in accordance with another embodiment of the present technology.

FIG. 45B shows another example of a stabilizing member 501 suitable to stabilize the anchoring member 110 and/or the valve support 120, and/or for spreading pressure gradient loads evenly over a greater area of the device 100 (e.g., during ventricular systole). As shown in FIG. 45B, the device 100 can include a plurality of sealing member septa 370 extending between the anchoring member 110 and the valve support 120. In the illustrated embodiment, the septa 370 can be extensions of the sealing member material configured to span between a sealing member 140, such as a skirt 144, coupled to the inner wall 141 of the anchoring member 110 and a sealing member 140, such as a sleeve 146, coupled to an interior or exterior surface 126, 127 of the valve support 120. Accordingly, the septa 370 can be formed of fabric or other flexible and biocompatible materials such as Dacron®, ePTFE, bovine pericardium, or other suitable materials. Similar to the embodiment illustrated in FIG. 45A, the septa 370 can assist in distributing forces evenly along the anchoring member 110 without deforming the valve support 120 or otherwise compromising the closure of the prosthetic valve 130. In some arrangements, the septa 370 can assist in preventing the device 100 from everting during ventricular systole. Accordingly, even with the incorporation of the septa 370, the valve support 120 is mechanically isolated from at least the upstream portion of the anchoring member 110.

Each of the elements and members of the device 100 may be made from any number of suitable biocompatible materials, e.g., stainless steel, nickel titanium alloys such as Nitinol™, cobalt chromium alloys such as MP35N, other alloys such as ELGILOY® (Elgin, Ill.), various polymers, pyrolytic carbon, silicone, polytetrafluoroethylene (PTFE), or any number of other materials or combination of materials depending upon the desired results. The arm members 510, sealing member 140, sleeves 146, anchoring member 110 and/or valve support 120 or other elements of device 100 may also be coated or covered with a material that promotes tissue in-growth (e.g., Dacron®, PTFE, etc.)

Delivery Systems

FIGS. 46A-46D illustrate one embodiment of a delivery system 10 suitable for delivery of the prosthetic heart valve devices disclosed herein. As used in reference to the delivery system, "distal" refers to a position having a distance farther from a handle of the delivery system 10 along the longitudinal axis of the system 10, and "proximal" refers to a position having a distance closer to the handle of the delivery system 10 along the longitudinal axis of the system 10.

Figure 46A:
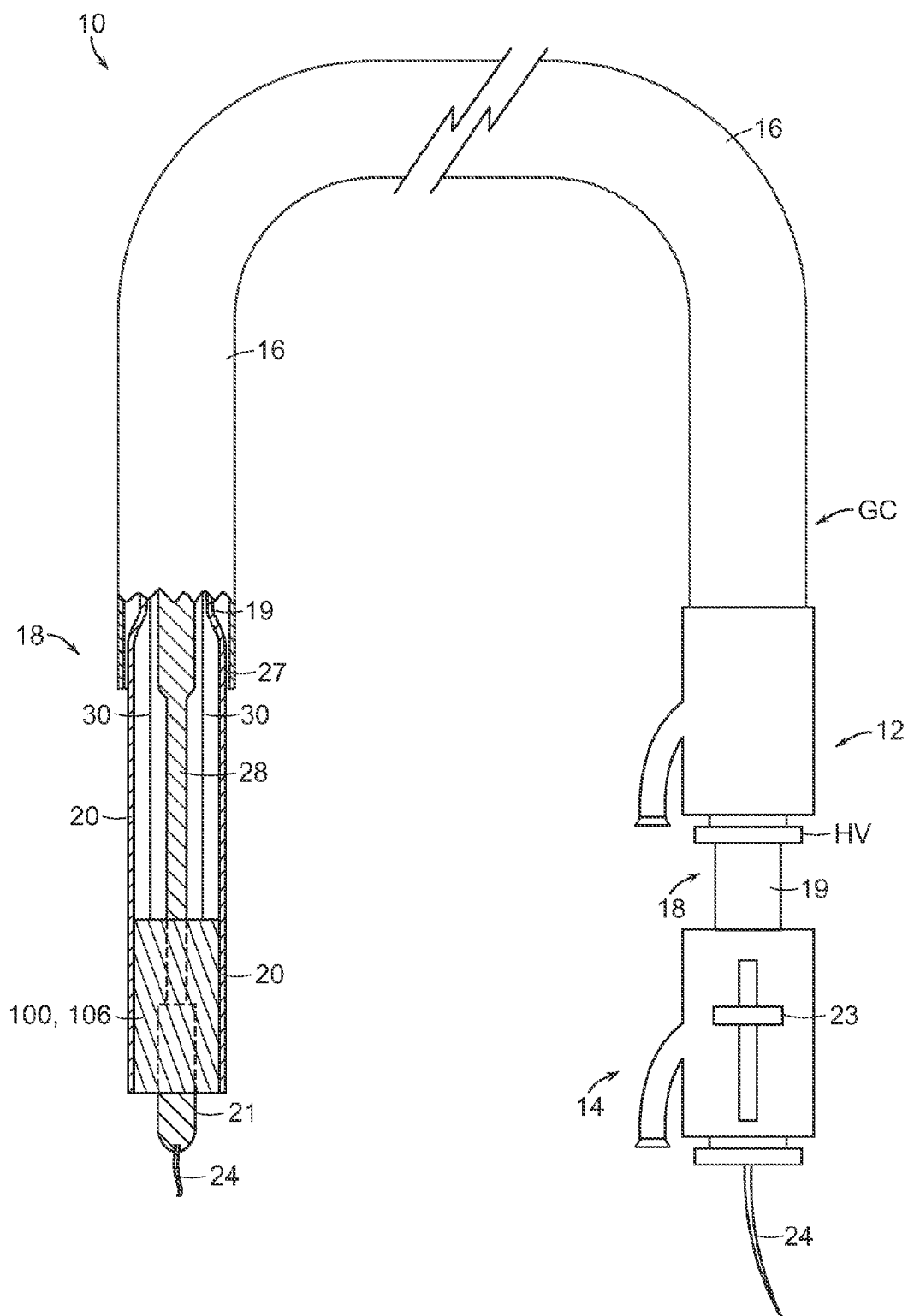
FIG. 46A is side partial cut-away view of a delivery system in accordance with an embodiment of the present technology.

FIG. 46A illustrates one embodiment of the delivery system 10 which may be used to deliver and deploy the embodiments of the prosthetic heart valve device 100 disclosed herein through the vasculature and to the heart of a patient. The delivery system 10 may optionally include a guiding catheter GC having a handle 12 coupled to a delivery shaft 16, which in one embodiment is 34 F or less, and in another embodiment, 28 F or less in diameter. The guiding catheter GC may be steerable or preshaped in a configuration suitable for the particular approach to the target valve. The delivery catheter 18 is placed through a hemostasis valve HV on the proximal end of guiding catheter GC and includes a flexible tubular outer shaft 19 extending to a delivery sheath 20 in which the device 100 is positioned in a collapsed or delivery configuration 106. A flexible inner shaft 28 is positioned slideably within outer shaft 19 and extends through the device 100 to a nosecone 21 at the distal end. The inner shaft 28 has a guidewire lumen through which a guidewire 24 may be slideably positioned. The device 100 is coupled to the inner shaft 28 and is releasable from the inner shaft 28 by release wires 30, as more fully described below. The delivery sheath 20 can protect and secure the device 100 in its collapsed configuration 106 during delivery. The outer shaft 20 is coupled to a retraction mechanism 23 on the handle 14 of the delivery catheter 18. Various retraction mechanisms 23 may be used, such as an axially-slidable lever, a rotatable rack and pinion gear, or other known mechanisms. In this way, the outer shaft 20 may be retracted relative to the inner shaft 28 to release (e.g., deploy) the device 100 from the sheath 20.

Figure 46B:
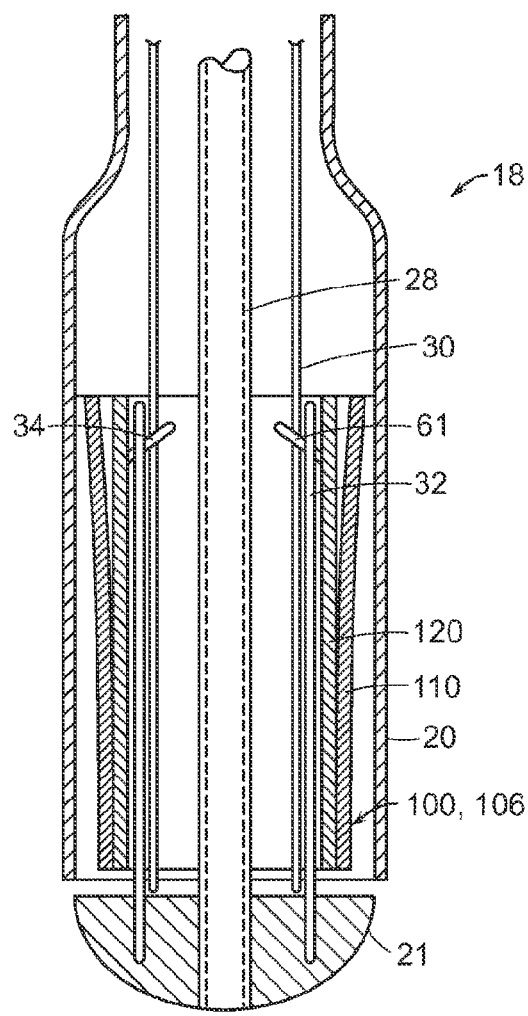
FIG. 46B is an enlarged cross-sectional view of a distal end of a delivery system in accordance with an embodiment of the present technology.
Figure 46C:
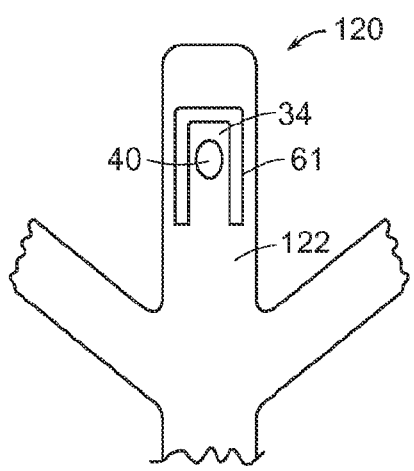
FIGS. 46C-46D are enlarged partial side views of a valve support configured for use with the delivery system of FIG. 46B in accordance with an embodiment of the present technology.
Figure 46D:
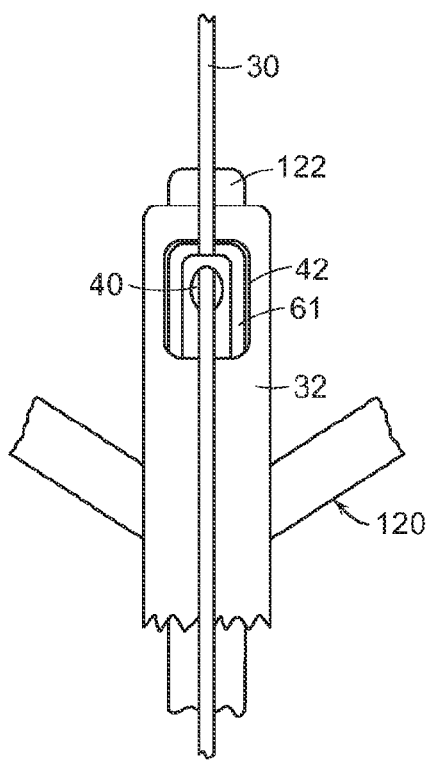

FIG. 46B shows the distal end of the delivery catheter 18 with the sheath 20 cut away to illustrate the coupling of the device 100 to the inner shaft 28. A plurality of locking fingers 32 are coupled to the nose cone 21 and extend proximally through the interior of the valve support 120 of the device 100. As shown in FIG. 46C, a selected number of posts 122 of the valve support 120 have a coupling element 61 comprising a tab 34 cut out from each post 122 at a proximal end thereof. The tab 34 may be deflected inwardly from the post 122 as shown in FIG. 46B and is configured to extend through a window 42 in the locking finger 32 as shown in FIG. 46D. The release wires 30 pass through the holes 40 in the tabs 34, which prevents the tabs 34 from being withdrawn from the windows 42 to secure the device 100 to the inner shaft 28. The pull-wires 30 can be sandwiched tightly between the tabs 34 and the locking fingers 32, such that friction temporarily prevents the pull-wire 30 from slipping in a proximal or distal direction. In this way, the sheath 20 may be retracted relative to the device 100 to permit expansion of the device 100 while the inner shaft 28 maintains the longitudinal position of the device 100 relative to the anatomy. The pull-wires 30 may extend proximally to the handle 14, for example, in between the inner shaft 28 and the outer shaft 19 or within one or more designated lumens. A suitable mechanism (not shown) on the handle 14 can allow the operator to retract the release wires 30 in a proximal direction until they are disengaged from the tabs 34. Accordingly, the device 100 can be released from the locking fingers 32 and expand for deployment at the target site.

Figures 47A, 47B:
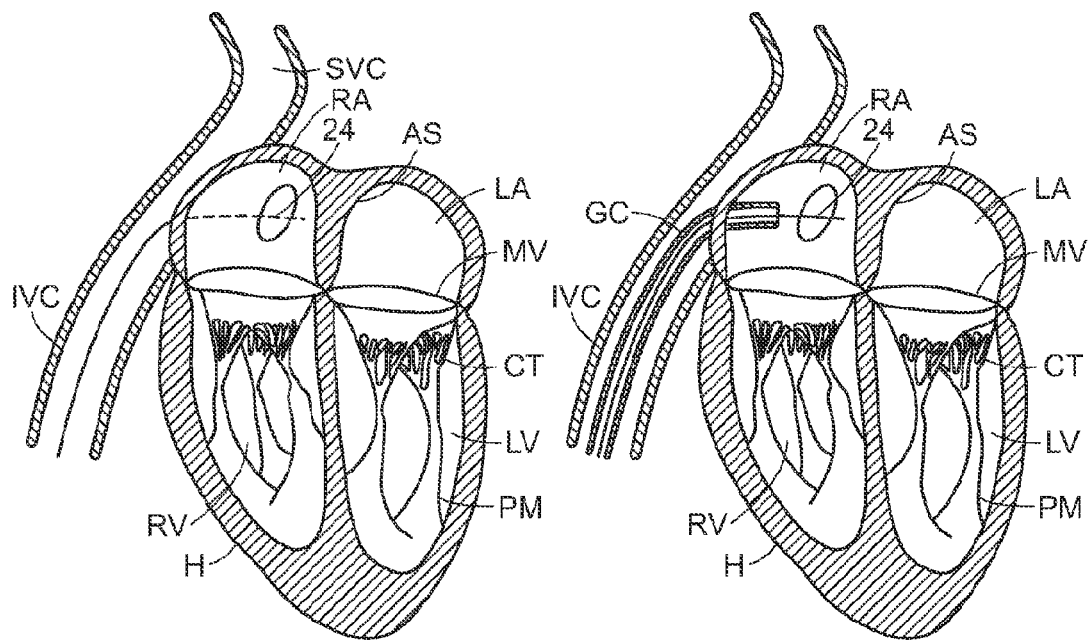
FIGS. 47A-47D are cross-sectional views of a heart showing an antegrade or trans-septal approach to the mitral valve in accordance with an embodiment of the present technology.
Figures 47C, 47D:
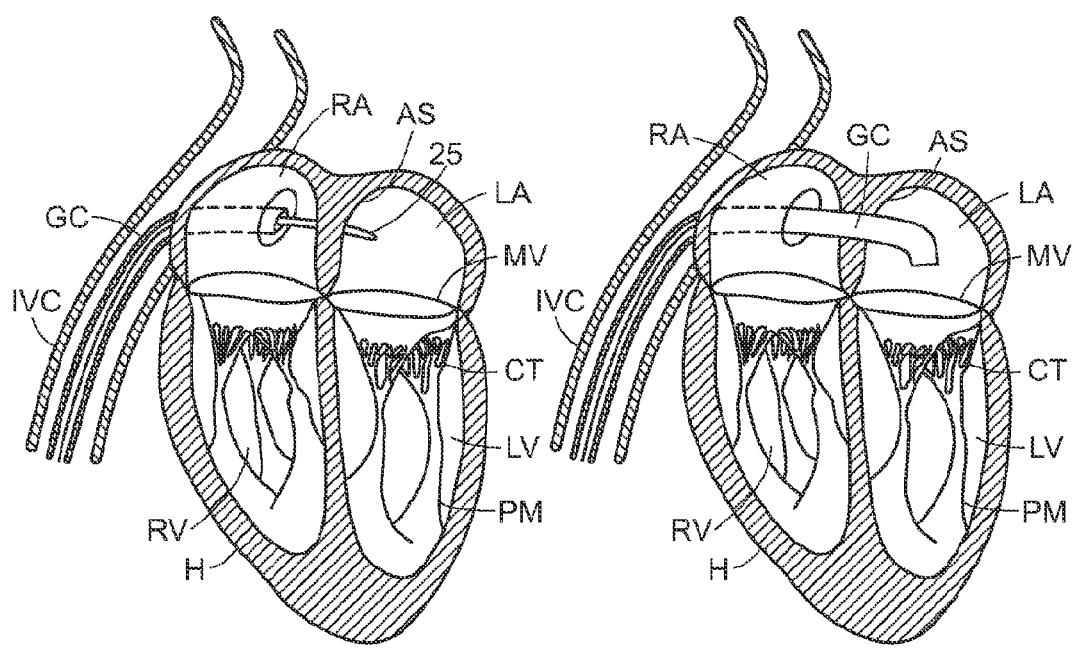

FIGS. 47A-47D are schematic, cross-sectional side views of a heart H showing a trans-septal or antegrade approach for delivering and deploying a prosthetic heart valve device 100. As shown in FIG. 47A, a guidewire 24 may be advanced intravascularly using any number of techniques, e.g., through the inferior vena cava IVC or superior vena cava SVC, through the inter-atrial septum IAS and into the right atrium RA. The guiding catheter GC may be advanced along the guidewire 24 and into the right atrium RA until reaching the anterior side of the atrial septum AS, as shown in FIG. 47B. At this point, the guidewire 24 may be exchanged for the needle 25, which is used to penetrate through the inter-atrial septum IAS (FIG. 47C). The guiding catheter GC may then be advanced over the needle 25 into the left atrium LA, as shown in FIG. 47D. The guiding catheter GC may have a pre-shaped or steerable distal end to shape or steer the guiding catheter GC such that it will direct the delivery catheter 18 (FIG. 46A) toward the mitral valve.

As an alternative to the trans-septal approach, the mitral valve may also be accessed directly through an incision in the left atrium. Access to the heart may be obtained through an intercostal incision in the chest without removing ribs, and a guiding catheter may be placed into the left atrium through an atrial incision sealed with a purse-string suture. A delivery catheter may then be advanced through the guiding catheter to the mitral valve. Alternatively, the delivery catheter may be placed directly through an atrial incision without the use of a guiding catheter.

Figure 48B:
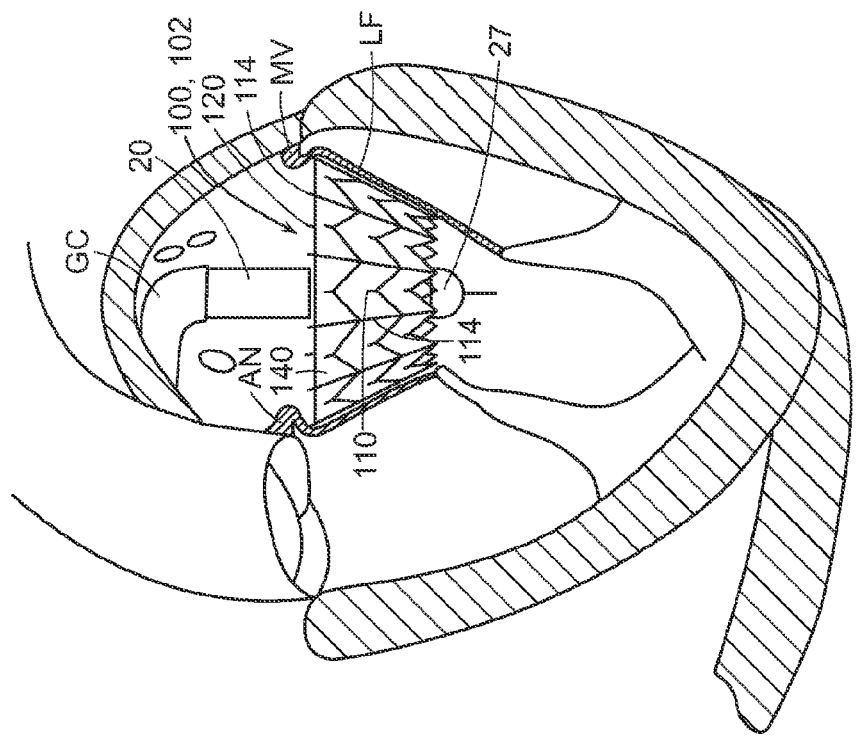
FIGS. 48A-48C are cross-sectional views of the heart illustrating a method of implanting a prosthetic heart valve device using a trans-septal approach in accordance with another embodiment of the present technology.
Figure 48A:
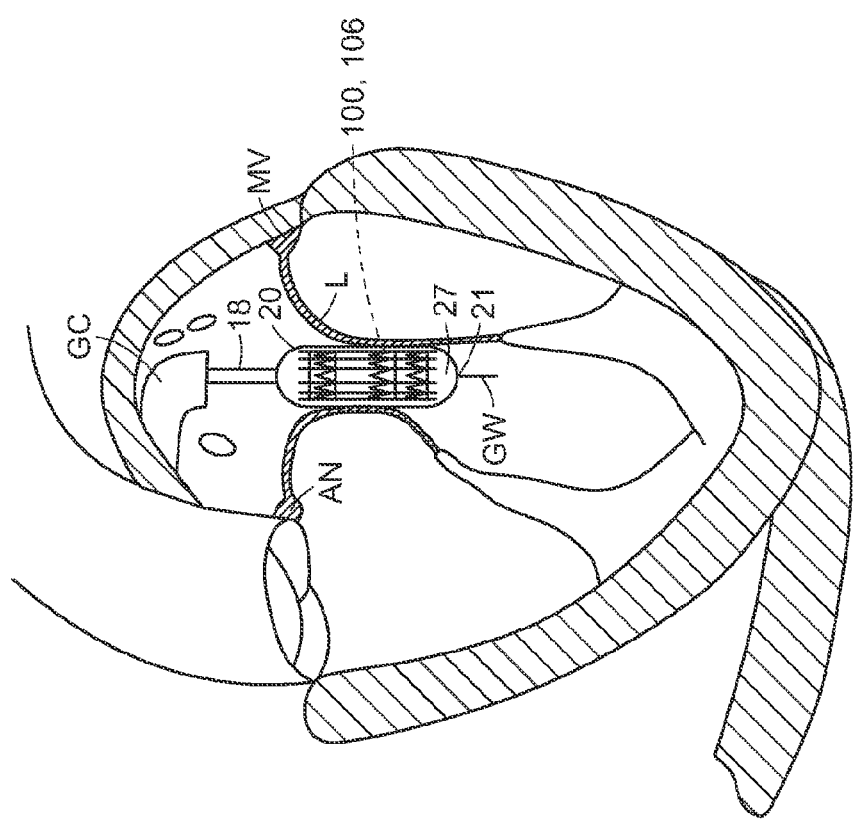
Figure 48C:
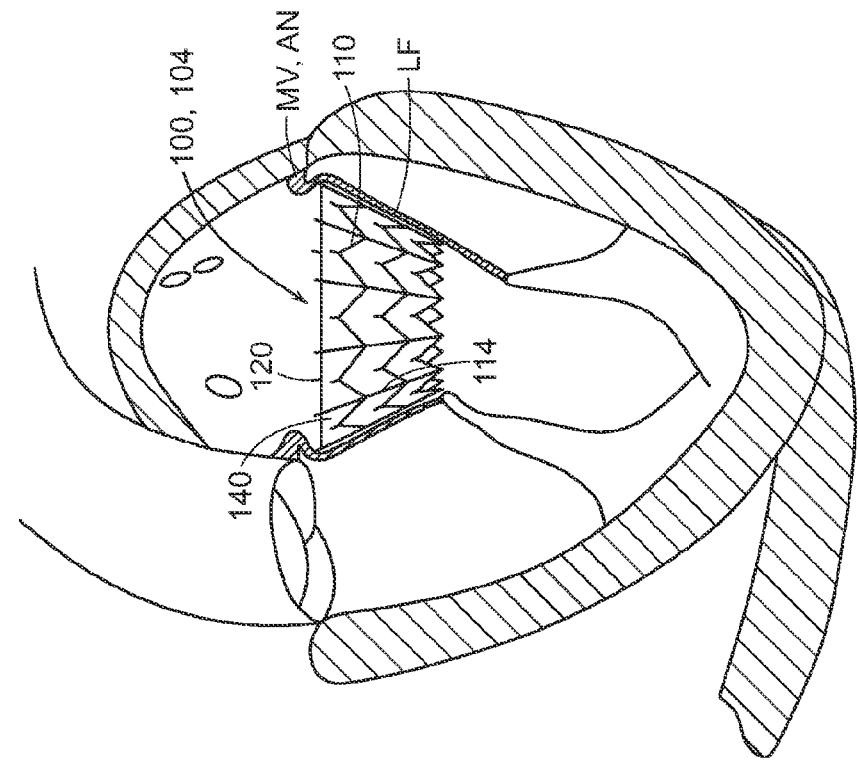

FIGS. 48A-48C are cross-sectional views of the heart illustrating a method of implanting a prosthetic heart valve device 100 using a trans-septal approach. Referring to FIGS. 48A-48C together, the distal end 21 of the delivery catheter 18 may be advanced into proximity to the mitral valve MV. Optionally, and as shown in FIG. 48A, a guidewire GW may be used over which catheter 18 may be slideably advanced over a guidewire GW. The sheath 20 of the delivery catheter 18, which contains the device 100 in a collapsed configuration 106, is advanced through the mitral valve annulus AN between native leaflets LF, as shown in FIG. 48A. Referring to FIG. 48B, the sheath 20 is then pulled back proximally relative to the distal nose cone 27 allowing the device 100 to expand such that anchoring member 110 pushes the leaflets LF outwardly to fold beneath the mitral valve annulus AN. The tips of the ribs 114 engage and may penetrate into or through the leaflet tissue to further engage the tissue of the annulus AN. After the sheath 20 has been removed and the device 100 allowed to expand, the delivery system can still be connected to the device 100 (e.g., system eyelets, not shown, are connected to the device eyelets 180, shown in FIG. 10A) so that the operator can further control the placement of the device 100 in the expanded configuration 102. For example, the device 100 may be expanded upstream or downstream of the target location then pushed downstream or upstream, respectively, into the desired target location before releasing the device 100 from delivery system 10. Once the device 100 is positioned at the target site, the pull-wires 30 (FIGS. 46A-46B) may be retracted in a proximal direction, to detach the device 100 in the deployed configuration 104 from the delivery catheter 18. The delivery catheter 18 can then be removed as shown in FIG. 48C. Alternatively, the device 100 may not be connected to the delivery system 10 such that the device 100 deploys and is fully released from the delivery system 10.

Figure 49B:
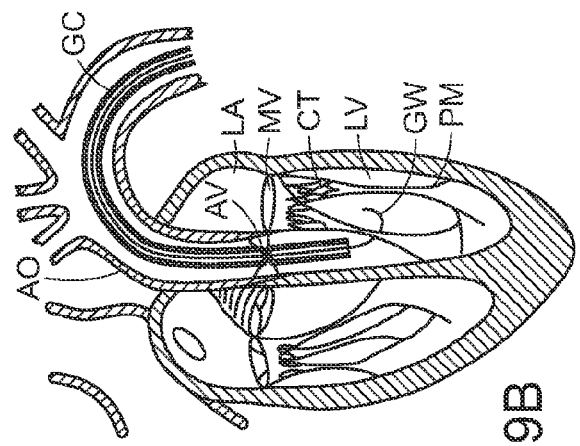
FIGS. 49A-49B are cross-sectional views of the heart showing a retrograde approach to the mitral valve via the aorta and left ventricle in accordance with a further embodiment of the present technology.
Figure 49A:
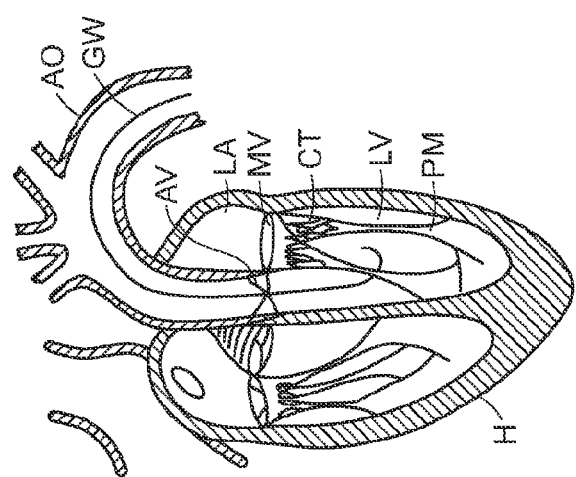

FIGS. 49A and 49B illustrate another variation for delivering and deploying one or more prosthetic heart valve devices 100 using a retrograde approach to the mitral valve via the aorta and left ventricle. In this example, the guidewire GW may be advanced intravascularly from a femoral or radial artery or through direct aortic puncture through the aorta AO and aortic valve AV, and into the left ventricle LV of the heart H (FIG. 49A). A guiding catheter GC, or alternatively, the delivery catheter 18, may be advanced along the guidewire GW until the distal end is positioned within the left ventricle in proximity to the mitral valve MV, as shown in FIGS. 49A and 49B. In many arrangements, the guiding catheter GC and/or the delivery catheter 18 will have a steering mechanism or a pre-shaped distal tip allowing it to be steered around the 180° turn from the aortic valve AV to the mitral valve MV. The distal end of the delivery catheter 18 may optionally be advanced at least partially through the mitral valve MV into the left atrium LA.

Figure 50B:
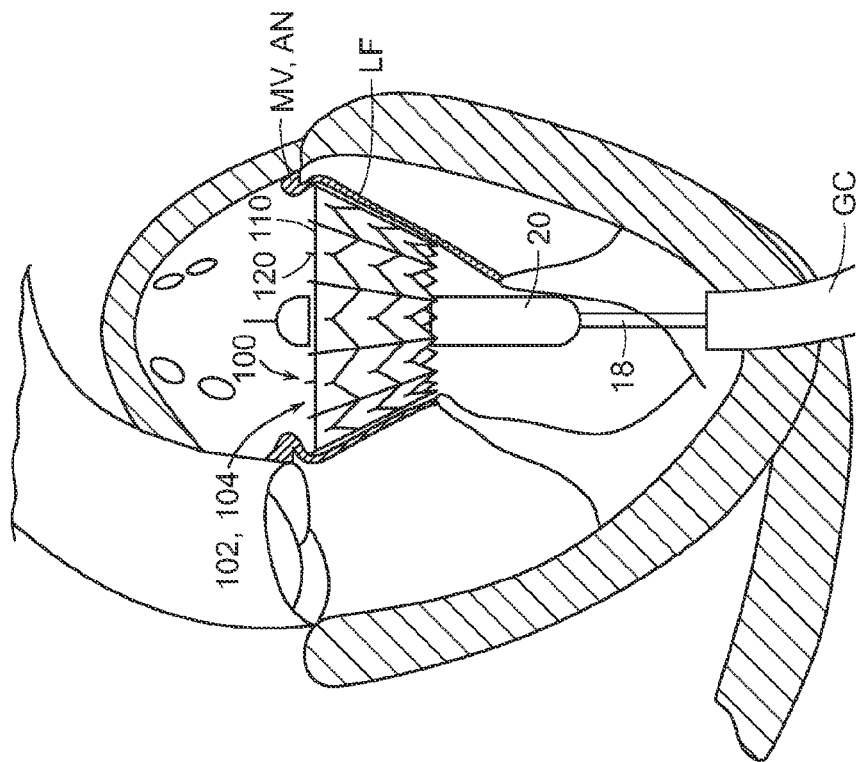
FIGS. 50A-50B are cross-sectional views of the heart illustrating a further embodiment of a method of implanting the prosthetic heart valve device using a trans-apical approach in accordance with aspects of the present technology.
Figure 50A:
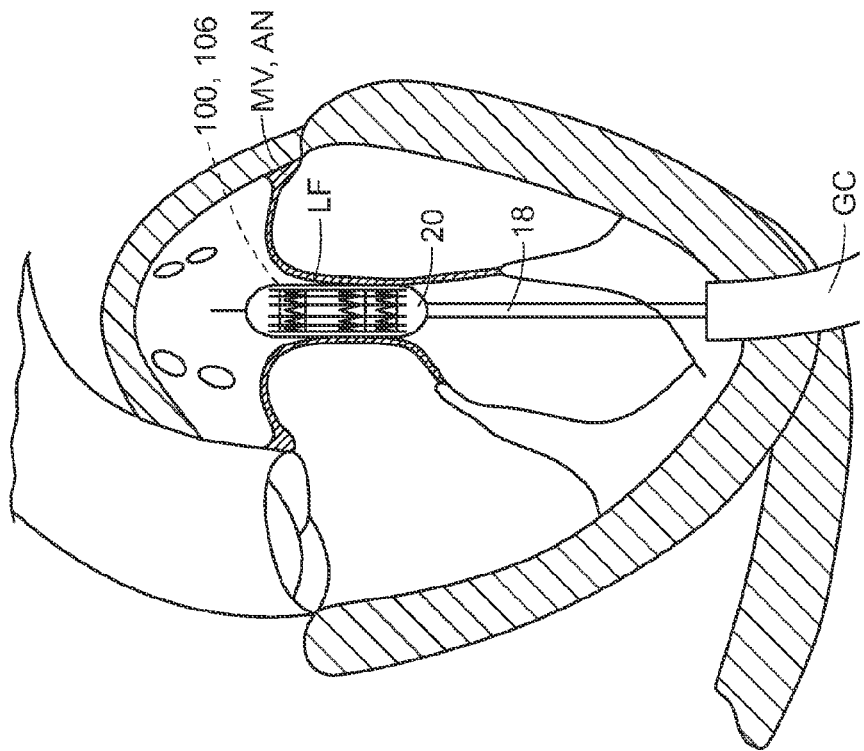

FIGS. 50A-50B illustrate delivery of the device 100 in the collapsed configuration 106 to the mitral valve MV in a trans-apical approach. Referring to FIG. 50A, the delivery catheter 18 is advanced through a guiding catheter GC that has been inserted into the left ventricle of the heart through a puncture in the left ventricle wall at or near the apex of the heart. The catheter can be sealed by a purse-string suture. Alternatively, the delivery catheter 18 may be placed directly through a purse-string-sealed trans-apical incision without a guiding catheter. The sheath 20 and the device 100 (e.g., in the collapsed configuration 106) within the sheath 20 are advanced through the mitral annulus AN between native leaflets LF as shown in FIG. 50A. Referring to FIG. 50B, the sheath 20 is pulled proximally such that the device 100 expands to the expanded and/or deployed configurations 102, 104. The delivery system 10 can remain connected to the device 100 (e.g., system eyelets, not shown, are connected to the device eyelets 180, FIG. 10A) after removing the sheath 20 so that the operator can control the placement of the device 100 while in the expanded configuration 102. The pull-wires 30 may be retracted in a proximal direction to release the device 100 from the delivery system 10, allowing the delivery system 10 to be removed and the device to be fully implanted at the mitral valve MV in the deployed configuration 104. In one embodiment, the device 100 may be expanded upstream or downstream of the desired target location then pulled or pushed downstream or upstream, respectively, into the target location before releasing the device 100 from delivery system 10. Alternatively, the device 100 may not be connected to the delivery system 10 such that the device 100 deploys and is fully released from the delivery system 10.

Figure 51A:
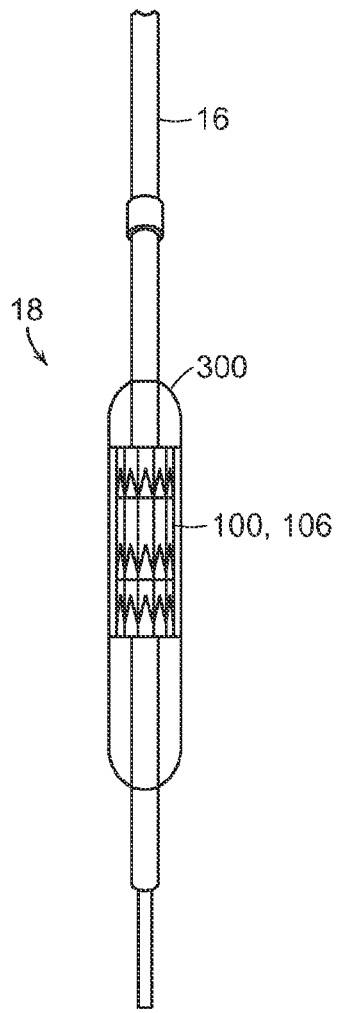
FIGS. 51A-51B are partial side views of a delivery system wherein a prosthetic heart valve device is mounted on an expandable balloon of a delivery catheter in accordance with another embodiment of the present technology.
Figure 51B:
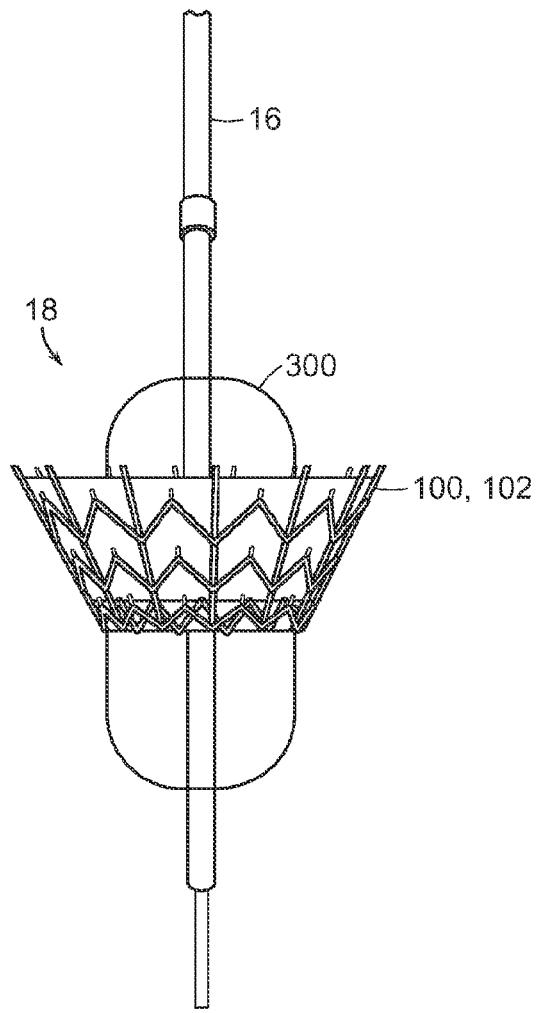

FIGS. 51A-51B are partial side views of a delivery system 10 wherein a prosthetic heart valve device 100 is mounted on an expandable balloon 300 of a delivery catheter 18 in accordance with another embodiment of the present technology. Referring to FIGS. 51A and 51B together, the device 100 can be mounted on an expandable balloon 300 of a delivery catheter while in a collapsed configuration 106 and delivered to the desired location at or near a native mitral valve (FIG. 51A). When the device 100 is released from the sheath 20 (FIGS. 46A-46B), the device 100 can be expanded to its expanded configuration 102 by inflation of the balloon 300 (FIG. 51B). When using a balloon 300 with the delivery system 10, the device 100 can be advanced from the delivery shaft 16 to initially position the device 100 in a target location. The balloon 300 can be inflated to fully expand the device 100. The position of the device 100 relative to the mitral valve may then be adjusted using the device locking hub to position the device into desired implantation site (e.g., just below the annulus of the native mitral valve). In another embodiment, the balloon 300 can initially be partially inflated to partially expand the device 100 in the left atrium. The delivery system 10 can then be adjusted to push or pull (depending on the approach) the partially expanded heart valve device 100 into the implantation site, after which the device 100 can be fully expanded to its functional size. In other alternative methods, the anchoring member 110 is a self-expanding construct which is first released from a sheath 20 (FIGS. 46A-46B) at the target site to engage the native anatomy, while the valve support 120 is a balloon-expandable element mounted on a balloon 300 which is then expanded to fully deploy the valve support 120 after the anchoring member 110 has been released.

Figure 52B:
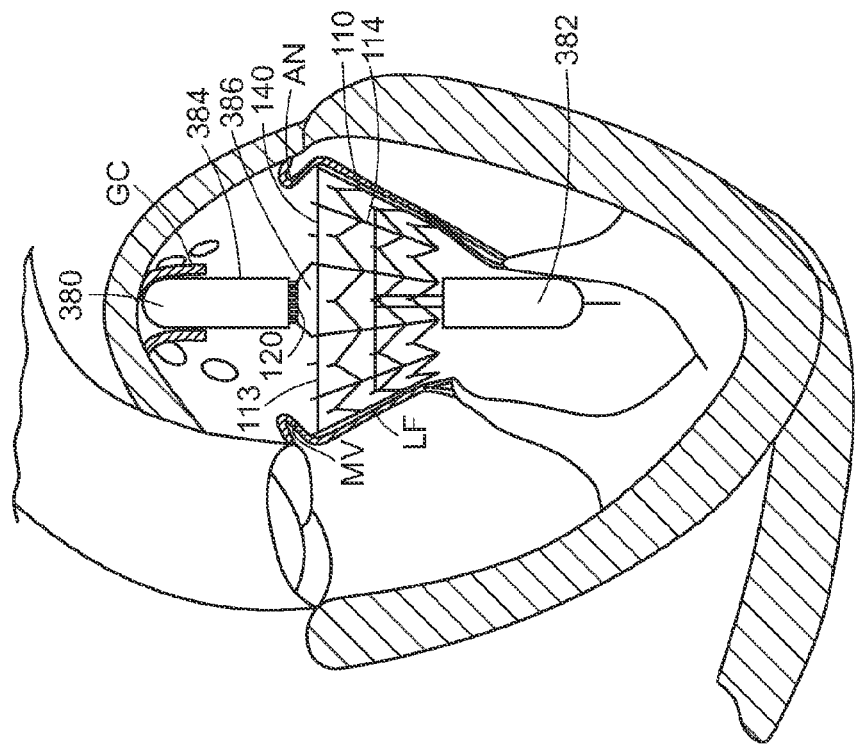
FIGS. 52A-52D are cross-sectional views of a heart showing a method of delivering a prosthetic heart valve device having a valve support movably coupled to an anchoring member in accordance with a further embodiment of the present technology.
Figure 52A:
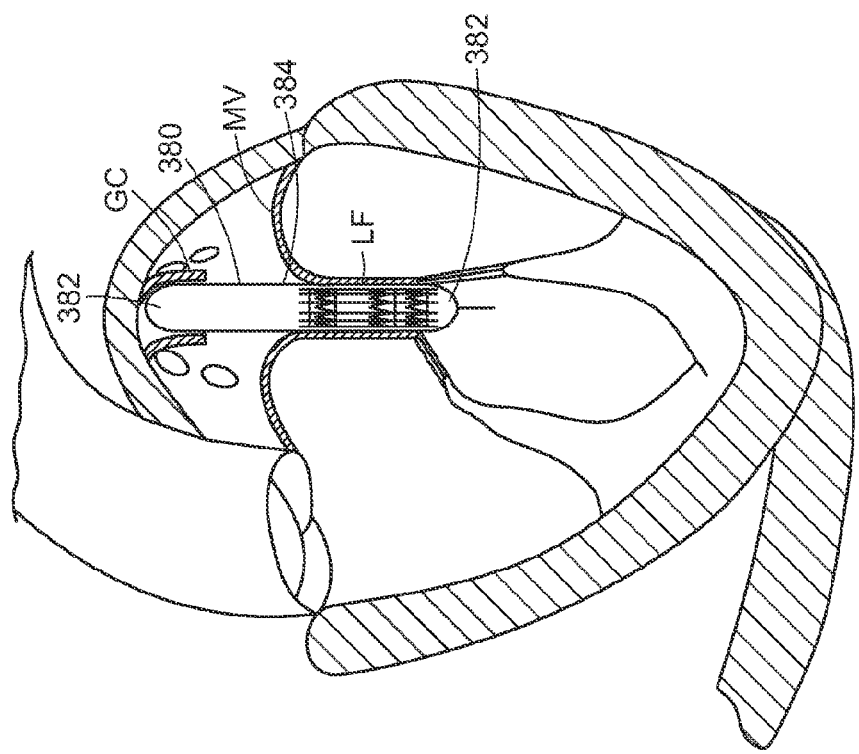
Figure 52C:
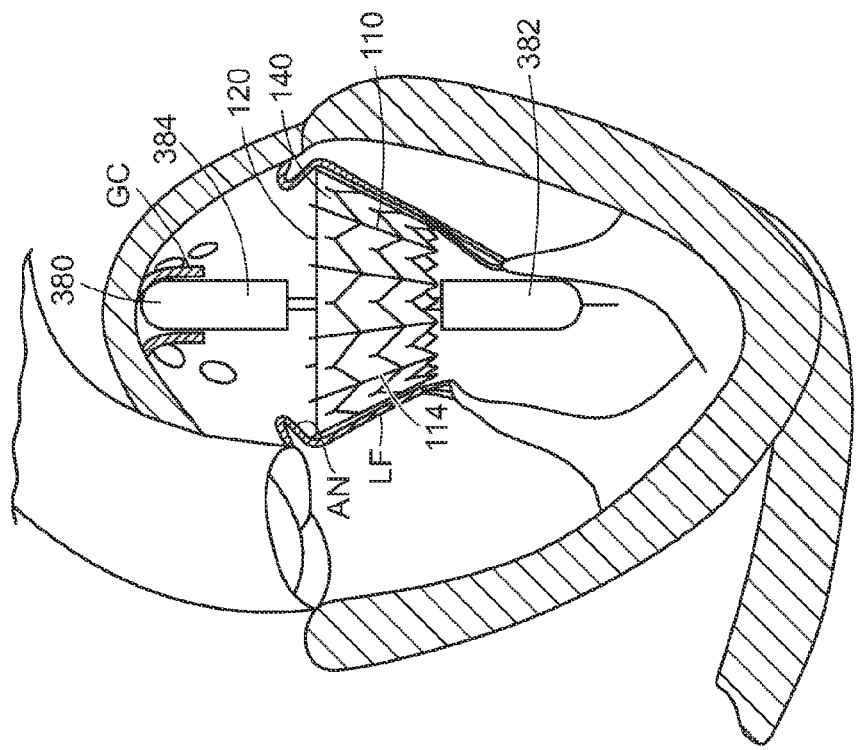
Figure 52D:
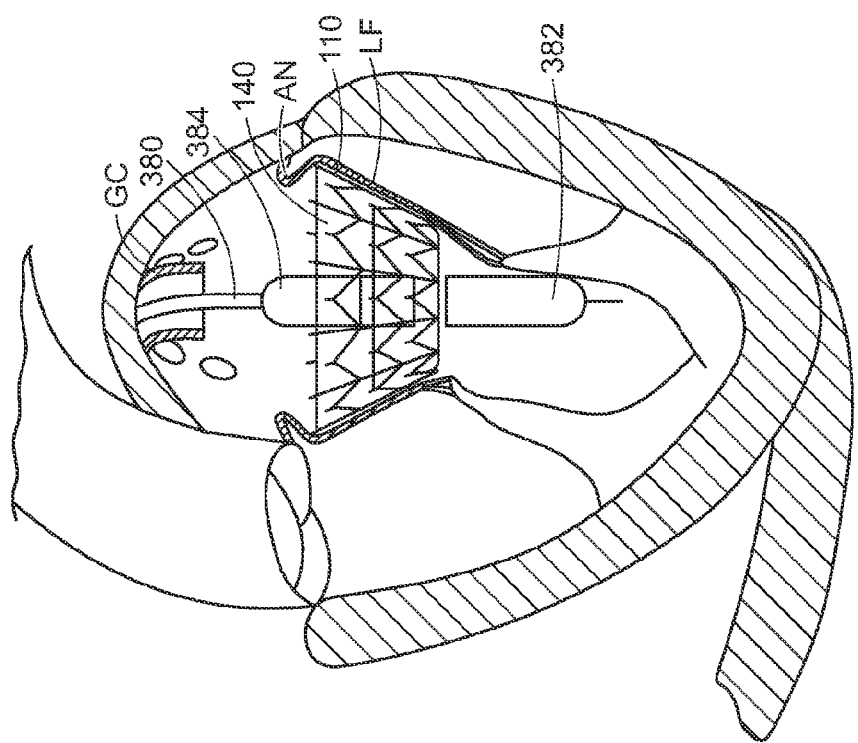

In still further embodiments, the valve support 120 of device 100 may be configured to be axially movable or detachable from the anchoring member 110. In such arrangements, the two components 110, 120 may be loaded in an axially separated configuration within the delivery system 10, thereby reducing the overall profile of the system 10. After delivery to the target valve site, the components 110, 120 can be assembled together. FIGS. 52A-52D show an embodiment of assembling the valve support 120 and anchoring member 110 in the heart. As shown in FIG. 52A, the delivery catheter 380 is advanced into the left atrium via a guiding catheter GC placed through the inter-atrial septum or the atrial wall. The delivery catheter 380 has a split sheath 382, 384 comprising a distal nose cone 382 and a proximal capsule 384. The delivery catheter 380 is advanced through the native valve MV until the nose cone 382 is positioned distally of the native annulus AN (FIG. 52A). The nose cone 382 is then advanced further distally while maintaining the position of the remainder of the delivery catheter 380 thereby releasing the anchoring member 110 from the nose cone 382 (FIG. 52B). The anchoring member 110 self-expands outward, engaging the native leaflets LF and folding them outward beneath the native annulus AN, as shown in FIG. 52B. The upstream tips of ribs 114 (FIG. 52B) engage the subannular tissue to anchor the device 100 in position. The sealing member 140 is fixed around the perimeter 113 of the anchoring member 110 and has a connecting portion 386 extending into the proximal capsule 384 where it is fixed to the valve support 120, which is still constrained within the proximal capsule 384. The delivery catheter 380 is then advanced so as to position the proximal capsule 384 within the anchoring member 110 as shown in FIG. 52C. By advancing the catheter 380 until the sealing member 140 becomes taught, the proper positioning may be attained. The proximal capsule 384 is then retracted relative to the nose cone 382 to release the valve support 120 from the proximal capsule 384. The valve support 120 can self-expand into engagement with the downstream end of anchoring member 110 to couple the two components together. The delivery catheter 380 may then be withdrawn from the patient.

FIGS. 53A-53H show various mechanisms that may be used for coupling the valve support 120 to the anchoring member 110 in the process shown in FIGS. 52A-52D. For example, as shown in FIG. 53A, the valve support 120 may include a circumferential ridge or detent 388 near its downstream end that engages in a groove 390 in the anchoring member 110 to inhibit detachment of the two components. Alternatively, valve support 120 may have a hook 392 formed at the downstream end of each post 122 which is configured to extend around a downstream end of anchoring member 110, e.g. around either the downstream tip of rib 114 or connectors 116, as shown in FIGS. 53B-53C. For example, the hook 392 may be configured to flex inwardly when it engages the inner surface of the rib 114 as the valve support 120 is advanced, and be configured to resiliently recoil to its outward configuration when extended beyond the downstream end of the rib 114, as shown in FIG. 53C. Optionally, a depth-limiting feature such as a stub 394 may extend outwardly from the valve support 120 which is configured to engage a complementary feature such as a bump or ridge 396 on the anchoring member 110 to prevent insertion of the valve support 120 beyond a predetermined depth.

In a further embodiment shown in FIGS. 53D-53F, the valve support 120 may have a coupling element 398 on its outer surface configured to slideably couple to the anchoring member 110. In a first configuration, the coupling element 398 comprises a loop 400, shown in FIG. 53E, through which a vertical guide member 402 on the anchoring member 110 may slide. The anchoring member 110 may have a plurality of such guide members 402 extending upwardly from its downstream end at locations spaced around its circumference. A bump 404 may be formed near the downstream end of each guide member 402 over which the loop 400 may slide to inhibit the valve support 120 from sliding back in the upstream direction (FIG. 53D). In an alternative configuration, shown in FIG. 53F, the guide member 402 has a vertical slot 406 into which a radially extending pin 408 on the valve support 120 can extend. The pin 408 may slide to the downstream end of the slot 406 where it may be urged through a waist 411, which prevents the pin 408 from sliding back in the upstream direction.

In a further embodiment shown in FIGS. 53G-53H, coupling elements 398 on the valve support 120 are configured to slideably receive the ribs 114, which themselves perform a similar function as the guide members 402 (described with respect to FIGS. 53D-53F). As shown in FIG. 53G, coupling of the ribs 114 to the valve support 120 helps restrain the ribs 114 in a radially compact configuration when the valve support 120 slides axially upward relative to the anchoring member 110. In the arrangement shown in FIGS. 53GG-53H, the delivery of the device 100 may not require the need for a separate sheath to constrain the ribs 114 during the delivery. As shown in FIG. 53H, the valve support 120 may slide in the downstream direction relative to the anchoring member 110 until the ribs 114 assume their radially outward configuration. As with guide members 402, each rib 114 may have a bump 412 formed near its downstream end past which coupling element 398 may be urged, but which then inhibits valve support 120 from sliding in the upstream direction (FIG. 53H).

FIGS. 54A-55C illustrate a delivery catheter 400 of a delivery system 40 in accordance with additional embodiments of the present technology. FIG. 54A is a cross-sectional side view of the delivery system 40 for the prosthetic heart valve device 100 and FIG. 54B is a partial cross-sectional side view of a distal portion of the delivery system 40 shown in FIG. 54A. As shown in FIGS. 54A and 54B, the delivery catheter 400 comprises a sheath 402 having an outer wall 403 and a closed distal nose 406 defining a blind annular cavity 408. An inner wall 405 extends proximally to the proximal end of the catheter (not shown), thus forming a tubular catheter shaft 407 defining an inner lumen extending axially therethrough in which a guidewire GW may be slideably positioned. A piston 412 is slideably disposed in the cavity 408 and has an O-ring 413 around its circumference to create a fluid seal with the wall of the cavity 408. A tubular piston shaft 414 extends proximally from piston 412 and is slideably mounted over the catheter shaft 407. The piston shaft 414 is oversized relative to the catheter shaft 407 so as to define a fluid lumen 416 which is in communication with the cavity 408. The device 26 is retained in its radially collapsed delivery configuration within cavity 408, with piston shaft 414 and catheter shaft 407 extending through the interior of the valve support 120 (shown in FIGS. 55A-55C). Preferably, the device 100 is releasably coupled to piston 412 by, for example, pins (not shown) extending radially outwardly from piston shaft 414.

The sheath 402 may have features that limit its travel. For example, a wire (not shown) may tether the protective sheath to a handle on the proximal end of catheter 400. The wire may be attached to an adjustable stop on the handle, allowing the length of piston travel to be adjusted. When fluid is injected into cavity 408, piston 412 will travel until this stop is reached. In this manner, the deployment progression can be controlled.

To ease the retraction of sheath 402 through the valve of the device 100 following deployment, a tapered feature may advance to abut the proximal end of the sheath 402 (see FIG. 56). Alternatively, piston 412 may have a taper or soft bumper material affixed directly to the back of piston 412 facing in the proximal direction. In this way the proximal side of the piston would itself provide an atraumatic leading surface to ease retraction of the sheath 402 through the valve support 120.

Features intended to control and smooth the deployment of device 100 can be incorporated. For example, a common problem during deployment of self-expanding stents is a tendency of the deployed device to "pop" or jump forward or backward as the final elements exit the deployment device. Features to prevent the sheath 402 from being thrust forward by the expanding skeletons of the device 100 may be important in order to prevent accidental damage to the ventricle or other tissue. Such features may incorporate stops or tethers within the deployment system designed to retain the position of the sheath 402 relative to the deployed device 100. For example, the proximal edge of the sheath 402 could be swaged slightly inward to prevent the piston from exiting the sheath and to precisely locate the taper or bumper features described above to ease withdrawal of the system through the deployed valve. Alternatively or additionally, a spring mechanism (not shown) could be built into the delivery system 40 so that when the last features of the device 100 leave the sheath 402, the sheath actively retracts slightly into the downstream end of the newly deployed device 100.

Figure 55A:
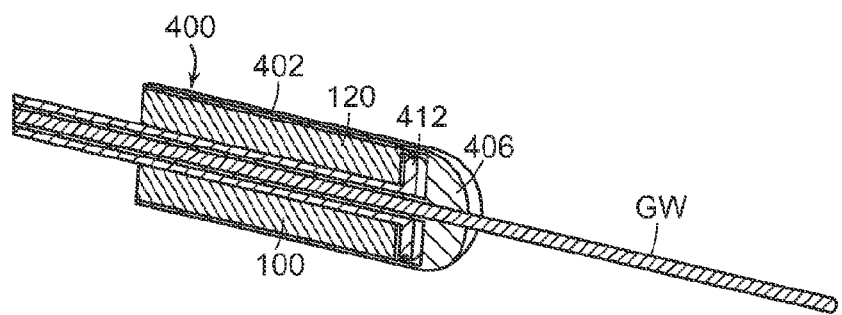
FIGS. 55A-55C are perspective views of the delivery system of FIG. 46 illustrating the steps of delivering the prosthetic treatment device of the invention.
Figure 55B:
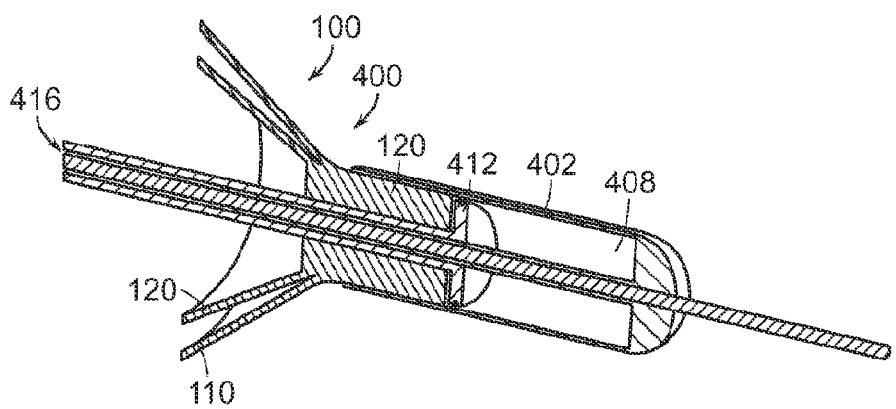
Figure 55C:
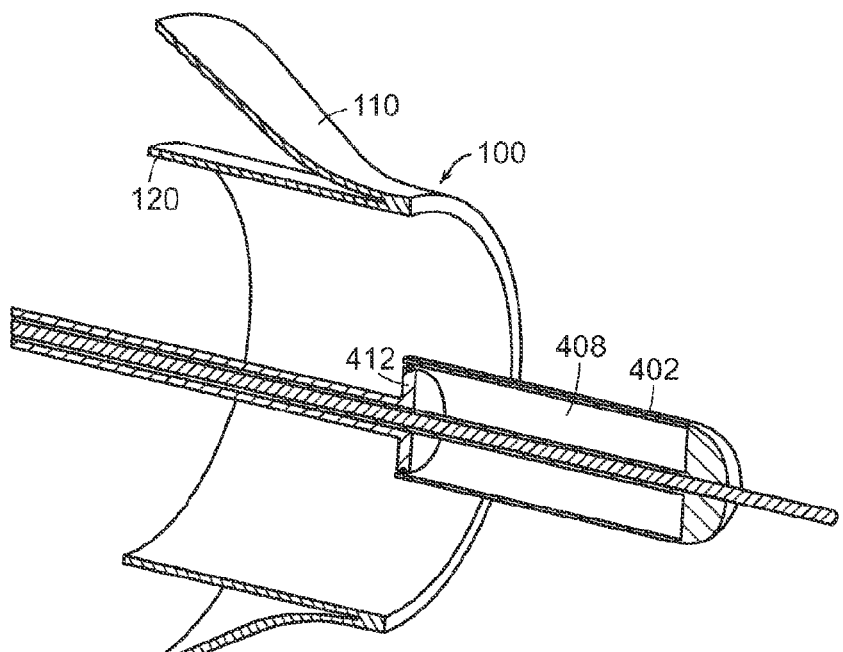

The operation of the delivery catheter 400 is illustrated in FIGS. 55A-55C. The delivery catheter 400 is positioned at the target valve site using one of the approaches described elsewhere herein. The delivery catheter 400 is particularly well suited to placement through the native valve from the upstream direction. The catheter 400 is advanced until the sheath 402 is positioned downstream of the native annulus (FIG. 55A). Fluid can then be injected through fluid lumen 416 into the cavity 408, distal to the piston 412 (FIG. 55B). This drives the sheath 402 distally, releasing the device 100 from the cavity 408 (FIG. 55C). The delivery catheter 400 and the device 100 may remain in a stationary longitudinal position relative to the native valve while the device 100 is deployed, thereby increasing the precision of deployment. In addition, the device 100 may be deployed in a slow and controlled manner, avoiding sudden and uncontrolled jumps of the device 100. Further, such hydraulic actuation allows the sheath 402 to be moved in incremental steps to only partially deploy the device 100, allowing the operator to assess its position relative to the native valve and reposition as needed before complete deployment.

In one embodiment, the piston 412 can be hydraulically actuated, however, in another embodiment, the piston 412 could be operated by manual retraction of the piston shaft 414 or advancement of the sheath 402. The delivery catheter 400 may be equipped with a handle on its proximal end having a retraction mechanism coupled to the piston shaft 414 and/or catheter shaft 407. Such a mechanism may use gears or pulleys to provide a mechanical advantage to reduce the force required to retract the piston or advance the sheath.

The delivery catheters in accordance with aspects of the present technology may further be configured to be reversible, to allow the device 100 to be retracted back in to the catheter 400 after a full or partial deployment. One embodiment of such a catheter is illustrated in FIG. 56, wherein the delivery catheter 400 of FIGS. 54A-55C is adapted to retract the device 100 back into the sheath 402 after being fully or partially deployed therefrom. The piston 412 has at least a first pulley 420 coupled thereto, while distal nose 406 has at least a second pulley 422 coupled thereto. A plurality of additional pulleys 423 may also be provided at locations around the circumference of the piston 412 for additional mechanical assistance. A cable 424, which may comprise a length of wire or suture, extends through the fluid lumen 416 and cavity 408, passes around first and second pulleys 420, 422 and any additional pulleys 423, and is secured to piston 412. The device 100 can be releasably coupled to the piston shaft 414 by a plurality of pins 426 extending radially from the piston shaft 414 into engagement with the device 100, preferably near a downstream end 428 thereof.

To deploy the device 100, the delivery catheter 400 of FIG. 56 operates similarly as described above in connection with FIGS. 55A-55C; however, in an additional embodiment and before the downstream end 428 has been fully released from the sheath 402, the operator can checks the location of the device 100. Upon deployment, the upstream end 430 of the device 100 will expand toward its expanded configuration. An operator can view, using ultrasound, fluoroscopy, MRI, or other means, the position and shape of the deployed device 100 in the native tissue. Following positioning, the sheath 402 may be further advanced relative to the piston 412 to fully deploy the device 100 from the sheath 402, whereupon the downstream end 428 fully expands and pins 426 are disengaged from device 100. In situations where the operator desires to recover the device 100 back into the sheath 402 for repositioning or other reasons, the cable 424 is pulled so as to move the piston 412 in the distal direction relative to the sheath 402. The pins 426 pull the device 100 with the piston 412 back into the sheath 402 and the device 100 is collapsed as it is pulled in the sheath 402. The delivery catheter 400 may then be repositioned and the device redeployed.

In one embodiment, the prosthetic heart valve device 100 may be specifically designed for a specific approach or delivery method to reach the mitral valve, or in another embodiment, the device 100 may be designed to be interchangeable among the approaches or delivery methods.

Additional Embodiments of Prosthetic Heart Valve Devices, Delivery Systems and Methods FIGS. 57A-57E are isometric views of prosthetic heart valve devices 600 shown in an expanded configuration 602 and configured in accordance with additional embodiments of the present technology. The prosthetic heart valve devices 600 include features generally similar to the features of the prosthetic heart valve device 100 described above with reference to FIGS. 10A-56. For example, the prosthetic heart valve device 600 includes the valve support 120 configured to support a prosthetic valve 130 and an anchoring member 610 coupled to the valve support 120 in a manner that mechanically isolates the valve support 120 from forces exerted upon the anchoring member 610 when implanted at the native mitral valve. However, in the embodiments shown in FIGS. 57A-57E, an upstream region 612 of the anchoring member 610 is coupled to the valve support 120 such that a downstream region 611 of the anchoring member 610 is configured to engage native tissue on or downstream of the annulus so as to prevent migration of the device 600 in the upstream direction.

Figure 57A:
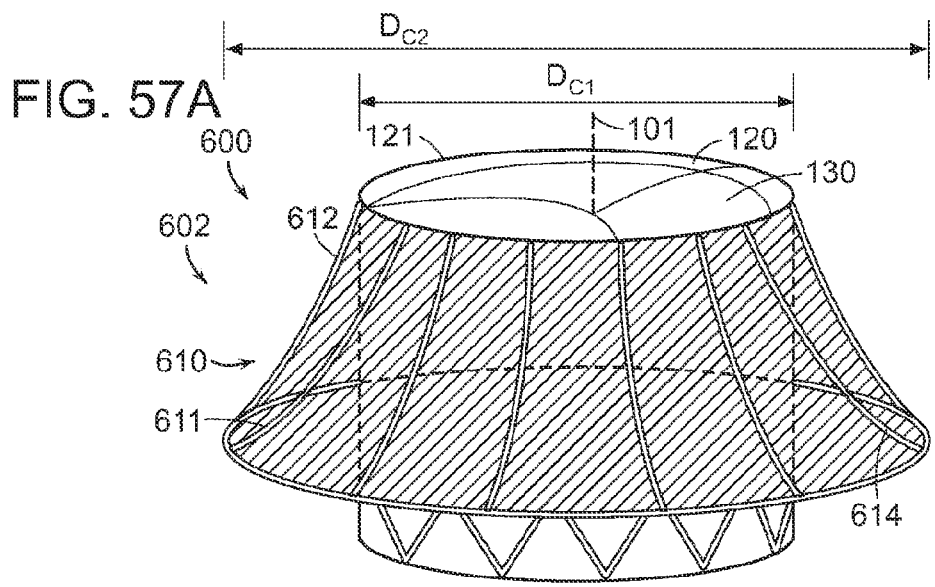
FIGS. 57A-57D are isometric views of prosthetic treatment devices in accordance with additional embodiments of the present technology.
Figure 57B:
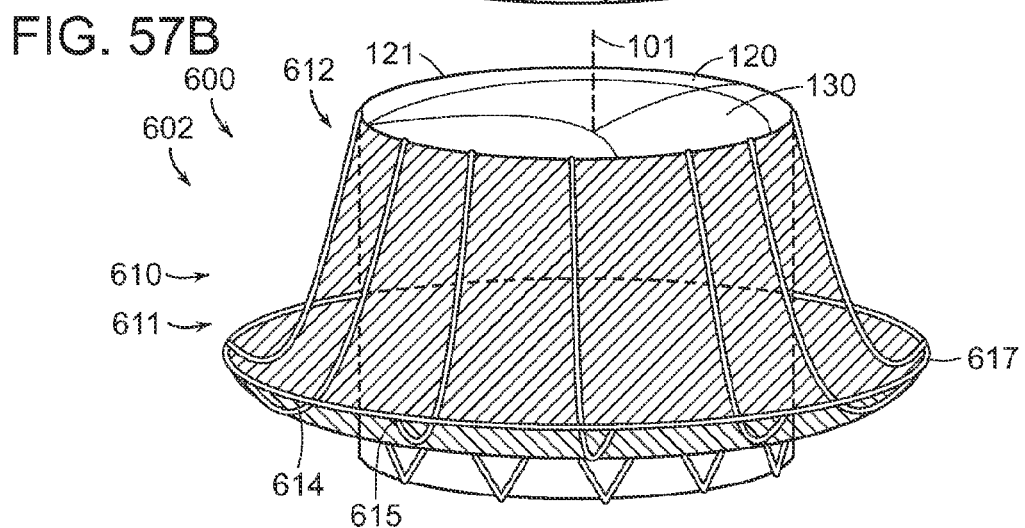

FIGS. 57A and 57B illustrate embodiments of the device 600 wherein the anchoring member 610 includes a plurality of longitudinal ribs 614 coupled to the upstream end 121 of the valve support 120 and extending in a downstream to distal direction. As shown in FIG. 57A, the ribs 614 can project radially outward away from the longitudinal axis 101 at the downstream region 611 of the anchoring member 610 such that the downstream region 611 is flared outward for engaging subannular tissue below the mitral annulus. FIG. 57B illustrates an embodiment of the device 600 having an anchoring member 610 with an upward-facing lip 617 at the downstream region. In this embodiment, the ribs 614 can be formed such that the downstream region is generally flared outwardly from the longitudinal axis 101 but the tips 615 of the ribs 614 reorient to point in an upstream direction at the lip 617. The lip 617 may assist the anchoring member 610 in engaging subannular tissue and can be configured to include tissue engaging elements (not shown) as described above with respect to device 100. The anchoring member 610 can also be coupled to the valve support 120 at a position desirable for positioning the valve support 120 and prosthetic valve 130 within the native valve. For example, FIG. 57C illustrates an embodiment of the device 600 in which the anchoring member 610 can be coupled to the valve support 120 at a location downstream from the upstream end 121.

Figure 57C:
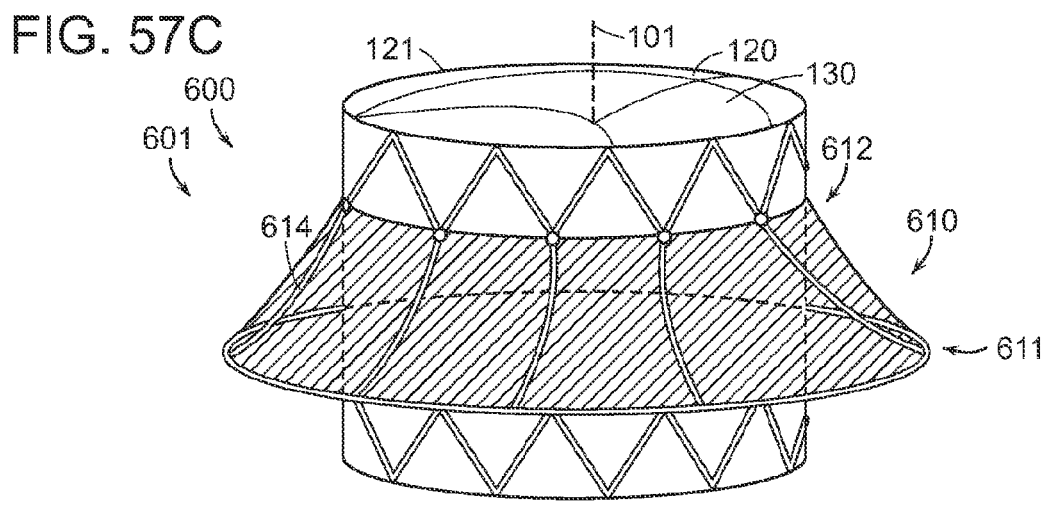

Referring to FIGS. 57A-57C together, the anchoring member 610 can have a first cross-sectional dimension $D_{C1}$ at the upstream region 612 that is less than a second cross-sectional dimension $D_{C2}$ at the downstream region 611. Additionally, the valve support 120 is radially separated from the downstream region 611 of the anchoring member 610 such that when the device 600 is deployed, the downstream region 611 can deform inwardly without deforming the upstream portion of the valve support 120. Additionally, the anchoring member 610 can have a generally oval or D-shape, or other irregular shape such as those described above with respect to FIGS. 16A-17C, while the valve support 120 can be generally cylindrical in shape. In such embodiments, the second cross-sectional dimension $D_{C2}$ can be greater than a corresponding cross-sectional dimension (e.g., MVA1 or MVA2) of the annulus of the native mitral valve (FIG. 5C).

Figure 57D:
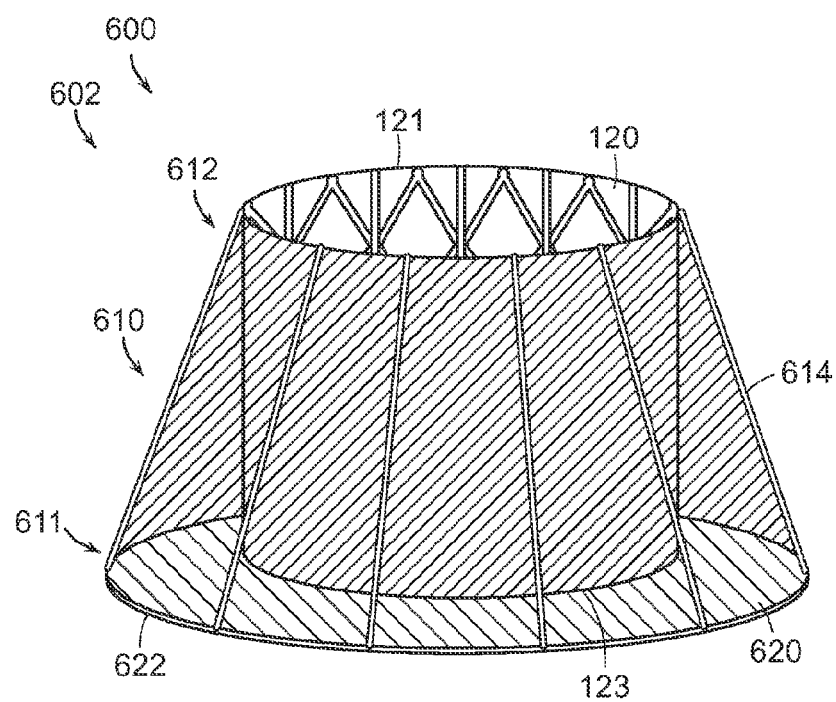

FIG. 57D illustrates yet another embodiment of the device 600 in an expanded configuration 602. As shown, the valve support 120 can include a flange 620 at the downstream end 123 of the valve support 120. The flange 620 can extend radially outward from the longitudinal axis 101 at the downstream end 123 to radially engage subannular tissue. The anchoring member 610 can include a plurality of ribs 614 coupled to the upstream end 121 of the valve support 120 and extending radially outward in the downstream direction to attach to an outer rim 622 of the flange 620. The anchoring member 610 can be configured to engage subannular tissue, such as inward-facing surfaces of the leaflets. In this embodiment, the ribs 614 can be flexible such that deformation of the anchoring member 610 between the coupling at the upstream region 612 and the coupling to the flange 620 at the lower region 611 will not substantially deform the valve support 120 wherein a prosthetic valve is connected.

Figure 57E:
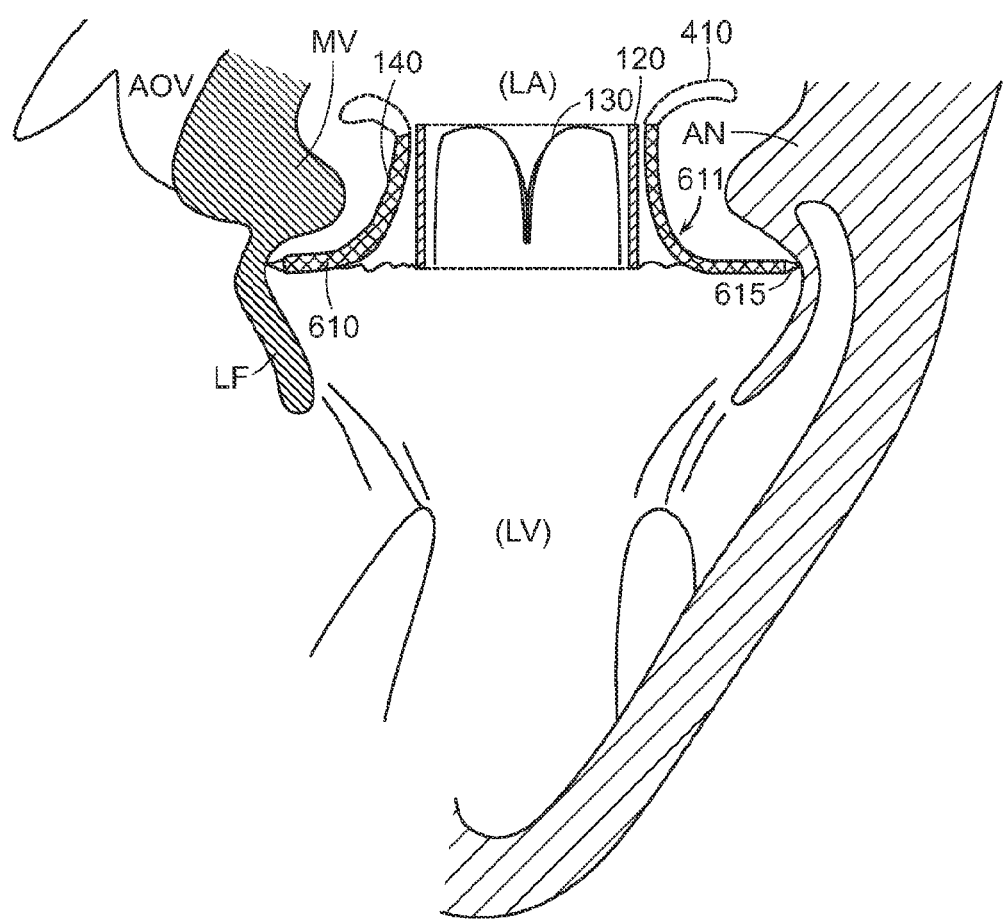
FIG. 57E is a schematic cross-sectional view of the prosthetic heart valve device of FIG. 57A implanted at a native mitral valve in accordance with an embodiment of the present technology.

FIG. 57E is a schematic cross-sectional view of the prosthetic heart valve device 600 of FIG. 57A implanted at a native mitral valve MV in accordance with an embodiment of the present technology. As shown, the flared downstream region 611 of the anchoring member 610 can engage the subannular tissue, e.g., inward-facing surfaces of the leaflets LF, a subannular surface, etc. The ribs 614 can incorporate tissue engaging elements 170 on the rib tips 615 for penetrating and/or partially penetrating the tissue. Further, the anchoring member 610 can expand radially outward to seal (not shown) against the tissue to prevent migration of the device 600 in the upstream or downstream direction and/or to prevent paravalvular leaks between the tissue and the device 600. Accordingly, the device 600 can incorporate one or more sealing members 140 as described above with respect to device 100. Additionally, the device 600 can also include an atrial extension member or atrial retainer 410 (shown in dotted lines) as described above with respect to the device 100. The atrial retainer, if present, can be configured to engage tissue above the annulus AN such as a supra-annular surface or some other tissue in the left atrium LA to inhibit downstream migration of the device (e.g., during atrial systole).

Figure 58A:
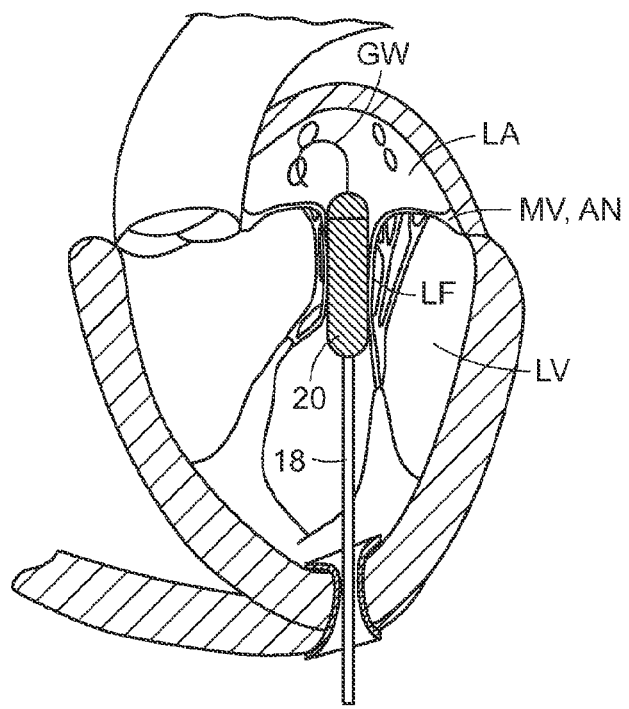
FIGS. 58A-58D are cross-sectional views of a heart showing a method of delivering a prosthetic heart valve device to a native mitral valve in the heart using a transapical approach in accordance with another embodiment of the present technology.
Figure 58B:
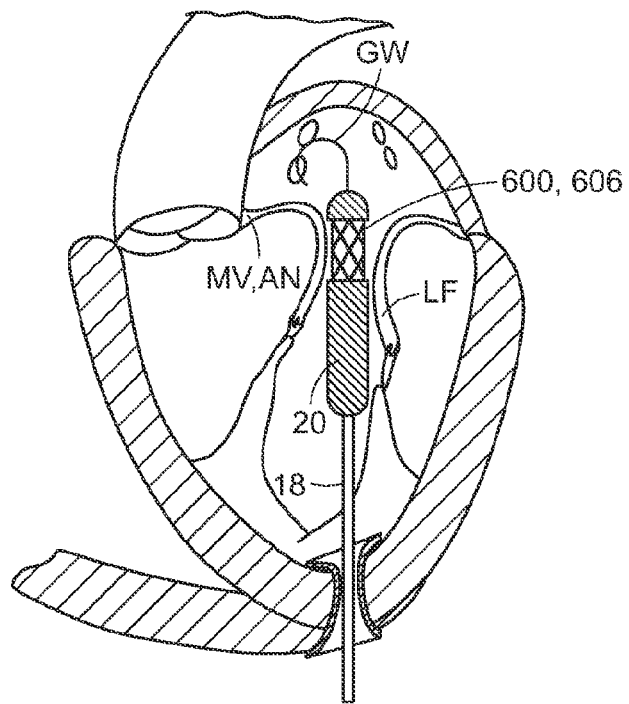
Figure 58C:
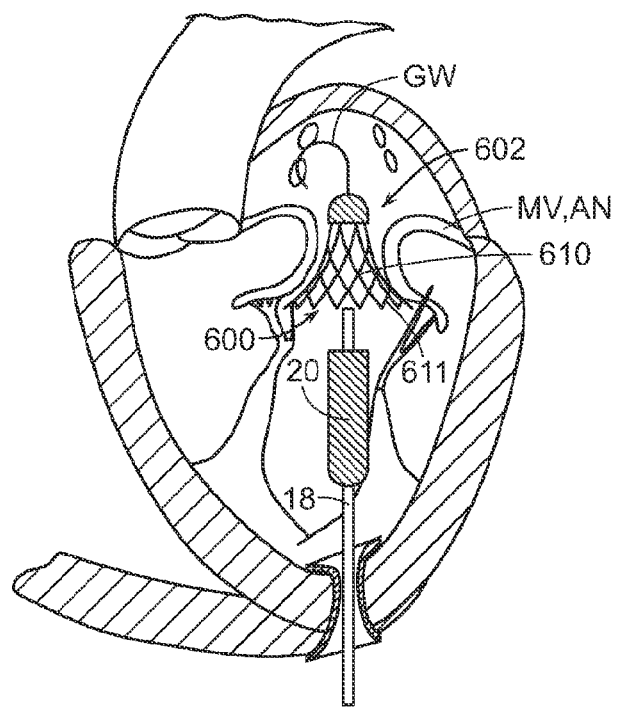
Figure 58D:
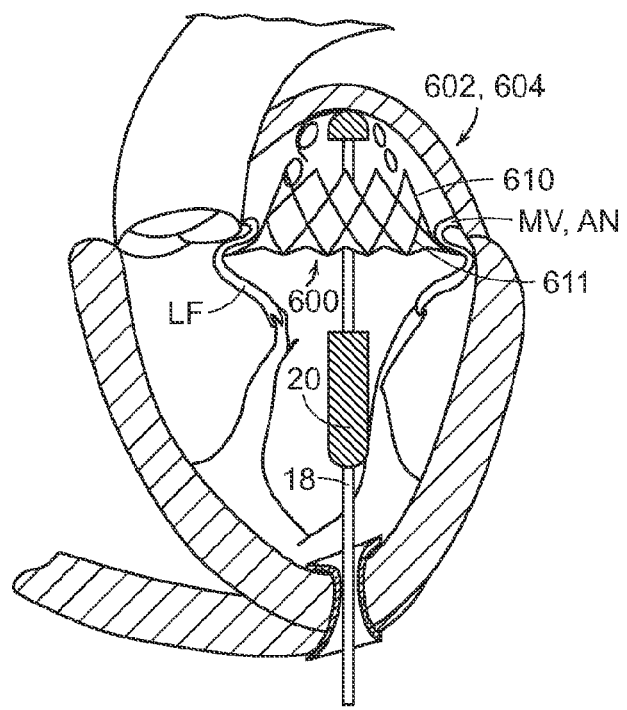

FIGS. 58A-58D are cross-sectional views of a heart showing a method of delivering a prosthetic heart valve device 600 to a native mitral valve MV in the heart using a trans-apical approach in accordance with another embodiment of the present technology. Referring to FIG. 58A, the delivery catheter 18 is advanced through guiding catheter (not shown) which enters the left ventricle LV of the heart through a puncture in the left ventricle wall at or near the apex of the heart and is sealed by a purse-string suture. Alternatively, the delivery catheter 18 may be placed directly through a purse-string-sealed trans-apical incision without a guiding catheter. The sheath 20, containing a collapsed device 600, 606 (shown in FIG. 58B), is advanced through the mitral annulus AN between native leaflets LF as shown in FIG. 58A. Referring to FIGS. 58B-58D together, the sheath 20 is pulled proximally to allow the device 600 to expand to the expanded and/or deployed configurations 602, 604 (FIGS. 58C and 58D).

Although the sheath 20 can be retracted and the device 600 allowed to expand, the delivery system can remain connected to the device 600 (e.g., system eyelets, not shown, are connected to the device eyelets, not shown) such that the operator can control the placement of the device 600 while in the expanded configuration 602 (FIGS. 58C and 58D). For example, as the sheath 20 is disengaged from the device 600, the upstream region 612 of the anchoring member 610 can remain collapsed within the sheath preventing the anchoring member 610 from fully expanding (FIG. 58C). During this phase of the delivery, the position of the device 600 within the mitral valve area can be adjusted or altered. After the device 600 is located at the target site, the sheath 20 can be fully removed from the device 600 and the anchoring member 610 of the device 600 can expand outwardly at the downstream region 611 to engage subannular tissue, such as the leaflets LF, and to retain the device 600 in the desired target location. The pull-wires (not shown) may be retracted in a proximal direction to release the device 600 from the delivery system, allowing the delivery system to be removed and the device to be fully implanted at the mitral valve MV in the deployed configuration 104. Alternatively, the device 600 may be expanded upstream or downstream of the desired target location then pulled or pushed downstream or upstream, respectively, into the target location before releasing the device 600 from delivery system.

Figure 59A:
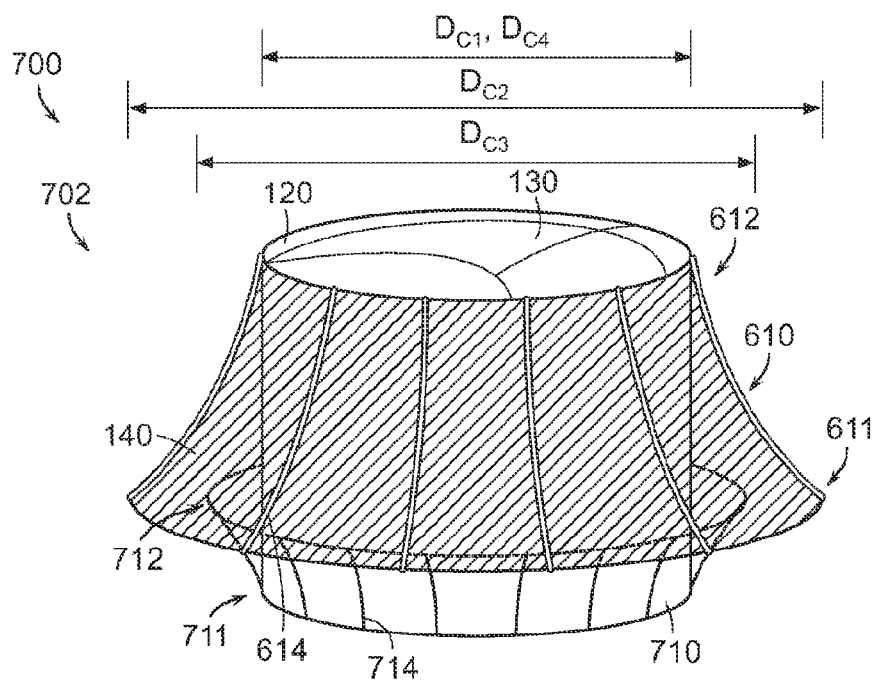
FIGS. 59A-59C are isometric views of prosthetic treatment devices in accordance with additional embodiments of the present technology.
Figure 59B:
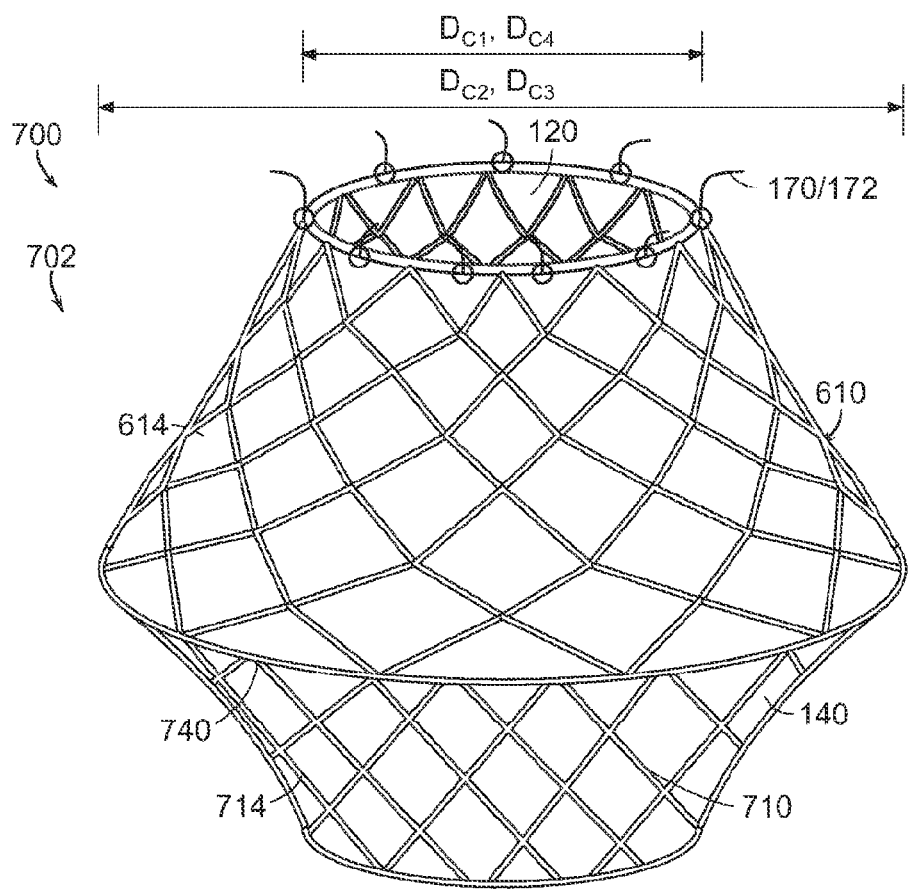
Figure 59C:
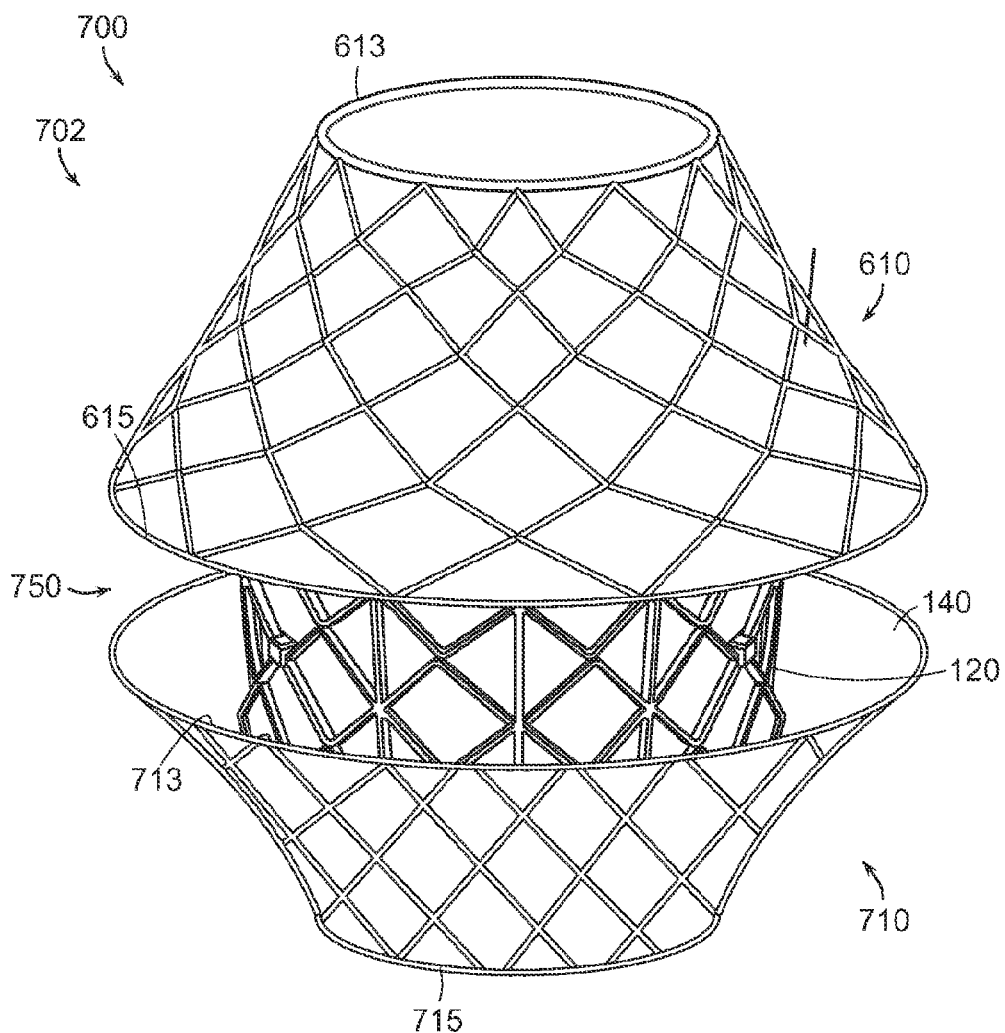

FIGS. 59A-59C are isometric views of prosthetic heart valve devices 700 shown in an expanded configuration 702, and FIG. 59D is a schematic cross-sectional view of the prosthetic heart valve device 700 implanted at a native mitral valve configured in accordance with further embodiments of the present technology. The prosthetic heart valve devices 700 include features generally similar to the features of the prosthetic heart valve devices 100 and 600 described above with reference to FIGS. 10A-58D. For example, the prosthetic heart valve device 700 includes the valve support 120 configured to support a prosthetic valve 130 and a first anchoring member 610 coupled to the valve support 120 in a manner that mechanically isolates the valve support 120 from forces exerted upon the first anchoring member 610 when implanted at the native mitral valve. Particularly, the upstream region 612 of the first anchoring member 610 is coupled to the valve support 120 and the downstream region 611 of the first anchoring member 610 is configured to flare outwardly to engage native tissue on or downstream of the annulus so as to prevent migration of the device 600 in the upstream direction. However, in the embodiments shown in FIGS. 59A-59D, the device 700 also includes a second anchoring member 710 having a downstream region 711 coupled to the valve support 120, and an upstream region 712 extending radially outward in the upstream direction. Accordingly, the device 700 includes both the first and second anchoring members 610 and 710 for engaging tissue on or under the annulus of the mitral valve.

Referring to FIGS. 59A-59D together, the first anchoring member 610 can have the first cross-sectional dimension $D_{C1}$ at the upstream region 612 that is less than the second cross-sectional dimension $D_{C2}$ at the downstream region 611. The second anchoring member 710 can have a third cross-sectional dimension $D_{C3}$ at the upstream region 712 that is greater than a fourth cross-sectional dimension $D_{C4}$ at the downstream region 711. In some embodiments, the third cross-sectional dimension $D_{C3}$ is less than the second cross-sectional dimension $D_{C2}$ such that the second anchoring member 710 can be partially surrounded by the first anchoring member 610 (FIG. 59A). In such an embodiment, the upstream region 712 can apply radial outward pressure against an inner wall (not shown) of the first anchoring member 610 and further support the fixation of the first anchoring member 610 to the tissue on or under the annulus. In another embodiment shown in FIG. 59B, the third cross-sectional dimension $D_{C3}$ can be approximately the same as the second cross-sectional dimension $D_{C2}$ such that the first and second anchoring members 610, 710 meet at a flared junction 740. In one embodiment, the first and second anchoring members 610 and 710 can be coupled at the flared junction 740; however, in other embodiments, the first and second anchoring members 610 and 710 are not coupled. FIG. 59C shows another embodiment of the device 700 wherein the downstream region 615 of the first anchoring member 610 is separated from the upstream region 713 of the second anchoring member 710 by a gap 750. In one embodiment, the device 700 shown in FIG. 59C can be implanted at the native heart valve such that the first anchoring member 610 can engage supra-annular tissue or other cardiac tissue upstream of the annulus and the second anchoring member 710 can engage subannular tissue or other cardiac tissue downstream of the annulus such that the annulus is retained or captured within the gap 750.

In a further embodiment illustrated in FIG. 59D, the third cross-sectional dimension $D_{C3}$ is greater than the second cross-sectional dimension $D_{C2}$ such that the second anchoring member 710 can partially surround the first anchoring member 610. In such an embodiment, the downstream region 611 of the first anchoring member 610 can apply radial outward pressure against an inner wall 741 of the second anchoring member 710 and further support the fixation of the second anchoring member 710 to the tissue on or under the annulus AN.

Additionally, the valve support 120 can be radially separated from the downstream region 611 of the first anchoring member 610 as well as the upstream region 712 of the second anchoring member 710 such that when the device 700 is deployed, the downstream region 611 and/or the upstream region 712 can deform inwardly without substantially deforming the valve support 120 or without deforming a support region 734 of the valve support 120 supporting the prosthetic valve 130. Additionally, the first and second anchoring members 610, 710 can have a generally oval or D-shape, or other irregular shape such as those described above with respect to FIGS. 16A-17C, while the valve support 120 can be generally cylindrical in shape. Moreover, additional features may be incorporated on the device 700, such as sealing membranes 140 and tissue engaging elements 170 as described above with respect to the device 100.

FIGS. 60A-60B are cross-sectional side views of a distal end of a delivery catheter 18 for delivering the prosthetic heart valve device 700 of FIG. 59C to a native mitral valve in the heart in accordance with another embodiment of the present technology. As shown in FIGS. 60A-60B the prosthetic heart valve device 700 is collapsed into a delivery configuration 706 and retained within a two portion delivery sheath 70 at the distal end of the catheter 18 (FIG. 60A). Upon delivery of the distal end of the catheter 18 to the desired location at or near a native mitral valve, the device 700 can be released from the two portion sheath 70 by retracting an upper portion 72 in a distal direction and/or retracting a lower portion 74 in a proximal direction (shown with arrows in FIG. 60A) thereby separating the sheath and exposing the collapsed device 700 from within the sheath 70. In one embodiment, the device 700 can self-expand to its expanded configuration 702 following retraction of the sheath 70 (FIG. 60B). As illustrated in FIG. 60B, when the sheath 70 is retracted in both the proximal and distal directions, the first and second anchoring members 610, 710 can self-expand outwardly to engage the native tissue. When using a balloon 300 to expand the support valve 120, the balloon 300 can be inflated to fully expand the device 700.

Figure 61:
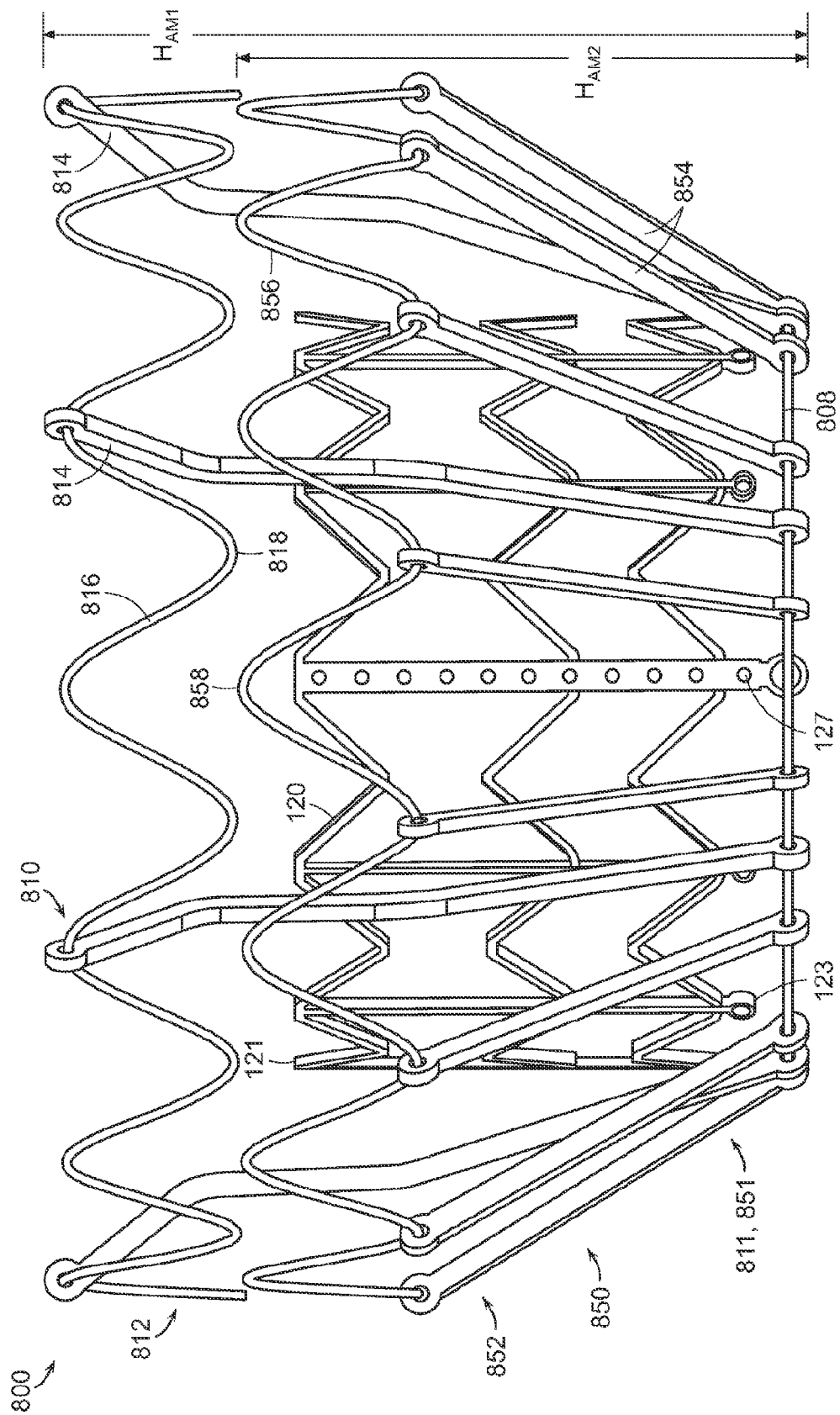
FIG. 61 is a side view of a prosthetic heart valve device having first and second anchoring members for engaging supra-annular and subannular tissue of the mitral valve, respectively, in accordance with yet another embodiment of the present technology.

FIG. 61 illustrates a prosthetic heart valve device 800 configured in accordance with another embodiment of the present technology. FIG. 61 is a side view of the device 800 that includes features generally similar to the features of the prosthetic heart valve devices 100, 600, 700 described above with reference to FIGS. 10A-60B. For example, the device 800 includes a support valve 120 having upstream and downstream ends 121, 123 and an interior in which a valve (not shown) may be coupled. The device also includes first and second anchoring members 810 and 850. The first anchoring member 810 has a first flared upstream portion 812 and a first downstream portion 811 that is coupled to an outer or exterior surface 127 of the valve support 120. The first flared upstream portion 812 can be mechanically isolated from the valve support 120. Additionally, the first flared upstream portion 812 can be configured to engage supra-annular tissue of the native mitral valve. The second anchoring member 850 can be configured to at least partially surround the first anchoring member 810 and to have a second flared upstream portion 852 for engaging the sub-annular tissue of the native mitral valve. The second anchoring member 850 can also have a second downstream portion 851 coupled to the outer surface 127 of the valve support 120 in a manner that mechanically isolates the valve support 120 from at least the second upstream portion 852.

As shown in FIG. 61, the first anchoring member 810 can have a plurality of first longitudinal ribs 814 and the second anchoring member 850 can have a plurality of second longitudinal ribs 854. In one embodiment, each of the individual first ribs 814 are longer than each of the individual second ribs 854 such that the first anchoring member 810 has a height $H_{AM1}$ greater than a height $H_{AM2}$ of the second anchoring member 850. Accordingly, the height $H_{AM2}$ can be selected to orient the second anchoring member 850 to engage subannular tissue, while the height $H_{AM1}$ can be selected to orient the first anchoring member 810 to extend through the mitral valve from the left ventricle to engage supra-annular tissue in the left atrium.

FIG. 61 illustrates one embodiment of the device 800 that can include a lower ring 808 on which the ribs 814, 854 can be interconnected. The lower ring 808 can allow the ribs 814, 854 to expand radially outward away from the valve support 120 at the upstream portions 812, 852. The device 800 can also include a first upper ring member 816 coupled to the plurality of first longitudinal ribs 814. The first upper ring member 816 can be shaped and or patterned to have a downward oriented rim 818 for engaging supra-annular tissue. The device can further include a second upper ring member 856 coupled to the plurality of second longitudinal ribs 854. The second upper ring member 856 can be shaped and or patterned to have an upward oriented rim 858 for engaging subannular tissue.

Figure 62C:
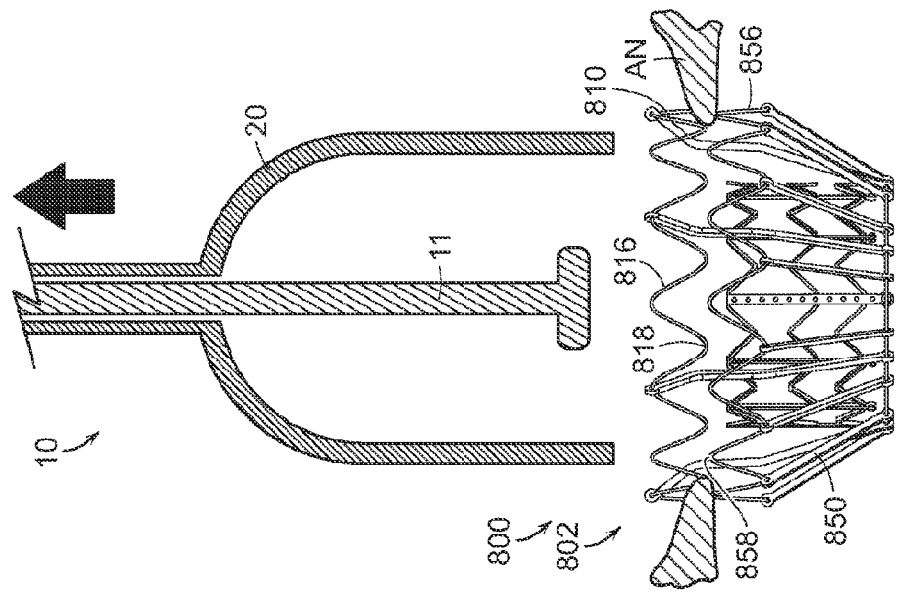
FIGS. 62A-62C are partial cross-sectional side views of a distal end of a delivery system showing delivery of the prosthetic heart valve device of FIG. 61 at a mitral valve in accordance with another embodiment of the present technology.
Figure 62B:
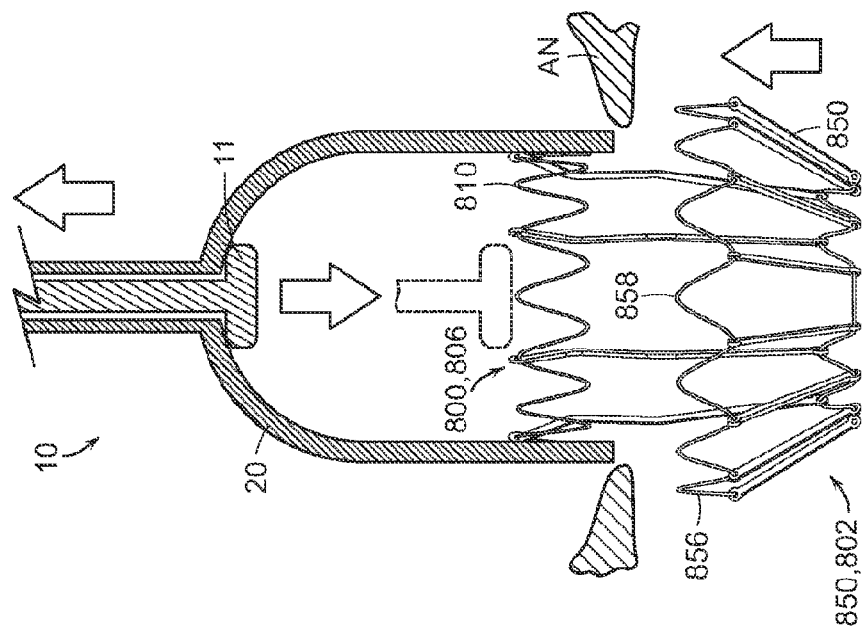
Figure 62A:
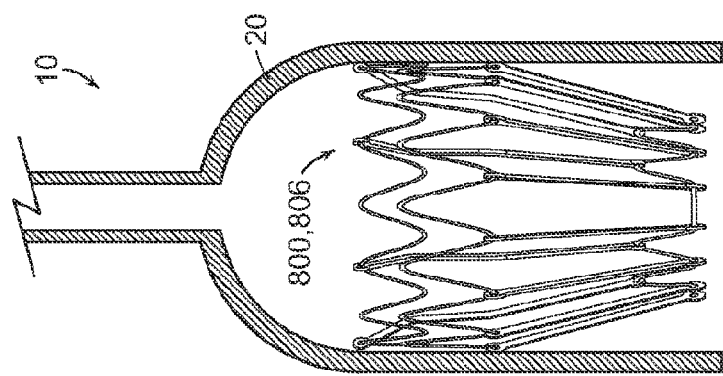

FIGS. 62A-62C are partial cross-sectional side views of a distal end of a delivery system 10 showing delivery of the prosthetic heart valve device 800 of FIG. 61 at a mitral valve MV in accordance with another embodiment of the present technology. The device 800 can be retained in a collapsed configuration 806 within a sheath 20 of the delivery system (FIG. 62A). When the distal end of the delivery system engages the target location, the sheath 20 can be retracted proximally from the device 800, thereby releasing the features of the device 800 to expand into the expanded configuration 102 (FIGS. 62B-62C). As shown in FIG. 62B, the second anchoring member 850 can be released first from the retracting sheath 20 and the upward oriented rim 858 of the second upper ring member 856 can be positioned to engage the subannular tissue. The sheath 20 can prevent the first anchoring member 810 from disengaging from the delivery system 10 and/or moving outside the sheath 20 until the rim 858 of the second anchoring member 850 is moved into position to engage the subannular tissue. Referring to FIG. 62C, a plunger 11 can engage the first anchoring member 810 (as shown by downward arrow in FIG. 62B) and/or the sheath 20 can be disengaged/retracted (shown by upward arrow in FIG. 62C) from the first anchoring member 810 thereby allowing the second anchoring member 850 to move radially outward to the expanded configuration 802. The downward oriented rim 818 of the first upper ring member 816 can be positioned to engage the supra-annular tissue (FIG. 62C). Once deployed, the rings 816, 856 can sandwich the annulus AN of the mitral valve and inhibit movement of the device 800 in both upstream and downstream directions.

Figure 63:
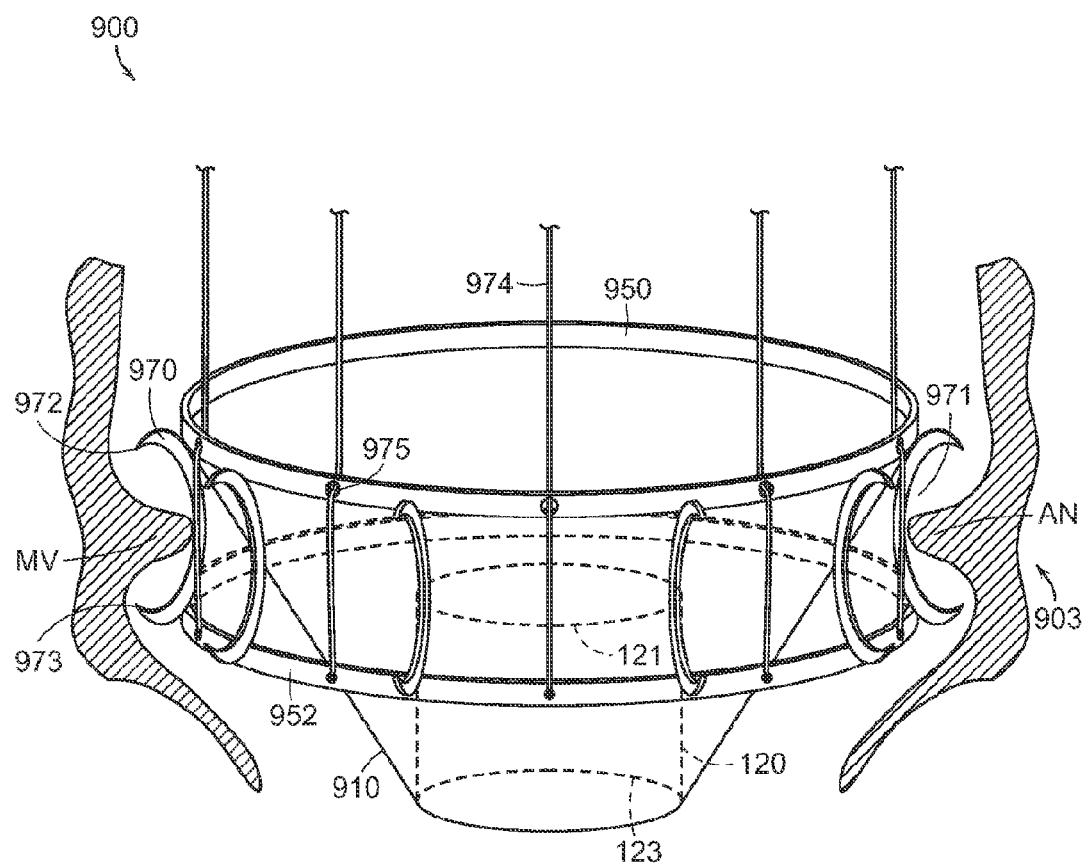
FIG. 63 is an isometric side view of a prosthetic heart valve device having an anchoring member with a supra-annular engaging rim and a subannular engaging ring in accordance with a further embodiment of the present technology.

FIG. 63 is an isometric side view of a prosthetic heart valve device 900 in accordance with a further embodiment of the present technology. The device 900 includes features generally similar to the features of the prosthetic heart valve devices 100, 600, 700 and 800 described above with reference to FIGS. 10A-62C. For example, the device 900 includes a support valve 120 having upstream and downstream ends 121, 123 and an interior in which a valve (not shown) may be coupled. The device 900 includes an anchoring member 910 that has a flared upstream portion 912 and a downstream portion 911 coupled to the valve support 120. However, the device 900 also includes upper and lower rings 950, 952 and a plurality of flexible annulus engaging elements 970 distributed around a circumference 980 of the anchoring member 910 and configured to couple the upper ring 950 to the lower ring 952. The flexible annulus engaging elements 970 can have a shape such as a C-shape or U-shape that is oriented to have an open portion outward from the device 900 such that the native annulus AN can be engaged in recesses 971 of the annulus engaging elements 970. The annulus engaging elements 970 can also include points 972, 973 for engaging and potentially piercing supra-annular and subannular tissue, respectively. The annulus engaging elements 970 can be suitably flexible to bend in a manner that brings the points 972, 973 close together for securing the device 900 to the annulus AN when the device 900 is deployed.

Figure 64B:
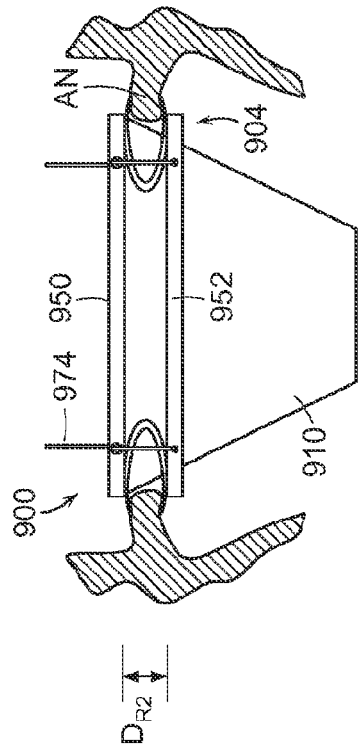
FIGS. 64A-64D are side views of the prosthetic heart valve device of FIG. 63 showing embodiments of methods for deploying the device at the mitral valve annulus in accordance with aspects of the present technology.
Figure 64A:
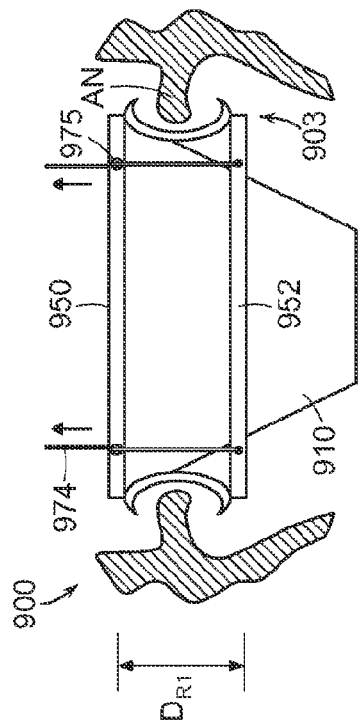

FIGS. 64A-64B illustrate a method for deploying the device 900 at the native mitral valve. Referring to FIGS. 63 and 64A-64B together, the annulus engaging elements 970 can be generally relaxed or have a wide recess 971 in an open state 903. As such, the upper ring 950 can rest above the lower ring 952 a first distance $D_{R1}$ when the elements 970 are in the open state 903. The device 900 can also include a plurality of pull-wires 974 that are slideably engaged with the upper ring 950 (e.g., through holes 975) and secured to the lower ring 952. When the wires 974 are pulled in an upward or upstream direction, the lower ring 952 moves in an upward/upstream direction toward the upper ring 950. As the lower ring 952 approaches the upper ring 950, the annulus engaging elements 970 can bend such that the points 972, 973 are brought closer together and/or engage or pierce the annulus tissue (FIG. 64B). Accordingly, when the device 900 is in the deployed state 904, the upper ring 950 can be held by the pull-wires 974 at a second distance $D_{R2}$ above the lower ring 952, wherein the second distance $D_{R2}$ is less than the first distance $D_{R1}$.

Figure 64D:
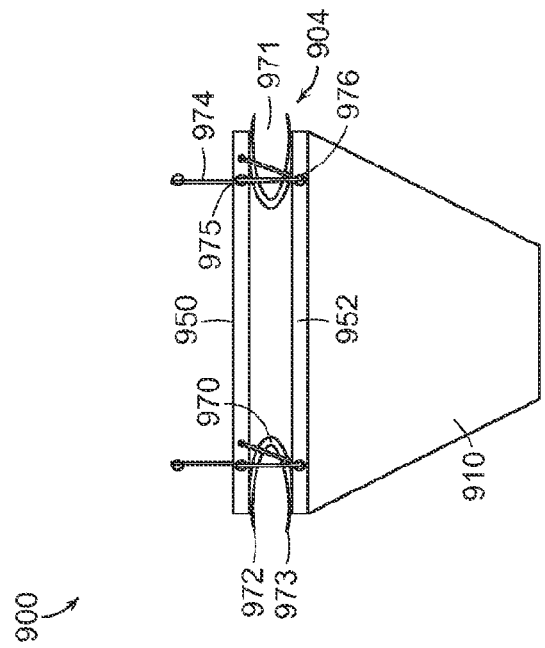
Figure 64C:
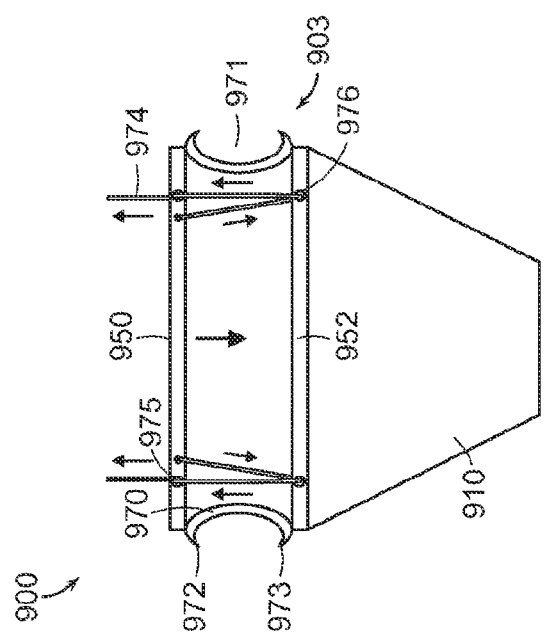

FIGS. 64C-64D show an alternative arrangement of the pull-wires 974 in which the wires 974 are secured to the upper ring 950 and are slideably engaged with the lower ring 952 (e.g., through holes 976). The pull-wires 974 can also be slideably engaged with the upper ring 950 (e.g., such as through holes 975) such that the pull-wires can be pulled in an upward direction to bring the rings 950, 952 closer together in the deployed state 904.

Figure 65A:
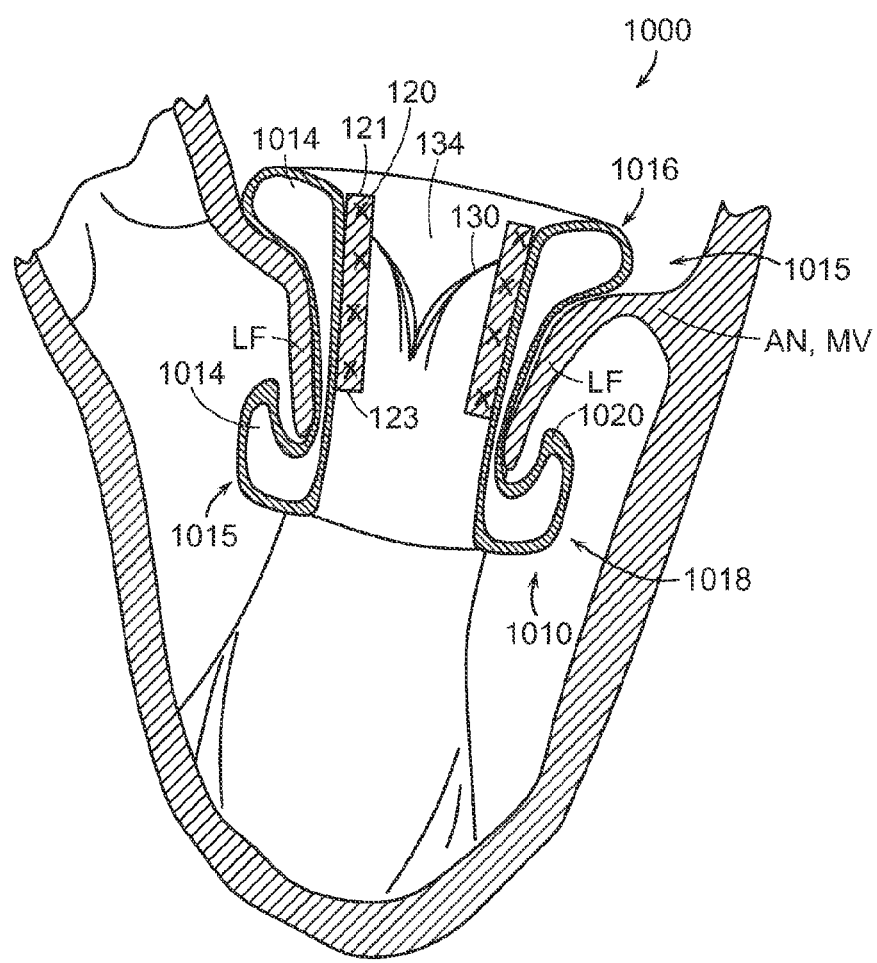
FIG. 65A is a cross-sectional view of a prosthetic heart valve device having an inflatable anchoring member and shown implanted in a native mitral valve of a heart in accordance with another embodiment of the present disclosure.

FIG. 65A is an isometric side view of a prosthetic heart valve device 1000 in accordance with a further embodiment of the present technology. The device 1000 includes features generally similar to the features of the prosthetic heart valve devices 100, 600, 700, 800 and 900 described above with reference to FIGS. 10A-64D. For example, the device 1000 includes a support valve 120 having upstream and downstream ends 121, 123 and an interior 134 in which a valve 130 may be coupled. However, the device 1000 includes an inflatable anchoring member 1010 coupled to and at least partially surrounding the valve support 120. The inflatable anchoring member 1010 can be configured to inflate/expand upon deployment and engage native tissue at the desired target location. As shown in FIG. 65A, the inflatable anchoring member 1010 can have one or more fillable chambers 1014 for receiving a fill substance such as a solution (e.g., saline or other liquid) or gas (e.g., helium, $CO_2$ or other gas) following implantation of the device 1000. In other embodiments, the fillable chambers 1014 can be filled with a hardening material (e.g., epoxy, cement, or other resin).

In one embodiment, the fillable chambers 1014 and/or the anchoring member 1010 can be formed of polytetrafluoroethylene (PTFE), urethane, or other expandable polymer or biocompatible material. The fillable chambers 1014 can have a predetermined shape such that the fillable chambers 1014, when inflated, form fixation elements 1015 for engaging the native anatomy. For example, the fixation elements 1015 can include a supra-annular flange 1016 for engaging a surface of the annulus AN within the left atrium LA. The elements 1015 may also include subannular flanges 1018 for engaging subannular tissue and/or arms 1020 for engaging leaflets LF (e.g., behind leaflets). Accordingly, the chambers 1014 can be incorporated or shaped such that the anchoring member 1010 engages supra-annular tissue, subannular tissue, leaflets or other tissue at or near the mitral valve MV while mechanically isolating the valve support 120 from distorting diastolic and systolic forces generated in the heart and particularly radial forces exerted on the device 1000 at or near the native mitral valve. For example, following deployment, the inflatable anchoring member 1010 can absorb pulsatile loading and other forces generated against the device 1000 such that deformation of the anchoring member 1010 does not substantially deform the valve support 120.

Figure 65B:
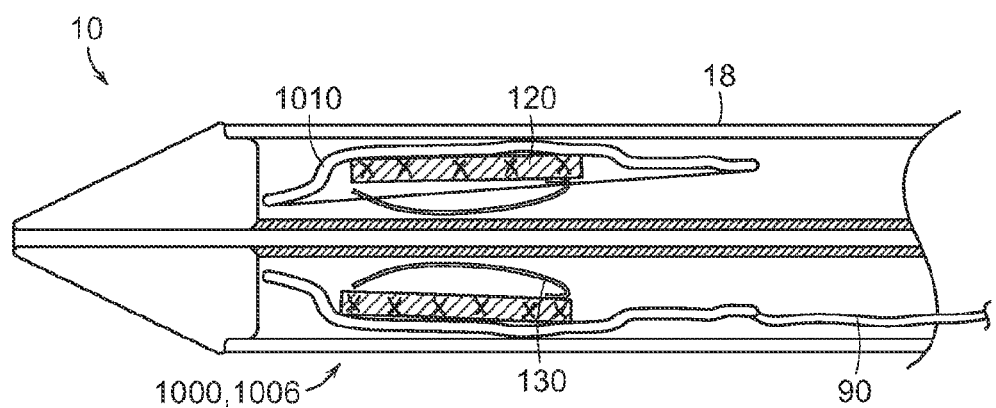
FIG. 65B is a partial cross-sectional side view of a distal end of a delivery system suitable for delivery of the prosthetic heart valve device of FIG. 65A in accordance with another embodiment of the present technology.

FIG. 65B is a partial cross-sectional side view of a distal end of a delivery system 10 suitable for delivery of the prosthetic heart valve device 1000 of FIG. 65A in accordance with another embodiment of the present technology. As shown in FIG. 65B, the delivery system 10 can include a delivery catheter 18 configured to retain the device 1000 in a collapsed configuration 1006. In the collapsed configuration 1006, the inflatable anchoring member 1010 is deflated. The delivery system 10 can also include a fill tube 90 suitable to deliver the fill substance when the device 1000 is in position and ready for deployment. Referring to FIGS. 65A-65B together, and in one embodiment, the inflatable anchoring member 1010 can be partially filled with the fill substance such that the position of the device 1000 at the implant site can be adjusted to align the fixation elements 1015 with the native tissue features before fully expanding and/or inflating the anchoring member 1010 to hold the device 1000 in place at the target location.

Figure 66D:
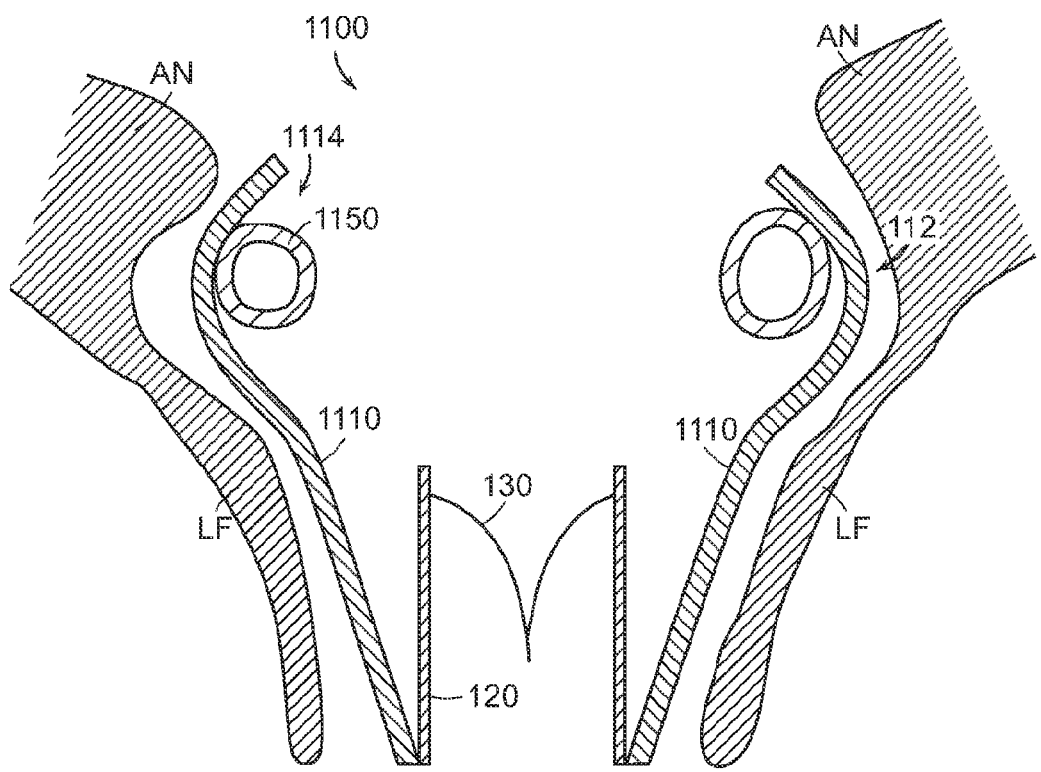

FIGS. 66A-66D are cross-sectional views of prosthetic heart valve devices 1100 having fillable chambers 1114 in accordance with additional embodiments of the present technology. Similar to the device 1000 discussed with respect to FIGS. 65A-65B, the devices 1100 include features such as the valve support 120 having an interior 134 in which a valve 130 is coupled and include an expandable anchoring member 1110 coupled to the valve support 120 in a manner that mechanically isolates the valve support 120 from forces exerted upon the anchoring member 1110 when implanted at the native mitral valve. The anchoring member 1110 can be coupled to the valve support 120 such that an upstream region 1112 of the anchoring member 1110 is configured to engage native tissue on or downstream of the annulus so as to prevent migration of the device 1100 in the upstream direction. In the embodiments shown in FIGS. 66A-66D, the devices 1100 can also include one or more fillable chambers 1114 configured to expand and/or inflate in an outward direction to support an outward expansion of the anchoring member 1100 (FIGS. 66A, 66C-66D), or to engage native tissue (FIG. 66B). In one embodiment, the fillable chambers 1114 and/or the anchoring member 1010 can be formed of polytetrafluoroethylene (PTFE), urethane, or other expandable polymer or biocompatible material. The fillable chambers 1114 can have a predetermined shape such that the fillable chambers 1114, when inflated, form fixation elements for engaging the native anatomy (as shown in FIG. 66B) or for engaging the anchoring member 1110 (as shown in FIGS. 66A, 66C and 66D).

Referring to FIG. 66A, the fillable chamber 1114 can be chambers 1114 created with a space between the valve support 120 and the anchoring member 1110. Following expansion of the device 1100, the fillable chambers 1114 can be filled with a fill substance such as a solution (e.g., saline or other liquid) or gas (e.g., helium, $CO_2$ or other gas). In other embodiments, the fillable chambers 1114 can be filled with a hardening material (e.g., epoxy, cement, or other resin). In other embodiments, the fillable chambers 1114 can be a separate component of the device 1100, such a ring-shaped chamber 1150 coupled to an outer surface 1142 of the anchoring member 1110 (FIG. 66B) or to an inner surface 1141 of the anchoring member 1110 or to an exterior surface 127 of the support valve 120. In FIGS. 66C-66D, for example, the ring-shaped chamber 1150 can provide additional support to the anchoring member 1110 such that inward deformation is counteracted by the presence of the ring-shaped chamber 1150. Additionally, as shown in FIG. 66D, the fillable chamber 114 can be a ring-shaped chamber 1150 that deforms the anchoring member 1110 in an outward direction against the native tissue.

Figure 67A:
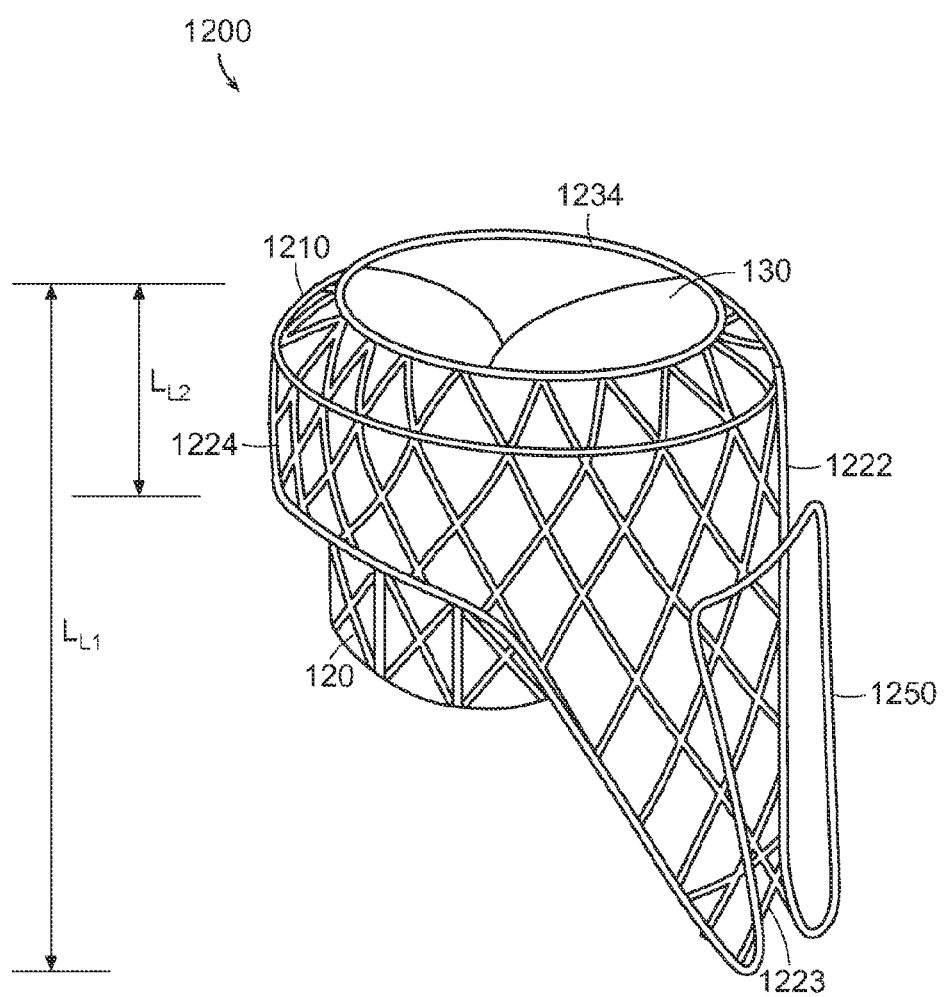
FIGS. 67A-67B are isometric views of additional embodiments of prosthetic heart valve devices in accordance with aspects of the present technology.
Figure 67B:
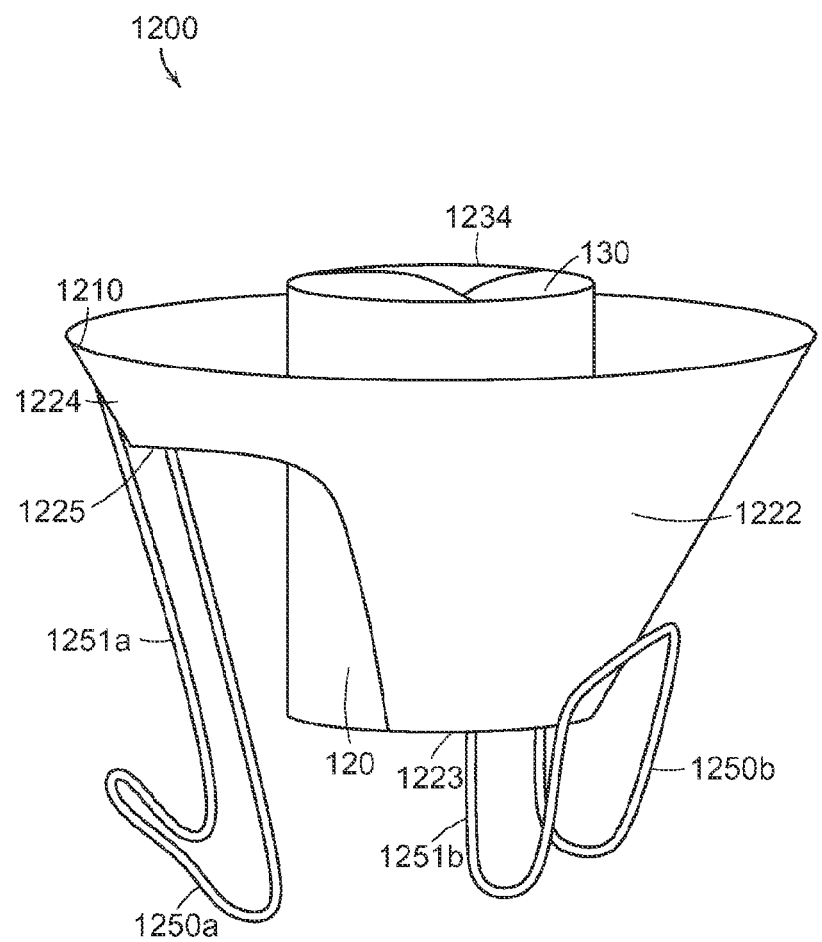

In accordance with another aspect of the present technology, FIGS. 67A-67B illustrates other embodiments of a prosthetic heart valve device 1200. Referring to FIGS. 67A-67B together, the device 1200 can include a radially expandable anchoring member 1210 configured to engage native tissue on or downstream of the annulus, and a support valve 120 and/or a prosthetic valve 130 coupled to an interior portion 1234 of the anchoring member 1210. The anchoring member 1210 can have a first longitudinal length $L_{L1}$ on a posterior leaflet-facing side 1222 of the anchoring member 1210 and have a second longitudinal length $L_{L2}$ on an anterior leaflet-facing side 1224 of the anchoring member 1210. As shown in FIG. 67A, the first length $L_{L1}$ is greater than the second length $L_{L2}$ such that occlusion of a left ventricle outflow tract (LVOT) is limited. Accordingly, in one embodiment, the posterior leaflet-facing side 1222 can provide suitable fixation and support for the anchoring member 1210 by engaging the thicker ventricular wall and tissue on the posterior leaflet side of the mitral valve. Concurrently, the shorter anterior leaflet-facing side 1224 of the anchoring member 1210 can have sufficient sealing and conformability to engage the anterior leaflet and/or subannular tissue aligned with the anterior leaflet of the native valve.

Optionally, the device 1200 can also include one or more stabilizing elements such as an arm 1250 coupled to the anchoring member 1210 for engaging a leaflet and/or a subannular surface. In FIG. 67A, the arm 1250 can be coupled to a downstream end 1223 of the anchoring member 1210 on the posterior leaflet-facing side 1222 of the anchoring member 1210 and be configured to extend behind the posterior leaflet. In one embodiment, the arm 1250 can be configured to sandwich the posterior leaflet between the arm 1250 and the anchoring member 1210.

In FIG. 67B, the device 1200 can include first and second arms (individually identified as 1250*a* and 1250*b*) coupled to the anchoring member 1210 for engaging leaflets and/or subannular surfaces. For example, the first arm 1250*a* can be coupled to the downstream end 1223 at the anterior leaflet-facing side 1224 of the anchoring member 1210 with extension 1251*a* and can be configured to further extend behind the anterior leaflet. The second arm 1250*b* can be coupled to the downstream end 1223 of the posterior leaflet-facing side 1222 of the anchoring member 1210 with extension 1251*b* and be configured to extend behind the posterior leaflet. In the illustrated embodiment, the extensions 1251*a* and 1251*b* can vary with respect to each other and be selected based on the anatomy of the target tissue. In other embodiments, not shown, the arm 1250 and or the anchoring member 1210 can include tissue engaging elements as described above with respect to device 100 for further positioning and stabilizing of the device 1200 at the desired target location. One of ordinary skill will recognize that the valve support 120 can also be uneven or have sides having different lengths such that the valve support will not substantially occlude the left ventricle outflow tract (LVOT).

FIGS. 68A-68B are side views of prosthetic heart valve devices 1300 shown in an expanded configuration 1302 and configured in accordance with an additional embodiment of the present technology. The prosthetic heart valve devices 1300 include features generally similar to the features of the prosthetic heart valve device 100 described above with reference to FIGS. 10A-56. For example, the prosthetic heart valve device 1300 includes the valve support 120 configured to support a prosthetic valve 130 and an anchoring member 110 coupled to the valve support 120 in a manner that mechanically isolates the valve support 120 from forces exerted upon the anchoring member 110 when implanted at the native mitral valve. However, in the embodiments shown in FIGS. 68A-68B, the device 1300 also includes a positioning element 1350 configured to adjust or maintain a desired position of the device 1300 within or near the native mitral valve (e.g., away from the LVOT). The positioning element 1350 can be coupled to the downstream portion 111 of the anchoring member 110 (as shown in FIGS. 68A-68B), the upstream portion 112 of the anchoring member 110, or to the valve support 120, at an element connection point 1352 and extend outward from the element connection point 1352 to engage ventricular tissue at a desired location. In one embodiment, the positioning element 1350 can extend outward from the device 1300 in a direction approximately transverse to the longitudinal axis 101. In other embodiments, not shown, the positioning element 1350 can extend outwardly from the device 1300 at an obtuse or an acute angle relative to the longitudinal axis 101 for engaging the ventricular tissue at the desired location.

In the embodiment shown in FIG. 68A, the positioning element 1350 can include a positioning arm 1354 and a tissue engaging portion 1356 coupled to the distal arm end 1358 of the positioning arm 1354. The positioning arm 1354 and tissue engaging portion 1356 together can extend a desired positioning distance $D_{P1}$ away from the element connection point 1352 on the device 1300 (e.g., from the anchoring member 110) such that the distal end 1360 of the positioning element 1350 can engage ventricular tissue, such as a ventricular wall. In some embodiments, the positioning distance $D_{P1}$ can be selected to be greater than a distance between the implanted device 1300 and the ventricular tissue such that the positioning element 1350, after engaging the ventricular tissue, extends the distance between the implant device 1300 and the ventricular tissue. In this way, the device 1300 can be positioned, aligned and maintained in an alternate position within or near the mitral valve.

The tissue engaging portion 1356 can be configured to contact the ventricular tissue, or other tissue (e.g., annular tissue, leaflet tissue, etc.), in an atraumatic manner such that the tissue engaging portion 1356 does not penetrate or pierce the tissue. In one embodiment, the tissue engaging portion 1356 can be resilient and/or be formed of a shape memory material (e.g., Nitinol) that can be partially deformed when engaging tissue. For example, the tissue engaging portion 1356 can be configured to absorb forces generated by the ventricular tissue (e.g., ventricular wall) during e.g., systole, without translating movement or altering a desired position of the device 1300 with respect to the native mitral valve. In other embodiments, the distal end 1360 of the positioning element 1350 can have other shapes or configurations that penetrate the ventricular tissue. The device 1300 can include one or more positioning elements 1350 disposed around the device 1300 for positioning and/or maintaining a desired position of the device 1300 with respect to native anatomy. For example, it may be desirable to increase the distance between the device 1300 and the left ventricular outflow tract (LVOT), and a positioning element 1350 can be configured to engage ventricular tissue to push or encourage the device 1300 a selected distance away from the LVOT.

In the embodiment shown in FIG. 68B, the positioning element 1350 can include a looped tissue engaging portion 1358 coupled to the device 1300 at the connection point 1352. The looped tissue engaging portion 1358 can extend the desired positioning distance $D_{P1}$ away from the element connection point 1352 on the device 1300 (e.g., from the anchoring member 110) such that the distal end 1360 of the looped tissue engaging portion 1358 can engage ventricular tissue, such as a ventricular wall. The looped tissue engaging portion 1358 can be configured to absorb radially contracting forces or other forces generated and transmitted by the ventricular tissue (e.g., within the left ventricle) such that they are not transmitted to or can change the position of the device 1300 with respect to the native heart valve. Accordingly, the device 1300 can be positioned, aligned and maintained in an alternate position within or near the mitral valve.

In another embodiment, not shown, a positioning structure, separate from the prosthetic heart valve device 100, can be implanted or otherwise positioned in the left ventricle (e.g., at or near the LVOT) and which can be configured to engage portions of the device 100, such as the anchoring member 110. Accordingly, such a positioning structure can be provided to prevent the device 100 from obstructing or partially obstructing the LVOT. In one embodiment, not shown, the positioning structure could be a stent-like cylinder or cage that expands into engagement with the ventricular wall and keeps the LVOT clear to allow blood to flow freely from the left ventricle through the aortic valve. In one example, the positioning structure could be delivered by catheter that is inserted through the aorta and the aortic valve into the left ventricle, or through the apex or the left atrium via the same delivery catheter used for delivering and implanting the device 100.

FIGS. 69A-69E are cross-sectional and side views of prosthetic heart valve devices 1400 shown in an expanded configuration 1402 and configured in accordance with an additional embodiment of the present technology. The prosthetic heart valve devices 1400 include features generally similar to the features of the prosthetic heart valve devices 100, 600 described above with reference to FIGS. 10A-57E. For example, the prosthetic heart valve devices 1400 include the valve support 120 configured to support a prosthetic valve 130 and an anchoring member 110 or 610 coupled to the valve support 120 in a manner that mechanically isolates the valve support 120 from forces exerted upon the anchoring member 110 when implanted at the native mitral valve. However, in the embodiments shown in FIGS. 69A-69E, the devices 1400 also includes a an expandable tissue-engaging ring 1450 coupled to a tissue engaging portion of the anchoring member 110 and configured to provide additional contact surface for engaging native tissue at or near the annulus of the heart valve.

In one embodiment, shown in FIGS. 69A-69B, the expandable tissue-engaging ring 1450 can be coupled to an upstream perimeter 113 of the anchoring member 110 and have a tissue-engaging surface 1452 facing in an outward direction relative to the device 1400. In some embodiments, the tissue-engaging surface 1452 can have tissue-engaging elements 170 for engaging and/or piercing the tissue. In another embodiment, shown in FIG. 69C, the expandable tissue-engaging ring 1450 can be coupled to a downstream perimeter 115 of the anchoring member 1410 and have a tissue-engaging surface 1452 facing in an outward direction relative to the device 1400. In another embodiment shown in FIG. 69D, the expandable tissue-engaging ring 1450 may include a plurality of fibrous elements 1454 (e.g., fiber elements) that can be configured to encourage tissue ingrowth, thrombus and/or be configured to provide a seal between the anchoring member 110 and the tissue. In various arrangements, the expandable tissue-engaging ring 1450 can expand and contract between various deployment and delivery configurations.

Figure 69E:
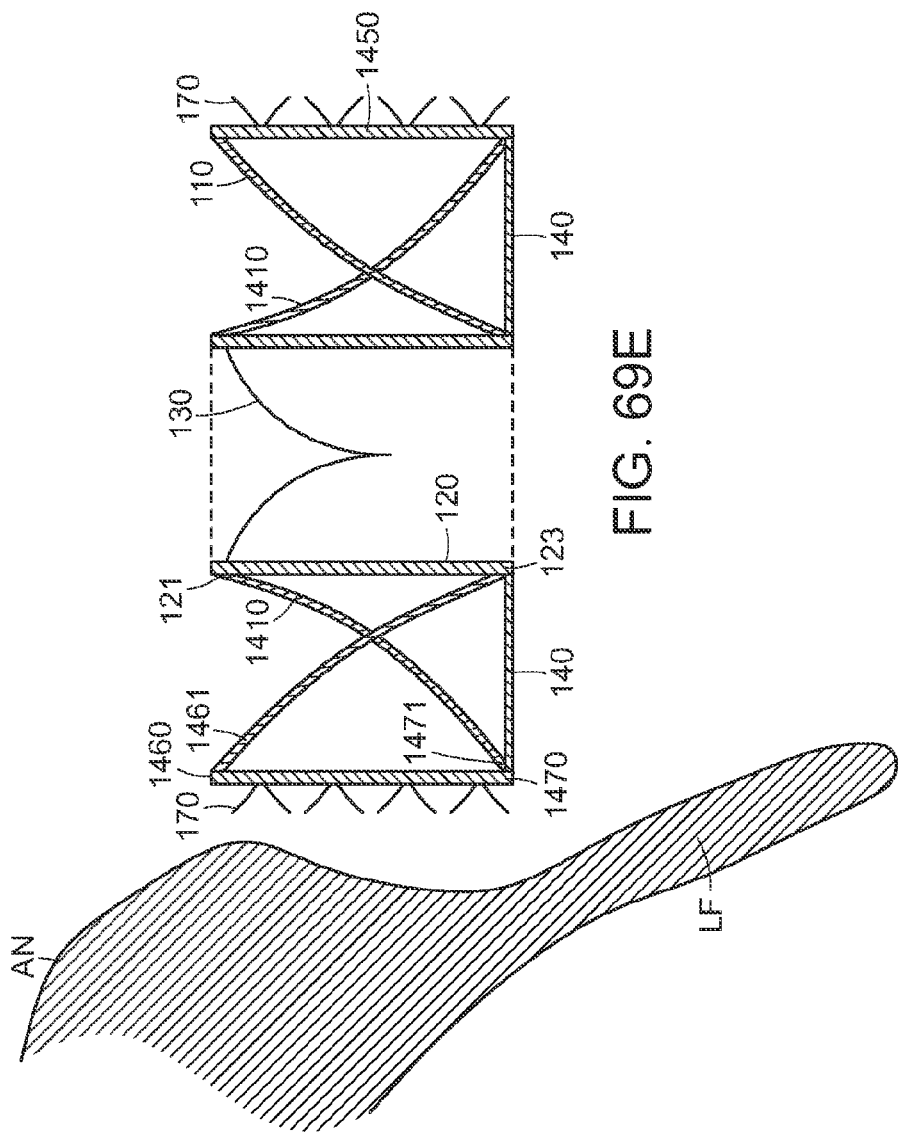

FIG. 69E shows another embodiment of the prosthetic heart valve device 1400 having the expandable tissue-engaging ring 1450. In this embodiment, the device 1400 can have a valve support 120 coupled to a first anchoring member 110 and a second anchoring member. In one embodiment, the first anchoring member 110 can be coupled to the valve support 120 at the downstream end 123 and extends outward and in an upstream direction. The second anchoring member 1410 can be coupled to the valve support 120 at the upstream end 121 and extend outward and in a downstream direction. The expandable tissue-engaging ring 1450 can be coupled to the distal portions of the first and second anchoring members 110, 1410 and have the tissue-engaging surface 1452 facing in an outward direction relative to the device 1500 for engaging tissue at or near the annulus AN or leaflets LF. In a particular example, the expandable tissue-engaging ring 1450 can have a first end 1460 coupled to an upstream end 1461 of the first anchoring member 110. The expandable tissue-engaging ring 1450 can also have a second end 1470 coupled to a downstream end 1471 of the second anchoring member 1410. The tissue-engaging surface 1452 may also include tissue engaging elements 170 for engaging and/or piercing the tissue at the target location.

Referring to FIGS. 69A-69E together, the outward radial force of the expandable tissue-engaging ring 1450 against the tissue and supported by the anchoring members 110 and/or 1410 can prevent the device 1400 from migrating in an upstream direction. Additionally, the expandable tissue-engaging ring 1450 along with at least the portions of the anchoring members 110 and/or 1410 that are uncoupled from the valve support 120 can effectively mechanically isolate the valve support 120 and the valve 130 from compromising radially compressive forces exerted on the device 1400 from the heart valve tissue.

Figure 70:
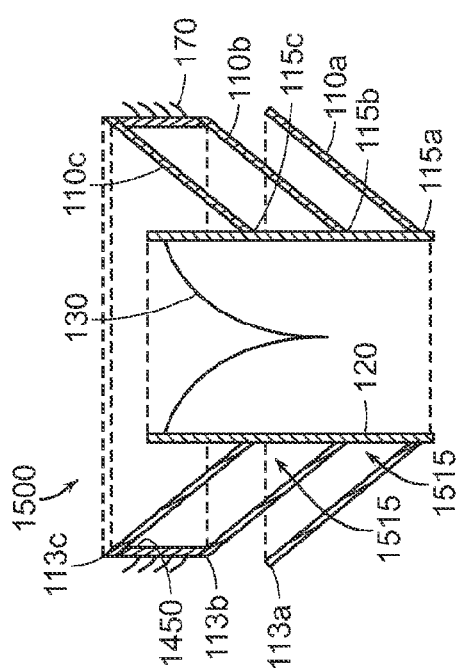
FIG. 70 is a cross-sectional side view of another prosthetic heart valve device configured in accordance with an embodiment of the present technology.

FIG. 70 is a cross-sectional side view of another prosthetic heart valve device 1500 configured in accordance with an embodiment of the present technology. The device 1500 can also include features as described above including a valve support 120 and a prosthetic valve 130 retained within the valve support 120. The device 1500 can also include a plurality of anchoring members (individually identified as 110a-c). The anchoring members 110a-c can be coupled at respective downstream perimeters 115a-c to the valve support 120 and be separated by gaps 1515 such that respective upstream perimeter 113a-c can engage cardiac tissue at variable target locations at the native valve. Optionally, the device 1500 can also include the expandable tissue-engaging ring 1450 (FIGS. 69A-D) such as those having tissue engaging features 170 for further engaging tissue at the native valve. In one embodiment, the expandable tissue-engaging ring 1450 can be coupled to the upstream perimeter of more than one anchoring member (e.g., the upstream perimeters 113b and 113c of anchoring members 110b and 110c). However, in other arrangements, the device 1500 will not have the expandable tissue-engaging ring 1450.

Figure 71:
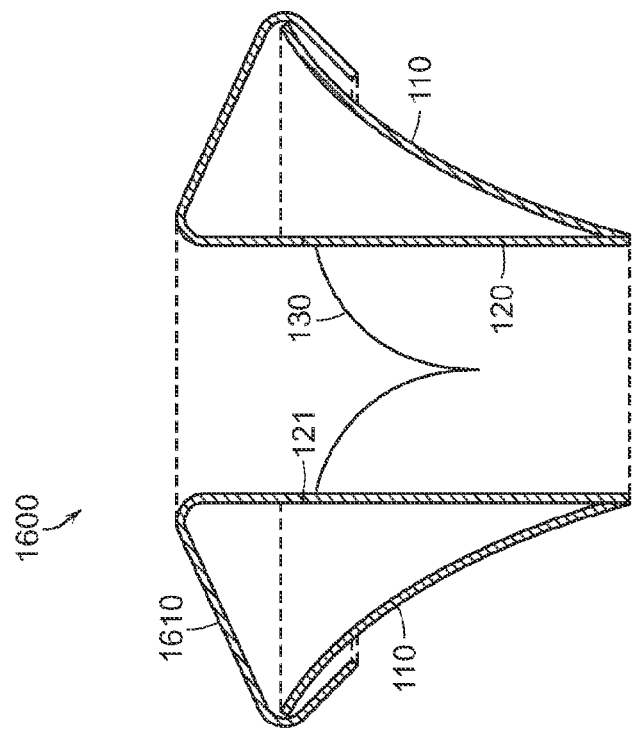
FIG. 71 is a cross-sectional side view of yet another prosthetic heart valve device configured in accordance with an embodiment of the present technology.

FIG. 71 is a cross-sectional side view of yet another prosthetic heart valve device 1600 configured in accordance with an embodiment of the present technology. The device 1600 can also include features as described above including a valve support 120 and a prosthetic valve 130 retained within the valve support 120. The device 1500 can also include the anchoring member 110. However, the device 1600 can also include an expandable retainer 1610 for further engaging tissue at or near the native valve annulus. In one embodiment, the retainer 1610 can be an extension of upstream end 121 of the valve support 120, however, in another embodiment, the retainer 1610 can include a separate expandable feature coupled to the upstream end 121 of the valve support. In some arrangements, the retainer 1610 can be mechanically isolated from the valve support 120 such that forces generated at the native valve are absorbed or otherwise translated by the retainer 1610. In this manner, the retainer 1610 may be deformed by radial forces exerted on the retainer 1610 while the valve support remains substantially undeformed.

In one embodiment, as shown, the anchoring member 110 can be configured to engage the retainer 1610; however, in other embodiments, the anchoring member 110 can be positioned differently such that the anchoring member 110 contacts tissue different than that of the retainer 1610. For example, the anchoring member 110 may extend outside a radius (not shown) of the retainer to contact subannular tissue. Additional details and embodiments regarding the structure, delivery and attachment of retainers 1610 suitable for use with the prosthetic heart valve devices disclosed herein can be found in International PCT Patent Application No. PCT/US2012/61215, entitled "DEVICES, SYSTEMS AND METHODS FOR HEART VALVE REPLACEMENT," filed Oct. 19, 2012, the entire contents of which are incorporated herein by reference.

Figure 72:
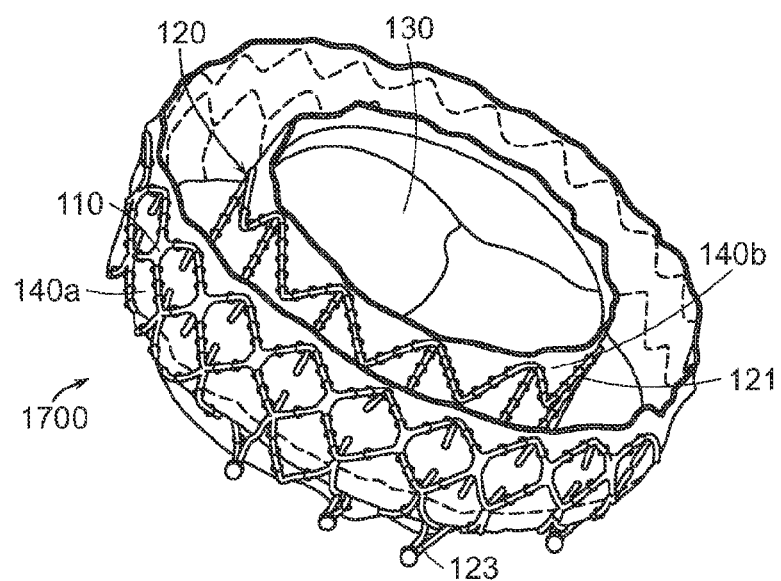
FIG. 72 is an isometric view of a prosthetic heart valve device in accordance with another embodiment of the technology.

FIG. 72 is an isometric view of a prosthetic heart valve device 1700 in accordance with another embodiment of the present technology. The device 1700 can include an anchoring member 110, a valve support 120 positioned radially within at least a portion of the anchoring member 110, and a prosthetic valve 130 retained within the valve support 120. The device 1700 can further include a first sealing member portion 140a coupled to an inner wall of the anchoring member 110 and a second sealing member portion 140b coupled to the inner wall of the valve support 120. In other embodiments, the first sealing member portion 140a can be coupled to the outer wall of the anchoring member 110 and/or the second sealing member portion 140b can be coupled to the outer wall of the valve support 120. The first and second sealing member portions 140a and 140b can be integral portions of a single sealing member, or the first and second sealing member portions 140a and 140b can be separate sealing members that are attached independently to the anchoring member 110 and the valve support 120. The first and second sealing member portions 140a and 140b will in any event together form a sealed bather between the valve support 120 and the anchoring member 110 to inhibit or prevent blood from flowing outside of the valve support 120 as blood flows from the atrium to ventricle or vice versa. As with several embodiments described above, an upstream portion 121 of the valve support 120 is spaced radially inward from the anchoring member 110, and a downstream portion 123 of the valve support 120 is coupled to the anchoring member 110.

Figure 73:
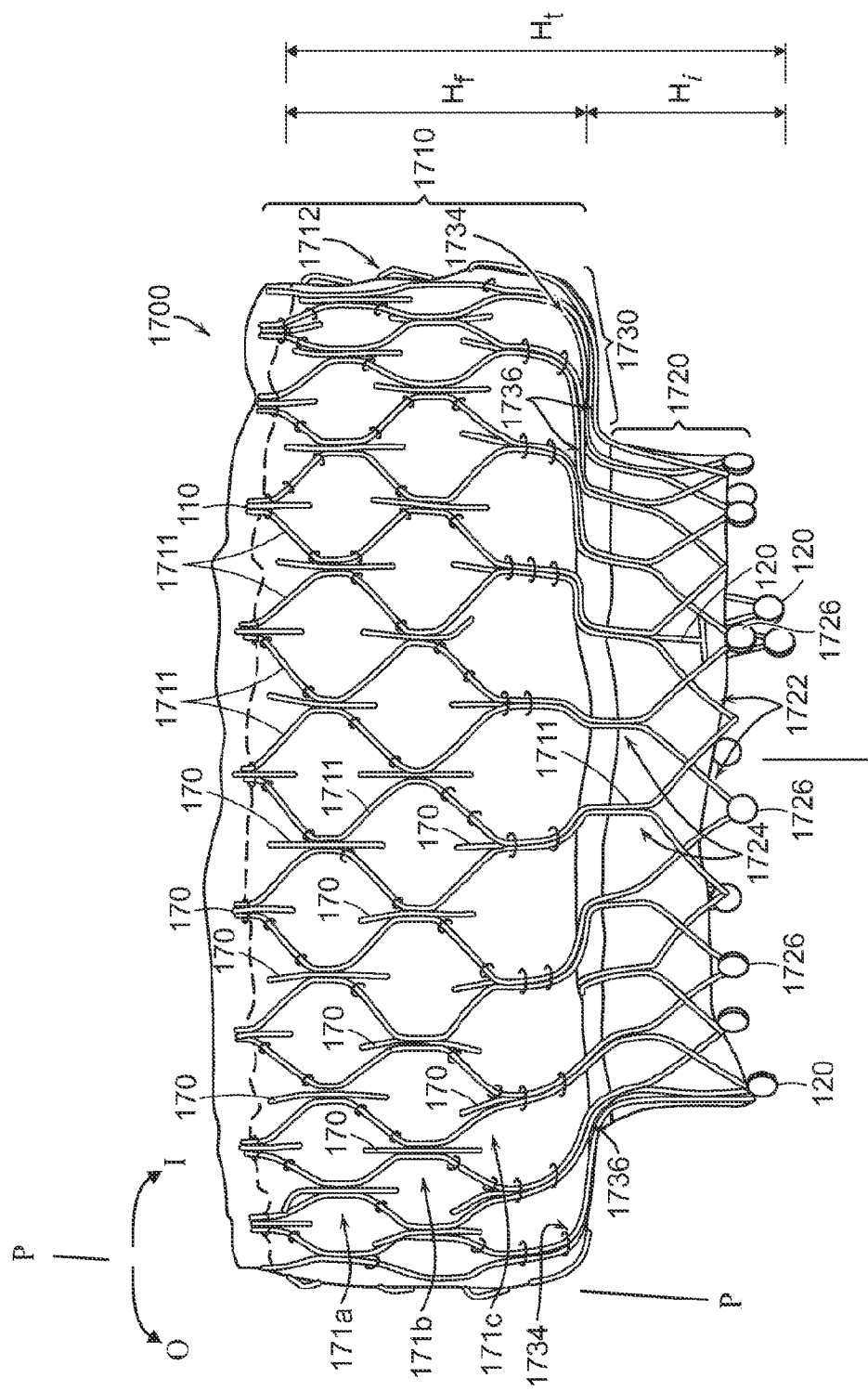
FIG. 73 is a side view of the prosthetic heart valve device of FIG. 72.
Figure 74:
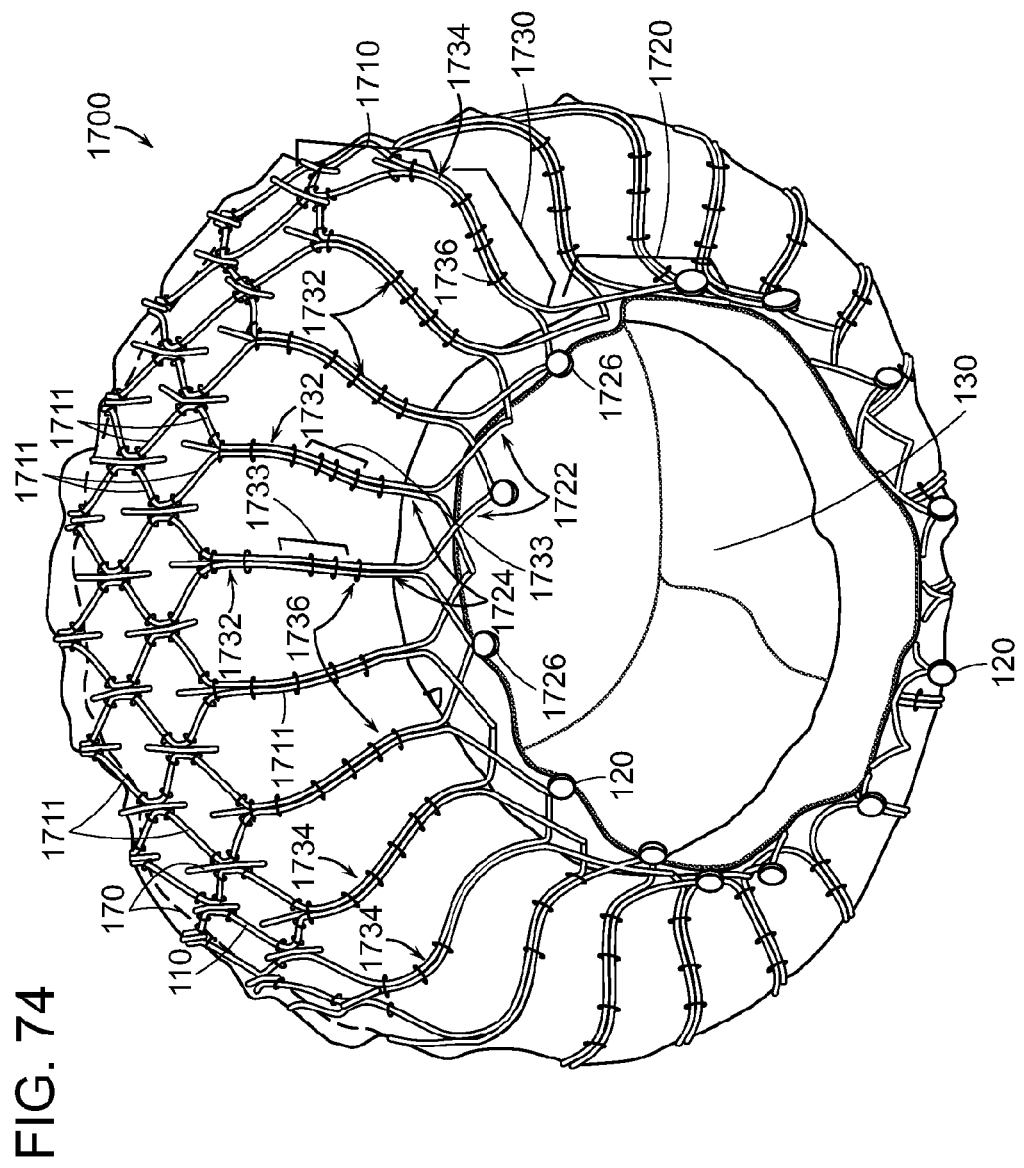
FIG. 74 is a bottom view of the prosthetic heart valve device of FIG. 72.

FIG. 73 is a side view of the prosthetic heart valve device 1700, and FIG. 74 is a bottom isometric view of the prosthetic heart valve device 1700. The anchoring member 110 can include a fixation portion 1710 configured to securely fix the anchoring member 110 to tissue at a native heart valve, an integration region 1720 configured to integrate the anchoring member 110 with the valve support 120, and a lateral portion 1730 between the fixation portion 1710 and the integration region 1720. The fixation portion 1710, integration region 1720, and lateral portion 1730 can be formed by a plurality of structural elements 1711 that can extend from the fixation portion 1710 to the integration region 1720. The integration region 1720 and the lateral region 1730 can collectively or individually define a connection structure that positions and controls the fixation portion 1710 relative to the valve support 120. The structural elements 1711 can be shaped and connected to form diamond-shaped or other structural configurations that provide the desired strength and flexion. The structural elements 1711 can be struts or other structural features formed from metal, polymers, or other suitable materials that can self-expand or be expanded by a balloon or other mechanical expander.

Several embodiments of the fixation portion 1710 can be a generally cylindrical fixation ring having an outwardly facing engagement surface 1712, which may be a large, generally cylindrical surface for engaging tissue at or near the annulus of a native valve. For example, the outer surface of the fixation portion 1710 can extend in a direction P-P that is at least substantially parallel to a longitudinal axis L-L, or the fixation portion 1710 can be inclined to converge from the lateral portion 1730 toward the longitudinal axis L-L such that all or a portion of the fixation ring is tapered in the upstream direction. For example, the fixation portion 1710 can be inclined inwardly (arrow I) toward the longitudinal axis L-L in the upstream direction at an angle of 0 to −30° relative to the longitudinal axis L-L. In other embodiments, the fixation portion 1710 can be inclined outwardly (arrow O) from the longitudinal axis L-L by an angle of 0 to 45° to increase the outward radial force. In several embodiments, the fixation portion 1710 can be parallel to an outwardly facing surface of the valve support 120.

Several embodiments of the anchoring member 110 are configured to press the engagement surface 1712 against tissue at an implant site on or below a native annulus of the native heart valve when the orientation of the fixation portion 1710 is at least generally parallel to the longitudinal axis L-L or tapered inwardly in the upstream direction. The fixation portion 1710 may have such a configuration in an unbiased state before implantation, or it may assume this inwardly tapered configuration through deformation imposed by engagement with tissue at the implant site. For example, the fixation portion 1710 can be deflectable through a range of angles relative to the longitudinal axis L-L such that upon engagement with the tissue the fixation portion 1710 moves from an unbiased state to the implanted orientation in which it is orientated at least substantially parallel to or tapered in the upstream direction toward the longitudinal axis L-L. As explained in more detail below, the large, generally cylindrical area of the outer surface of the fixation portion 1710 and the orientation of the fixation portion 1710 in a direction P-P provide good fixation to the annulus and subannular tissue of a native mitral valve or other heart valve. In several embodiments, the fixation portion can have a height ($H_f$) of 10 mm-20 mm.

The fixation portion 1710 of the anchoring member 110 may have different regions of radial stiffness along the P-P axis. These regions can conform to and exert an outward radial force on the surrounding anatomy to provide fixation and sealing. In one example, the radial stiffness may be greater in the region of the fixation portion that is downstream of the annulus and lesser in the region that is in contact with and upstream of the annulus. This combination would provide a region downstream of the annulus that resists compression and ensures that the device maintains its fixation with respect to the anatomy when subjected to a systolic pressure gradient and a region at the annulus that allows some compression (preventing dilation of the annulus), but maintains sufficient radial outward force to keep the fixation portion in contact with the anatomy to provide sealing between the device and the anatomy.

Radial stiffness may be controlled by the design of the structural elements of the attachment portion 1720 and/or the lateral portion 1730, the taper angle or curve between these regions and the fixation portion 1710, or a combination of those properties. The design of the structural elements 1711 of the fixation portion 1710 may have different properties (wall thickness, width, length, angle, etc.) along with the P-P axis to provide regions of different radial stiffness. Additionally, the fixation portion 1710 can have a first flexibility and the integration region 1720 and/or the lateral portion 1730 can have a second flexibility different than the first flexibility. The fixation portion 1710 can itself have a downstream region with a first flexibility and an upstream region with a second flexibility different than the first flexibility.

The fixation portion 1710 can further include a plurality of tissue engaging elements 170 configured to penetrate into the annulus and/or subannular tissue. The prosthetic heart valve device is preferably anchored solely by the engagement of fixation portion 1710 with the native tissue, which resists the high forces of blood against the device during ventricular systole. Other means of anchoring, such as tissue-engaging arms or tethers coupled to the native tissue, are not required. Thus, the tissue engaging elements 170 are configured to engage the native tissue to reliably resist movement of the device without fully penetrating or perforating the leaflets or heart wall tissue, or otherwise causing undue trauma as the heart beats. Because the upstream forces during ventricular systole are so high, the tissue engaging elements 170 will preferably project at least in the upstream direction to inhibit movement of anchoring member 110 in the upstream direction relative to the native tissue. Smaller forces are exerted on the device in the downstream direction during diastole, so in some cases downstream-projecting tissue engaging elements may also be desirable (e.g., project superiorly in the case of a mitral valve). In one embodiment, the fixation portion 1710 can include an upper row 171a of tissue engaging elements that project superiorly and inferiorly, a second row 171b of tissue engaging elements that also extend superiorly and inferiorly, and a third row 171c of tissue engaging elements that extend superiorly. The tissue engaging elements 170 can be barbs, tines, pins, or other elements that penetrate into or otherwise grip the tissue of the native annulus and/or native subannular tissue. In several embodiments, the tissue engaging elements 170 project radially outward from the structural elements 1711 of the fixation portion 1710 by a distance of approximately 0.5-5 millimeters.

The integration region 1720 of the anchoring member 110 can be formed from the lower portions of the structural elements 1711. In the embodiment illustrated in FIGS. 73 and 74, the integration region 1720 has a plurality of diamond-shaped structures 1722 and vertical members 1724. In the illustrated embodiment, each of the vertical members 1724 can include a portion of two of the structural elements 1711. In several embodiments, the anchoring member 110 and the valve support 120 are made from separate struts, and the integration region 1720 is an attachment portion or fastening portion of the anchoring member 110 that is attached to the valve support 120. For example, when the anchoring member 110 and the valve support 120 are separate components, the integration region 1720 can be an attachment portion including a plurality of connecting points 1726 where the integration region 1720 is coupled to the valve support 120. In one embodiment, the integration region 1720 of the anchoring member 110 can be connected to the valve support 120 at a plurality of connecting points 1726 (e.g., 12) using Nitinol rivets. In other embodiments, threads, adhesives, solder, laser welding, metal bolts or other mechanical features, or other types of fasteners can be used to secure the valve support 120 to the integration region 1720. The integration region 1720 can thus be a fastening portion.

In other embodiments, the anchoring member 110 and the valve support 120 are integrally formed together from common struts, or a number of struts can be integrally formed with both the anchoring member 110 and the valve support 120. In these embodiments, the integration region 1720 is the structure that transitions from the anchoring member 110 to the valve support 120 without otherwise being fastened together. For example, the integration region 1720 can be a curved or otherwise bent portion of such struts between a cylindrically shaped valve support 120 and the portion of the anchoring member 110 that projects away from the valve support 120.

Figure 75:
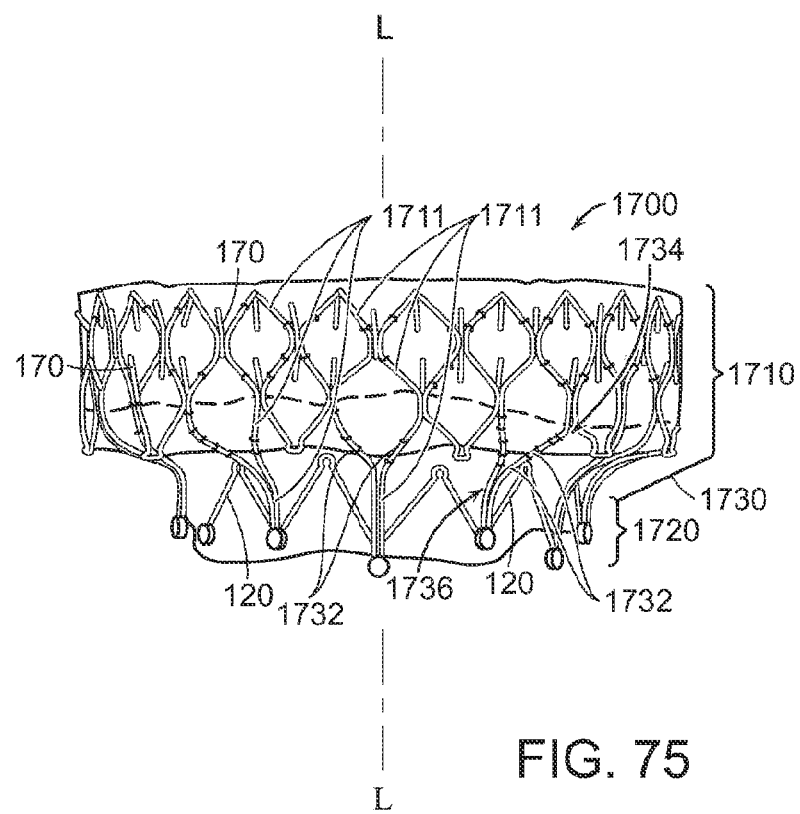
FIG. 75 is a side view of a prosthetic heart valve device in accordance with another embodiment of the technology.

The lateral portion 1730 extends between the upper region of the integration region 1720 and the lower region of the fixation portion 1710 in the embodiment shown in FIGS. 72-74. The lateral portion 1730, for example, extends laterally outward from the integration region 1720 to the fixation portion 1710. In one embodiment, the lateral portion 1720 includes a plurality of connectors 1732 having lateral sections 1733 (FIG. 74) formed from a portion of the structural elements 1711. The lateral sections 1733 of the connectors 1732 extend laterally, which in several embodiments is a direction transverse to the longitudinal axis L-L in an outwardly straight, conical, curved, or outwardly angled (e.g., flared) configuration. Additionally, "traverse direction" includes any non-parallel direction relative to the longitudinal axis L-L. The connectors 1732 can have a first transition zone 1734 that curves from the orientation of the fixation portion 1710, which is generally parallel to or canted inwardly toward the longitudinal axis L-L, to the lateral sections 1733 of the connectors 1732 that are transverse to the longitudinal axis L-L. In many embodiments the lateral sections 1733 of the connectors 1732 are nearly perpendicular or perpendicular to the longitudinal axis L-L. The connectors 1732 can also have second transition zone 1736 that curves from the lateral sections 1733 of the connectors 1732 to the orientation of the integration region 1720 that extends at least generally parallel to the longitudinal axis L-L (FIG. 73). In the embodiment shown in FIG. 73, the first transition zone 1734 is an inward and/or superior bend at an angle of approximately 60°-160° (e.g., approximately 90°) from the lateral sections 1733 to the orientation of the engagement surface 1712 of the fixation portion 1710. The second transitional zone 1736 can be a downward and/or inferior bend at an angle in the range of 75°-160° (e.g., approximately 90°) from the lateral sections 1733 of the connectors 1732 to the integration region 1720. The smaller angles result in an S-Shape; the larger angles result in a tapered transition as shown in FIG. 75. The first transition zone 1734 can thus be a concave curve with respect to the longitudinal axis L-L, and similarly the second transition zone 1736 can be a convex curve with respect to the longitudinal axis L-L. The curves of the first transition zone 1734 and the second transitional zone 1736 enable the fixation portion 1710 to present a large engagement surface 1712 to contact the annulus and leaflets of the native heart valve to provide good fixation of the device 1700. The connectors 1732 also enable the fixation portion 1710 to flex based on the shape of the native annulus and the contraction of the left ventricle without transmitting the full forces of such flexure of the fixation portion 1710 to the upstream portion 121 of the valve support 120 where the prosthetic valve 130 is attached. The device 1700 accordingly provides enhanced fixation to the native tissue and sufficient mechanical isolation between the fixation portion 1710 and the upstream portion 121 of the valve support 120 such that the prosthetic leaves of the prosthetic valve 130 maintain sufficient contact with each other to inhibit backflow after the anchoring member 110 has been implanted at a native mitral valve and during left ventricular contraction.

In several embodiments, as explained above, the integration region 1720 and the lateral portion 1730 can individually or collectively define a connecting structure that interconnects the anchoring member 110 and valve support 120. The connecting structure can comprise a plurality of struts that each have an inner end connected to or integral with the valve support 120 and an outer end connected to or integral with the anchoring member 110. For example, the connecting structure can be a flared portion that flares outwardly from the valve support 120 in the upstream direction, and in selected embodiments the connecting structure can be configured to be disposed entirely downstream of the native annulus when the anchoring member is at the implant site. The connecting structure can have an upstream end connected to the anchoring member such that the upstream end is positioned below the native annulus when the anchoring member is at the implant site.

The anchoring member 110 can thus include the fixation portion 1710 and the connection structure 1720/1730, and the connection structure 1720/1730 can have an inner end connected to the valve support 120, an outer end connected to the fixation portion 1710, and an intermediate portion between the inner end and the outer end which flares outwardly from the valve support 120. The intermediate portion, for example, can flare outwardly in an upstream direction.

The fixation portion 1710 can have a skirt covering an inward-facing surface of the fixation portion 1710, and in additional embodiments the skirt can further cover an inward-facing side of the connecting structure. Additionally, the device 1700 can further include a tubular valve cover extending around the valve support, and the skirt can be attached to the tubular valve cover. In additional embodiments, the valve cover is disposed on an inward facing surface of the valve support.

Figure 76:
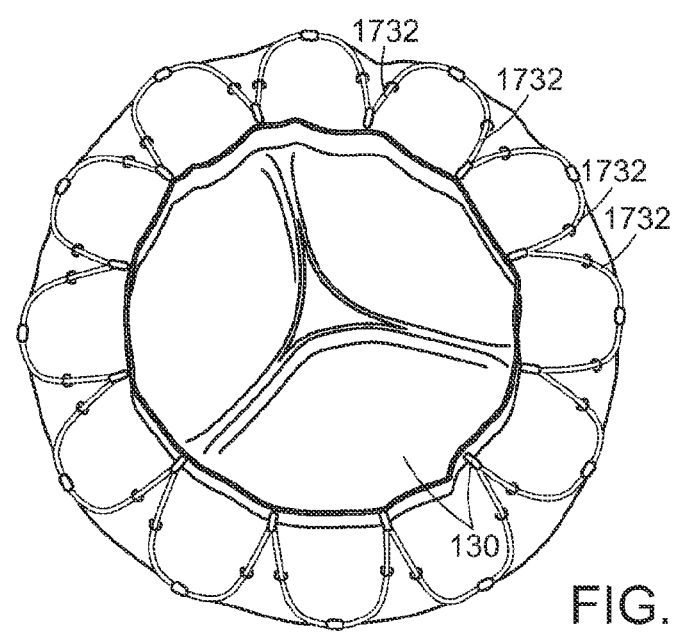
FIG. 76 is a bottom view of the prosthetic heart valve device of FIG. 75.

FIG. 75 is a side view of another embodiment of the prosthetic heart valve device 1700, and FIG. 76 is a bottom view of the prosthetic heart valve device 1700 shown in FIG. 75. In this embodiment, the connectors 1732 of the lateral portion 1730 are defined by laterally extending portions of individual structural elements 1711 that extend between the fixation portion 1710 and the integration region 1720. Referring to FIG. 76, each connector 1732 includes a single one of the structural elements 1711 as opposed to two structural elements 1711 as shown in FIGS. 72-74. Additionally, the connectors 1732 are inclined at a non-perpendicular angle with respect to the longitudinal axis L-L of the device 1700. The connectors 1732 nonetheless each include a first transition 1734 bending from the connectors 1732 to the fixation portion 1710, and a second transition zone 1736 bending from the connectors 1732 to the integration region 1720.

Figure 77:
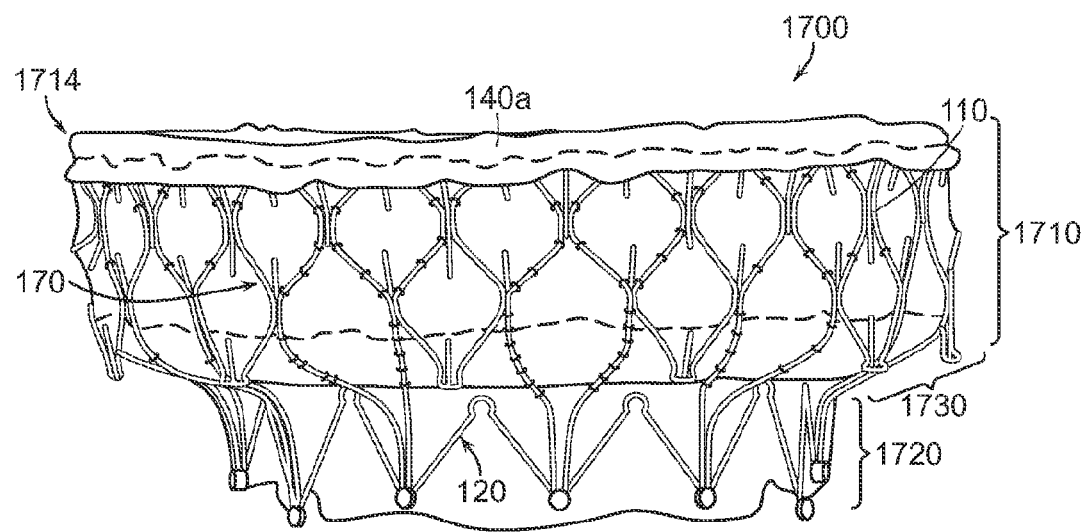
FIG. 77 is a side view of a prosthetic heart valve device in accordance with another embodiment of the technology.

FIG. 77 is a side view of the prosthetic heart valve device 1700 in accordance with another embodiment of the present technology. In this embodiment, the device 1700 wraps a portion of the first sealing member portion 140a around a rim 1714 of the fixation portion 1710 of the anchoring member 110. The section of the first sealing portion 140a wrapped over the rim 1714 provides an atraumatic edge to protect the roof of the left atrium during implantation and use.

Figure 78:
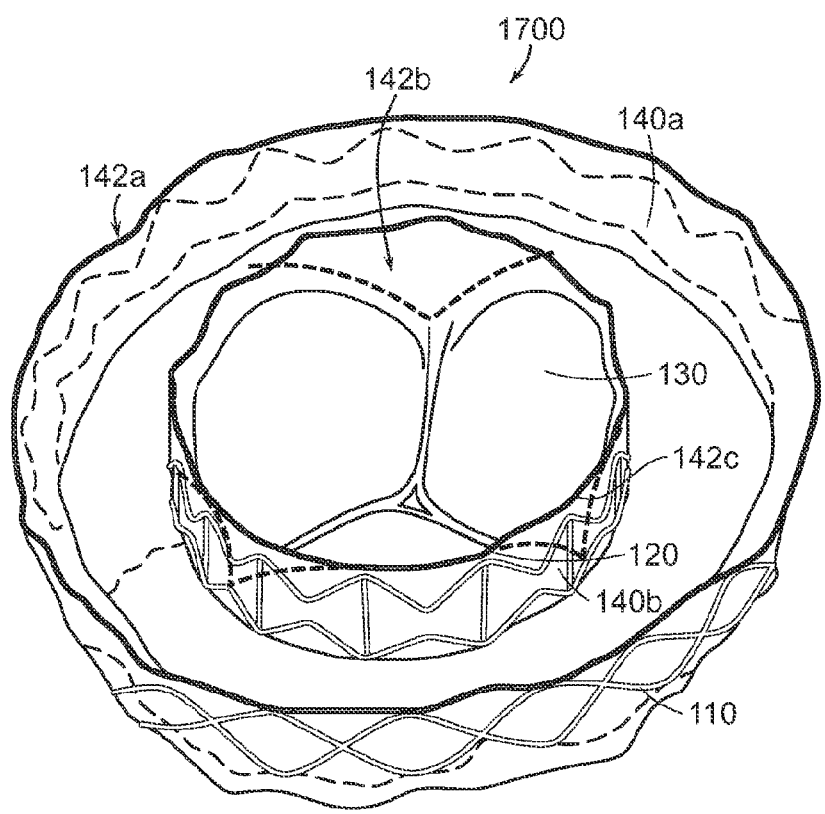
FIG. 78 is an isometric view of a prosthetic heart valve device in accordance with another embodiment of the technology.

FIG. 78 is an isometric view of the prosthetic heart valve device 1700 in accordance with yet another embodiment of the present technology. In this embodiment, the material of the second sealing portion 140b on the inside of the valve stent 120 has openings 142a-142c spaced apart from each other around the perimeter of the valve support 120. The openings 142a-142c are spaced between the commissures where the prosthetic valve 130 is attached to the second sealing portion 140b. In operation, the open areas 142a-142c are expected to decrease static blood volume on the atrial side of the device 1700 to reduce fibrin and thrombus deposition and to provide better flow dynamics.

Figure 79A:
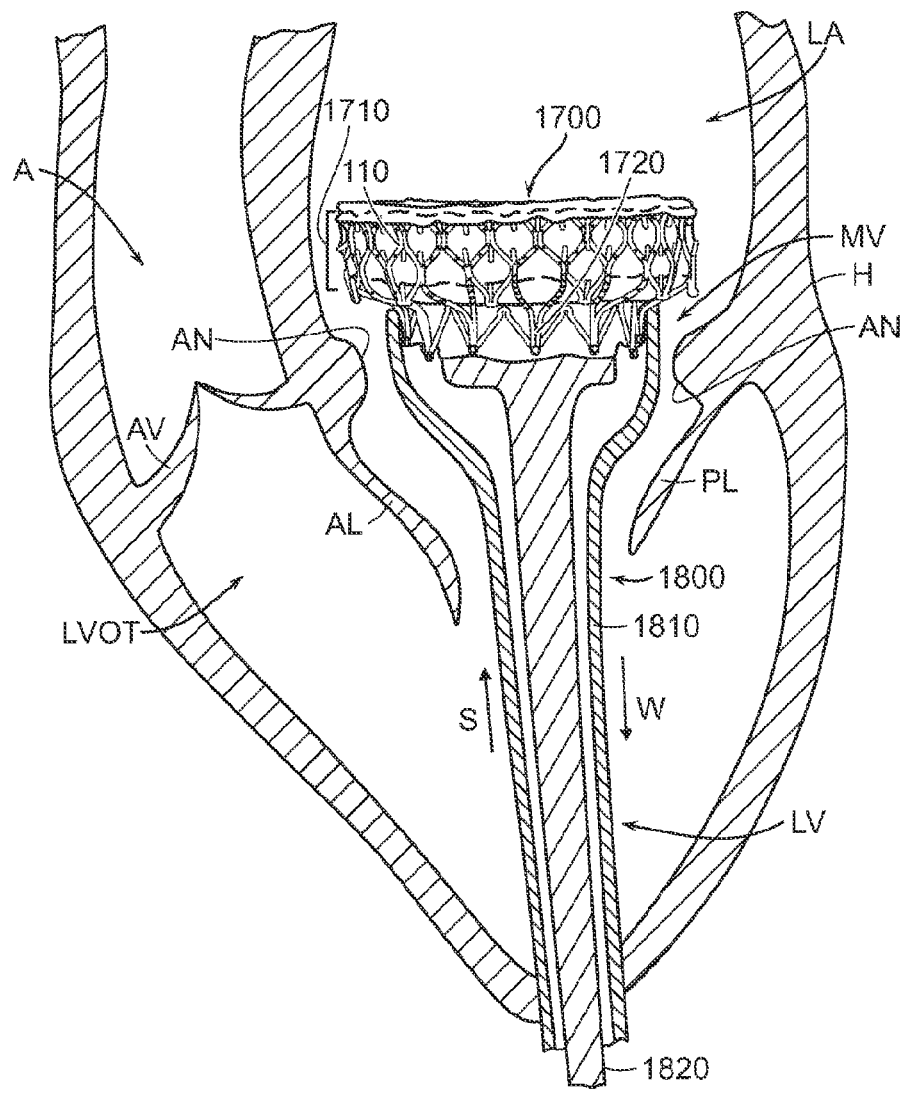
FIGS. 79A and 79B are partial anatomical cross-sections of a heart (H) and side views of an embodiment of a prosthetic heart valve device being implanted in accordance with a method of the present technology.
Figure 79B:
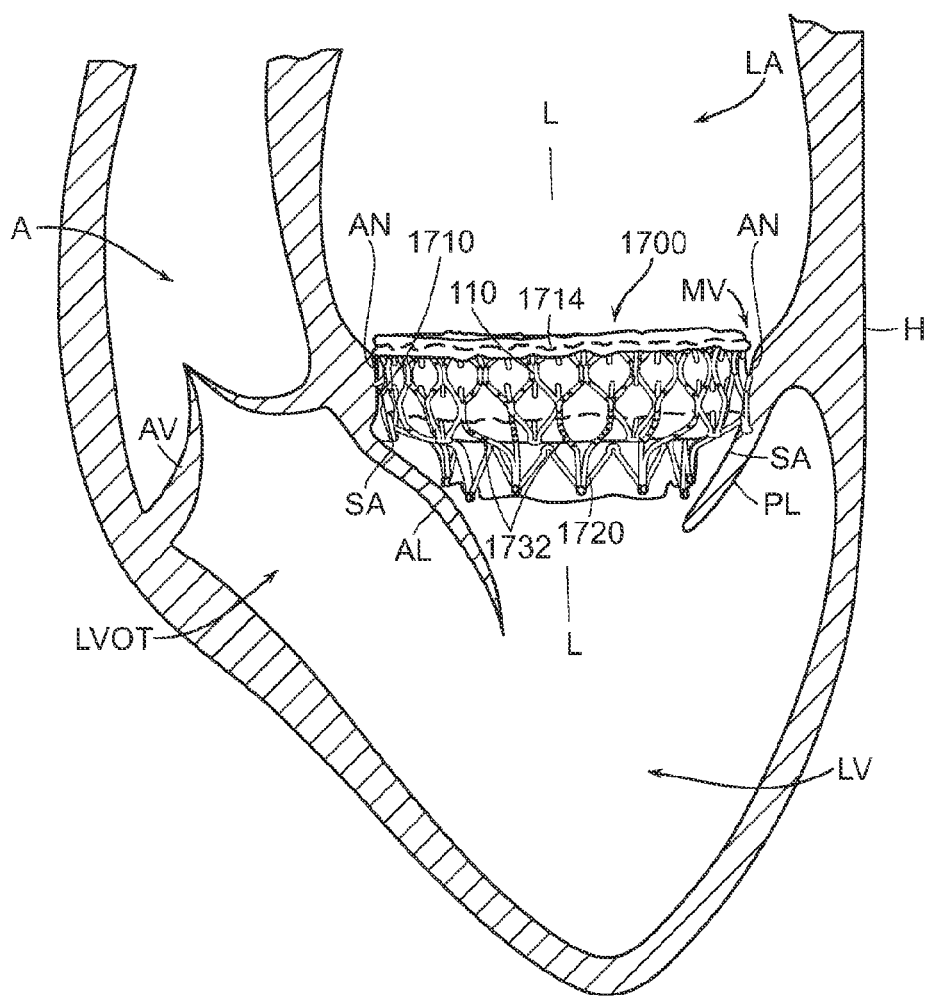

FIGS. 79A and 79B are partial cross-sectional views of a heart (H) and side views of an embodiment of the prosthetic heart valve device 1700 showing an embodiment of a method for implanting the prosthetic heart valve device 1700 in accordance with the present technology. Referring to FIG. 79A, the device 1700 is attached to a delivery device 1800 (shown schematically) and inserted into the heart (H) via a transapical approach in a low-profile configuration (not shown). The device 1700 is inserted superiorly (arrow S) through the native mitral valve (MV). The fixation portion 1710 of the device 1700 can be positioned in the left atrium (LA) at this stage of the procedure, and then relative movement between an outer member 1810 and an inner member 1820 of the delivery device 1800 can release the fixation portion 1710 from the delivery device 1800. The fixation portion 1710 can then self-expand or be expanded using a balloon or other mechanical expander to a partially deployed state in which the integration region 1720 remains attached to the delivery device 1800. In the partially deployed state shown in FIG. 79A, the fixation portion can have a diameter that is larger than the opening defined by the annulus (AN) of the mitral valve (MV). In selected embodiments, the outer diameter of the fixation portion 1710 of the device 1700 can be between approximately 38 mm and 56 mm depending on the size and shape of the native annulus (AN) of the mitral valve (MV). It will be appreciated that other sizes can be used depending on the specific anatomy of a patient.

FIG. 79B illustrates the prosthetic heart valve device 1700 after it has been positioned at a desired location with respect to the annulus (AN) of the native mitral valve (MV). The device 1700 reaches the position shown in FIG. 79B by moving the delivery device 1800 (FIG. 79A) inferiorly (arrow W) until the fixation portion 1710 contacts and fixedly engages the annulus (AN). In some embodiments, the rim 1714 of the fixation portion 1710 can project slightly superior of the annulus (AN). The rim 1714 can accordingly be positioned approximately 1-5 mm above the native annulus (AN) at the anterior leaflet (AL) side of the atrium (LA) in such embodiments. In other embodiments, the rim 1714 of the fixation portion 1710 can be positioned at or below the upper rim of the annulus (AN) such that the fixation portion 1710 contacts at least the annulus (AN) and potentially a portion of the anterior leaflet (AL) and/or the posterior leaflet (PL) of the mitral valve (ML). In still other embodiments, the rim 1714 of the fixation portion 1710 can be positioned at a subannular (SA) location underneath the annulus (AN) (not shown in FIG. 79B). After the device 1700 is positioned at a desired location relative to the annulus (AN) of the mitral valve (MV), the delivery device 1800 (FIG. 79A) is withdrawn inferiorly (arrow W in FIG. 79A) and removed from the patient.

In the embodiment shown in FIG. 79B, the device 1700 is implanted such that the rim 1714 is approximately 1-5 mm above the native annulus (AN). Since the diameter of the fixation portion 1710 in the expanded configuration is greater than that of the native annulus (AN), the outer surface of the fixation portion 1710 and the tissue engaging members 170 securely hold the anchoring member 110 with respect to the mitral valve (MV).

Figure 79C:
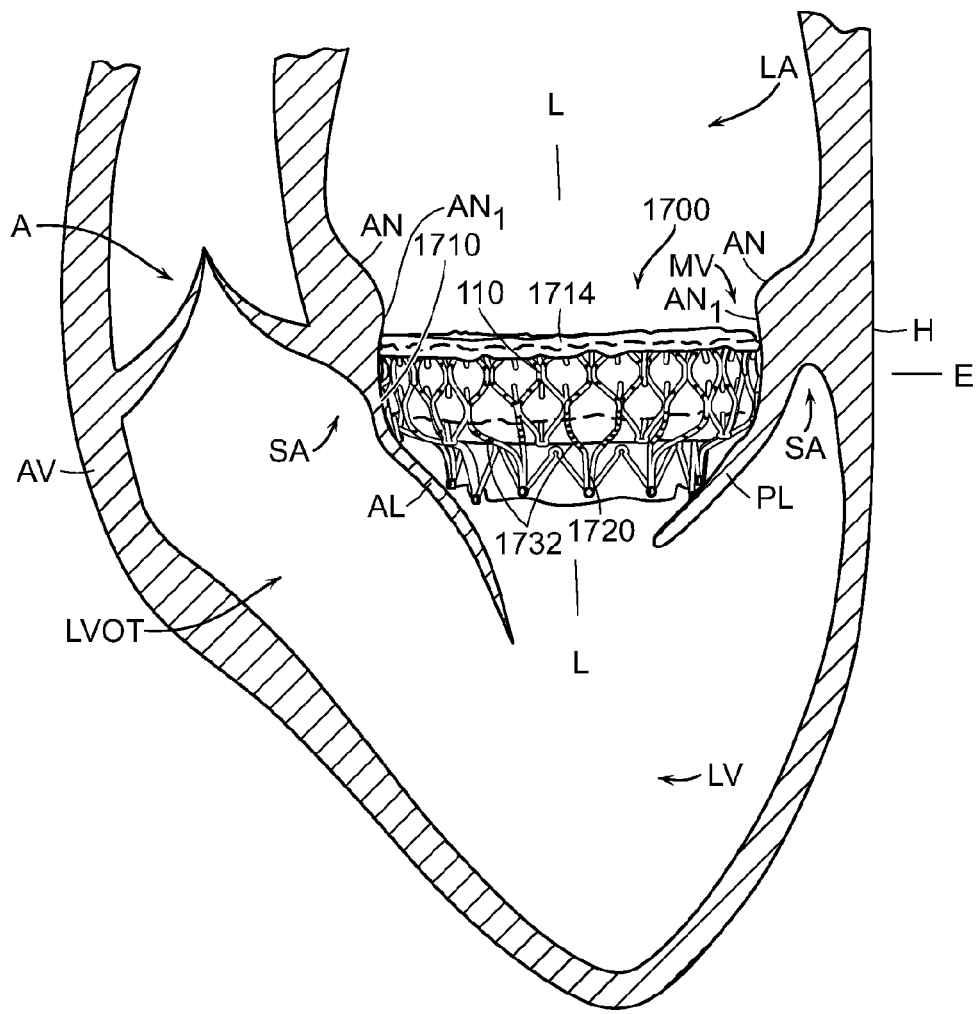
FIG. 79C is a partial anatomical cross-section of a heart (H) showing the placement of the prosthetic heart valve device in accordance with an embodiment of the technology.

FIG. 79C is an anatomical cross-section view of a heart (H) showing the device 1700 implanted at a location slightly lower than the position shown in FIG. 79B such that the rim 1714 of the fixation portion 1710 pushes outward under a portion (AN1) of the native annulus (AN). The device 1700 can also be implanted lower than the elevation shown in FIG. 79C. For example, the rim 1714 of the fixation portion 1710 can be positioned at an elevation E-E at the bottom of the annulus (AN) or even at the subannular space (SA). In all of these embodiments, the portion of the native annulus (AN) over the rim 1714 further restricts the device 1700 from moving upwardly into the left atrium (LA) during ventricular systole.

Figure 79D:
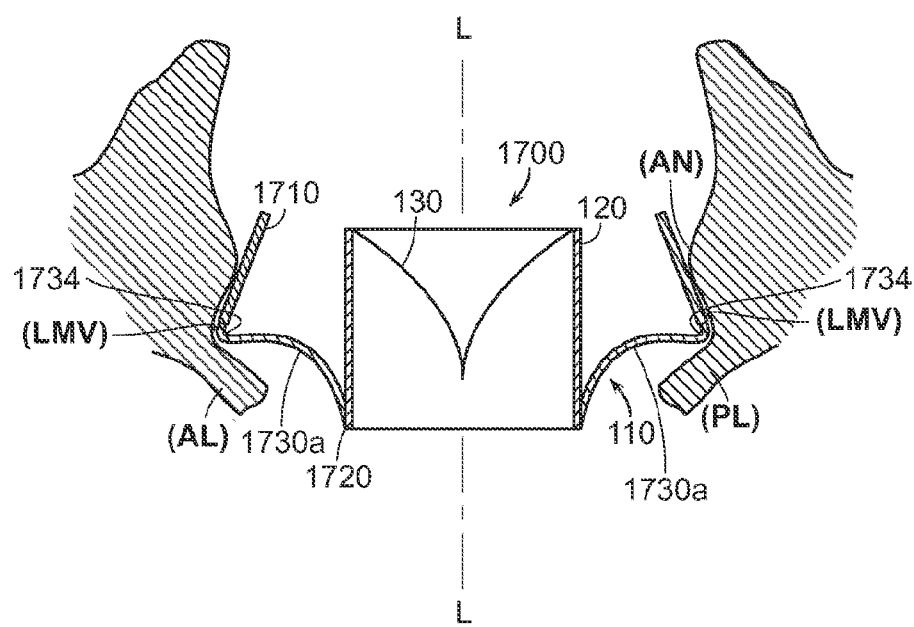
FIG. 79D is a partial anatomical cross-section of a heart (H) showing the placement of the prosthetic heart valve device in accordance with an embodiment of the technology

FIG. 79D is a schematic view showing an aspect of implanting the device 1700 as shown above in FIG. 79B or 79C, or in many other applications as well. Referring to FIG. 79D, the outwardly-projecting portion of the anchoring member 110 that extends from the valve support 120 to the fixation portion 1710, which can be the laterally curved connection structure 1730*a* in FIG. 79D, is preferably located entirely downstream of the native annulus (AN) as shown in FIGS. 79B and 79C. For example, the transition zone 1734 between the connecting structure 1730*a* and the fixation portion 1710 can be located inferiorly of the lower portion (LMV) of the mitral valve annulus (AN) to urge or drive the downstream end of fixation portion 1710 outwardly below the annulus (AN). This allows the anchoring member 110 to engage tissue on the downstream surface of the native annulus so that upstream forces against the prosthetic device 1700 during ventricular systole are resisted by both the resulting upward force against the annulus (AN) as well as the outward pressure of the fixation portion 1710 against the annulus (AN), friction between the fixation portion 1710 and the annulus (AN), and the engagement of tissue engaging elements 170 with the native tissue.

The anchoring member 110 and the valve support 120 can be configured such that the downstream end of the valve support 120 is disposed not more than 26 mm downstream of the native annulus (AN). Additionally, the fixation portion 1710 can be configured such that the engagement surface has a width (e.g., height) of at least about 10-20 mm. The connecting structure can additionally have a height ($H_t$ in FIG. 73) of not more than about 0-15 mm downstream from the end at the valve support 120 to the outer end at the fixation portion 1710. The total height ($H_t$, FIG. 73) of the device 1700 can be approximately 16-26 mm.

The large contact area of the engagement surface 1712 (FIG. 73) that faces the tissue located at or near the annulus (AN) provides exceptionally good fixation to hold the device 1700 at a desired location, and the tissue engaging elements 170 around the fixation portion 1710 further enhance the fixation of the device 1700 to the region of the annulus (AN). The transverse orientation of the connectors 1732 further provides significant outward support of the fixation portion 1710 to exert a sufficient outward force against the annulus (AN), yet the orientation and configuration of the connectors 1732 in combination with attaching the valve support (not shown in FIG. 79B) to the terminus of the integration region 1720 isolates the upstream portion of the valve support from forces exerted by the fixation portion 1710 to accommodate for the irregular shapes and motion of the mitral valve (MV) after implantation. Also, as noted above, the anchoring member further secures the device 1700 to the anatomy by compressing upwardly against the bottom or lower portion of the native annulus (AN) in combination with the friction and radial hoop force exerted by the fixation portion 1710 and the tissue engaging elements as described above with reference to FIGS. 79B-79D. Tests of the device 1700 further show that tissue grows in and around the fixation portion 1710, which further secures the device 1700 to the desired location relative to the annulus (AN).

Figures 80A, 80B:
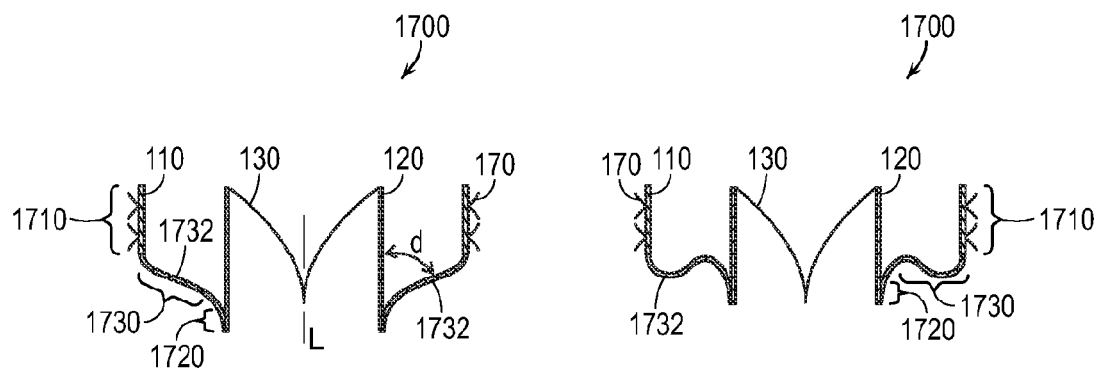
FIGS. 80A-80Q are schematic cross-sectional views of several embodiments of prosthetic heart valve devices in accordance with the present technology.
Figures 80C, 80D:
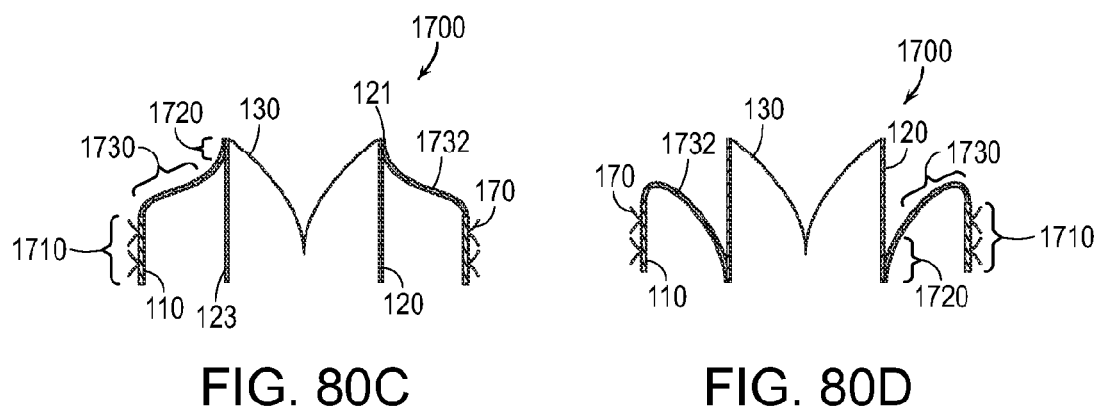
Figures 80E, 80F:
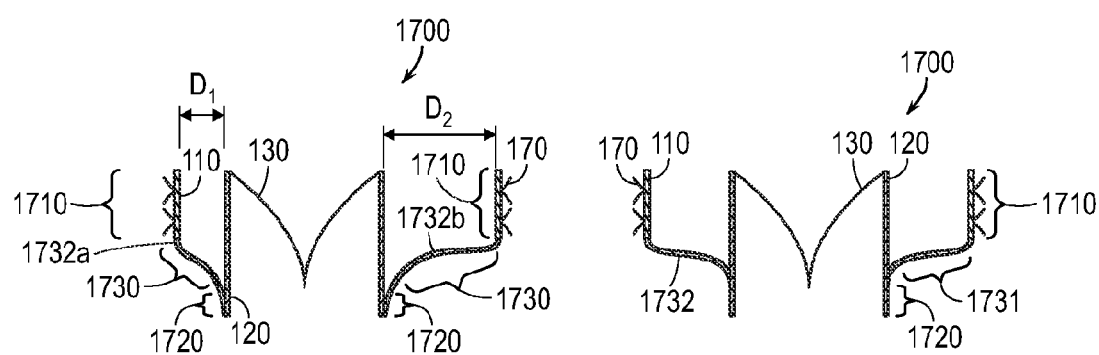
Figure 80G:
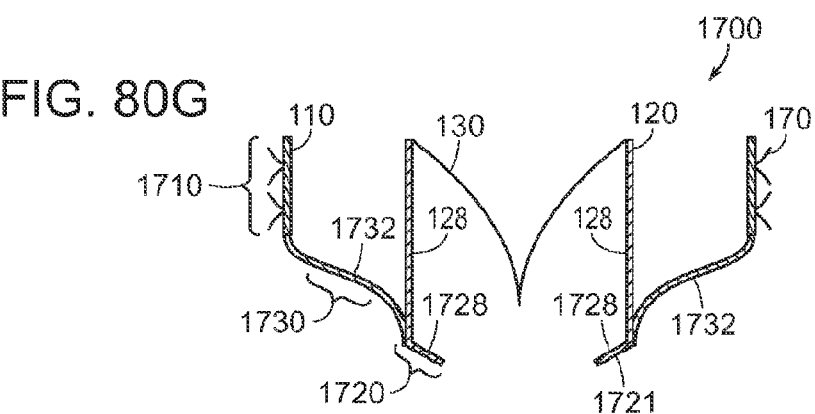
Figure 80H:
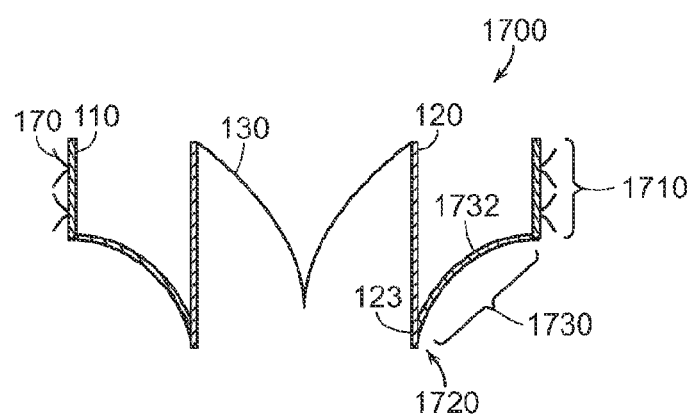
Figure 80I:
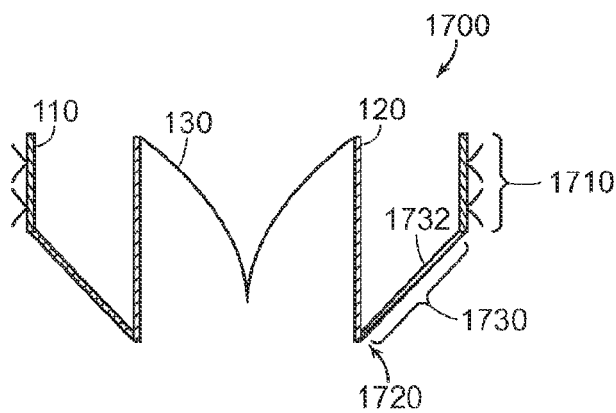
Figure 80J:
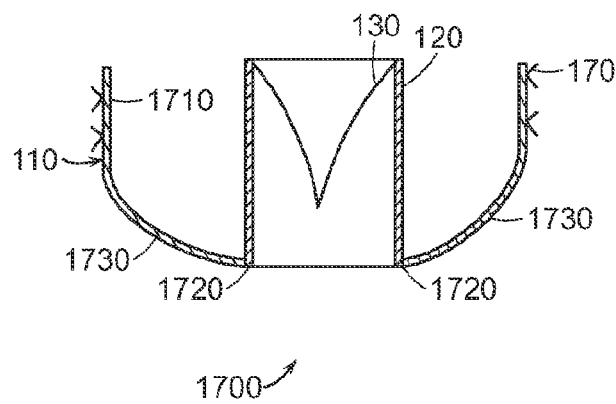
Figure 80K:
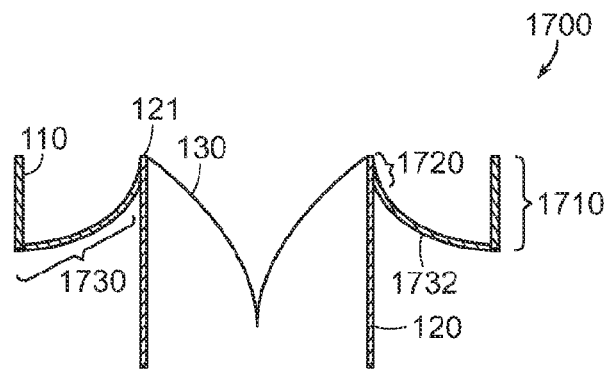
Figure 80L:
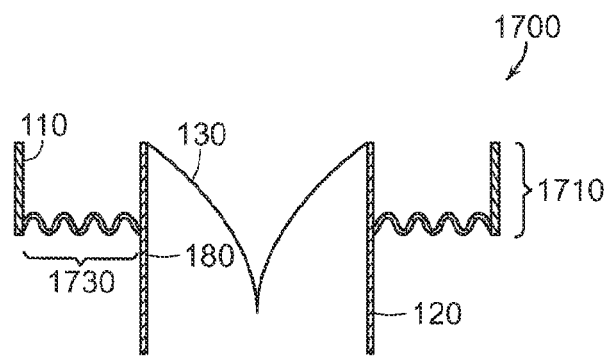
Figure 80M:
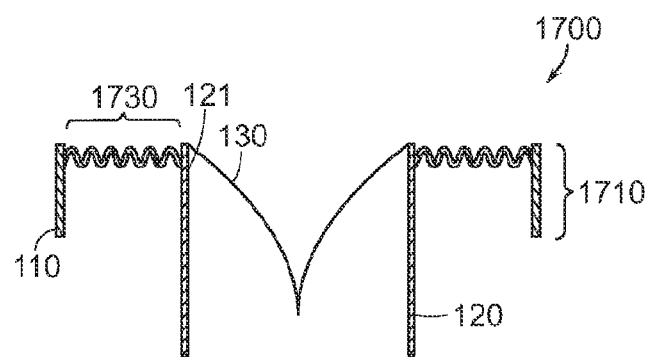
Figure 80N:
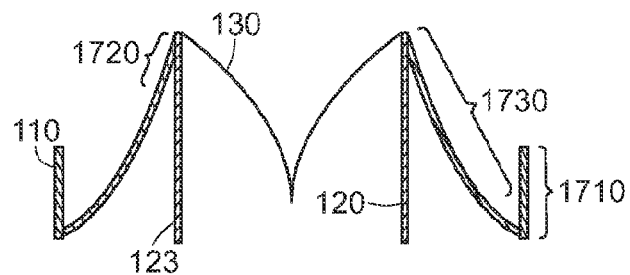
Figure 80O:
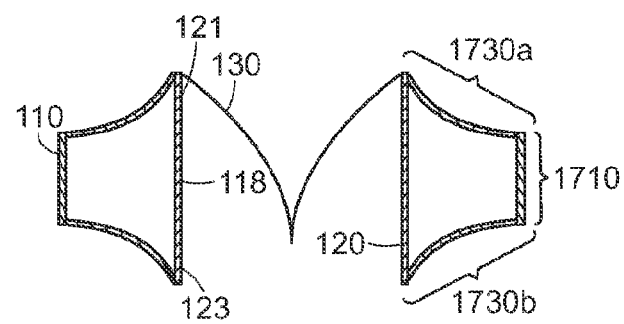
Figure 80P:
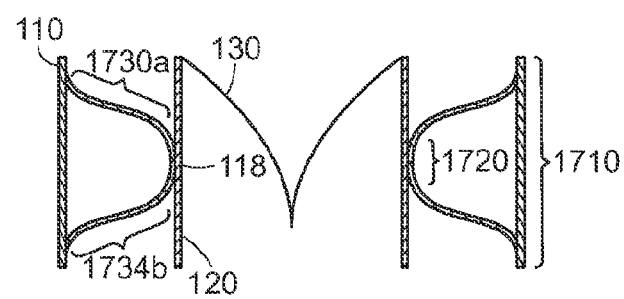
Figure 80Q:
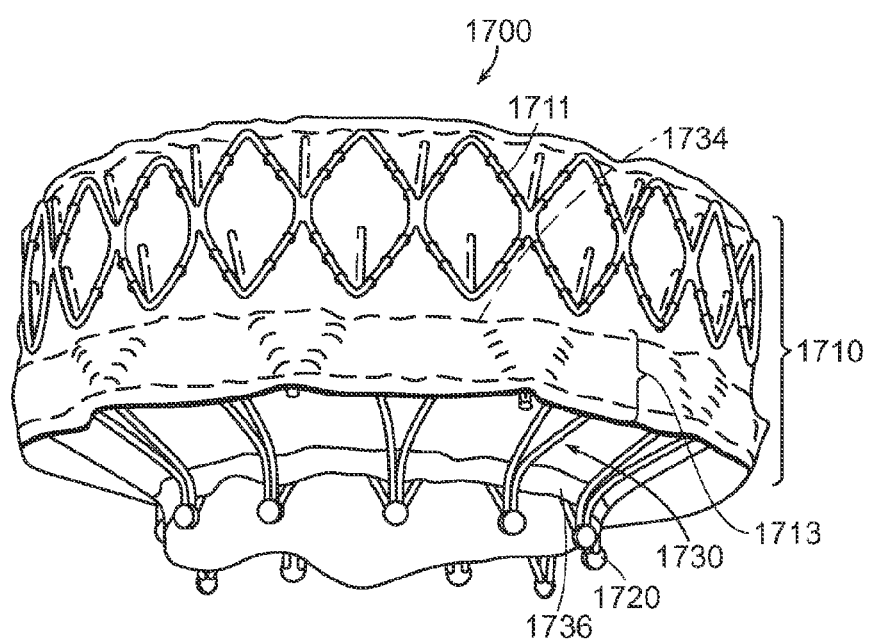

FIGS. 80A-80P are schematic cross-sectional views and FIG. 80Q is an isometric view of several additional embodiments of prosthetic heart valve devices 1700 in accordance with the present technology. Like reference numbers refer to similar or identical components in FIGS. 72-80Q. The embodiment of the device 1700 illustrated in FIG. 80A represents several of the embodiments described above with reference to FIGS. 72-79D. In this embodiment, the connectors 1732 extend at an angle α of 30°-90° with respect to the longitudinal dimension L-L of the device 1700. As the angle α approaches 90 degrees, the loads from the fixation portion 1710 to the valve support 120 increase relative to angles that are less than 90 degrees. As such, a greater taper (e.g., lower angle α) reduces the loads transmitted to the valve support 120 and the prosthetic valve 130.

FIG. 80B illustrates an embodiment of the device 1700 in which the connectors 1732 have an S-shape. One advantage of having S-shaped connectors 1732 is that the valve support 120 can be shortened to mitigate the extent that the device 1700 protrudes into the left ventricle and interrupts flow through the LVOT. As noted above, the lower end of the device 1700 can interfere with the flow through the LVOT during ventricular contraction.

FIG. 80C illustrates an embodiment of the device 1700 in which the anchoring member 110 is inverted such that the fixation portion 1710 is located around the downstream portion 123 of the valve support 120 and the integration region 1720 is attached to the upstream portion 121 of the valve support 120. This embodiment of the device 1700 positions the valve support 120 further into the left atrium as opposed to the left ventricle.

FIG. 80D illustrates an embodiment of the device 1700 in which the fixation portion 1710 is orientated downwardly to be positioned at the elevation of the downstream portion of the valve support 1720. This embodiment is expected to inhibit loads from being transmitted from the fixation portion 1710 to the valve support 120, and it also positions the valve support 120 to reduce the valve support 120 from protruding into the left ventricle.

FIG. 80E illustrates an embodiment of the device 1700 in which the valve support 120 is offset relative to different areas of the fixation portion 1710. In this device, the anchoring member 110 can include first connectors 1732*a* between the fixation portion 1710 and the valve support 120 at one side of the device 1700, and second connectors 1732*b* between the valve support 120 and the fixation portion 1710 at another side of the device 1700. The first connectors 1732*a* can be shorter than the second connectors 1732*b* such that the valve support 120 is closer to the fixation portion 1710 at the one side of the device compared to another side of the device. The embodiment of the device 1700 illustrated in FIG. 80E may advantageously position the valve support 120 and prosthetic valve 130 further away from the LVOT to mitigate interference with blood flow during ventricular contraction. Additionally, the embodiment of the device 1700 shown in FIG. 80E is expected to provide a more uniform load distribution to accommodate for the non-circular shape and saddle profile of the mitral valve annulus.

FIG. 80F illustrates an embodiment of the device 1700 in which the integration region 1720 of the anchoring member 110 is attached to an intermediate portion of the valve support 120 as opposed to the end of the valve support 120. The embodiment of the device 1700 illustrated in FIG. 80F may reduce the interaction between the fixation portion 1710 and valve function.

FIG. 80G illustrates another embodiment of the device 1700 in which the valve support 120 has commissural attachment structures 128 that have extensions 1728 that project radially inwardly from the downstream end of the commissural attachment structures. The extensions 1728 can converge inwardly at a desired angle toward the central axis of the device 1700. In one embodiment, the angle of the extensions 1728 maintains an appropriate minimum required bend radius so that the extensions 1728 can be linearized to minimize valve diameter during placement. The integration region 1720 of the anchoring member 110 can be attached to the extensions 1728. The embodiment of the device 1700 illustrated in FIG. 80G is expected to increase the minimum required bend radius for the connectors 1732, and reduce the height of the fixation portion 1710 for a given taper angle. The inward extensions 1728 might also provide an advantageous attachment point for the commissures of the valve tissue. By moving this attachment point further into the ventricle and further towards the centerline of the valve, the overall stresses on the valve tissue will be reduced. If the free edges of the valve leaflets are slightly shorter than the commissures, they will not touch these extensions 1728 in the open position. Therefore blood flow will not be impeded, and the leaflets will not be damaged by repeatedly touching the extensions.

FIG. 80H is a cross-sectional view of another embodiment of the prosthetic heart valve 1700 in accordance with the present technology. In this embodiment, the lateral portion 1730 has a continuously outwardly flared shape from the downstream end 123 of the valve support 120, and the integration region 1720 is at the terminus of the lateral portion 1730 where the anchoring member 110 is attached to the valve support 120. The first transition zone 1732 of the lateral portion 1730 bends superiorly from the lateral portion 1730 to the orientation of the fixation portion 1710 such that the fixation portion 1710 is configured to face the tissue of a native mitral valve. This embodiment thus shows a flared laterally extending lateral portion 1730.

FIG. 80I is a cross-sectional view of another embodiment of the prosthetic heart valve 1700 in accordance with the present technology. In this embodiment, the lateral portion 1730 has an outwardly projecting conical shape from the downstream end 123 of the valve support 120, and the integration region 1720 is at the terminus of the lateral portion 1730 where the anchoring member 110 is attached to the valve support 120. The first transition zone 1732 of the lateral portion 1730 bends superiorly from the lateral portion 1730 to the orientation of the fixation portion 1710 such that the fixation portion 1710 is configured to face the tissue of a native mitral valve. This embodiment thus shows a conical laterally extending lateral portion 1730.

FIG. 80J is a cross-sectional view of another embodiment of the prosthetic heart valve 1700 in accordance with the present technology. In this embodiment, the lateral portion 1730 has arms that are slightly convex when viewed from the downstream end, or concave when viewed from the upstream end. In this embodiment, the systolic blood pressure against the valve and valve support imparts a compressive column loading on each of the arms. Due to the slightly bent shape of the arms, this imparts a slight bending load on the arms in the downstream direction. At the same time, the systolic blood pressure against the arms themselves and the attached sealing portions imparts a slight bending load on the arms in the upstream direction. By optimizing the curvature of the arms, the net bending load on the arms due to blood pressure can be minimized or eliminated.

FIG. 80K is a cross-sectional view of another embodiment of the prosthetic heart valve 1700 in accordance with the present technology. In this embodiment, the lateral portion 1730 has a continuously outwardly flared shape from a location at or near the upstream end 121 of the valve support 120, and the integration region 1720 is at the peak of the lateral portion 1730 where the anchoring member 110 is attached to the valve support 120. The first transition zone 1732 of the lateral portion 1730 bends from the lateral portion 1730 to the orientation of the fixation portion 1710 such that the fixation portion 1710 is configured to face the tissue of a native mitral valve. This embodiment thus shows an inverted flared laterally extending lateral portion 1730. Lateral portion 1730 may be integrally formed with fixation portion 1710, or it may be a separate structure that is attached to fixation portion 1710 by welding or other suitable means. In the latter case, the transition zone 1732 may bend either upwardly so that the tip of lateral portion 1730 points in an upstream direction, or downwardly so the tip of lateral portion 1730 points in a downstream direction.

FIGS. 80L and 80M are cross-sectional views of additional embodiments of the prosthetic heart valve 1700 in accordance with the present technology. In these embodiments, the lateral portion 1730 extends radially from a mid-section 118 of the valve support 120 (FIG. 80L) or from the upstream end 121 of the valve support 120 (FIG. 80M). In other embodiments lateral portion 1730 may extend radially from a point at or near the downstream end of valve support 120. Referring to FIGS. 80L and 80M, the lateral portions 1730 can be have a serpentine or zig-zag cross-section and/or other configuration that is radially compressible or deflectable to permit radial movement of the fixation portion 1710 toward and away from the valve support 120, and that is resilient so as to bias the fixation portion 1710 radially away from the valve support 120.

FIG. 80N is a cross-sectional view of another embodiment of the prosthetic heart valve 1700 in which the anchoring member 110 is inverted such that the fixation portion 1710 is located around the downstream portion 123 of the valve support 120 and the integration region 1720 is attached to the upstream portion 121 of the valve support 120. In this embodiment, the lateral portion 1730 has a continuously outwardly flared shape from a point at or near the upstream end 121 of the valve support 120. This embodiment of the device 1700 positions the valve support 120 further into the left atrium as opposed to the left ventricle.

FIG. 80O is a cross-sectional view of another embodiment of the heart valve 1700 in which the fixation portion 1710 of the anchoring member 110 is located around the mid-section 118 of the valve support 120. In this embodiment, the anchoring member 110 is attached to the valve support by a first lateral portion 1730a having a continuously outwardly flared shape from a point at or near the upstream end 121 of the valve support 120, and by a second lateral portion 1730b having a continuously outwardly flared shape from a point at or near the downstream end 123 of the valve support 120.

FIG. 80P is a cross-sectional view of another embodiment of the heart valve 1700 in which the fixation portion 1710 of the anchoring member 110 is proportioned to be substantially coextensive with the valve support 120 in the axial or longitudinal direction. In this embodiment, the anchoring member 110 is attached to the valve support 120 by a first lateral portion 1730a extending from the integration region 1720 located at the mid-section 118 of the valve support 118 and by a second lateral portion 1730b extending from the integration region 1720 at the mid-section 118. The first and second lateral portions 1730a, 1730b may be integrally formed with each other and/or with the fixation portion 1710.

FIG. 80Q is an isometric view of another embodiment of the prosthetic heart valve device 1700 in accordance with the present technology. In this embodiment, the fixation portion 1710 includes an extension 1713 that extends downstream from the first transition zone 1734. The extension 1713 can be formed by extensions of selected structural elements 1711 that project downstream beyond the area where the transition zone 1734 comes into the fixation portion 1710. The extension 1713 increases the height of the fixation portion 1710, and it further enhances sealing and ingrowth at the downstream portion of the fixation portion 1710. For example, the extension 1713 can enhance the ingrowth at the ventricular portion of the fixation portion 1710 of a mitral valve device.

Figure 81A:
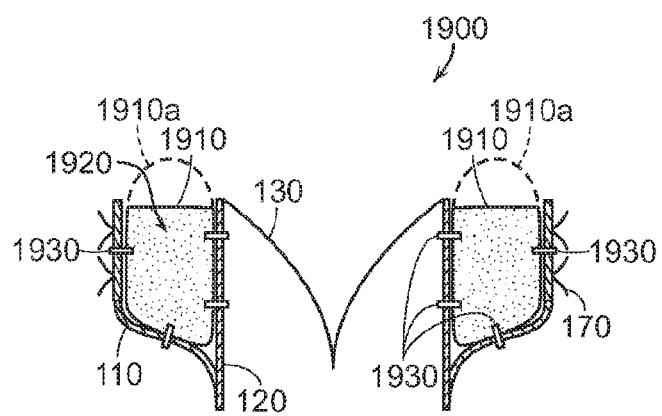
FIG. 81A is a cross-sectional view of a prosthetic heart valve device in accordance with another embodiment of the present technology.

FIG. 81A is a cross-sectional view schematically showing a prosthetic heart valve device 1900 in accordance with another embodiment of the present technology. The device 1900 can include an anchoring member 110, valve support 120, and prosthetic valve 130. The device 1900 can further include a compartment 1910 attached to one or both of the anchoring member 110 and the valve support 120. The compartment 1910 can be configured to fit between the anchoring member 110 and the valve support 120. The compartment 1920 can extend around only a portion of the circumference of the anchoring member 110, or the compartment 1910 can extend around the entire inner circumference of the anchoring member 110. The compartment 1910 can further include a second portion 1910a that projects towards the left atrium to provide more space for packing into a low-profile configuration.

In one embodiment, the compartment 1910 is made from a fabric, mesh, braid, porous material, or other suitable material that can contain a material 1920. The fabric, mesh, or other material might be optimized on one end to minimize blood flow through it during the initial period after implantation, while the other end might be more open to allow more aggressive tissue ingrowth and even vascularization of the compartment 1910. The material 1920, for example, can be a time-released agent that inhibits or prevents clotting (e.g., clopidogrel or aspirin), a healing agent (ascorbic acid), or other agents that promote tissue and growth. The material 1920 can alternatively include structural filler elements, such as small spheres, random intermeshed fibers, foam, swellable hydrogels, etc., either in lieu of or in addition to anti-clotting and healing agents. These small spheres, fiber, foam etc. might be optimized for their compressibility. In this way the structural filler elements can provide structural support between the anchoring member 110 and the valve support 120 without transmitting fully forces from the anchoring member 110 to the valve support 120. The compartment 1910 can be attached to the anchoring member 110 or the valve support 120 by fasteners 1930, such as clasps, threaded ties, or other suitable fasteners. The material 1920 might be introduced into the device after the device has been deployed into the patient, for example via a tube which extends from the compartment 1910 to the proximal end of the delivery system. Once the compartment 1910 has been filled with material 1920, the tube can be pulled out of compartment 1910, with a self-sealing valve preventing leakage of material 1920 from the compartment.

Figure 81B:
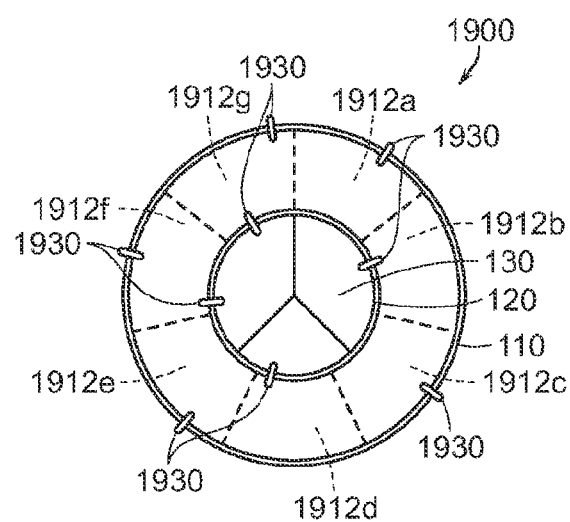
FIG. 81B is a top view of the prosthetic heart valve device of FIG. 81A.

FIG. 81B is a top view of the prosthetic heart valve device 1900 illustrating an embodiment in which the compartment 1910 has a plurality of separate cells 1912 (identified individually as cells 1912a-1912g). Each of the cells 1912 can include the same material 1920 (FIG. 81A), or a number of the cells can include different materials 1920. For example, cells 1912a, 1912c, 1912e, and 1912g can include an anticlotting agent, and cells 1912b, 1912d, and 1912f can include a healing agent to promote healing of connective tissues.

Figure 82A:
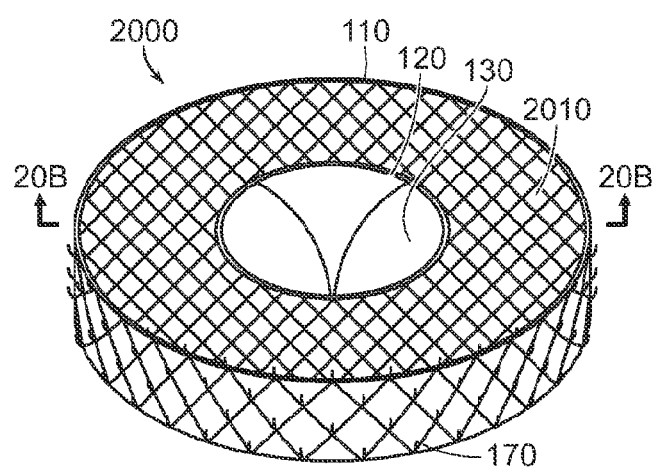
FIG. 82A is an isometric view of a prosthetic heart valve device in accordance with another embodiment of the present technology.
Figure 82B:
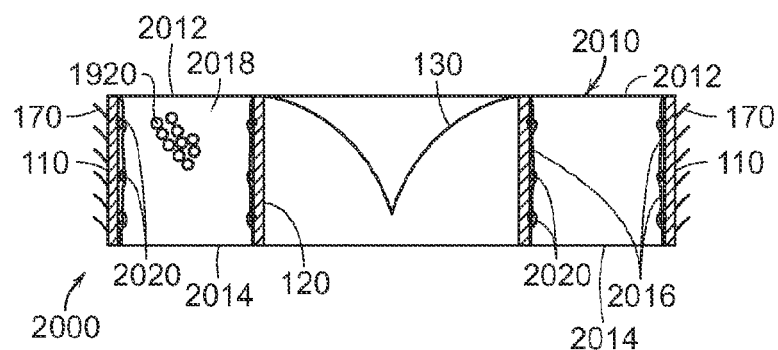
FIG. 82B is a cross-sectional view of the prosthetic heart valve device of FIG. 82A taken along line 20B-20B.

FIG. 82A is an isometric view of a prosthetic heart valve device 2000 in accordance with another embodiment of the present technology, and FIG. 82B is a cross-sectional view of the device 2000 along line 20B-20B in FIG. 20A. The device 2000 can include an anchoring member 110 having a frame and a plurality of tissue engaging elements 170 similar to the fixation portion 1710 of the devices 1700 described above. The device 2000 can further include one or more fibers or webs 2010 that flexibly couple the anchoring member 110 to the valve support 120. The webs 2010, for example, can be a fabric, mesh, braid, sheet, or other material formed form a textile, polymer, metal, natural fiber, or other suitable materials. These webs might have a variety of orientations.

Referring to FIG. 82B, the web 2010 can include a first portion 2012 at the upstream end of the valve support 120, a second portion 2014 at the downstream end of the valve support 120, and side portions 2016 attached to the anchoring member 110 and the valve support 120 by fasteners 2020. The web 2010 illustrated in FIG. 82B can form an enclosed compartment 2018 that can be filled with a material such as a time-release agent and/or filler elements as described above. The fasteners 2020 can be sutures, other threaded ties, clasps, rivets or other suitable fastening means. Additional fibers or webs might extend from the downstream end of the anchoring member to the upstream end of the valve support, from the upstream end of the anchoring member to the downstream end of the valve support, or in other directions. Alternatively, vertical radially-oriented planar webs may extend from the anchoring member to the valve support.

The device 2000 illustrated in FIGS. 82A and 82B may provide very good force isolation between the anchoring member 110 and the valve support 120 because there is no metal-to-metal interface and the suture-type fasteners 2020 add further stability and potentially better fatigue life. The device 2000 has the potential for further improving fatigue life because of the robust materials that can be used for the web 2010 (e.g., Kevlar®, a trademark of E. I. du Pont de Nemours and Company) and the flexibility of the web 2010.

Figure 83:
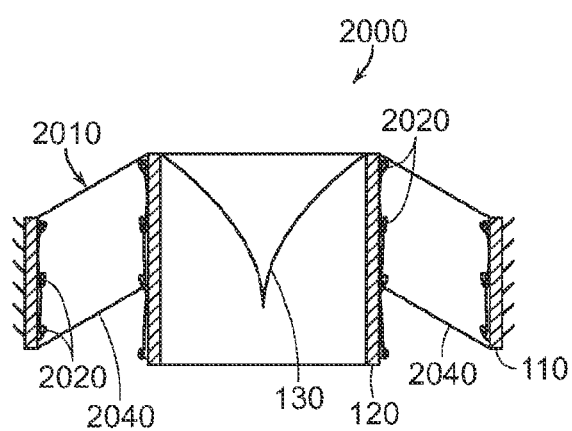

FIG. 83 is a schematic cross-sectional view of the device 2000 in accordance with another embodiment of the present technology. In this embodiment, the web 2010 has a top portion between the upstream ends of the anchoring member 110 and the valve support 120, and the side portions are connected to the anchoring member 110 and the valve support 120 by fasteners 2020. The device 2000 in this embodiment further includes tethers 2040 attached to the downstream end of the anchoring member 110 and to an intermediate area of the valve support 120.

Figure 84A:
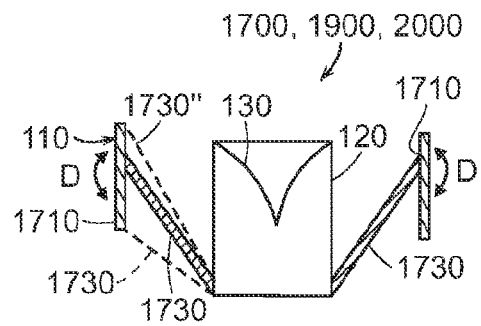
Figure 84B:
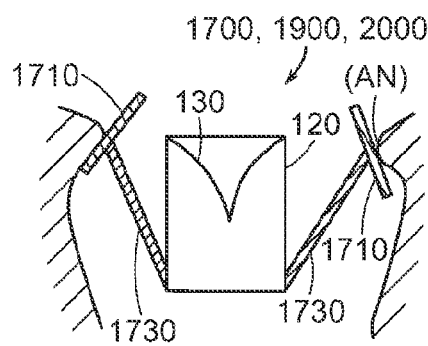
Figure 84C:
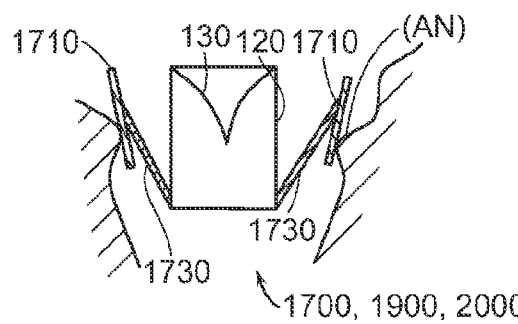

FIGS. 84A-84C are schematic cross-sectional views illustrating an aspect of several embodiments of the prosthetic heart valve devices 1700, 1900 and 2000 in accordance with the present technology. Referring to FIG. 84A, the device 1700 can have a fully expanded state in which the fixation portion 1710 extends from the lateral portion 1730 (e.g., connecting structure) by an angel of 45° outwardly away from the longitudinal axis of the device 1700 to an angle of −30° inwardly toward the longitudinal axis of the device. The fixation portion 1710 extends approximately parallel to the longitudinal axis of the device in the embodiment shown in FIG. 84A. The device 1700 can have such a fully expanded state outside of the body or after the device 1700 has been implanted at a native valve. The fixation portion 1710, however, can flex or otherwise deform upon implantation such that the fixation portion 1710 at least partially adapts to the shape of the native valve location and deflects (arrow D) inwardly or outwardly to also at least partially adapt to the angular orientation of tissue at the native valve location. FIG. 84B, for example, shows deflection of the fixation portion 1710 inwardly to adapt to the angle of the tissue at the underside of the native annulus (AN), and FIG. 84C shows deflection of the fixation portion 1710 outwardly to adapt to the angle of the tissue on the other side of the native annulus (AN). Such double conformability enhances the fixation of the device to the native tissue. Additionally, the fixation portion 1710 need not deflect with respect to the lateral portion 1730 at a mid-section of the fixation portion 1710 as shown in solid lines in FIG. 84A, but rather the fixation portion 1710 can deflect around areas that are at or near the ends of the fixation portion as shown by the transition areas of lateral sections 1730' and 1730" shown in broken lines in FIG. 84A.

Figure 85A:
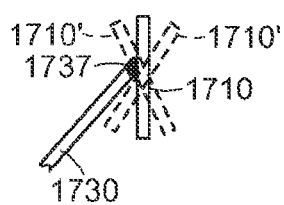
Figure 85B:
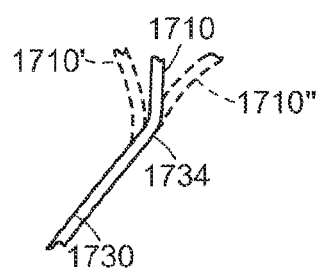
Figure 85C:
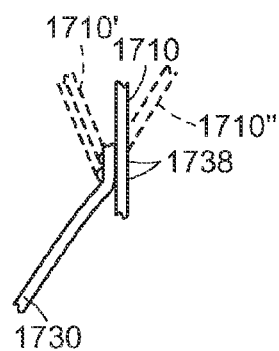

FIGS. 85A-85C are side views illustrating selected embodiments of the deflection of the fixation portion 1710 relative to the lateral portion 1730. Referring to FIG. 85A, the fixation portion 1710 can be connected to the outer end of the lateral portion 1730 by a hinge 1737. In the embodiment shown in FIG. 85B, the fixation portion 1710 deflects about the first transition zone 1734 where the lateral portion 1730 bends to the fixation portion 1710. FIG. 85C shows an embodiment in which the fixation portion 1710 is attached to the lateral portion 1730 by mechanical fasteners 1738, such as pins, bolts, rivets, or other fasteners. In any of these embodiments, the fixation member can pivot, rotate, flex or otherwise deflect to an inward orientation 1710' or to an outward orientation 1710" depending on the tissue at the implant site.

Figure 86A:
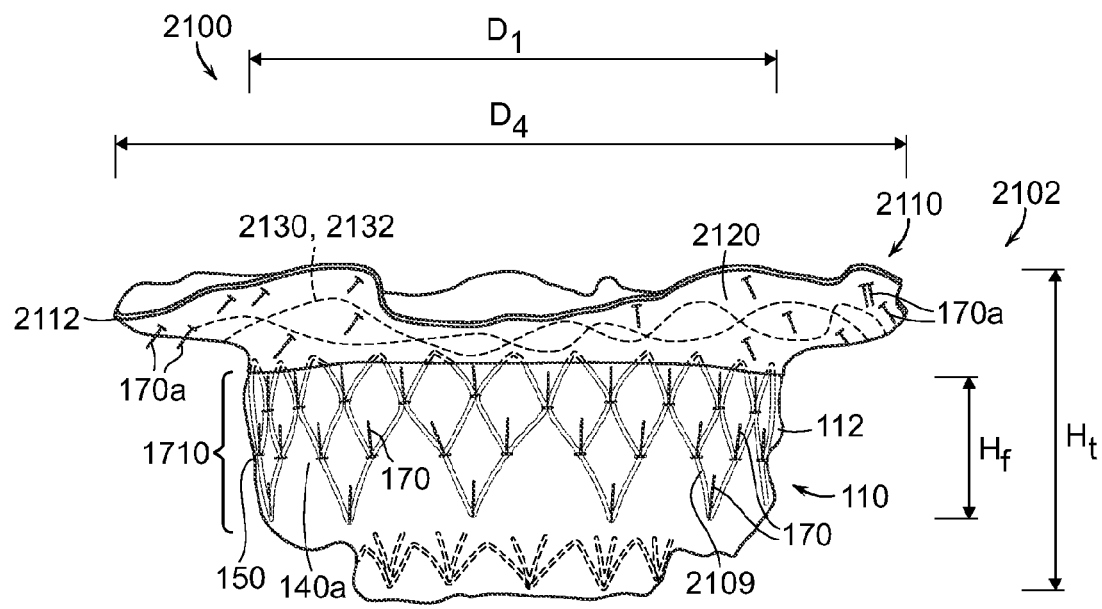
Figure 86B:
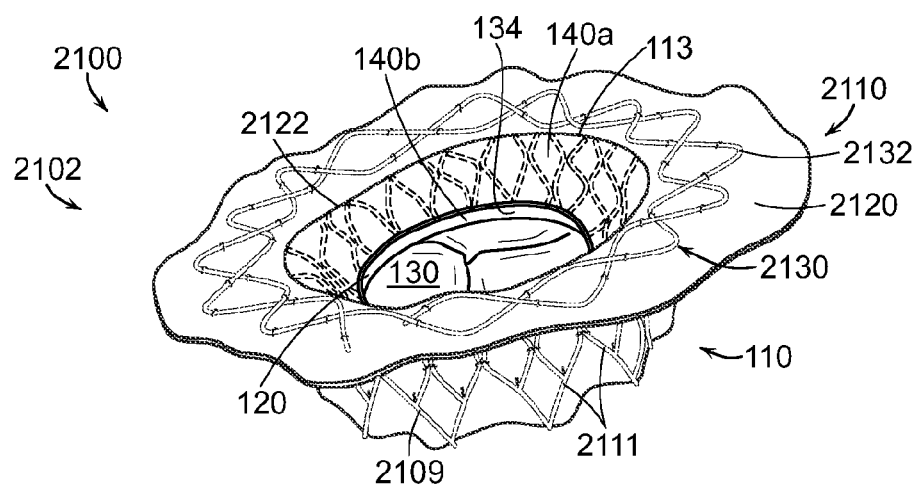

FIGS. 86A-107B illustrate prosthetic heart valve devices 2100 having extension members 2110 in accordance with additional embodiments of the present technology. Similar to the devices discussed above with respect to FIGS. 10A-85C, the devices 2100 include features such as the valve support 120 (e.g., FIG. 86B) having an interior 134 in which a prosthetic valve 130 (e.g., FIG. 86B) is coupled and an expandable anchoring member 110 (e.g., fixation member having a tubular fixation frame) coupled to the valve support 120 in a manner that mechanically isolates the valve support 120 from forces exerted upon the anchoring member 110 when implanted. FIG. 86A is a side view and FIG. 86B is an isometric view of the device 2100 that includes features generally similar to the features of the prosthetic heart valve device 1700 described above with reference to FIGS. 72-85C. Similar to the device 1700, the anchoring member 110 can be coupled to the valve support 120 such that a fixation portion 1710 of the anchoring member 110 is configured to engage native tissue on or downstream of the annulus so as to prevent migration of the device 2100 in the upstream direction.

In the embodiment illustrated in FIGS. 86A and 86B, the device 2100 also includes an extension member 2110 extending from the anchoring member 110 (e.g., from the fixation portion 1710 of the anchoring member 110). The extension member 2110 can be a brim, flange, shoulder or expansion ring projecting from or tethered to the fixation portion 1710 of the anchoring member 110. In one embodiment, the extension member 2110 is configured to be positioned and to engage tissue upstream of the native annulus while the anchoring member 110 is configured to engage tissue at or near the annulus or leaflets. In some arrangements, the extension member 2110 is a self-expanding retainer configured to engage tissue in the upstream heart chamber (e.g., left atrium) to (a) align and position the device 2100 within the native valve region such that the device 2100 is accurately seated within the native valve to ensure proper engagement and retention by the surrounding tissue; and/or (b) assist in visualization and detection of device position relative to the anatomy during implantation by deflecting, deforming, or otherwise moving in response to engagement with native tissue in a manner that can be visualized using fluoroscopy, echocardiography, or other visualization methods; and/or (c) inhibit the device 2100 from moving in a downstream direction during operative use as a prosthetic valve in the heart of a patient.

Referring to FIG. 86A, the extension member 2110 can have an outer circumference 2112 with a cross-sectional transverse dimension $D_4$ that is greater than the cross-sectional transverse dimension D1 of the outer circumference 150 of the upstream portion 112 (e.g., fixation portion 1710) of the anchoring member 110 when the device 2100 is in the expanded configuration 2102. In other embodiments, the extension member 2110 may have a cross-sectional transverse dimension $D_4$ at least as large or even larger that the major axis 55 of the native annulus (FIG. 14A). In some embodiments, the outer circumference 2112 of the extension member 2110 has a cross-sectional transverse dimension $D_4$ that is greater than the supra-annular surface such that the extension member 2110 is deflected by the walls of the atrium in an upstream direction when the extension member 2110 is deployed above the annulus. In some embodiments, the cross-sectional transverse dimension $D_4$ of the extension member 2110 can be approximately 1.2 to 3 times the cross-sectional dimension $D_1$ of the fixation portion 1710 of the anchoring member 110 when in a fully expanded, undeformed condition. In a specific example, the extension member 2110 in a fully expanded, unbiased, undeformed condition, may have a transverse dimension $D_4$ in the range of about 40 mm to about 150 mm, or about 40 mm to about 80 mm, for adult human patients. In some embodiments, extension member 2110 may be non-circular in a transverse/horizontal plane (e.g. oval or D-shaped) and in such embodiments may have a major diameter in a range of about 40 to about 150 mm, preferably about 40 to about 80 mm, the major diameter being about 1.2 to 2 times its minor diameter. Also in accordance with aspects of the present technology, the extension member 2110 may be provided in multiple transverse dimensions and/or shapes to fit various native valve sizes allowing a surgeon to select the appropriate size and shape for each patient.

In some embodiments the extension member 2110 can be configured to align the device 2100 relative to the native annulus by engaging the tissue upstream of the native annulus. As the device is delivered to the target site via a delivery catheter (not shown), and as described in more detail below, the extension member 2110 expands within the atrial chamber before the anchoring 110 member and valve support 120 are released from the delivery catheter at or near the annulus. In these embodiments, the extension member 2110 can be rested on or pulled down against the supra-annular surface before the remainder of the device 2100 (e.g., anchoring member 110 and valve support 120) is released from a delivery device. The total height ($H_t$, FIG. 86A) of the device 2100 and/or the fixation height ($H_f$, FIG. 86A) of the fixation portion 1710 can be configured such that when the extension member 2110 is engaging the supra-annular surface, the fixation portion 1710 is properly aligned longitudinally with respect to the native valve such that the fixation portion 1710 engages the desired annular and/or leaflet tissue. In other embodiments, the extension member 2110 is configured to deflect or deform when it engages the atrial walls or supra-annular surface while the remainder of the device 2100 is advanced in a downstream direction. The degree of deflection or deformation is correlated with the longitudinal position of the fixation portion 1710 relative to the native annulus such that, by visualizing the extension member 2110 using fluoroscopy, echocardiography, or other means, the position of the device 2100 may be accurately determined prior to full deployment.

The extension member 2110 can be, in some examples, an extension of material either directly or indirectly coupled to the upstream portion 112 (e.g., upper rim or upstream perimeter 113) of the anchoring member 110 and which projects in a non-coaxial (or transverse) direction relative to the anchoring member 110 when the device 2100 is in an expanded configuration 2102. In a deployed configuration 2104 (see, e.g., FIG. 89B) at a native mitral valve, the extension member 2110 can extend upstream through the annulus AN and into a supra-annular space within the atrium and engage the supra-annular surface or other atrial tissue with an outwardly extending flange or brim 2120.

The extension member 2110 may include the brim 2120 comprising a covering or sheet of material, such as a flexible fabric, ring, disk, or web (e.g., a weave, braid or grating of fabric, shape-memory polymeric material, and/or shape-memory metal). In one embodiment, and as shown in FIGS. 86A and 86B, the brim 2120 can include a sheet of flexible material coupled to the anchoring member 110 near the upstream end or portion 112 and extends radially outward from the anchoring member 110. In one example, the device 2100 can include a first sealing member portion 140a (FIG. 86B) coupled to a wall of the anchoring member 110 (e.g., inner wall) and a second sealing member portion 140b coupled to a wall of the valve support 120 (e.g., inner wall, outer wall). As described above with respect to the device 1700 illustrated in FIG. 72, the first and second sealing member portions 140a and 140b can be integral portions of a single sealing member or can be separate sealing members that are attached independently to the anchoring member 120 and the valve support 120. Likewise, in one embodiment, the brim 2120 can have an inner edge 2122 that is coupled to the first sealing member portion 140a. For example, the brim 2120 and the first sealing member portion 140a can be a continuous sheet of material. In another example, the brim 2120 and the first sealing member portion 140a can be coupled using an attachment means, such as stitching, sutures, rivets, adhesive or other mechanical coupling fasteners or features known in the art. In such embodiments, the brim 2120 and the first sealing member portion 140a may be formed of the same material or different materials. In a particular example, the first sealing member portion 140a and the brim 2120 can be formed of an impermeable material for preventing perivascular leaks between the device 2100 and the adjacent tissue and/or to promote in-growth of tissue of adjacent tissue (e.g., Dacron® or tissue such as pericardium). In another example, the brim 2120 can be formed of a different material having a desired flexion or shape-memory feature (e.g., shape-memory metal), or a combination of metal, fabric, tissue and/or other materials.

The extension member 2110 may further include tissue engaging elements 170a, such as barbs, bumps, tines, rods or similar structures, integrated therewith, or bonded or otherwise attached thereto, similar to those optionally included on the sealing member 140 as described above in connection with FIG. 43A-43B. These tissue engaging elements 170a may be configured to engage atrial wall or supra-annular tissue to inhibit movement of the device 2100 in a downstream direction (toward the ventricle). The tissue engaging elements 170a may be non-penetrating or may penetrate the tissue surface slightly to inhibit movement. In exemplary embodiments, the tissue engaging elements can be oriented to point preferentially in a downstream direction to have higher retention force against movement in the downstream direction than in the upstream direction. Alternatively or additionally, the outer, tissue-facing surface of the extension member 2110 may be coated with a permanent or temporary adhesive or other material to enhance friction and/or to adhere to the native tissue, at least until tissue in-growth has occurred sufficiently to inhibit device movement.

In some embodiments, the extension member 2110 can also include a support structure 2130 coupled to or, in other embodiments, integral with the brim 2120 (FIG. 86B). The support structure 2130 can provide the extension member 2110 with additional rigidity as the extension member 2110 extends radially out from the anchoring member 110 when the device 2100 is in the expanded configuration 2102. In several arrangements, the support structure 2130 can be a stiffening member formed from metal and/or a polymeric material that is sewn, sutured, or adhered to the brim 2120. In some embodiments, the support structure 2130 can include a resilient metal or polymer mesh, ring or series of rings coupled to or otherwise integrated into a portion of the brim 2120. In certain embodiments, the support structure 2130 can be formed from a deformable material or a resilient or shape memory material (e.g., Nitinol). In other embodiments, the support structure 2130 can include one or more stiffening members, such as wires 2132 or struts that are secured to the outer surface or positioned within the material of the brim 2120 (FIG. 86B).

In one embodiment, the support structure 2130 can be separate from the frame 2109 and/or the anchoring member 110. For example, FIG. 86B illustrates an embodiment in which the support structure 2130 includes wires 2132 (e.g., a plurality of struts) formed in a crisscrossing serpentine configuration that form a continuous ring around the extension member 2110 and in which the wires 2132 are not in direct contact with the frame 2109. In this embodiment, the extension member 2110 is connected to the anchoring member 110 (e.g., at the fixation portion 1710) by the material of the brim 2120 (e.g. fabric or tissue). In some embodiments, the extension member 2110 (including the brim 2120 and any support structure 2130) is connected to the anchoring member 110 only by fabric, suture, or other highly flexible, non-metal elements. Accordingly, in this embodiment, the wires 2132 are structurally independent from the anchoring member 110 such that the support structure 2130 is indirectly coupled to the frame 2109 by the brim 2120 (e.g., fabric, material, etc.). As such, the support structure 2130, in an undeformed or unbiased condition, is spaced apart from the frame 2109 of the anchoring member 110 and is mechanically isolated from the frame 2109. While the embodiment illustrated in FIG. 86B illustrates a generally concentric arrangement of the wires forming a crisscrossing serpentine pattern (e.g., zig-zag pattern, diamond pattern), other arrangements and patterns (e.g., serpentine, wavy, radial arms, square, etc.) can also be formed to provide a desired rigidity to the extension member 2110, and as described below with respect to FIGS. 87A-107B.

Figure 87B:
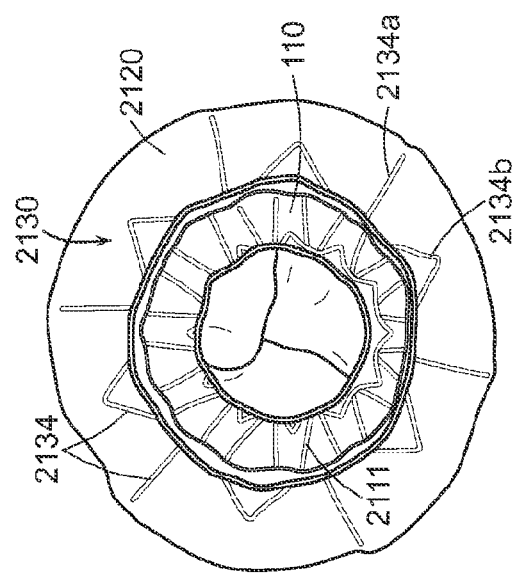
Figure 87A:
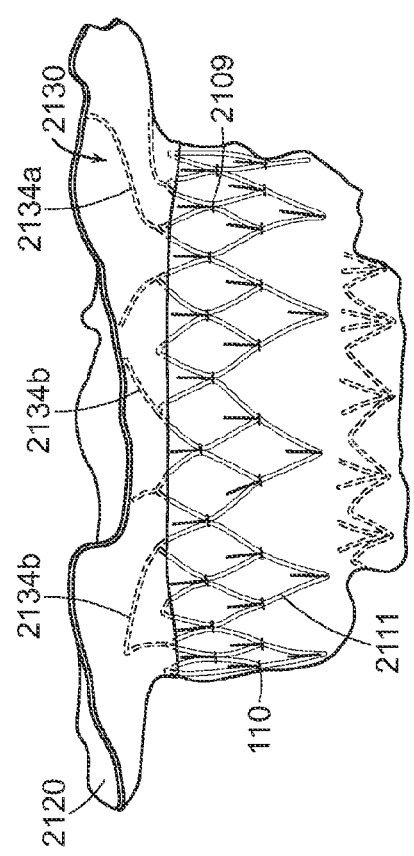

In a further embodiment, and as illustrated in FIGS. 87A and 87B, the support structure 2130 can be integral with the frame 2109 (e.g., Nitinol frame) of the anchoring member 110. FIGS. 87A and 87B are side and top views, respectively, of a device 2100 having an extension member 2110 that includes a support structure 2130 formed from an extension of the frame 2109. For example, the support structure 2130 includes integral wires 2134 (e.g., struts) extending from the structural elements 2111 of the frame 2109 into the brim 2120 (FIG. 87A, dotted lines). As illustrated in FIG. 87B, the integral wires 2134 can be arranged in a pattern (e.g., a combination of straight, outwardly projecting struts 2134*a* and triangular-oriented struts 2134*b*) for providing a desired combination of rigidity and flexibility about the brim 2120. In some embodiments, the integral wires 2134 connecting the support structure 2130 to the frame 2109, due to their number, dimensions, geometrical arrangement, or other aspect, are individually or collectively substantially more flexible than the structural elements of the frame 2109 so that the extension member 2109 is comparatively easily deflected or deformed when it engages native tissue. For example, the number of integral wires 2134 interconnecting extension member 2110 to frame 2109 around the circumference of the device 2100 may be substantially fewer than the number of structural elements 2111 around the circumference.

In another embodiment, the support structure 2130 can be connected to the frame 2109 at one or more connection points using rivets, (e.g. Nitinol rivets), threads, adhesives, solder, laser welding, metal bolts or other mechanical features, or other types of fasteners can be used to secure the support structure 2130 to the frame 2109 of the anchoring member 110. In some arrangements, the support structure 2130 can be coupled to the frame 2109 with a plurality of flexible connecting members (not shown) that are substantially less rigid than the frame 2109. In this embodiment, the flexibility of the extension member 2110 can allow the extension member 2110 to distort without distorting the anchoring member 110 and/or the valve support 110. Various aspects of this arrangement can allow the extension member 2110 to be conformable and, in some embodiments, more atraumatic to the supra-annular tissue and atrial wall. In some embodiments, the wires 2132 or struts can have a rigidity or stiffness that is less than the rigidity of stiffness of the structural elements 2111 of the frame 2109. In these embodiments, the extension member 2110 may be deformed by the surrounding supra-annular tissue and/or atrial walls without transmitting forces to the more rigid frame structure of the anchoring member 110.

Figure 88A:
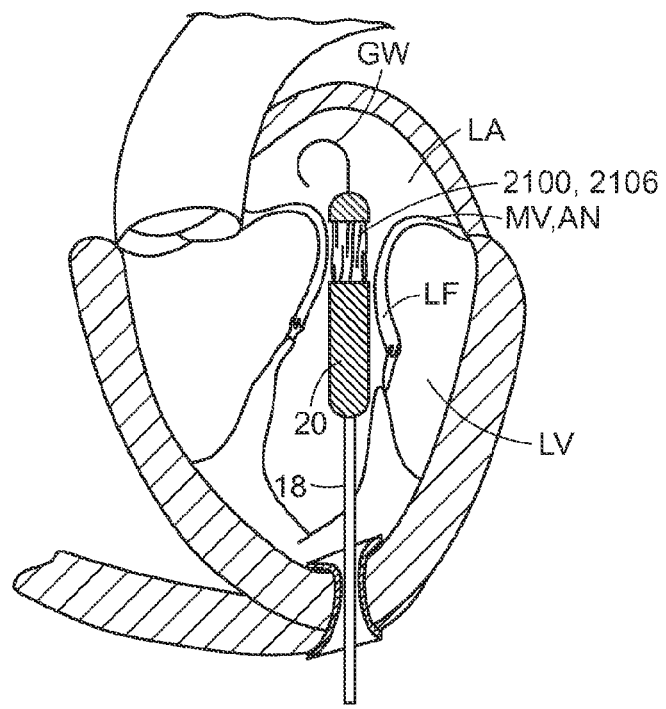
Figure 88B:
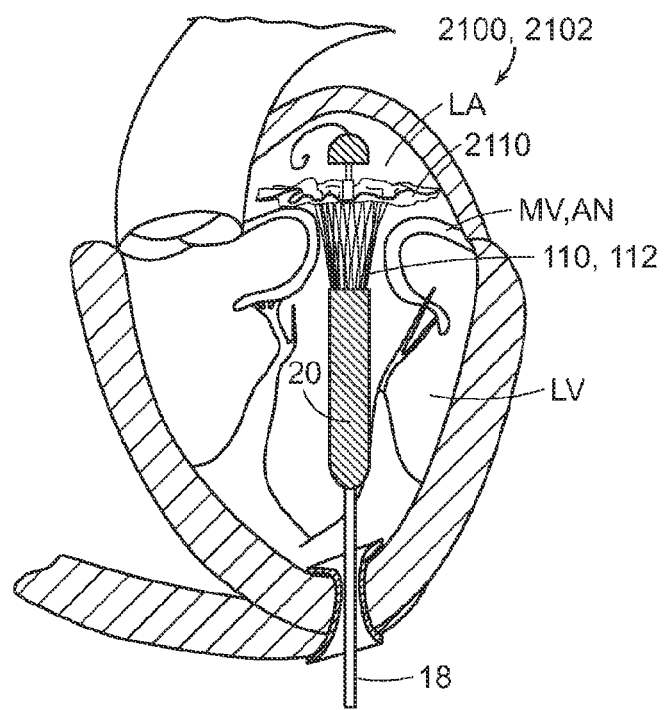
Figure 88C:
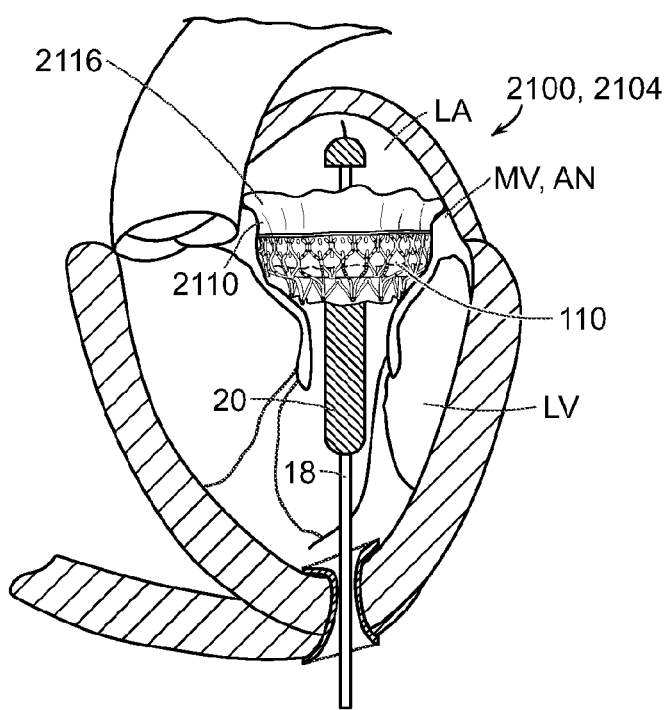

FIGS. 88A-88C are cross-sectional views of a heart showing a method of delivering a prosthetic heart valve device 2100 to a native mitral valve MV in the heart using a trans-apical approach in accordance with another embodiment of the present technology. Referring to FIG. 88A, the delivery catheter 18 is advanced through guiding catheter (not shown) which enters the left ventricle LV of the heart through a puncture in the left ventricle wall at or near the apex of the heart and is sealed by a purse-string suture. Alternatively, the delivery catheter 18 may be placed directly through a purse-string-sealed trans-apical incision without a guiding catheter. The sheath 20, which contains a collapsed device 2100 in a radially contracted delivery configuration 2106, is advanced through the mitral annulus AN between native leaflets LF as shown in FIG. 88A. The valve support 120, the anchoring member 110 and the extension member 2110 (e.g., brim, flange, shoulder, expansion ring, etc.) have a low profile configured for delivery through the delivery catheter 18 positioned at or near the native mitral valve when in the delivery configuration 2106. Referring to FIGS. 88B-88C together, once the device is positioned so that the extension member 2110 is located in the atrium, the sheath 20 is pulled proximally to allow the device 2100 to expand to the radially expanded and/or deployed configurations 2102, 2104 (FIGS. 88B and 88C).

As with other devices disclosed herein, retraction of the sheath 20 allows the device 2100 to expand while the delivery system remains connected to the device 2100 (e.g., system eyelets, not shown, are connected to the device eyelets, not shown). In this manner, an operator can control the placement of the device 2100 while at least portions of the device 2100 (e.g., the extension member 2110, upstream portion 112 of the anchoring member 110) are in the expanded configuration 2102 (FIGS. 88B and 88C). For example, as the sheath 20 is disengaged from the device 2100, the extension member 2110 can expand within the left atrium while the upstream region 112 of the anchoring member 110 is retained within the sheath 20 (FIG. 88B). During this phase of the delivery, the position of the device 2100 within the mitral valve area can be adjusted or altered.

In one embodiment, the extension member 2110 can have an indicator portion 2116 (FIGS. 88C and 89B) that can be visualized during device implantation to determine the position of the device 2100 relative to the native annulus. In one embodiment, deflection of the indicator portion 2116 caused by engagement of the extension member 2110 with a wall of the left atrium (e.g., when treating the mitral valve) can be visualized to accurately determine the position of the device 2100 relative to the native annulus. In some arrangements, the indicator portion 2116 preferably deflects about an axis generally parallel to a plane containing the native annulus. In another arrangement, the indicator portion 2116 forms an angle with a plane containing the native annulus, wherein the angle increases as the indicator portion 2116 is deflected. In a particular positioning and deployment step, the extension member 2110 can be placed such that the indicator portion 2116 forms a first angle with the plane during the visualization step and then the device 2100 is moved such that the indicator portion 2116 forms a second angle with the plane less than the first angle before the anchoring member 110 is deployed. Because the position of the fixation portion 1710 (FIG. 86A) relative to the extension member 2110 is known for a given degree of deflection, the position of the fixation portion 1710 relative to the native annulus can be determined based upon degree of deflection (i.e. second angle) of the extension member 2110. The indicator portion 2116, for example, can include a radiopaque material coupled to or integrated with the brim 2120 and/or the support structure 2130, and the radiopaque material can visualized using fluoroscopy.

In another example, the indicator portion 2116 can include an echogenic material that is visualized using ultrasound. The indicator portion may include, in a further embodiment, one or more metallic members. In some embodiments, the device 2100 can also include gas (e.g. $CO_2$) pockets or chambers (not shown) within or associated with the extension member 2110 that enhance echocardiographic visibility. For example, the extension member 2110 can be made of closed cell foam or other material with trapped gas pockets. In another embodiment, the extension member 2110 (e.g., the support structure 2130) can include a platinum core wire for enhancing fluoroscopic visibility. The platinum core wire can be removable such that once the device 2100 is properly positioned and implanted, the platinum core wire can be removed to avoid a galvanic response with NiTi wires.

After the device 2100 is located at the target site, the sheath 20 can be fully removed from the device 2100 and the anchoring member 110 of the device 2100 can expand outwardly to engage subannular tissue, such as the leaflets LF, and to retain the device 2100 in the desired target location. Following positioning and deployment of the device 2100 where the extension member 2110 is positioned and conformed to tissue above the annulus and the anchoring member 110 is engaging the annular and/or subannular tissue, the pull-wires (not shown) may be retracted in a proximal direction to release the device 2100 from the delivery system. The delivery system can then be removed to thereby fully implant the device 2100 at the mitral valve MV in the deployed configuration 2104. Alternatively, the device 2100 may be expanded upstream or downstream of the desired target location then pulled or pushed downstream or upstream, respectively, into the target location before releasing the device 2100 from delivery system.

Figure 89A:
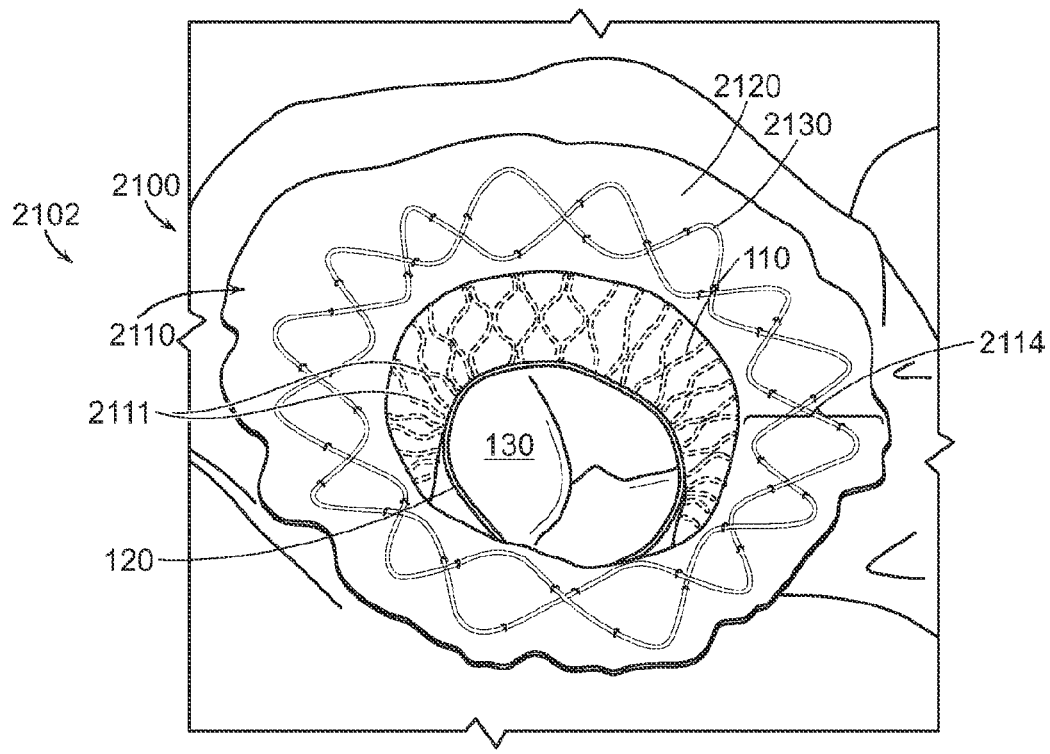
Figure 89B:
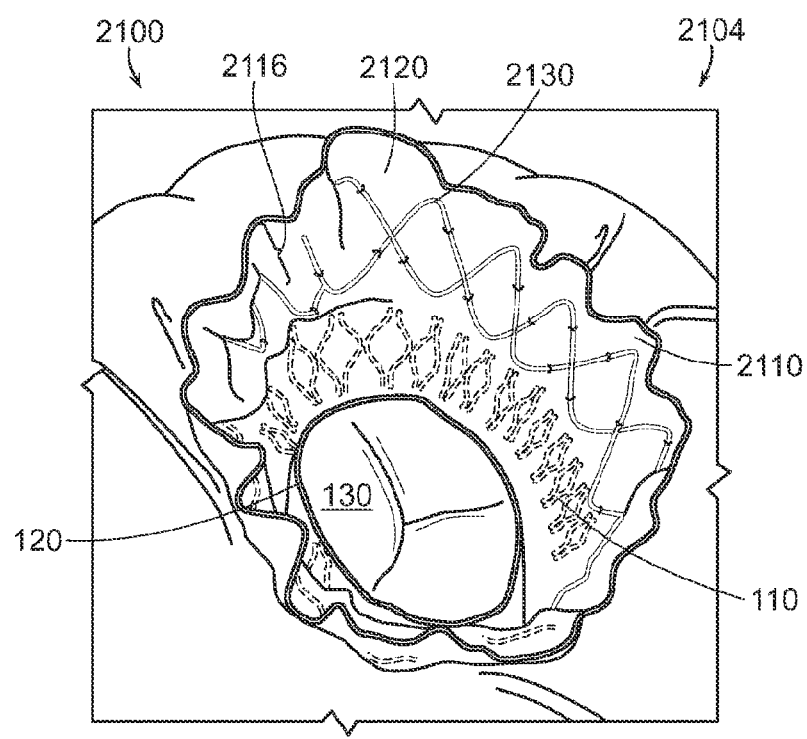

FIGS. 89A and 89B are schematic top views of a native mitral valve in the heart viewed from the left atrium and showing the prosthetic treatment device of FIGS. 86A and 86B implanted at the native mitral valve in accordance with an embodiment of the present technology. During deployment, the device 2100 is configured to transition from a radially contracted delivery configuration (FIG. 88A) to an unbiased/expanded configuration 2102 (FIG. 89A) in which the extension member 2110 expands radially outward from the anchoring member 110 (e.g., the upstream perimeter 113 and/or the fixation portion 1710) over the supra-annular surface of the native valve and/or the atrial wall surrounding the native valve. Prior to completely releasing the device 2100 from the delivery catheter, the catheter may be moved in a downstream direction (toward the ventricle) to position the fixation portion at the desired location relative to the native annulus (FIGS. 88B-88C). In doing so, the outer portion of the extension member 2110 may be deflected upward and radially inward due to contact with the atrial tissue (FIGS. 88C and 89B). This deflection can be visualized using fluoroscopy and/or echocardiography, thereby indicating to the practitioner the longitudinal position of the device 2100. As illustrated in FIG. 89B, the device 2100 can assume a final deployed configuration 2104 in which at least a portion of the extension member 2110 engages and is at least partially deformed by a supra-annular surface or tissue above the native valve (e.g., an atrial wall).

In many embodiments, the extension member 2110 can have sufficient flexibility such that the extension member 2110 conforms to supra-annular and atrial wall anatomy when in the deployed configuration 2104 (FIG. 89B). Accordingly, during implantation at a native valve (e.g., native mitral valve), the extension member 2110 can be deformed or deflected by the native tissue from its bias toward the expanded configuration 2102 to the deployed configuration 2104 in which it extends further in an upstream direction (FIG. 89B). Although the extension member 2110 is deflectable in an upstream direction (FIG. 89B), the extension member 2110 is resiliently biased to return to the unbiased configuration (FIGS. 86A-87B and 89A) where it to radially extends and pushes downward against the supra-annular surface. This bias contributes to the retention of the extension member 2110 in the atrium (e.g., resist movement toward the left ventricle under axial compressive forces during diastole and/or atrial contraction) and the maintenance of the positioning of the device 2100 with respect to the native valve annulus. Furthermore, the resulting compression fit between the extension member 2110 and the supra-annular surface and/or atrial walls or other structures helps create a long-term bond between the tissue and the device 2100 by encouraging tissue ingrowth (e.g., into the brim 2120) and encapsulation.

The flexible characteristics of the structural elements 2111 of the frame 2109 (FIG. 86A) having the first sealing member portion 140*a* and the support structure 2130 and brim 2120 can allow for the flexibility and conformability of the anchoring member 110 and extension member 2110, respectively, to engage and seal the device 2100 against uneven and uniquely-shaped native tissue at the native mitral valve. Although the extension member 2110 and the anchoring member 110 are deformable in response to forces exerted by the native anatomy, the valve support 120 can be substantially isolated from such deformation and/or can have sufficient rigidity to maintain a circular or other original cross-sectional shape, thus ensuring proper coaptation of the leaflets of the prosthetic valve 130 when implanted. The mechanical isolation of the prosthetic valve 130 from the forces exerted by the native tissue may be achieved by the independent deformability of the portion of the anchoring member 110 that is spaced apart from the valve support 102 as well as the independent deformability and atrial positioning of the extension member 2110.

As described above, mechanical isolation of the valve support 120 from the anchoring member 110 may be attributed to several aspects of the prosthetic heart valve devices disclosed herein. Some of these aspects can include, but not be limited to, (a) the relative high flexibility of the anchoring member 110, or flexibility of the transverse elements connecting the fixation portion 1710 of the anchoring member 110 to the valve support 120, compared with the lower flexibility of the valve support 120; (b) radial spacing between the anchoring member 110 and the valve support 120, particularly in some embodiments, at the upstream portion/upstream end where the anchoring member 110 engages the native annulus and/or subannular tissue; and (c) the coupling mechanisms employed to attach the anchoring member 110 to the valve support 120 (e.g. connection structure 1720/1730, FIG. 73) can be configured (e.g., to be flexible, compressible, or moveable) so as to reduce the transmission of forces from the anchoring member 110 to the valve support 120.

In the device 2100, the anchoring member 110 can also be mechanically isolated from the extension member 2110. When deployed at a native mitral valve, the extension member 2110 is more substantially influenced by anatomical tissue forces of the atrium and by atrial diastolic forces, whereas the anchoring member 110 is more substantially influenced by anatomical tissue forces at or near (e.g., below) the annulus and/or by ventricular systolic forces. The device 2100 is configured to conform to the shape and motion of the anatomy under these separate forces by mechanically isolating the anchoring member 110 from the extension member 2110 as well as from the valve support 120. In one embodiment, the extension member 2110 can have a relative high flexibility compared to the flexibility of the anchoring member 110 and/or the valve support 120 such that the extension member 2110 can deform significantly when deployed and in when in operation without substantially affecting the deformation of the anchoring member 110. In another embodiment, the extension member 2110 can have a deformable portion 2114 (FIG. 89A) that is mechanically isolated from the anchoring member 110 such that the deformable portion 2114 is radially and/or longitudinally deformable without substantially deforming the anchoring member 110. The extension member 2110 can also be coupled to the anchoring member 110 in a manner and at a location (e.g., upper rim or upstream perimeter 113)

that allows for deformability of the extension member 2110 without substantially affecting the shape of the anchoring member 110 or the valve support 120. Moreover, the coupling mechanisms employed to attach the extension member 2110 to the anchoring member 110 can be configured (e.g., to be flexible or moveable) so as to reduce the transmission of forces from the extension member 2110 to the anchoring member 110 or vice versa.

FIGS. 90A-90F are schematic illustrations showing how the prosthetic heart valve device mechanically isolates the valve support 120 from the forces exerted by the native tissue in accordance with additional embodiments of the present technology. Reference to forces exerted by the native tissue can include, in some examples, the diastolic and systolic forces generated in the beating heart, or in other examples, can include forces exerted by anatomical differences in the native valve that can vary patient to patient. In one embodiment, shown in FIG. 90A, lateral forces $F_{H1}$ exerted on the device 2100 are absorbed by the anchoring member 110 and/or the extension member 2110, such that the valve support 120 is not deformed by the forces $F_{H1}$. In this embodiment, the device 2100 can have a central longitudinal axis L-L and the lateral forces $F_{H1}$ can deform or otherwise move the anchoring member 110 and extension member 2110 into different laterally offset positions relative to the axis L-L, while the valve support 120 does not substantially move with respect to the axis L-L. The extension member 2110 is also mechanically isolated from the anchoring member 110 such that the anchoring member 110 can be moved a first distance $DIS_1$ in a direction transverse to longitudinal axis L-L and the extension member 2110 can move a second distance $DIS_1$ in the transverse direction that is greater than, equal to or, in another embodiment, less than the distance $DIS_1$. In some cases, all three elements (anchoring member 110, extension member 2110, and valve support 120) can be in three different offset positions in the transverse direction relative to axis L-L.

In another embodiment, multiple moment forces $F_{A1}$ and $F_{A2}$ exerted on the device 2100 from the native tissue can also be absorbed by the anchoring member 110 and/or the extension member 2110 (FIG. 90B). For example, the moment forces $F_{A1}$, $F_{A2}$ exerted by the native tissue can independently alter the positioning (e.g., X-Y positioning, rotational positioning, etc.) with respect to the central longitudinal axis of the anchoring member 110, extension member 2110 and valve support 120 such that each element is at a different angle relative to the longitudinal axis L-L. As illustrated in FIG. 90B, the extension member 2110 can deform, tilt, or move angularly independently of the deformation or angle of the anchoring member 110, and vice versa.

In a further embodiment, the anchoring member 110 and extension member 2110 can undergo relative shape changes with respect to the expanded configuration 2102 (e.g., FIGS. 86A and 86B) when forces transmitted from the surrounding tissue are absorbed by the anchoring member 110 and the extension member 2110. In the examples illustrated in FIGS. 90C-90E, transverse compressive forces, can be absorbed by portions of the anchoring member 110 and/or the extension member 2110, such that the device 2100 is positioned and retained at the native valve site and so that the valve support 120 remains substantially un-deformed under the same conditions. In one embodiment, absorption of transverse compressive forces $F_{H2}$ and $F_{H3}$ by the anchoring member 110 can cause the upstream portion 112 of the anchoring member 110 to deform inwardly without or less deformation of the extension member 2110 under the same and/or different applied forces (FIG. 90C). Alternatively, the downstream end of the extension member 2110 may be deformed in the transverse direction without or with less deformation of the upstream end of the anchoring member 110.

In other embodiments, as illustrated in FIGS. 90D and 90E, forces can change the shape of the extension member 2110 in the horizontal plane into a shape that is different than the shape of the anchoring member 110 resulting from the same or different forces. For example, the extension member 2110 can be subjected to different horizontal forces $F_{H4}$ and $F_{H5}$ (e.g., within the atrium) than the forces $F_{H2}$ and $F_{H3}$ (e.g., at the annulus or downstream of the annulus) exerted on the anchoring member 110 (FIG. 90D). As a result, extension member 2110 may be ovalized with its major axis in a first direction, while anchoring member 110 is ovalized with its major axis in a second direction transverse to the first direction. FIG. 90E illustrates another embodiment in which lateral forces $F_{H2}$, $F_{H3}$, $F_{H4}$ and $F_{H5}$ are absorbed by the extension member 2110 and the anchoring member 110 such that the extension member 2110 is deformed into a D-shape, while the anchoring member 110 has a different shape—e.g. circular, oval, or a non-aligned D-shape—in the horizontal plane.

FIG. 90F illustrates an embodiment in which the anchoring member 110 and extension member 2110 undergo relative shape changes in the expanded configuration 2102 when longitudinal forces $F_{L1}$ and $F_{L2}$ transmitted from the surrounding tissue are absorbed by the anchoring member 110 and the extension member 2110. In this embodiment, longitudinal mechanical forces $F_{L1}$ and $F_{L2}$ can cause distortion of the extension member 2110 and the anchoring member 110, such that these elements have side profiles with different shapes along a transverse axis T-T of the device 2100. For example, extension member 2110 may have a saddle shape corresponding to the shape of the supra-annular surface of the native valve, while anchoring member 110 remains substantially cylindrical or is deformed into a different shape, e.g. with an arched side profile.

Figure 91A:
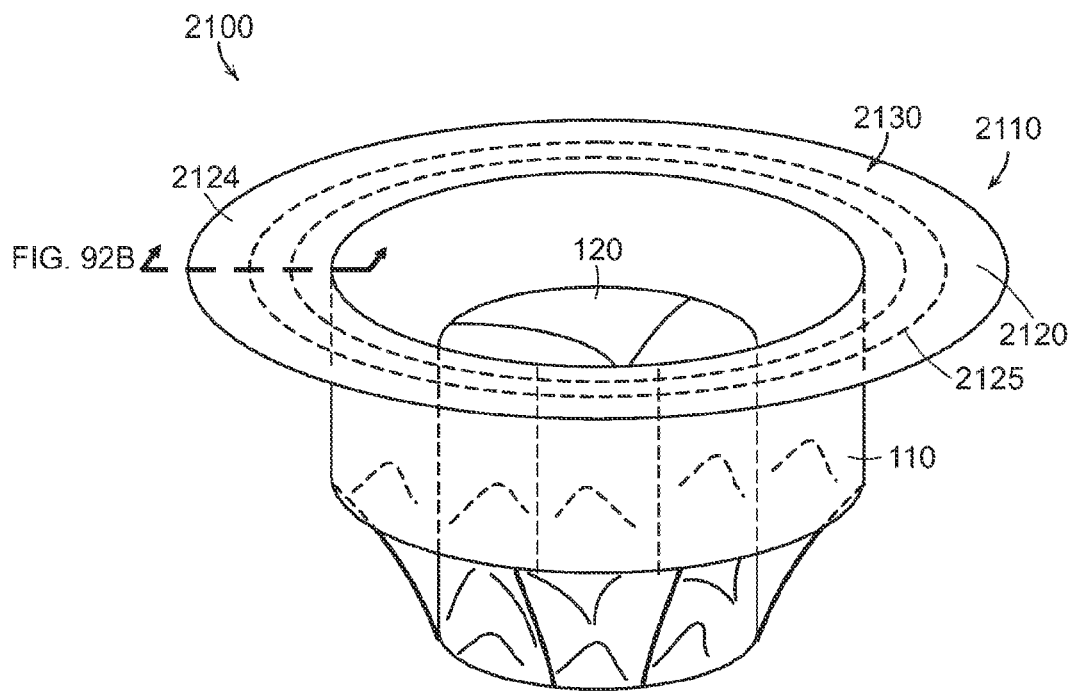

FIG. 91A is an isometric illustration of another device 2100 having an extension member 2110 in accordance with the present technology. The extension member 2110 shown in FIG. 91A includes the brim 2120 formed of fabric or another suitable material, wherein the brim material 2124 has structure features such as folds 2125 in the fabric that are at least in part configured to provide the support structure 2130 of the extension member 2110. The folds 2125 can be sewn, sutured, secured with adhesive, or formed using other mechanical features such as staples. The folds 2125 in the brim material 2124 can be patterned or positioned for desired strength, rigidity and/or flexibility. For example, folds 2125 can have concentric, radial, zig-zag, serpentine, diamond, square or other patterns in the brim 2120. Optionally, one or more structural elements (e.g., metal wires, plastic elements, etc.) can be sewn or attached to the brim 2120 and/or placed within the fold(s) 2125 to provided added structure.

Figure 91B:
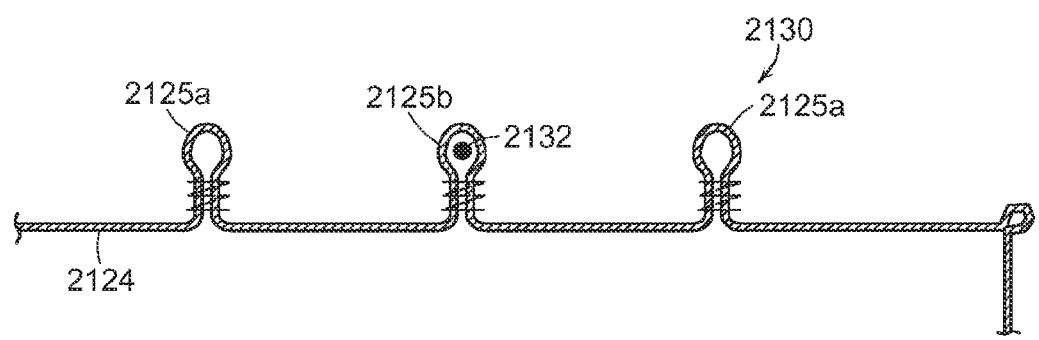

FIG. 91B is a cross-sectional view of the folds 2125 in the extension member 2110 shown in FIG. 91A. The folds 2125 can be sewn or secured portions of the brim material 2124 arranged in a spaced-apart manner circumferentially, radially or in another pattern about the brim 2120. Some folds 2125a do not have additional elements incorporated, while other folds 2125b may have structural elements such as wires 2132 positioned within the fold 2125b (FIG. 91B). In some embodiments, the structural elements or other elements can be radiopaque to assist visualization of the device during and post implantation at the native valve. The device 2100 illustrated in FIGS. 91A and 91B, provides a compliant, easily compressible, and atraumatic extension member 2110 that does not apply or transmit deforming forces to the anchoring member 110 or the valve support 120.

Figure 92:
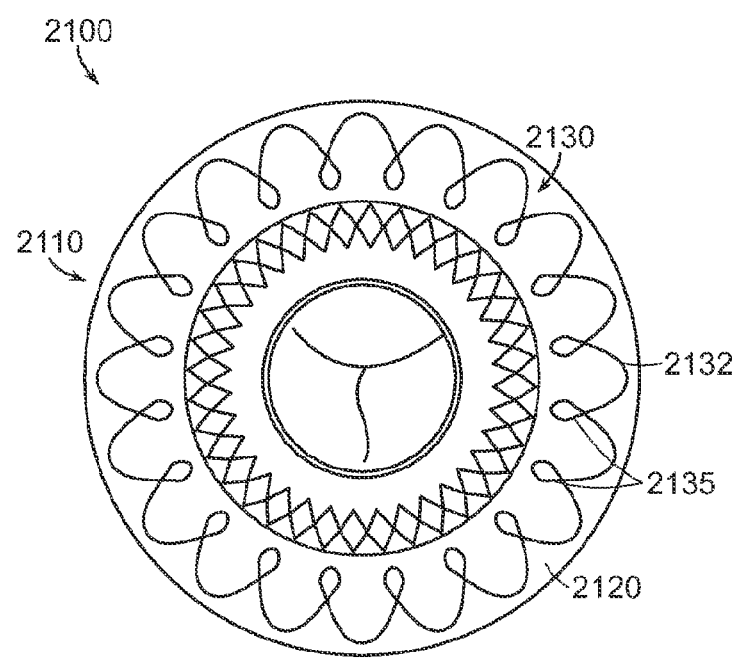

FIGS. 92-95B are schematic top views of several additional embodiments of prosthetic heart valve devices 2100 in accordance with the present technology. Like reference numbers refer to similar or identical components in FIGS. 86A-95B. The embodiment of the device 2100 illustrated in FIG. 92 represents several of the embodiments described above with reference to FIGS. 86A-91B. In this embodiment, the extension member 2110 includes a support structure 2130 including a wire 2132 forming a series of loops 2135 positioned circumferentially around the brim 2120. The loops 2135 may provide increased resilience in the brim 2120 while still providing sufficient flexibility for the extension member 2110 to be deflected in an upstream direction. Moreover, the loops 2135 may provide a support structure 2130 that atraumatically engages tissue.

Figure 93:
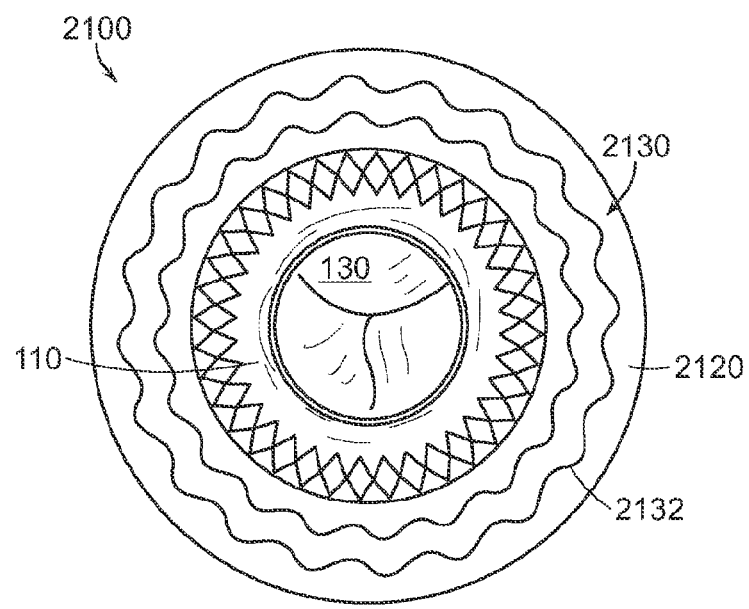

FIG. 93 illustrates an embodiment of the device 2100 in which the support structure 2130 includes a plurality of wavy, concentric wires 2132 positioned circumferentially around the brim 2120. FIG. 94 illustrates an embodiment of the device 2100 in which the support structure 2130 includes a spiral/helical formed wire 2132, 2136 positioned circumferentially around the brim 2120. While the illustrated embodiment of FIG. 94 includes a single wire 2132 formed in a concentric spiral/helical pattern, other wires (not shown) could be included to form the spiral/helical pattern or another pattern (e.g., a double helix, double spiral, etc.). The support structures 2130 illustrated in FIGS. 93 and 94 can provide axial strength while maintaining sufficient flexibility to conform and deflect relative to the anchoring member 110 about an axis transverse to the direction of blood flow through the prosthetic valve 130.

FIGS. 95A and 95B illustrate additional embodiments of the device 2100 in which the support structure 2130 includes a plurality of spirally projecting spokes 2136 connected to or otherwise integral with the frame 2109 of the anchoring member 110 and extending radially toward the outer circumference 2112 of the extension member 2110. The spokes 2136 can have an atraumatic tip 2137 and/or tissue engaging portion such that the supra-annular tissue and/or atrial wall is undamaged during deployment or engagement by the extension member 2110. In some embodiments the atraumatic tip 2137 can be a looped portion 2137a at the end of the spoke 2136 (FIG. 95A). In other embodiments, the atraumatic tip 2137 can be a bent portion 2137b.

FIGS. 96A-96C illustrate another embodiment of the device 2100 having a support structure 2130 with atraumatic features. As shown in FIGS. 96A and 96B, the device 2100 includes a rounded or curvilinear extension member 2110 having a plurality of resilient coils 2138 coupled to the brim 2120. In one embodiment, the extension member 2110 shown in FIG. 96A is configured to conform to the native anatomy without inducing trauma. The extension member 2110 can also enhance self-alignment of the device 2100 (e.g., mitigate tilting relative to the annulus). For example, the extension member 2110 can counteract against forces that would cause the device 2100 to tilt during systole. Further, one or more components of the extension member 2110 can be used to visualize the shape of the extension member 2110 and thereby detect or locate the device 2100 during deployment.

The coils 2138 can extend from the frame 2109 of the anchoring member 110 toward the outer circumference 2112 of the extension member 2110 (FIG. 96B), or in another embodiment, the coils 2138 can be spaced apart from the frame 2109. In one embodiment, the coils 2138 are deflectable in at least an upward direction, but are biased toward a radially outward orientation with a rounded, downward oriented end 2139. In one embodiment, the coils 2138 can wound from Nitinol (NiTi), polyether ether ketone (PEEK) polymer, stainless steel or other suitable materials. In various embodiments, the coils 2138 include shape-memory metal. In a further embodiment, the extension member 2110 can include the brim 2120 formed from a fabric, woven material, knitted material, mesh or web made from polyester or other flexible materials (FIG. 96C). In yet a further embodiment, the brim 2120 can be formed from a web, mesh, knitted material or other woven material made from NiTi, stainless steel, (PEEK) polymer, or other suitable materials that can be used to form the brim 2120 alone or in combination with another material (e.g., integrated into the weave of) that is used to form the brim 2120. As shown in FIGS. 96A-96C, the extension member 2110 can be shaped to provide sealing between the native tissue and the device 2100 when the valve is closed and under pressure during ventricular systole. The extension member of FIGS. 96A-96C can also promote bio-integration of tissue into the material of the brim 2120, which can then promote long-term sealing of the device 2100 to the native tissue.

FIGS. 97A and 97B illustrate a further embodiment of the device 2100 in which the extension member 2110 includes a discontinuous brim 2120 around the upstream perimeter 113 of the anchoring member 110 in accordance with the present technology. FIGS. 97A and 97B are top and isometric views of a device 2100 having an extension member 2110 that includes a plurality of discreet extending petals 2140 or protrusions extending from the frame 2109 of the anchoring member 110. The petals 2140 can include wires 2132 or struts radially extending from the frame 2109 to form a plurality of spaced apart triangular-shaped petals 2140 around the upstream perimeter 113 of the anchoring member 110. The wires 2132 can be covered with fabric or other brim material 2124 in a continuous or discontinuous (FIGS. 97A and 97B) manner to define the brim 2120. The petals 2140 are mechanically isolated from each other petal 2140 and each petal 2140 is configured to be deflected and/or deformed independently of each other petal 2140 to provide enhanced conformity to the native tissue.

FIGS. 98A-98C illustrate additional embodiments of the device 2100 in which the extension member 2110 includes a plurality of petals 2140 radially extending from the frame 2109 of the anchoring member 110. For example, FIG. 98A illustrates a device 2100 having a plurality of circular-shaped wires 2141 forming individual petals 2140. The circular-shaped wires 2141 can be flexibly connected via a plurality of connectors 2142 to the frame 2109 around the upstream perimeter 113 of the anchoring member 110. Additionally, the circular-shaped wires 2141 can be covered or otherwise attached to brim material 2124 for forming the brim 2120 (see FIGS. 98B and 98C). In one embodiment, the extension member 2110 includes a fabric or other material over and/or under the circular-shaped wires 2141 and extending beyond the circular-shaped wires 2141 to form a continuous brim 2120 (FIG. 98B). FIG. 98C illustrates another embodiment in which the circular-shaped wires are adhered to discreet portions of brim material 2124 to form spaced apart circular-shaped petals 2140 around the upstream perimeter 113 of the anchoring member 110. In this example, each petal 2140 can be mechanically isolated from each adjacent petal 2140 and such that the petals 2140 can be deflected and/or deformed independently of each other petal 2140 to provide the extension member 2110 enhanced conformity to the surrounding native tissue. In further embodiments, the petals 2140 can be connected or hinged to adjacent petals 2140 (FIG. 98B) with links 2143 or other fasteners to provide some cohesive movement within the brim 2120 while still allowing more freedom for conformity of unique tissue anatomy engaged by the extension member 2110.

FIG. 99 illustrates an additional embodiment of the device 2100 having an extension member 2110 formed of a polymeric sheet 2118 or other panel. In various arrangements, the polymeric sheet 2118 can provide sufficient strength or/or rigidity such that the extension member 2110 does not need support wires and/or can allow for fewer wires or smaller wires to be used to form a support structure (not shown). To provide flexibility to the extension member 2110, certain embodiments of the polymeric sheet 2118 include a plurality of holes 2119 through the polymeric sheet material. The holes 2119 can be selected for density, size and/or position on the polymeric sheet 2118 can be varied to increase and/or decrease flexibility of selected regions the extension member 2110. For example, FIG. 99 illustrates an embodiment of the device 2100 in which holes 2119 are placed in the polymeric sheet 2118 at greater density toward the outer circumference 2112 when compared to the density at an inner portion 2113 of the polymeric sheet 2118. In this example, the flexibility of the extension member 2110 is greater towards the outer circumference 2112 than at the inner portion 2113 allowing the region at or near the outer circumference 2112 to more readily deform and conform to the native tissue. In some embodiments, not shown, the density and/or size of the holes 2119 can be unevenly distributed across the polymeric sheet 2118 to form a non-uniform extension member 2110. For example, it may be desirable to provide greater flexibility (e.g., greater density of holes 2118) on the side engaging the anterior leaflet than on the side engaging the posterior leaflet such that the device 2100 will not substantially occlude the LVOT.

FIGS. 100A and 100B illustrate another embodiment of the device 2100 having an extension member 2110 with variable flexibility during and following implantation in accordance with the present technology. FIG. 100A illustrates the expanded device 2100, 2102 after release from a delivery catheter 18, and FIG. 100B is a schematic top view of the device 2100. Referring to FIGS. 100A and 100B together, the support structure 2130 can include a combination of wires having variable stiffness (e.g., flexibility). For example, the support structure 2130 can include flexible wires 2144 (e.g., thin, floppy) and include relatively stiffer wires 2145 that are less flexible than the flexible wires 2144. The stiffer wires 2145 may also have higher radiopacity than the flexible wires 2144 so as to facilitate enhanced visualization during device placement. In some embodiments, the stiffer wires 2145 can be positioned within pockets or sleeves 2146 within or attached to the brim 2120 such that the stiffer wires 2145 can be removable during or after implantation of the device 2100. The sleeves 2146 may be oriented such the stiffer wires 2145 provide radial support to the extension member 2110 during deployment and implantation (FIG. 100B); however other orientations and arrangements are also possible. As shown in FIG. 100A, the stiffer wires 2145 can remain connected to the delivery catheter 18. After placement of the extension member 2110 upstream of the native valve, the stiffer wires 2145 can be removed from the sleeves 2146 and retracted through the deliver catheter 18. In some embodiments, all the stiffer wires 2145 can be removed, however, in other arrangements, a portion of the stiffer wires 2145 or select stiffer wires can remain within the extension member 2110 following implantation. The flexible wires 2144 can remain coupled to the brim 2120 to provide an atraumatic support structure 2130 having increased flexibility once implanted.

FIG. 101 illustrates an embodiment of the device 2100 in which the support structure 2130 includes one or more inflatable chambers 2147 within the brim 2120 that can be inflated with fluid to provide radial stiffness to the extension member 2110. The brim material 2124 can be a fabric, polymer or other material, for example, that provides the inflatable chambers 2147 (e.g., internal channels). One or more independent or interconnected inflatable chambers 2147 can be arranged in a continuous ring around the extension member 2110, or in other arrangements (e.g., radially extending arms, zig-zags, etc.) In one embodiment, the chambers 2147 are fillable with fluid (e.g., saline, $CO_2$, air, gel, contrast agent, etc.) via a port 2148 provided on the brim 2120 either before, during, or after deployment of the device 2100. In one embodiment, the chambers 2147 can be at least partially filled during deployment and the volume of the internal fluid can be adjusted after deployment of the extension member 2110 and/or the device 2100 to provide a desired degree of flexibility. In various embodiments, the chambers 2147 can be inflated temporarily, permanently, or be deflated before the release of the device 2100 from the delivery catheter (not shown). In one embodiment, the extension member 2110 has radial stiffness only when inflated. The extension member 2110 can be structurally independent from the anchoring member 110, for example, attached via the brim material 2124 or via flexible connectors (not shown). In some embodiments, the inflation chambers 2147 may provide improved visibility by contrast echocardiography if the chambers 2147 are filled with a gas (e.g., $CO_2$) or other material more visible by echocardiogram.

FIG. 102 illustrates an embodiment of the device 2100 in which the extension member 2110 can include multiple layers 2150 of brim materials 2124 and/or support structures 2130. Although, for purposes of clarity, layers 2150 are shown separated in FIG. 102, layers 2150 are preferably stacked in contact with each other without intervening spaces In a particular example, multiple layers 2150 of woven fabric of polymeric sheets with one or more layers of wires 2132 can provide the extension member 2110 with a selectable degree of compliance or conformity to the native tissue. Individual layers 2150 of brim materials 2124 can be formed of the same materials or a combination of materials. Likewise, the support structure 2130 can include layers of wires 2132 having the same or different arrangements on the layers 2150 of brim materials 2124. The wires 2132 can also include a combination of flexible wires (e.g., smaller, less stiff) and stiffer wires. Accordingly the multiple layers 2150 may include wires 2132 having different wire diameters, geometries, overall size and stiffness. In another embodiment, the layers 2150 can provide the extension member 2110 with an asymmetric degree of flexibility. In one example, the lower layers 2151 (e.g., closer to the ventricle) can be more stiff (e.g., less flexible) than the upper layers 2152 that contact atrial chamber tissue. In another example, the extension member 2110 can have an asymmetric degree of flexibility between the side engaging the anterior leaflet (e.g., greater flexibility) and the sides engaging the posterior leaflet or commissures (e.g., less flexibility) such that the device 2100 will not substantially occlude the LVOT. In a further embodiment, the extension member 2110 can also include radiopaque markers 160 (e.g., metallic strips, rings) placed on or between the layers 2150 to assist in visualization of the device 2100 during and after implantation.

FIG. 103 illustrates an embodiment of the device 2100 having a funnel-shaped extension member 2110 extending from the anchoring member 110 in shape that diverges outwardly in an upstream direction. In one embodiment, the extension member 2110 can include an inverted funnel-shaped brim 2126 or tube that includes the brim material 2124 (e.g., fabric) coupled to the anchoring member 110 and/or integral with the first sealing member portion 140a. In another embodiment, the extension member 2110 can include the inverted funnel-shaped brim 2126 further supported by support structure comprising struts or wires (not shown).

FIGS. 104A and 104B illustrate an embodiment of the device 2100 in which the anchoring member 110 includes a plurality of upstream extending lobes 2170 and the extension member 2110 positioned beneath (e.g., downstream) the lobes 2170. In one embodiment, the lobes 2170 can be spaced apart radial struts 2171 (FIG. 104A), or in another embodiment, the lobes 2170 can be spaced apart loops 2172 (FIG. 104B). The lobes 2170 can be pre-shaped and connected to or integral with the frame 2109 of the anchoring member 110. In one embodiment, the lobes 2170 can include metal or other material visible by fluoroscopy or echocardiogram imaging systems (not shown) for visualizing the placement of the device 2100.

Referring to FIGS. 104A and 104B together, the lobes 2170 can define the expected final deployed position of the extension member 2110. As such, the lobes 2170 may limit deflection of the extension member as the device 2100 is pulled (e.g., moved downstream) into position. Alternatively or additionally, the lobes 2170 may provide a reference marker, visible using fluoroscopy, relative to which the degree of deflection of the extension member 2110 that may be assessed. As illustrated in FIGS. 104A and 104B, the angle α is the angle between the radially extended extension member 2110 and the lobes 2170. When the angle α is small, the extension member 2110 extends more longitudinally (e.g., low-profile), and the angle α increases as the extension member 2110 extends outwardly. Visualizing the angle α during deployment and implantation of the device 2100 can allow a practitioner to better visualize the position of the device 2100 relative to the native valve anatomy before the anchoring member 110 and valve support with prosthetic valve (not shown) is deployed from the delivery catheter (not shown). For example, in operation, the extension member 2110 can be at least partially deployed from the delivery catheter (not shown) such that the angle α becomes large (e.g., full extension). The device 2100 can then be pulled/pushed downstream through the native annulus. As the device 2100 is pulled/pushed downstream, the extension member 2110 is deflected by the native tissue inwardly thereby decreasing the angle α. Visualization of the decreasing angle α can allow the practitioner to see the extent of the inward deflection as the device 2100 is implanted and, as such, ensure correct positioning of the device at the native valve.

FIG. 105 illustrates an embodiment of the device 2100 in which the extension member 2110 includes an expansion ring 2153 separate from the anchoring member 110 in accordance with the present technology. The expansion ring 2153 can be flexibly coupled to the anchoring member 110 by one or more tethers 2154 or other lines (e.g., sutures, fabric material etc.) spanning a desired distance between the expansion ring 2153 and the upstream perimeter 113 of the anchoring member 110. In one embodiment, the expansion ring 2153 may be formed of a wire frame or metal mesh. In another embodiment, the expansion ring 2153 may be a cylindrical stent connected to the upstream perimeter 113 and/or the frame 2109 of the anchoring member 110 by the tethers 2154. In certain embodiments, a cover or other material can be coupled to the expansion ring 2153. In various arrangements, the expansion ring 2153 is structurally independent (e.g., mechanically isolated) from the anchoring member 110 and can also provide a device delivery positioning aid to ensure the proper position of the anchoring member 110 before deployment.

FIGS. 106A and 106B illustrate embodiments of the device 2100 wherein the extension member 2110 is attached to or otherwise extends from a portion of the valve support 120 (e.g., at a location downstream from the upstream portion 112 of the anchoring member 110). In some embodiments this may allow for higher placement of the device 2100 within the native annulus (not shown). In the embodiments shown in FIGS. 106A and 106B, the extension member 2110 can be connected and/or attached (e.g., via stitching, sutures, rivets, adhesive or other mechanical coupling fasteners or features known in the art) to the valve support frame 136 and/or to the second sealing member portion 140b coupled to the valve support frame 136 at an upstream end 121 (FIG. 106B) or at an intermediate portion 2155. As illustrated in FIGS. 106A and 106B, and in certain embodiments, the extension member 2110 may also, or alternatively, be attached and/or sealed to the anchoring member 110 at the upstream portion 112 to provide a cover over the gap 2108 between the anchor member 110 and the valve support 120 (e.g., inner skeleton). The extension member 2110 may include a brim material 2124 that is impervious to blood or, alternatively, may contain holes to allow fluid to easily pass into the gap 2108. Or the extension member 2110 could have holes (not shown) with flap valves (not shown) or other suitable one-way valves to allow blood or fluid flow only into the gap 2108 where the fluid becomes trapped in the space between the anchoring member 110 and the valve support 120, thus "inflating" the space to add additional radial rigidity.

FIGS. 107A and 107B illustrate an embodiment of the device 2100 having a separate extension member 2180 that is a separately deployable component in accordance with the present technology. The separate extension member 2180 can have a brim 2120 and support structure (not shown) similar to the extension members 2110 described above. In other arrangements (not shown), the separate extension member 2180 can include a support structure (e.g., spiral-shaped wire) that is delivered above the annulus (not shown). Additionally, the separate extension member 2180 can also include one or more docking features 2182 (e.g., hooks, latches, barbs, pins, etc.) configured to engage the anchoring member 110 (e.g., at corresponding hooks, on frame 2109, etc.). In one embodiment, the separate extension member 2180 can be delivered by delivery catheter 18 to the native valve NV before delivering the anchoring member 110 carrying the prosthetic valve (FIG. 107A) to the target site. In some embodiments, the separate extension member 2180 can engage the supra-annular surface above the annulus A when deployed. Following deployment of the separate extension member 2180, the anchoring member 110 and valve support 120 can be released from the delivery catheter 18 to engage and be retained by the separate extension member 2180 in proper position within the native valve NV (FIG. 107B). In one embodiment, the separate extension member 2180 can remain implanted at the native valve NV; however, in other embodiments, the separate extension member 2180 can be removed after the prosthetic valve device 2100 is implanted. In other arrangements, the separate extension member 2180 and the anchoring member 110 can be delivered as a single component and the valve support 120 carrying the prosthetic valve can be delivered separately.

Referring back to FIGS. 86A-107B, and in the case of mitral valve replacement, the device 2100 is delivered in a low-profile delivery configuration 2106 such that the extension member 2110 is positioned in the left atrium and the anchoring member 110 (e.g., fixation portion 1710) is positioned at the native valve annulus. The device 2100 is partially deployed such that the extension member 2110 is release from the delivery catheter 18 and allowed to expand radially while the anchoring member 110 is retained in the delivery catheter 18. In many of the foregoing embodiments, the extension member 2110 readily folds relative to the anchoring member 110. As such, the device 2100 is then drawn toward the left ventricle which causes the extension member 2110 to fold inwardly. The extension member 2110 exerts a force that properly aligns the anchoring member 110 with the native valve annulus, and the relative position between the extension member 2110 and the anchoring member 110 can be readily visualized through known imaging techniques to enable the practitioner to accurately position the device 2100 relative to the native valve structure.

Additionally, as discussed above, the extension member 2110 can have many different embodiments including a brim 2120 or shoulder that extends from the anchoring member 110, or an expansion ring 2153 that is coupled to the anchoring member 110 by at least one line (e.g., tether 2154). The brims 2120, shoulders, and/or rings are configured to expand to have a larger diameter than the anchoring member 110 and to flex, flap, and/or fold relative to the anchoring member 110. The extension member 2110 is accordingly configured to enhance the positioning, orientation/alignment, and visualization of the device 2100 relative to the native valve anatomy. In some embodiments, but not necessarily all, the extension member 2110 can provide additional fixation and sealing of the device 2100.

Additional Embodiments

Features of the prosthetic heart valve device components described above and illustrated in FIGS. 10A-107B can be modified to form additional embodiments configured in accordance with the present technology. For example, the prosthetic heart valve device 1100 illustrated in FIGS. 65A-65B without flared anchoring members can include anchoring members that are coupled to the valve support or other feature and are configured to extend radially outward to engage subannular tissue. Similarly, the prosthetic heart valve devices described above and illustrated in FIGS. 57A-71 can include features such as sealing members as well as stabilizing features such as arms and tissue engaging elements.

Features of the prosthetic heart valve device components described above also can be interchanged to form additional embodiments of the present technology. For example, the anchoring member 1210 of the prosthetic heart valve device 1200 illustrated in FIG. 67A can be incorporated into the prosthetic heart valve device 600 shown in FIGS. 57A-57C. Additionally, many features of the prosthetic heart valve devices 1700, 1900, 2000 and 2100 described above with reference to FIGS. 72-107B can be used with the prosthetic heart valve devices described above with reference to FIGS. 10-71A, and vice versa. In a particular embodiment, extension members 2110 shown in FIGS. 86A-107B can be incorporated, for example, in the device 100 (FIG. 10A).

The following Examples are illustrative of several embodiments of the present technology.

EXAMPLES

1. A prosthetic heart valve device, comprising:
a valve support having an upstream region and a downstream region relative to blood flow through a native heart valve of a human heart, the upstream region being configured to support a prosthetic valve, the prosthetic valve having a plurality of leaflets and having an undeformed shape in which the leaflets coapt sufficiently to prevent backflow through the prosthetic valve;
an anchoring member having a longitudinal dimension and including a tissue fixation portion, an integration region coupled to the valve support, and a plurality of lateral connectors between the tissue fixation portion and the integration region, wherein the tissue fixation portion is configured to (a) engage tissue at an implant site located at and/or downstream of a native annulus of the native heart valve and (b) be at least partially deformable into a non-circular shape to adapt to a shape of the tissue at the implant site in a deployed state, and wherein the lateral connectors have a lateral section extending in a transverse direction relative to the longitudinal dimension of the anchoring member and at least a first transition zone that bends in a direction different than the transverse direction such that the tissue fixation portion faces the tissue at the implant site in the deployed state; and wherein the tissue fixation portion of the anchoring member is mechanically isolated from the upstream region of the valve support such that the upstream region of the valve support maintains the undeformed shape if the anchoring member has deformed in the non-circular shape.

2. A prosthetic heart valve device, comprising:
an anchoring member having a longitudinal dimension and including a tissue fixation portion having a first cross-sectional dimension in a deployed state, an integration region having a second cross-sectional dimension in the deployed state less than the first cross-sectional dimension, and a lateral portion between the tissue fixation portion and the integration region, wherein—
the tissue fixation portion is configured to (a) engage tissue located at and/or downstream of a native annulus of a heart valve in a human and (b) be at least partially deformable into a non-circular shape to adapt to a shape of the tissue engaged by the tissue fixation portion in a deployed state, and
the lateral portion extends in a direction transverse with respect to the longitudinal dimension of the anchoring member and has at least a first transition zone that bends from the transverse direction to the tissue fixation portion such that the tissue fixation portion is configured to face the native annulus in the deployed state; and
a valve support having a first region and a second region, the first region having a cross-sectional shape in the deployed state configured to support a prosthetic valve such that prosthetic leaflets of the prosthetic valve contact each other in the deployed state, and the second region of the valve support being coupled to the fixation portion of the anchoring member.

3. The prosthetic heart valve device of any of examples 1-2, wherein the connectors or lateral portion further include a second transition zone that bends from the lateral section or lateral portion to the integration region.

4. The prosthetic heart valve device of any of examples 1-3, wherein the anchoring member has a first end at the tissue fixation portion and a second end at the integration region, and wherein the first transition zone bends from the lateral section or lateral portion toward the first end of the anchoring member and second transition zone bends from the lateral section or lateral portion toward the second end of the anchoring member.

5. The prosthetic heart valve device of any of examples 1-4, wherein the connectors or lateral portion further include a second transition zone, and wherein the first transition zone bends superiorly and the second transition zone bends inferiorly relative to the heart.

6. The prosthetic heart valve device of any of examples 1-5, wherein the first transition zone has a concave curvature with respect to the longitudinal dimension of the anchoring member.

7. The prosthetic heart valve device of example 6, wherein the connectors further comprise a second transition zone that bends from the lateral section or lateral portion to the integration region, and wherein the second transition zone has a convex curvature with respect to the longitudinal dimension of the anchoring member.

8. The prosthetic heart valve device of any of examples 1-7, wherein the tissue fixation portion extends at least substantially parallel to the longitudinal dimension of the anchoring member.

9. The prosthetic heart valve device of any of examples 1-8 wherein the longitudinal dimension is a central longitudinal axis of the anchoring member, and the tissue fixation portion extends at angle inclined inwardly toward the central longitudinal axis.

10. The prosthetic heart valve device of any of examples 1-9, wherein the tissue fixation portion comprises a ring having right cylindrical shape and a plurality of barbs projecting from the ring.

11. The prosthetic heart valve device of any of examples 1-10, wherein the tissue fixation portion has a height of 10-20 mm and a generally flat outer surface along the height.

12. The prosthetic heart valve device of any of examples 1-11, wherein the anchoring member has a first end at the tissue fixation portion and a second end at the integration region, and the second end of the anchoring member is connected to the downstream region of the valve support.

13. The prosthetic heart valve device of any of examples 1-11, wherein the anchoring member has a first end at the tissue fixation portion and a second end at the integration region, and the second end of the anchoring member is connected to the upstream region of the valve support.

14. The prosthetic heart valve device of any of examples 1-13, further comprising a compartment between the anchoring member and the valve support, and a material in the compartment.

15. The prosthetic heart valve device of example 14, wherein the compartment comprises a fabric container attached to the anchoring member and/or the valve support, and the material includes at least one of an anti-clotting agent and/or a healing agent.

16. The prosthetic heart valve device of any of examples 1-15, wherein the lateral portion comprises an outwardly flared section, and the fixation portion extends at least substantially parallel to the longitudinal dimension of the anchoring member.

17. The prosthetic heart valve device of any of examples 1-15, wherein the lateral portion comprises an outwardly extending conical section, and the fixation portion extends at least substantially parallel to the longitudinal dimension of the anchoring member.

18. A device for implantation at a native mitral valve, the native mitral valve having a non-circular annulus and leaflets, comprising:
 a valve support having a first region configured to be attached to a prosthetic valve with a plurality of prosthetic leaflets and a second region;
 an anchoring member having a longitudinal dimension and including a first portion configured to contact tissue at the non-circular annulus and a second portion having a lateral portion between the first portion and the valve support;
 wherein the second portion of the anchoring member is attached to the second region of the valve support while in a low-profile configuration in which the anchoring member and the valve support are configured to pass through vasculature of a human;
 wherein the lateral portion is transverse to the longitudinal dimension; and
 wherein the anchoring member and the valve support are configured to move from the low-profile configuration to an expanded configuration in which the first portion of the anchoring member at least partially adapts to the non-circular annulus of the native mitral valve and the first region of the valve support is spaced inwardly from the first portion of the anchoring member relative to the longitudinal dimension of the anchoring member such that a shape of the first region of the valve support is at least partially independent of a shape of the first portion of the anchoring member.

19. The device of example 18, wherein the first portion of the anchoring member comprises a tissue fixation portion and the second portion of the anchoring member comprises an integration region.

20. The device of any of examples 18-19, wherein the lateral portion comprises a plurality of lateral connectors, and individual connectors include a lateral section extending in a transverse direction relative to the longitudinal dimension of the anchoring member and at least a first transition zone that bends in a direction different than the transverse direction such that the first portion or the tissue fixation portion of the anchoring member faces tissue at the implant site in the deployed state.

21. The device of any of examples 18-20, wherein the connectors or lateral portion further include a second transition zone that bends from the lateral section or lateral portion to the valve support.

22. The device of any of examples 18-21, wherein the first portion or the tissue fixation portion of the anchoring member extends at least substantially parallel to the longitudinal dimension of the anchoring member.

23. The prosthetic heart valve device of any of examples 18-21 wherein the longitudinal dimension is a central longitudinal axis of the anchoring member, and the first portion or the tissue fixation portion of the anchoring member extends at angle inclined inwardly toward the central longitudinal axis.

24. The prosthetic heart valve device of any of examples 18-23, wherein the first portion or the tissue fixation portion of the anchoring member comprises a ring having right cylindrical shape and a plurality of barbs projecting from the ring.

25. The prosthetic heart valve device of any of examples 18-24, wherein the anchoring member has a first end at the first portion or the tissue fixation portion and a second end at the second portion or the integration region, and the second end of the anchoring member is connected to a downstream region of the valve support.

26. The prosthetic heart valve device of any of examples 18-24, wherein the anchoring member has a first end at the first portion or the tissue fixation portion and a second end at the second portion or the integration region, and the second end of the anchoring member is connected to an upstream region of the valve support.

27. The prosthetic heart valve device of any of examples 18-26, further comprising a compartment between the anchoring member and the valve support, and a material in the compartment.

28. The prosthetic heart valve device of any of examples 27, wherein the compartment comprises a fabric container attached to the anchoring member and/or the valve support, and the material includes at least one of an anti-clotting agent and/or a healing agent.

29. The prosthetic heart valve device of any of examples 18-28, wherein the lateral portion comprises an outwardly flared section, and the first portion or the fixation portion of the anchoring member extends at least substantially parallel to the longitudinal dimension of the anchoring member.

30. The prosthetic heart valve device of any of examples 18-28, wherein the lateral portion comprises an outwardly extending conical section, and the first portion or the fixation portion of the anchoring member extends at least substantially parallel to the longitudinal dimension of the anchoring member.

31. A method for operating of a prosthetic heart valve wherein the prosthetic heart valve device including an anchoring member and a valve support coupled to the anchoring member in a heart of a human, and wherein the anchoring member has a tissue fixation portion, an integration region attached to the valve support, and a lateral portion between the tissue fixation portion and the integration region, and wherein the method comprises:
expanding the anchoring member and the valve support such that a tissue fixation portion has a size and shape that is spaced apart from the valve support;
moving the anchoring member and the valve support such that the tissue fixation portion deforms to a non-circular shape; and
wherein a support region of the valve support is mechanically isolated from the tissue fixation portion of the anchoring member such that the support region of the valve support has a predetermined cross-sectional shape that supports a prosthetic valve so that prosthetic leaflets of the prosthetic valve contact each other sufficiently to inhibit backflow through the prosthetic valve.

32. The method of example 31, wherein the tissue fixation portion of the anchoring member comprises a right cylinder having an outer surface that extends at least substantially parallel to a longitudinal axis of the anchoring member.

33. The method of any of examples 31-32, wherein the lateral portion has a lateral section that extends transverse with respect to the valve support or the longitudinal axis of the anchoring member and at least a first transition zone having a first bend from the lateral section to the tissue fixation portion.

34. The method of example 32, wherein the lateral portion further includes a second transition zone having a second bend from the lateral section to the integration region.

35. The method of any of examples 33 and 34, wherein the lateral portion projects outwardly from the integration region and the first bend is angled superiorly from the lateral portion.

36. The method of any of examples 33 and 34, wherein the lateral portion projects outwardly from the integration region and the first bend is angled inferiorly from the lateral portion.

37. A method for replacement of a native heart valve having an annulus and leaflets coupled to the annulus, the method comprising:
positioning a prosthetic heart valve device including an anchoring member and a valve support at a native mitral valve location in a heart of the patient, wherein the anchoring member has a first portion and a second portion, and the valve support has a first region and a second region; and
expanding the anchoring member and the valve support while the second portion of the anchoring member is coupled to the second region of the valve support such that the first portion of the anchoring member engages tissue on or downstream of the annulus and at least partially adapts to a shape of the annulus at the native mitral valve location;
wherein, upon expansion, the first region of the valve support is spaced inwardly apart from the first portion of the anchoring member and the first region of the valve support holds a prosthetic valve having prosthetic leaflets such that the prosthetic leaflets contact each other sufficiently to inhibit backflow through the prosthetic valve after the first portion of the anchoring member has adapted to the shape of the annulus of the native mitral valve.

38. A prosthetic heart valve device, comprising:
a valve support having an upstream region and a downstream region relative to blood flow through a native heart valve of a human heart, the upstream region being configured to support a prosthetic valve, the prosthetic valve having a plurality of leaflets and having an undeformed shape in which the leaflets coapt sufficiently to prevent backflow through the prosthetic valve;
an anchoring member including an outwardly-facing engagement surface configured to engage tissue at an implant site on or below a native annulus of the native heart valve and extend in an upstream direction at an angle generally parallel to a longitudinal axis of the anchoring member or tapering inwardly in the upstream direction, the fixation portion being deformable into a non-circular shape to adapt to a shape of the tissue at the implant site in a deployed state; and
a connection structure interconnecting the anchoring member to the valve support;
wherein the tissue fixation portion of the anchoring member is mechanically isolated from the upstream region of the valve support such that the upstream region of the valve support maintains the undeformed shape if the anchoring member has deformed into the non-circular shape.

39. The prosthetic heart valve device of example 38 wherein the connection structure comprises a plurality of struts each having an inner end connected to the valve support and an outer end connected to the anchoring member.

40. The prosthetic heart valve device of any of examples 38-39 wherein the connection structure has a flared portion that flares outwardly in the upstream direction.

41. The prosthetic heart valve of example 40 wherein the connection structure is configured such that the flared portion is disposed entirely downstream of the native annulus when the anchoring member is at the implant site.

42. Prosthetic heart valve device of any of examples 38-41 wherein the connection structure has an upstream end connected to the anchoring member, the upstream end being configured for positioning below the native annulus when the anchoring member is at the implant site.

43. The prosthetic heart valve device of any of examples 38-42 further comprising a plurality of barbs on the fixation surface, the barbs pointing in the upstream direction and configured to engage the tissue to resist upstream movement of the anchoring member relative to the native annulus.

44. The prosthetic heart valve device of any of examples 38-43 wherein the fixation surface is deflectable through a range of angles relative to the longitudinal axis such that upon engagement with the tissue the fixation surface is movable from an unbiased orientation to an implanted orientation.

45. The prosthetic heart valve device of example 44 wherein the fixation surface is deflectable through a range of angles relative to the connecting structure.

46. The prosthetic heart valve device of any of examples 38-45 wherein the fixation portion has a first flexibility and the connecting structure has a second flexibility different than the first flexibility.

47. The prosthetic heart valve device of any of examples 38-45 wherein the fixation portion has a downstream region with a first flexibility and an upstream region with a second flexibility different than the first flexibility.

48. The prosthetic heart valve device of any of examples 38-47 wherein the fixation portion comprises a skirt covering an inward-facing surface thereof.

49. The prosthetic heart valve device of example 48 wherein the skirt further covers an inward-facing side of the connecting structure.

50. The prosthetic heart valve device of example 48 further comprising a tubular valve cover extending around the valve support, the skirt being attached to the valve cover so as to inhibit blood flow therebetween 51. The prosthetic heart valve device of example 50 wherein the valve cover is disposed on an inward facing surface of the valve support.

52. The prosthetic heart valve device of any of examples 38-51 wherein the fixation surface is disposed at an angle generally parallel to an outwardly facing surface of the valve support in an unbiased condition.

53. The prosthetic heart valve device of any of examples 38-52 wherein the valve support has a downstream end, the anchoring member being configured such that the downstream end is disposed no more than 16 mm downstream of the native annulus when the engagement surface is at the implant site.

54. The prosthetic heart valve device of any of examples 38-53 wherein the fixation surface has a width in a direction parallel to the longitudinal axis of at least about 10-20 mm.

55. The prosthetic heart valve device of 38-54 wherein the connecting structure extends a distance parallel to the longitudinal axis of less than about 15 mm from the inner end to the outer end.

56. A prosthetic heart valve device, comprising:
a valve support having an upstream region and a downstream region relative to blood flow through a native heart valve of a human heart, the upstream region being configured to support a prosthetic valve, the prosthetic valve having a plurality of leaflets and having an undeformed shape in which the leaflets coapt sufficiently to prevent backflow through the prosthetic valve; and
an anchoring member including a connection structure and a fixation portion, the connection structure having an inner end connected to the valve support, an outer end connected to the fixation portion, and an intermediate portion between the inner end and the outer end which flares outwardly in an upstream direction, the fixation portion having an outwardly-facing engagement surface configured to engage tissue at an implant site on or below a native annulus of the native heart valve with the flared portion of the connection structure disposed entirely downstream of the native annulus, the engagement surface extending in an upstream direction at an angle generally parallel to a longitudinal axis of the anchoring member or tapering inwardly in the upstream direction, the fixation portion being deformable into a non-circular shape to adapt to a shape of the tissue at the implant site in a deployed state;
wherein the fixation portion of the anchoring member is mechanically isolated from the upstream region of the valve support such that the upstream region of the valve support maintains the undeformed shape if the anchoring member has deformed into the non-circular shape.

57. A prosthetic heart valve device, comprising:
a valve support having an upstream region and a downstream region relative to blood flow through a native heart valve of a human heart, the upstream region being configured to support a prosthetic valve, the prosthetic valve having a plurality of leaflets and having an undeformed shape in which the leaflets coapt sufficiently to prevent backflow through the prosthetic valve; and
an anchoring member including a connection structure and a fixation portion, the connection structure having an inner end connected to the valve support and an outer end connected to the fixation portion, the fixation portion having an outwardly-facing engagement surface configured to engage tissue at an implant site on or below a native annulus of the native heart valve, the anchoring member having a downstream region with a first flexibility and an upstream region with a second flexibility different than the first flexibility, the fixation portion being deformable into a non-circular shape to adapt to a shape of the tissue at the implant site in a deployed state;
wherein the fixation portion of the anchoring member is mechanically isolated from the upstream region of the valve support such that the upstream region of the valve support maintains the undeformed shape if the anchoring member has deformed into the non-circular shape.

58. The prosthetic heart valve device of example 57 wherein the upstream region is in the fixation portion and the downstream region is in the connecting structure.

59. The prosthetic heart valve device of example 57 wherein the upstream region is in an upstream portion of the fixation portion and the downstream region is in a downstream portion of the fixation portion.

60. A prosthetic heart valve device comprising:
an anchoring member having a tubular fixation frame with an inlet end and an outlet end;
a tubular valve support having a first portion coupled to the anchoring member and a second portion mechanically isolated from the anchoring member such that the inlet end of the anchoring member is radially deformable without substantially deforming the second portion;

a valve coupled to the valve support and having at least one leaflet movable from a closed position in which blood flow is blocked through the valve support and an open position in which blood flow is allowed through the valve support in a downstream direction; and an extension member coupled to the fixation frame and extending radially outward therefrom, at least a deformable portion of the extension member being mechanically isolated from the anchoring member such that the deformable portion of the extension member is radially deformable without substantially deforming the anchoring member.

61. The prosthetic heart valve device of example 60 wherein the extension member includes a brim comprised of a sheet of flexible material coupled to the fixation frame and extending radially outward therefrom, and a support structure coupled to the brim, wherein the support structure is more rigid than the brim.

62. A prosthetic heart valve device comprising:
an anchoring member having a connection structure and a radially expandable fixation frame, wherein the connection structure has a first end coupled to the fixation frame, a second end coupled to a valve support and a lateral portion that spaces the fixation frame apart from the valve support;
a valve coupled to the valve support and having at least one leaflet movable from a closed position in which blood flow is blocked through the interior and an open position in which blood flow is allowed through an interior in a flow direction from an inlet end toward an outlet end; and
an extension member comprising:
a brim comprised of a sheet of flexible material coupled to the fixation frame and extending radially outward therefrom; and
a support structure coupled to the brim, the support structure being more rigid than the brim;
wherein the extension member is deflectable relative to the fixation frame about an axis transverse to the flow direction and the fixation frame is configured to deform at least partially independently of the valve support.

63. The prosthetic heart valve device of any of examples 61 and 62 wherein the support structure is resilient and is more flexible than the fixation frame.

64. The prosthetic heart valve device of any of examples 60-63 wherein the valve support comprises a generally cylindrical valve frame formed around a longitudinal axis extending between the inlet and outlet ends.

65. The prosthetic heart valve device of example 64 wherein the valve frame has an upper extremity and a lower extremity, and the anchoring member is coupled to the lower extremity of the valve frame.

66. The prosthetic heart valve device of example 65 further comprising a plurality of connecting members interconnecting the lower extremity of the valve frame and the anchoring member.

67. The prosthetic heart valve device of example 65 wherein an upstream end of the anchoring member is radially spaced apart from the upper extremity of the valve frame such that the upstream end of the anchoring member is radially deformable without substantially deforming the upper extremity of the valve frame.

68. The prosthetic heart valve device of any of examples 61-63 wherein the anchoring member comprises a cover of a flexible material coupled to the fixation frame and surrounding an interior thereof.

69. The prosthetic heart valve device of example 68 wherein the brim has an inner edge attached to a circumference of the cover.

70. The prosthetic heart valve device of example 68 wherein the brim and the cover comprise a continuous sheet of material.

71. The prosthetic heart valve device of any of examples 61 and 62 wherein the support structure comprises a plurality of struts.

72. The prosthetic heart valve device of example 71 wherein the struts are not directly connected to the fixation frame.

73. The prosthetic heart valve device of example 71 wherein the struts are spaced apart from the fixation frame.

74. The prosthetic heart valve device of example 71 wherein the struts are coupled directly to the fixation frame.

75. The prosthetic heart valve of any of examples 60-62 wherein the extension member has an unbiased configuration in which it extends radially outward from the anchoring member and is deflectable to a deflected configuration in which it extends further in an upstream direction, the extension member being resiliently biased to return to the unbiased configuration.

76. The prosthetic heart valve device of example 71 wherein the struts extend in a radial direction away from the fixation frame.

77. The prosthetic heart valve device of example 71 wherein the struts form a continuous ring around extension member.

78. The prosthetic heart valve device of example 77 wherein the struts form a wavy, zig-zag or diamond pattern around the extension member.

79. The prosthetic heart valve device of example 71 wherein the struts are sewn to the brim.

80. The prosthetic heart valve device of any of examples 60-63 wherein the extension member comprises a plurality of discreet petals extending from an upstream end of the anchoring member.

81. The prosthetic heart valve device of any of examples 60-63 wherein in a deployed state the fixation frame is configured to engage tissue downstream of a native annulus of a heart valve and the extension member is configured to engage tissue upstream of the native annulus.

82. The prosthetic heart valve device of example 81 wherein the extension member is configured align the heart valve device relative to the native annulus by engaging the tissue upstream of the native annulus.

83. The prosthetic heart valve device of any of examples 61-63 wherein the support structure comprises a resilient metal or polymer mesh.

84. The prosthetic heart valve device of any of examples 61-63 wherein the support structure is coupled to the fixation frame by a plurality of flexible connecting members, the connecting members being substantially less rigid than the fixation frame.

85. The prosthetic heart valve device of any of examples 61-63 wherein the extension member is coupled to the anchoring member only by the brim.

86. A prosthetic heart valve device comprising:
an anchoring member having a tubular fixation frame with an interior and having an upstream end and a downstream end;
a valve coupled to the anchoring member and having at least one leaflet movable from a closed position in which blood flow is blocked through the interior and an open position in which blood flow is allowed through the interior in a flow direction from the upstream end toward the downstream end; and an extension member comprising:
- a brim comprised of a sheet of flexible material coupled to the anchoring member near the upstream end thereof and extending radially outward therefrom; and
- a resilient support structure coupled to the brim and being structurally independent of the fixation frame;

wherein the extension member is radially deformable without substantially deforming the anchoring member.

87. A method of replacing a native heart valve comprising:

positioning a prosthesis in a first heart chamber upstream of a native annulus with a delivery device, the prosthesis being in a collapsed configuration;

deploying an extension member of the prosthesis in the first heart chamber so that the extension member at least partially expands into an expanded shape while an anchoring member of the prosthesis remains at least partially collapsed;

moving the prosthesis to cause an indicator portion of the extension member to deflect by engagement with a wall of the first heart chamber surrounding the native heart valve;

visualizing the indicator portion of the extension member to determine a position of the prosthesis relative to a native annulus based on the deflection of the indicator portion; and deploying the anchoring member of the prosthesis such that it expands into engagement with heart tissue downstream of the native annulus so as to anchor the prosthesis in place.

88. The method of example 87 wherein the indicator portion comprises a radiopaque material, the indicator portion being visualized using fluoroscopy.

89. The method of example 87 wherein the indicator portion comprises an echogenic material, the indicator portion being visualized using ultrasound.

90. The method of example 87 wherein the indicator portion comprises one or more metallic members.

91. The method of example 87 wherein the indicator portion deflects about an axis generally parallel to a plane containing the native annulus.

92. The method of example 87 wherein the indicator portion forms an angle with a plane containing the native annulus, the angle increasing as the indicator portion is deflected.

93. The method of example 92 wherein the indicator portion forms a first angle with the plane during the visualization step, further comprising moving the prosthesis after the visualization step such that the indicator portion forms a second angle with the plane less than the first angle before the anchoring member is deployed.

94. A method of replacing a native heart valve comprising:

positioning a prosthesis in a first heart chamber upstream of a native annulus with a delivery device, the prosthesis being in a collapsed configuration;

deploying an extension member of the prosthesis in the first heart chamber so that the extension member at least partially expands into an expanded shape while an anchoring member of the prosthesis remains at least partially collapsed;

deploying the anchoring member of the prosthesis such that it expands into engagement with heart tissue downstream of the native annulus so as to anchor the prosthesis in place; and allowing the extension member to radially deform to a greater extent than any deformation of the anchoring member.

95. The method of example 94 further comprising expanding a tubular valve support coupled to the anchoring member, the valve support having a valve coupled thereto.

96. The method of example 95 wherein the valve support has a lower extremity coupled to a downstream end of the anchoring member and an upper extremity which is mechanically isolated from an upstream end of the anchoring member.

97. The method of example 96 further comprising allowing the anchoring member to radially deform without substantially deforming the second end of the valve support.

98. The method of example 94 wherein the extension member is coupled to the anchoring member by a flexible coupling member, the coupling member being substantially less rigid than the anchoring member.

99. The method of example 98 wherein the coupling member is fabric.

100. A prosthetic heart valve device comprising:

an anchoring member having a radially expandable frame with an interior and having an upstream end and a downstream end, wherein the upstream end includes a tissue fixation portion configured to engage tissue located at and/or downstream of a native annulus of a heart valve in a subject and configured to be at least partially deformable to conform to a shape of the tissue;

a valve positioned relative to the anchoring member and having at least one leaflet movable from a closed position in which blood flow is blocked through the interior and an open position in which blood flow is allowed through the interior in a flow direction from the upstream end toward the downstream end, wherein the valve is spaced inwardly apart from the tissue fixation portion of the anchoring member such that the valve remains competent when the tissue fixation portion is deformed to conform to the shape of the tissue; and an extension member flexibly coupled to the anchoring member proximate the upstream end of the expandable frame, wherein the extension member extends longitudinally along the flow direction in a low-profile configuration and is biased to project laterally relative to the flow direction in a deployed configuration, the extension member being configured to deform relative to the expandable frame in the deployed configuration.

101. The prosthetic heart valve device of example 100 wherein the extension member comprises a brim projecting from the upstream end of the frame.

102. The prosthetic heart valve device of example 100 wherein the extension member comprises a shoulder.

103. The prosthetic heart valve device of example 100 wherein the extension member comprises an expansion ring separate from the anchoring member, and the device further includes a tether attached to the expansion ring and the anchoring member.

104. The prosthetic heart valve device of any of examples 101, 102 and 103 wherein the brim comprises a cover.

105. The prosthetic heart valve device of example 104 wherein the cover comprises a web material.

106. The prosthetic heart valve device of example 105 wherein the web comprises a woven, braided and/or grating of flexible material.

107. The prosthetic heart valve device of any of examples 105 and 106 wherein the web comprises a shape-memory polymeric material, a shape-memory metal, and/or a fabric.

108. The prosthetic heart valve device of any of examples 101-107 wherein the extension member further comprises a support structure attached to the brim.

109. The prosthetic heart valve device of example 108 wherein the support structure comprises a stiffening member more rigid than the brim.

110. The prosthetic heart valve device of example 109 wherein the stiffening member comprises a scaffold formed from a polymeric material and/or a metal.

111. The prosthetic heart valve device of example 110 wherein the scaffold has a serpentine, zig-zag, diamond pattern, and/or square pattern.

112. The prosthetic heart valve device of example 111 wherein the scaffold comprises a continuous strut.

113. The prosthetic heart valve device of example 111 wherein the scaffold comprises a plurality of struts that are connected together.

114. The prosthetic heart valve device of any of examples 108-113 wherein the support member is spaced apart from the expandable frame such that support member is only indirectly coupled to the anchoring member by the brim.

115. The prosthetic heart valve device of examples 108-113 wherein the support member is mechanically isolated from the expandable frame.

116. The prosthetic heart valve device of example 115 wherein the support member is spaced apart from the frame of the anchoring member and indirectly coupled to the anchoring member by the brim.

117. The prosthetic heart valve device of any of examples 108-113 wherein the support member is directly connected to the expandable frame.

118. A method of replacing a native heart valve comprising:
   positioning a prosthesis in a first heart chamber upstream of a native annulus with a delivery device, the prosthesis being in a collapsed configuration;
   deploying an extension member of the prosthesis in the first heart chamber so that the extension member at least partially expands into an expanded shape while a fixation member of the prosthesis remains at least partially collapsed;
   moving the prosthesis in a downstream direction such that the expanded extension member folds at least partially inwardly and positions the fixation member at a desired location relative to the native valve annulus; and
   deploying the fixation member of the prosthesis such that it expands into engagement with heart tissue downstream of the native annulus so as to anchor the prosthesis in place.

119. The method of example 118, further comprising visualizing via an imaging modality the extension member folding inwardly while moving the prosthesis downstream.

120. The method of any of examples 118 and 119, wherein the extension member causes the fixation member to align with the native valve annulus.

121. The method of any of examples 118-120 wherein the extension member is configured for tissue ingrowth such that the extension member provides additional fixation and sealing over time.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A prosthetic heart valve device for treating a native heart valve having a native annulus and native leaflets, comprising:
   a valve support having an upstream region and a downstream region relative to blood flow direction through a native heart valve of a human heart, the upstream region being configured to support a prosthetic valve, the prosthetic valve having a plurality of leaflets and having an undeformed shape in which the leaflets coapt sufficiently to prevent backflow through the prosthetic valve;
   an anchoring member arranged around the valve support and including an outwardly-facing fixation portion having an engagement surface configured to engage tissue at an implant site proximate the native annulus, the fixation portion having a first cross-sectional shape in an unbiased condition and being deformable into a second cross-sectional shape to adapt to a shape of the tissue at the implant site in a deployed state; and
   a connection structure interconnecting the fixation portion to the valve support, the fixation portion extending from the connection structure at a transition zone, and the transition zone being configured to be positioned at a subannular location below the native annulus and to allow the fixation portion to deflect angularly relative to the connection structure;
   wherein the tissue fixation portion of the anchoring member is mechanically isolated from the upstream region of the valve support such that the upstream region of the valve support maintains the undeformed shape if the anchoring member has deformed into the second cross-sectional shape.

2. The prosthetic heart valve device of claim 1 further comprising a plurality of barbs extending in an upstream direction from the fixation surface.

3. The prosthetic heart valve device of claim 1 wherein the fixation portion is biased radially outward to apply a compressive force to native tissue at the implant location.

4. The prosthetic heart valve device of claim 1 wherein, in an unbiased condition, the connection structure extends in a transverse direction relative to the blood flow direction, and the engagement surface is disposed in a longitudinal direction at a different angle relative to the blood flow direction than the connection structure.

5. The prosthetic heart valve device of claim 1 wherein the fixation portion has at least one tissue engagement feature configured to engage tissue on a subannular aspect of the native annulus.

6. The prosthetic heart valve device of claim 1 wherein the transition zone is configured to be positioned under the native annulus and the fixation portion is deflectable such that the engagement surface is tapering inward in the upstream direction.

7. The prosthetic heart valve device of claim 1 wherein the connection structure comprises a plurality of struts each having an inner end connected to the valve support and an outer end connected to the anchoring member.

8. The prosthetic heart valve device of claim 1 wherein the fixation portion and the connection structure comprise metal struts, and the transition zone comprises a bend in the metal struts from the connection structure to the fixation portion.

9. The prosthetic heart valve of claim 1 wherein the fixation portion is attached to the connection structure by a fastener configured to pivot, rotate or flex to an inward and/or outward orientation.

10. The prosthetic heart valve device of claim 1 wherein the connection structure has a flared portion that flares outwardly in the upstream direction.

11. The prosthetic heart valve of claim 10 wherein the flared portion of the connection structure extends inwardly in a downstream direction from the fixation portion such that the connection structure is disposed entirely downstream of the native annulus when the anchoring member is at the implant site.

12. The prosthetic heart valve device of claim 10 wherein the connection structure has an upstream end connected to the anchoring member, and the upstream end being configured for positioning at or below the native annulus when the anchoring member is at the implant site.

13. The prosthetic heart valve device of claim 1 wherein the connection structure comprises a flexible web coupling the fixation portion to the valve support.

14. The prosthetic heart valve device of claim 13 wherein the flexible web comprises a first portion at the upstream end of the valve support and a second portion at the downstream end of the valve support.

15. The prosthetic heart valve device of claim 1 wherein the engagement surface is deflectable through a range of angles relative to the connection structure.

16. The prosthetic heart valve device claim 1 wherein:
the fixation portion comprises a skirt covering an inward-facing surface thereof;
the valve support includes a tubular valve cover extending around the valve support; and
the skirt is attached to the valve cover so as to inhibit blood flow therebetween.

17. The prosthetic heart valve device of claim 1 wherein the fixation surface extends in a direction at least generally parallel to a longitudinal axis of the anchoring member.

18. The prosthetic heart valve device of claim 1 wherein the transition zone is configured to be positioned under the native annulus.

* * * * *